(12) United States Patent
Kilburn et al.

(10) Patent No.: US 11,358,971 B2
(45) Date of Patent: Jun. 14, 2022

(54) PRODRUGS OF MODULATORS OF THE NMDA RECEPTOR

(71) Applicant: H. Lundbeck A/S, Valby (DK)

(72) Inventors: John Paul Kilburn, Valby (DK); Erhad Ascic, Valby (DK); Mauro Marigo, Valby (DK); Laurent David, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/916,681

(22) Filed: Jun. 30, 2020

(65) Prior Publication Data

US 2021/0047342 A1 Feb. 18, 2021

(30) Foreign Application Priority Data

Jul. 3, 2019 (DK) .............................. PA201900822

(51) Int. Cl.
*C07D 495/04* (2006.01)
(52) U.S. Cl.
CPC .................................. *C07D 495/04* (2013.01)
(58) Field of Classification Search
CPC ................................................... C07D 495/04
See application file for complete search history.

(56) References Cited

U.S. PATENT DOCUMENTS

| | | | |
|---|---|---|---|
| 5,026,700 A | 6/1991 | Harrison et al. | |
| 7,754,896 B2 | 7/2010 | Azzaoui et al. | |
| 2014/0336108 A1 | 11/2014 | Guo et al. | |
| 2021/0002292 A1 | 1/2021 | Kilburn et al. | |

FOREIGN PATENT DOCUMENTS

| | | | |
|---|---|---|---|
| EP | 0581106 A1 | 2/1994 | |
| EP | 1708998 A1 | 10/2006 | |
| WO | WO 95/21612 A2 | 8/1995 | |
| WO | WO 96/40097 A1 | 12/1996 | |
| WO | WO 97/46511 A1 | 12/1997 | |
| WO | WO 98/56752 A1 | 12/1998 | |
| WO | WO 2004/048386 A2 | 6/2004 | |
| WO | WO 2005/070886 A1 | 8/2005 | |
| WO | WO 2006/030031 A1 | 3/2006 | |

OTHER PUBLICATIONS

Urwyler et al. in Journal of Medicinal Chemistry (2009), 52(16), 5093-5107 (Year: 2009).*
Peyrovian et al. disclose in Progress in Neuropsychopharmacology& Biological Psychiatry 92, 387-404 (2019) (Year: 2019).*
U.S. Appl. No. 16/916,769, filed Jun. 30, 2020, Pending.
PCT/EP2020/068522, Oct. 2, 2020, International Search Report and Written Opinion.
PCT/EP2020/068513, Oct. 2, 2020, International Search Report and Written Opinion.
PA 201900821, Oct. 9, 2019, Danish Search Report.
PA 201900822, Oct. 9, 2019, Danish Search Report.
International Search Report and Written Opinion dated Oct. 2, 2020 in connection with Application No. PCT/EP2020/068522.
International Search Report and Written Opinion dated Oct. 5, 2020 in connection with Application No. PCT/EP2020/068513.
Danish Search Report dated Oct. 9, 2019 in connection with Application No. PA 201900821.
Danish Search Report dated Oct. 9, 2019 in connection with Application No. PA 201900822.
Heresco-Levy et al., Controlled trial of D-cycloserine adjuvant therapy for treatment-resistant major depressive disorder. J Affect Disord. Jul. 2006;93(1-3):239-43. doi: 10.1016/j.jad.2006.03.004. Epub May 4, 2006.
Olden et al., Pilot Study of a Telehealth-Delivered Medication-Augmented Exposure Therapy Protocol for PTSD. J Nerv Ment Dis. Feb. 2017;205(2):154-160. doi: 10.1097/NMD.0000000000000563.
Peyrovian et al., The glycine site of NMDA receptors: A target for cognitive enhancement in psychiatric disorders. Prog Neuropsychopharmacol Biol Psychiatry. Jun. 8, 2019;92:387-404. doi: 10.1016/j.pnpbp.2019.02.001. Epub Feb. 6, 2019.
Urwyler et al., Drug design, in vitro pharmacology, and structure-activity relationships of 3-acylamino-2-aminopropionic acid derivatives, a novel class of partial agonists at the glycine site on the N-methyl-D-aspartate (NMDA) receptor complex. J Med Chem. Aug. 27, 2009;52(16):5093-107. doi: 10.1021/jm900363q.
Zhou et al., Targeting N-methyl-D-aspartate receptors for treatment of neuropathic pain. Expert Rev Clin Pharmacol. May 2011;4(3):379-88. doi: 10.1586/ecp.11.17.
International Search Report and Written Opinion dated Mar. 2, 2022 in connection with Application No. PCT/EP2021/085681.
Greenfield et al., Synthesis and biological activities of aryl-ether-, biaryl-, and fluoreneaspartic acid and diaminopropionic acid analogs as potent inhibitors of the high-affinity glutamate transporter EAAT-2. Bioorg Med Chem Lett. Nov. 15, 2005;15(22):4985-8.
Maolanon et al., Subtype-specific agonists for NMDA receptor glycine binding sites. ACS Chem Neurosci. Aug. 16, 2017;8(8):1681-1687. Epub May 3, 2017.
Nakada et al., Novel acyl coenzyme A (CoA): diacylglycerol acyltransferase-1 inhibitors: synthesis and biological activities of diacylethylenediamine derivatives. Bioorg Med Chem. Apr. 2010 1;18(7):2785-95. Epub Feb. 4, 2010.

* cited by examiner

*Primary Examiner* — Jared Barsky
(74) *Attorney, Agent, or Firm* — Wolf, Greenfield & Sacks, P.C.

(57) ABSTRACT

The present invention is directed to novel prodrugs of modulators of the NMDA receptor. Separate aspects of the inventions are directed to pharmaceutical compositions comprising said compounds and uses of the compounds to treat neurological disorders or neuropsychiatric disorders such as depression.

36 Claims, 7 Drawing Sheets

PRODRUGS OF MODULATORS OF THE NMDA RECEPTOR

CROSS-REFERENCE TO RELATED APPLICATION

This application claims priority to Danish Application No. PA201900822, filed Jul. 3, 2019, the entire contents of the aforementioned application is hereby incorporated herein by reference.

FIELD OF THE INVENTION

The present invention is directed to compounds that are prodrugs of modulators of the NMDA receptor, pharmaceutical compositions comprising said compounds, and their use in the treatment of neurological disorders or neuropsychiatric disorders such as depression, in particular major depressive disorder (MDD) and treatment-resistant depression (TRD).

BACKGROUND OF THE INVENTION

The World Health Organization estimates 350 million people will be affected with MDD and has projected that depression will constitute the largest health burden on society worldwide by 2030. A rough working estimate of prevalence is that depression affects ⅕th of the population at some point, affecting women in a higher proportion than men (5-9% and 2-3% incidence respectively in the US, representing an overall incidence of 6.6%). The North-American Center for Disease Control has reported that from 2005-2008, 8.9% of the US population was prescribed an antidepressant during any given month, antidepressants being also prescribed for anxiety, pain, and other non-mood disorders [Global Burden of Disease Study. Lancet. May 17, 1997; 349(9063): 1436-1442].

Antidepressants are marketed and thus known to the skilled person. Examples of different types of antidepressant are but not limited to, selective serotonin reuptake inhibitors (SSRs), Serotonin-norepinephrine reuptake inhibitors (SNRIs), Monoamine oxidase inhibitors (MAOIs), and Tricyclic antidepressants. Typical limitations of known antidepressants are delayed onset of efficacy and low remission rates after multiple courses of pharmacotherapy, and for some antidepressants severe side-effects [Antidepressants and the risk of suicidal behaviours. Jama. Jul. 21, 2004; 292(3):338-343].

In recent years, modulators of the N-Methyl-D-Aspartate (NMDA) receptors have received more attraction in treatment MDD, in particular treatment-resistant depression (TRD). Especially, ketamine, an antagonist of the NMDA receptor, is used for treating MMD due to its antidepressant effect and fast onset. However, MDD treatment with ketamine has the drawback of psychometric side effects and requirement of intravenous administration.

NMDA receptors are tetrameric ligand-gated ion channels which are also involved in essential physiological processes such as synaptic plasticity and development. NMDA receptors are heterotetramers comprising two GluN1 subunits and two GluN2/GluN3 subunits. This means that they assemble as either diheteromeric or triheteromeric receptors. The majority of native NMDA receptors consist of two GluN1 subunits and two GluN2 subunits. Activation of the NMDA receptors requires simultaneous binding at two different binding sites. Glutamate, the major excitatory neurotransmitter in the central nervous system, binds to the GluN2 subunits and glycine binds to the GluN1 and GluN3 subunits.

Another known modulator of the NMDA receptor is D-cycloserine, which is a partial glycine site agonist. D-cycloserine has been intensively studied due to its neuroactive properties and potential utility in treatment of depression and depression disorders such as MDD [Heresco-Levy, U., Javitt, D. C., Gelfin, Y., Gorelik, E., Bar, M., Blanaru, M., Kremer, I., 2006. Controlled trial of d-cycloserine adjuvant therapy for treatment-resistant major depressive disorder. J. Affect. Disord. 93, 239-243] and PTSD [Olden, M., Wyka, K., Cukor, J., Peskin, M., Altemus, M., Lee, F. S., Finkelstein-Fox, L, Rabinowitz, T., Difede, J., 2017. Pilot study of a telehealth-delivered medication augmented exposure therapy protocol for PTSD. J. Nerv. Ment. Dis. 205, 154-160]. However, treatment of D-cycloserine suffers from frequent complaints of psychopathological stimulation such as anxiety, euphoria, agitation, feeling stimulated, dizziness/drowsiness, fatigue, headache, and gastrointestinal disturbance [Schade, S., Paulus, W., 2016. D-Cycloserine in neuropsychiatric diseases: a systematic review. Int. J. Neuropsychopharmacol]

Urwyler et al., J. Med. Chem. 2009, 52, 5093-5107 discloses 3-acylamino-2-amonipropionic acid derivatives with affinity for the glycine site of the NMDA receptor.

Despite the longstanding interest in the field, there is evidently still an unmet need as regards developing efficient, well tolerated and active drugs for the treatment of depression in particular MDD and TRD. A prodrug of a compound being a modulator of the NMDA receptor, with improved permeability and brain exposure compared to the parent compound may fulfil such unmet needs.

SUMMARY OF THE INVENTION

With this background, it is an object of the invention to provide a prodrug of modulators of the NMDA receptor. Accordingly, the present invention relates to compounds of formula I, or a pharmaceutically acceptable salt thereof, wherein:

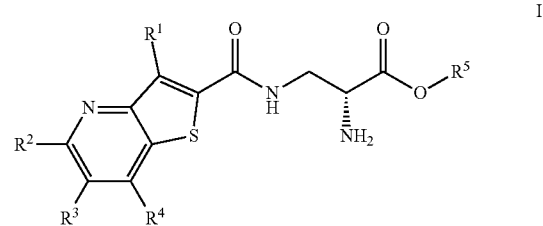

$R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $NR^aR^b$, $SR^cR^d$, $OR^6$, L-($OR^6$), and $R^7$;

$R^a$ and $R^b$ are independently selected from the group consisting of hydrogen, and $C_{1-4}$ alkyl;

$R^c$ and $R^d$ are independently selected from the group consisting of hydrogen, and $C_{1-4}$ alkyl;

$R^6$ is selected from the group consisting of hydrogen, halogen, $C_{1-4}$ alkyl, $C_{1-4}$ haloalkyl, $C_{1-4}$ hydroxyalkyl, and $C_{1-4}$ hydroxyhaloalkyl;

L represents $C_{1-3}$ alkylene;

$R^7$ is selected from the group consisting of $C_{3-6}$ cycloalkyl, phenyl, a 4, 5, or 6 membered heterocycle, and a 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F;

$R^5$ is selected from the group consisting of $C_{1-5}$ alkyl, $C_{1-4}$ haloalkyl, hydroxyalkyl, $C_{1-4}$ hydroxyhaloalkyl, $R^8$, $WR^8$, and $W(OR^9)$;

W is selected from the group consisting of $C_{1-3}$ alkylene and —$CH_2C(O)$—;

$R^8$ is selected from the group consisting of $C_{3-6}$ cycloalkyl, phenyl, a 4, 5, or 6 membered heterocycle, and a 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F; and $R^9$ is $C_{1-3}$ alkyl unsubstituted or substituted with 1, 2 or 3 F.

In a further aspect is provided a pharmaceutical composition comprising a compound of formula I or a pharmaceutically acceptable salt thereof, and one or more pharmaceutically acceptable carrier or diluents.

In a further aspect is provided a method for the treatment of depression comprising the administration of a therapeutically effective amount of a compound of formula I, or acceptable salt thereof, or a pharmaceutical composition to a patient in need thereof.

In a further aspect is provided a compound of formula I, or a pharmaceutically acceptable salt thereof for use as a medicament.

In a further aspect is provide a compound of formula I, or a pharmaceutically acceptable salt thereof, or a pharmaceutical composition for use in the treatment of depression.

In a further aspect is provided a use of a compound of formula I, or a pharmaceutically acceptable salt thereof, or a pharmaceutical composition comprising a compound of formula I, or a pharmaceutically acceptable salt thereof for the manufacture of a medicament for use in the treatment of depression.

These and other aspects of the invention will become apparent upon reference to the following detailed description. It should be understood that the various aspects, embodiments, implementations and features of the invention mentioned herein may be claimed separately, or in any combination.

All references, including publications, patent applications and patents, cited herein are hereby incorporated by reference in their entirety and to the same extent as if each reference were individually and specifically indicated to be incorporated by reference and were set forth in its entirety.

Headings and sub-headings are used herein for convenience only and should not be construed as limiting the invention in any way.

Significance levels for post-hoc comparisons (relative to the vehicle group) are indicated: *<0.05, <0.01, *<0.001.

Figure 2:
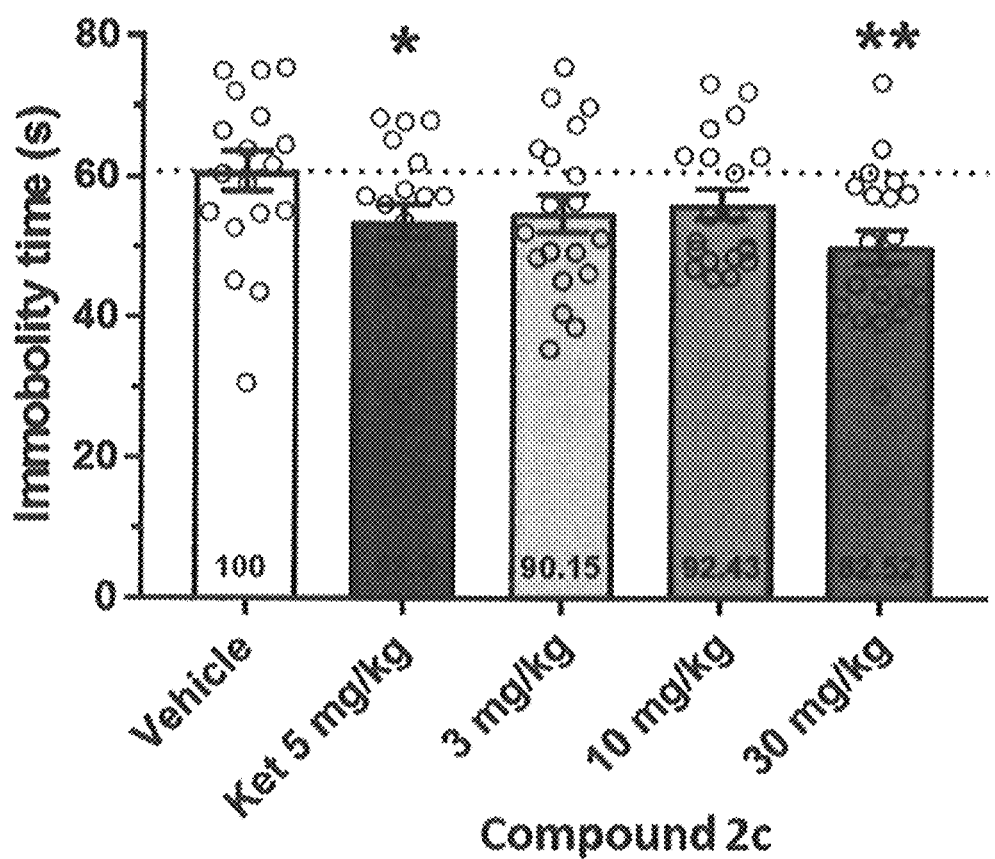

FIG. 2: Effects of compound 2c and ketamine in the forced swim test model.
Y-axis: Immobility time (s); X-axis: bar furthest to the left: Vehicle; bar second to the left: ketamine (5 mg/kg); bar in the middle: compound 2c (3 mg/kg); bar second to the right: compound 2c (10 mg/kg); bar furthest to the right: compound 2c (30 mg/kg)

Significance levels for post-hoc comparisons (relative to the vehicle group) are indicated: *<0.05, <0.01, *<0.001.

Figure 3A:
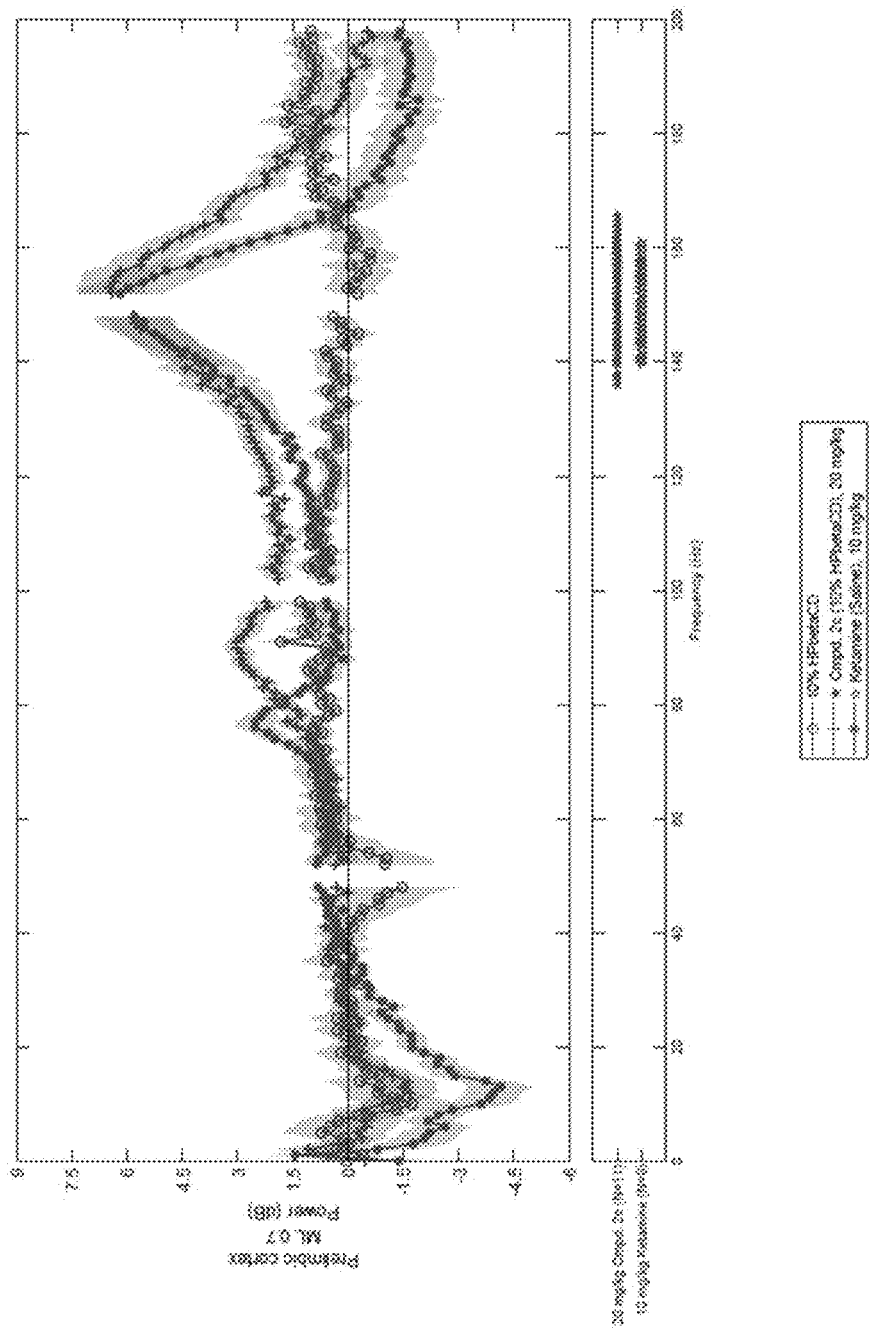

FIGS. 3A-3D: Effects of compound 2c and ketamine in Resting state Electroencephalography (rsEEG).
Y-axis: Baseline-normalized power (dB); X-axis: Frequency (Hz);

FIG. 3A: rsEEG obtained in the prelimbic cortex ML 0.7; 30-40 min after dosing of compound 2c (20 mg/kg in 10% HPβCD); ketamine (10 mg/kg in saline); or 10% HPβCD.
+: compound 2c; *: ketamine; O: 10% HPβCD.

Figure 3B:
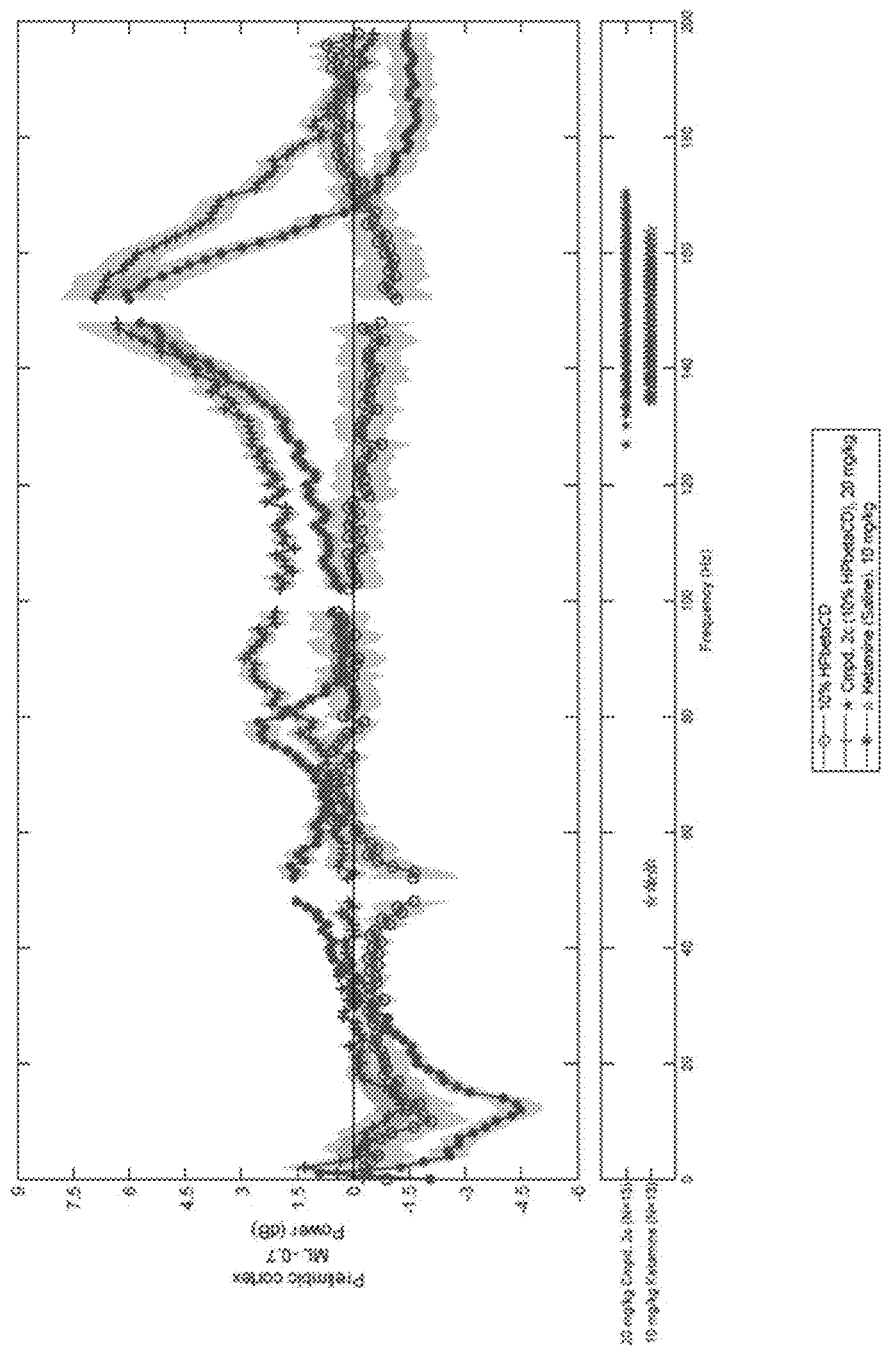

FIG. 3B: rsEEG obtained in the prelimbic cortex ML –0.7; 30-40 min after dosing of compound 2c (20 mg/kg in 10% HPβCD); ketamine (10 mg/kg in saline); or 10% HPβCD.
+: compound 2c; *: ketamine; O: 10% HPβCD.

Figure 3C:
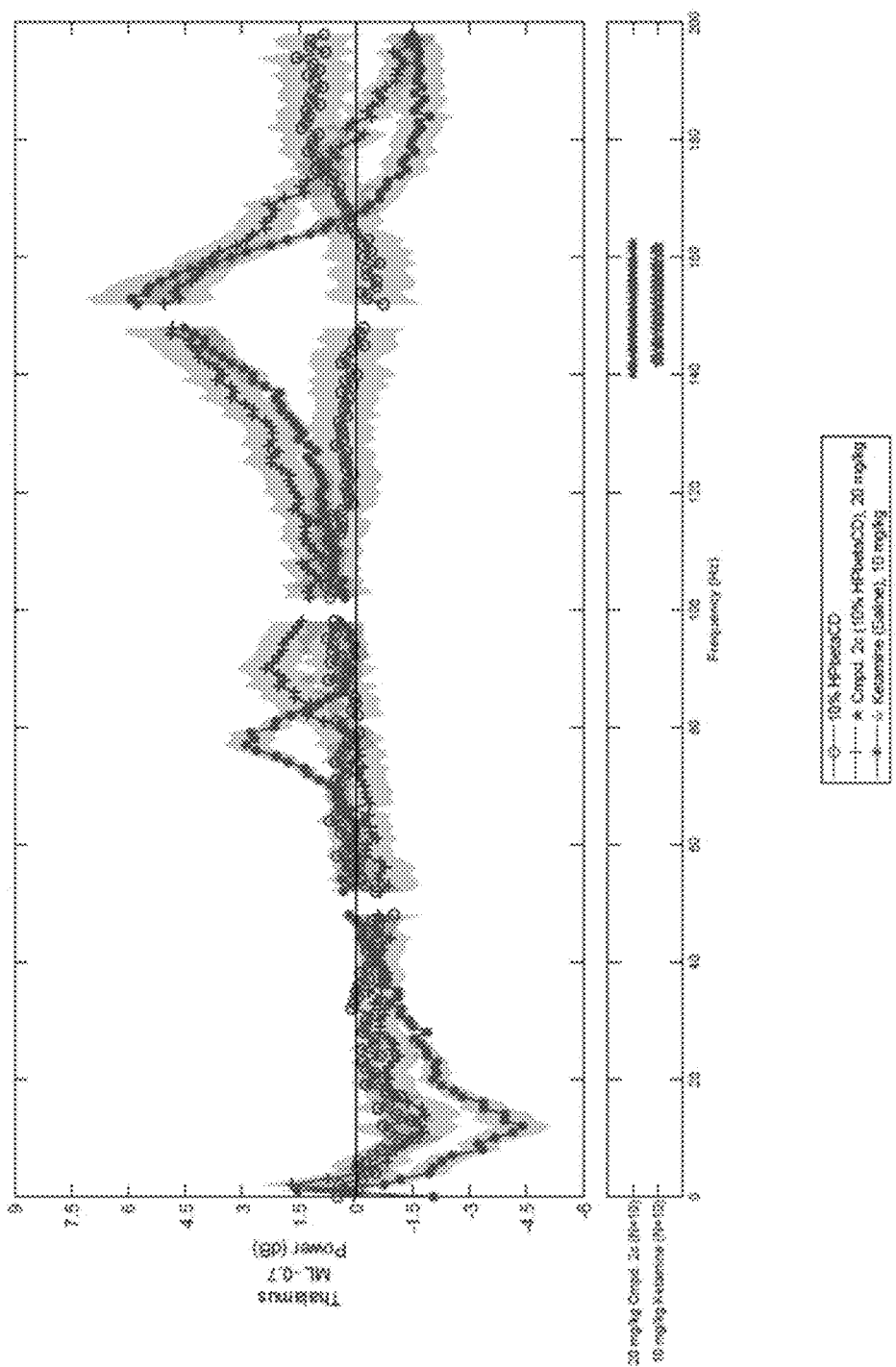

FIG. 3C: rsEEG obtained in the Thalamus ML –0.7; 30-40 min after dosing of compound 2c (20 mg/kg in 10% HPβCD); ketamine (10 mg/kg in saline); or 10% HPβCD.
+: compound 2c; *: ketamine; O: 10% HPβCD.

Figure 3D:
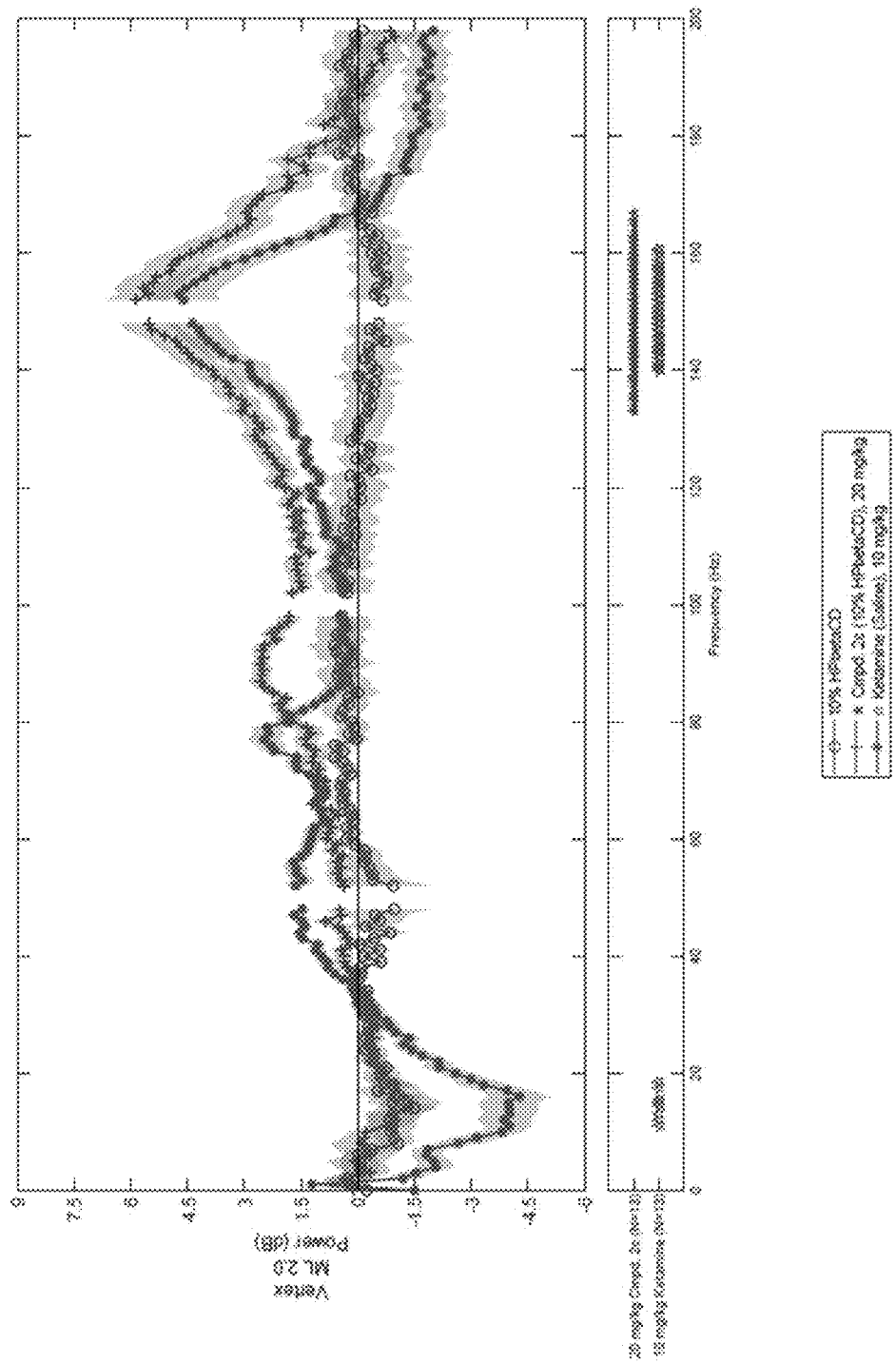

FIG. 3D: rsEEG obtained in the Vertex ML 2.0; 30-40 min after dosing of compound 2c (20 mg/kg in 10% HPβCD); ketamine (10 mg/kg in saline); or 10% HPβCD.
+: compound 2c; *: ketamine; O: 10% HPβCD.

Significance levels for post-hoc comparisons (relative to the vehicle group) are indicated:
*<0.05, <0.01, *<0.001.

Figure 4:
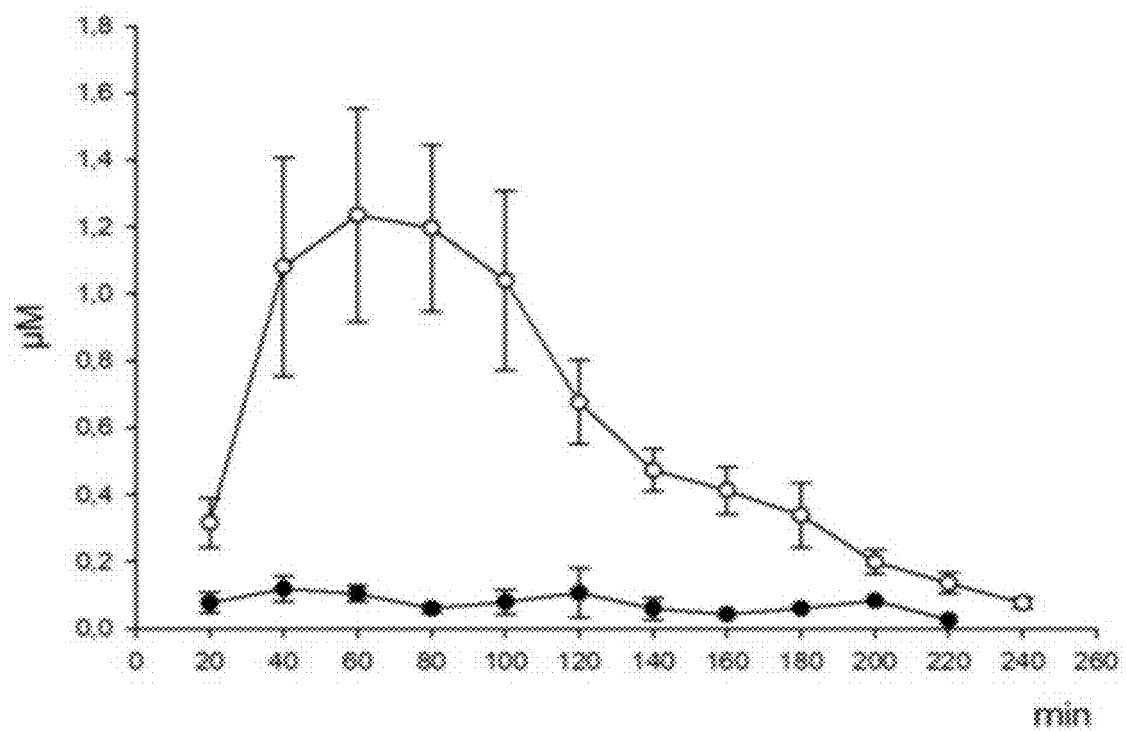

FIG. 4: Micro dialysis studies in rats after systemic administration of compound 1c.
X-axis: time (minutes); Y-axis: concentration of tested compound in the rat ventral hippocampus (µM); O: Compound 1c; •: Compound 2c.

DETAILED DESCRIPTION OF THE INVENTION

The present invention relates to ester prodrugs of the parent compounds with the Formula V or a pharmaceutically acceptable salt thereof, wherein:

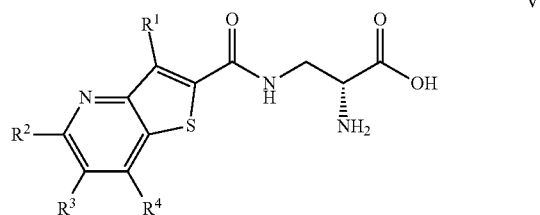

V $R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $NR^aR^b$, $SR^cR^d$, $OR^6$, $L\text{-}(OR^6)$, and $R^7$;

$R^a$ and $R^b$ are independently selected from the group consisting of hydrogen and $C_{1-4}$ alkyl;

$R^c$ and $R^d$ are independently selected from the group consisting of hydrogen and $C_{1-4}$ alkyl;

$R^6$ is selected from the group consisting of hydrogen, $C_{1-4}$ alkyl, $C_{1-4}$ haloalkyl, $C_{1-4}$ hydroxyalkyl, and $C_{1-4}$ hydroxyhaloalkyl;

L represents a $C_{1-3}$ alkylene; and $R^7$ is selected from the group consisting of $C_{3-6}$ cycloalkyl, phenyl, 4, 5, or 6 membered heterocycle, and 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F.

The inventors observed that dosing of the prodrug of the invention gave a significant response in the forced swim test and Maximal Electro Shock Threshold test compared to vehicle.

The inventors observed that the prodrugs of the invention have an improved permeability compared to the parent compounds of the invention as shown in table 3a and 3b.

The inventors observed that the administration of compound 2c dosed at 20 mg/kg subcutaneously showed significant effects in resting state Electroencephalography and showing similarities to that observed with ketamine as shown in FIGS. 3A-3D.

1. Definitions

As used herein, the terms "$C_{1-3}$ alkyl", "$C_{1-4}$ alkyl", "$C_{1-5}$ alkyl", "$C_{1-6}$ alkyl", "$C_{1-7}$ alkyl" and "$C_{1-8}$ alkyl" refers to a linear (i.e. unbranched) or branched saturated hydrocarbon having from one up to eight carbon atoms, inclusive. Examples of such groups include, but are not limited to methyl, ethyl, 1-propyl, 2-propyl, 1-butyl, 2-butyl, 2-methyl-2-propyl, 2-methyl-1-butyl, n-hexyl, isopropyl, isobutyl, isopentyl, n-heptyl and n-octyl.

As used herein, the term "alkoxy" refers to a moiety of the formula —OR', wherein R' indicates alkyl as defined above. In particular "$C_{1-4}$ alkoxy" refers to such moiety wherein the alkyl part has 1, 2, 3 or 4 carbon atoms. Examples of "$C_{1-4}$ alkoxy" include methoxy, ethoxy, n-butoxy and tert-butoxy.

As used herein, the term "alkoxyalkyl," as used herein, refers to an alkoxy group, as defined herein, appended to the parent molecular moiety through an alkyl group, as defined herein. Examples include, but are not limited to, methoxymethyl and ethoxymethyl.

As used in the context of the present invention, the terms "halo" and "halogen" are used interchangeably and refer to an atom of the group consisting of F, Cl, I and Br.

As used herein, the term "$C_{1-6}$ fluoroalkyl" refers to a straight chained or branched saturated hydrocarbon having from one to six carbon atoms inclusive substituted with one or more fluorine atoms. Examples include, but are not limited to, trifluoromethyl, pentafluoroethyl, 1-fluoroethyl, 1,2-difluoroethyl and 3,4 difluorohexyl.

Similarly, the term "$C_{1-4}$ fluoroalkyl" refers to a saturated hydrocarbon of straight chained or branched $C_{1-4}$ fluoroalkyl having from one to four carbon atoms inclusive substituted with one or more fluorine atoms per carbon atom.

As used herein, the term "cyano", refers to a CN group appended to the parent molecule through the carbon atom of the CN group.

The term "phenyl" is intended to mean a benzene radical, with one H removed at the attachment point.

The term "heteroaryl," as used herein, refers to an aromatic monocyclic ring. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, pyrrolidinyl, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, and isoxazolidinyll.

The term "cycloalkyl," as used herein, refers to a carbocyclic ring system containing three to ten carbon atoms, zero heteroatoms and zero double bonds. The cycloalkyl may be monocyclic or bicyclic, wherein the two rings are bridged, fused, or spirocyclic. Representative examples of cycloalkyl include, but are not limited to, cyclopropyl, cyclobutyl, cyclopentyl, cyclohexyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

In the present context, the term an NMDA receptor partial glycine agonist is intended to indicate a compound that binds to and activates the NMDA receptor through the orthosteric glycine binding site and elicits partial efficacy relative to glycine.

In the present context, the term "therapeutically effective amount" of a compound is intended to indicate an amount sufficient to cure, alleviate or partially arrest the clinical manifestations of a given disease (e.g. depression) and its complications in a therapeutic intervention comprising the administration of said compound. An amount adequate to accomplish this is defined as "therapeutically effective amount". Effective amounts for each purpose will depend on the severity of the disease (e.g. depression) or injury as well as the weight and general state of the subject. It will be understood that determining an appropriate dosage may be achieved using routine experimentation, e.g. by constructing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease (e.g. depression) from which the patient is suffering, such as administration of the active compound to alleviate the symptoms or complications, to delay the progression of the disease (e.g. depression), to alleviate or relief the symptoms and complications, and/or to cure or eliminate the depression disease. The patient to be treated is preferably a mammal, in particular a human being. In the present context, "disease" can be used synonymous with disorder, condition, malfunction, dysfunction and the like.

In the present context, the terms "prodrug" or "prodrug derivative" indicates a compound that, after administration to a living subject, such as a mammal, preferably a human is converted within the body into a pharmacologically active moiety. The conversion preferably takes place within a mammal, such as in a mouse, rat, dog, minipig, rabbit, monkey and/or human.

In the present context, the terms "parent compound" and "parent molecule" indicate the pharmacologically active moiety obtained upon conversion of a corresponding prodrug or administered as the active moiety to the patient. For example, the "parent compound" is to be understood as a compound of formula V exemplified with compound 1a, 1b, 1c, 1d, 1e, 1f, 1g, 1h, 1i, 1j, 1k, 1l, 1m, 1n, 1o, or 1p.

2. Embodiments of the Invention

In the following, embodiments of the invention are disclosed. The first embodiment is denoted E1, the second embodiment is denoted E2 and so forth.

E1. A compound of Formula I, or a pharmaceutically acceptable salt thereof, wherein:

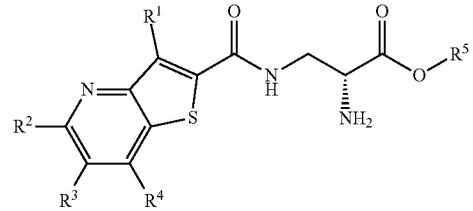

$R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $NR^aR^b$, $SR^cR^d$, $OR^6$, L-($OR^6$), and $R^7$;

$R^a$ and $R^b$ are independently selected from the group consisting of hydrogen, and $C_{1-4}$ alkyl;

$R^c$ and $R^d$ are independently selected from the group consisting of hydrogen, and $C_{1-4}$ alkyl;

$R^6$ is selected from the group consisting of hydrogen, halogen, $C_{1-4}$ alkyl, $C_{1-4}$ haloalkyl, $C_{1-4}$ hydroxyalkyl, and $C_{1-4}$ hydroxyhaloalkyl;

L represents $C_{1-3}$ alkylene;

$R^7$ is selected from the group consisting of $C_{3-6}$ cycloalkyl, phenyl, a 4, 5, or 6 membered heterocycle, and a 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F;

$R^5$ is selected from the group consisting of $C_{1-5}$ alkyl, $C_{1-4}$ haloalkyl, hydroxyalkyl, $C_{1-4}$ hydroxyhaloalkyl, $R^8$, $WR^8$, and $W(OR^9)$;

W is selected from the group consisting of $C_{1-3}$ alkylene and —$CH_2C(O)$—;

$R^8$ is selected from the group consisting of $C_{3-6}$ cycloalkyl, phenyl, a 4, 5, or 6 membered heterocycle, and a 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F; and $R^9$ is $C_{1-3}$ alkyl unsubstituted or substituted with 1, 2 or 3 F.

E2. The compound according to embodiment E1, or a pharmaceutically acceptable salt thereof, wherein:

$R^1$ is selected from the group consisting of a hydrogen, halogen, and $C_{1-4}$ alkyl;

$R^2$ is selected from the group consisting of hydrogen, halogen, and $C_{1-4}$ alkyl;

$R^3$ is selected from the group consisting of hydrogen, halogen, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $OR^6$, and $R^7$;

R⁶ is selected from the group consisting of hydrogen, $C_{1-4}$ alkyl, and $C_{1-4}$ haloalkyl;

R⁷ is selected from the group consisting of $C_{3-6}$ cycloalkyl and phenyl, wherein said cycloalkyl and phenyl is independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F;

R⁵ is selected from the group consisting of $C_{1-5}$ alkyl, R⁸, WR⁸, and W(OR⁹);

W is $C_{1-3}$ alkylene;

R⁸ is selected from the group consisting of $C_{3-6}$ cycloalkyl, phenyl, wherein said cycloalkyl and phenyl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F; and R⁹ is $C_{1-3}$ alkyl unsubstituted or substituted with 1, 2 or 3 F.

E3. The compound according to any one of embodiments E1 to E2, or a pharmaceutically acceptable salt thereof, wherein R¹ is hydrogen.

E4. A compound according to any one of embodiments E1 to E3, or a pharmaceutically acceptable salt thereof, wherein R² is hydrogen.

E5. A compound according to any one of embodiments E1 to E4, or a pharmaceutically acceptable salt thereof, wherein R³ is selected from the group consisting of hydrogen, $C_{1-4}$ alkyl, and halogen.

E6. The compound according to embodiment E5, or a pharmaceutically acceptable salt thereof, wherein R³ is selected from the group consisting of hydrogen, fluoro, and methyl.

E7. The compound according to embodiment E6, or a pharmaceutically acceptable salt thereof, wherein R³ is hydrogen.

E8. The compound according to any of embodiments E1 to E2, or a pharmaceutically acceptable salt thereof, wherein R¹, R², and R³ are hydrogen.

E9. The compound according to any one of embodiments E1 to E8, or a pharmaceutically acceptable salt thereof, wherein R⁴ is $C_{1-4}$ alkyl.

E10. The compound according to any one of embodiments E1 to E9, or a pharmaceutically acceptable salt thereof, wherein R⁴ is methyl.

E11. The compound according to any one of embodiments E1 to E8, or a pharmaceutically acceptable salt thereof, wherein R⁴ is $C_{1-4}$ fluoroalkyl.

E12. The compound according to any one of embodiments E1 to E8, or a pharmaceutically acceptable salt thereof, wherein R⁴ is halogen.

E13. The compound according to any one of embodiments E1 to E8, or a pharmaceutically acceptable salt thereof, wherein R⁴ is phenyl unsubstituted or substituted with $C_{1-3}$ alkyl.

E14. The compound according to any one of embodiments E1 to E8, or a pharmaceutically acceptable salt thereof, wherein R⁴ is $C_{1-4}$ alkoxy.

E15. The compound according to any one of embodiments E1 to E7, or a pharmaceutically acceptable salt thereof, wherein R⁴ selected from the group consisting of $C_{1-4}$ alkyl, $C_1$-4 fluoroalkyl, $NR^aR^b$, $SR^cR^d$, $C_{1-4}$ hydroxyalkyl $C_{1-4}$ alkoxy, halogen, and phenyl unsubstituted or substituted with ethyl.

E16. The compound according to embodiment E15, or a pharmaceutically acceptable salt thereof, wherein R⁴ is selected from the group consisting of methyl, ethyl, isopropyl, cyclopropyl, fluoromethyl, difluoromethyl, trifluoromethyl, hydroxymethyl, isopropoxy, ethoxy, methoxy, bromo, fluoro, dimethylamino, methylthio, and ethylphenyl.

E17. A compound according to claim 1, having the formula Ia, or a pharmaceutically acceptable salt thereof, wherein:

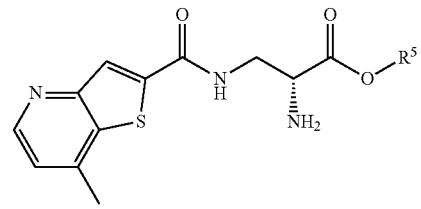

Ia

E18. The compound according to any one of embodiments E1 to E17, or a pharmaceutically acceptable salt thereof, wherein R⁵ is selected from the group consisting of methyl, ethyl, propyl, isopropyl, cyclopropyl, butyl, isobutyl, —CH₂-cyclopropyl, 2-methoxyethyl, isopentyl, benzyl, cyclohexyl, 2-oxo-2-(pyrrolidin-1-yl)ethyl and phenyl.

E19. The compound according to any one of embodiments E1 to E18, or a pharmaceutically acceptable salt thereof, wherein R⁵ is a $C_{1-5}$ alkyl.

E20. The compound according to any one of embodiments E1 to E19, or a pharmaceutically acceptable salt thereof, wherein R⁵ is selected from the group consisting of methyl, ethyl, propyl, butyl and isopropyl.

E21. The compound according to any one of embodiments E1 to E20, or a pharmaceutically acceptable salt thereof, wherein R⁵ is selected from the group consisting of methyl, ethyl, propyl, and butyl.

E22. The compound according to any one of embodiments E1 to E21, or a pharmaceutically acceptable salt thereof, wherein R⁵ is selected from the group consisting of methyl and ethyl.

E23. The compound according to any one of embodiments E1 to E22, or a pharmaceutically acceptable salt thereof, wherein R⁵ is methyl.

E24. The compound according to any one of embodiments E1 to E22, or a pharmaceutically acceptable salt thereof, wherein R⁵ is ethyl.

E25. The compound according to any one of embodiments E1 to E24 selected from the group consisting of:
methyl (R)-2-amino-3-(7-(difluoromethyl)thieno[3,2-b]pyridine-2-carboxamido)propanoate;
methyl (R)-2-amino-3-(7-cyclopropylthieno[3,2-b]pyridine-2-carboxamido)propanoate;
methyl (R)-2-amino-3-(7-methylthieno[3,2-b]pyridine-2-carboxamido)propanoate;
ethyl (R)-2-amino-3-(7-methylthieno[3,2-b]pyridine-2-carboxamido)propanoate;
propyl (R)-2-amino-3-(7-methylthieno[3,2-b]pyridine-2-carboxamido)propanoate;
isopropyl (R)-2-amino-3-(7-methylthieno[3,2-b]pyridine-2-carboxamido)propanoate;
cyclopropyl (R)-2-amino-3-(7-methylthieno[3,2-b]pyridine-2-carboxamido)propanoate;
butyl (R)-2-amino-3-(7-methylthieno[3,2-b]pyridine-2-carboxamido)propanoate;
isobutyl (R)-2-amino-3-(7-methylthieno[3,2-b]pyridine-2-carboxamido)propanoate;

cyclopropylmethyl (R)-2-amino-3-(7-methylthieno[3,2-b]pyridine-2-carboxamido)propanoate;
2-Methoxyethyl (R)-2-amino-3-(7-methylthieno[3,2-b]pyridine-2-carboxamido)propanoate;
isopentyl (R)-2-amino-3-(7-methylthieno[3,2-b]pyridine-2-carboxamido)propanoate;
benzyl (R)-2-amino-3-(7-methylthieno[3,2-b]pyridine-2-carboxamido)propanoate;
cyclohexyl (R)-2-amino-3-(7-methylthieno[3,2-b]pyridine-2-carboxamido)propanoate;
phenyl (R)-2-amino-3-(7-methylthieno[3,2-b]pyridine-2-carboxamido)propanoate;
(2-oxo-2-pyrrolidin-1-yl-ethyl) (R)-2-amino-3-[(7-methylthieno[3,2-b]pyridine-2-carboxamido)propanoate;
methyl (R)-2-amino-3-(7-(2-ethylphenyl)thieno[3,2-b]pyridine-2-carboxamido)propanoate;
methyl (R)-2-amino-3-(7-methoxythieno[3,2-b]pyridine-2-carboxamido)propanoate;
methyl (R)-2-amino-3-(7-(trifluoromethyl)thieno[3,2-b]pyridine-2-carboxamido)propanoate;
methyl (R)-2-amino-3-(7-isopropoxythieno[3,2-b]pyridine-2-carboxamido)propanoate;
methyl (R)-2-amino-3-(7-bromothieno[3,2-b]pyridine-2-carboxamido)propanoate;
methyl (R)-2-amino-3-(7-(hydroxymethyl)thieno[3,2-b]pyridine-2-carboxamido)propanoate;
methyl (R)-2-amino-3-(7-(fluoromethyl)thieno[3,2-b]pyridine-2-carboxamido)propanoate;
methyl (R)-2-amino-3-(6-fluoro-7-methyl-thieno[3,2-b]pyridine-2-carboxamido)propanoate; and
methyl (R)-2-amino-3-(6,7-dimethylthieno[3,2-b]pyridine-2-carboxamido)propanoate; or a pharmaceutically acceptable salt thereof.

E26. The compound according to embodiment E1 selected from the group consisting of:
methyl (R)-2-amino-3-(7-methylthieno[3,2-b]pyridine-2-carboxamido)propanoate;
ethyl (R)-2-amino-3-(7-methylthieno[3,2-b]pyridine-2-carboxamido)propanoate;
propyl (R)-2-amino-3-(7-methylthieno[3,2-b]pyridine-2-carboxamido)propanoate;
isopropyl (R)-2-amino-3-(7-methylthieno[3,2-b]pyridine-2-carboxamido)propanoate;
cyclopropyl (R)-2-amino-3-(7-methylthieno[3,2-b]pyridine-2-carboxamido)propanoate;
butyl (R)-2-amino-3-(7-methylthieno[3,2-b]pyridine-2-carboxamido)propanoate;
isobutyl (R)-2-amino-3-(7-methylthieno[3,2-b]pyridine-2-carboxamido)propanoate;
cyclopropylmethyl (R)-2-amino-3-(7-methylthieno[3,2-b]pyridine-2-carboxamido)propanoate;
2-Methoxyethyl (R)-2-amino-3-(7-methylthieno[3,2-b]pyridine-2-carboxamido)propanoate;
isopentyl (R)-2-amino-3-(7-methylthieno[3,2-b]pyridine-2-carboxamido)propanoate;
benzyl (R)-2-amino-3-(7-methylthieno[3,2-b]pyridine-2-carboxamido)propanoate;
cyclohexyl (R)-2-amino-3-(7-methylthieno[3,2-b]pyridine-2-carboxamido)propanoate; and
phenyl (R)-2-amino-3-(7-methylthieno[3,2-b]pyridine-2-carboxamido)propanoate; or a pharmaceutically acceptable salt thereof.

E27. The compound according to embodiment E1 selected from the group consisting of:
methyl (R)-2-amino-3-(7-methylthieno[3,2-b]pyridine-2-carboxamido)propanoate;
ethyl (R)-2-amino-3-(7-methylthieno[3,2-b]pyridine-2-carboxamido)propanoate;
propyl (R)-2-amino-3-(7-methylthieno[3,2-b]pyridine-2-carboxamido)propanoate; and
isobutyl (R)-2-amino-3-(7-methylthieno[3,2-b]pyridine-2-carboxamido)propanoate; or a pharmaceutically acceptable salt thereof.

E28. A pharmaceutical composition comprising a compound, or a pharmaceutically acceptable salt thereof, according to any one of embodiments E1 to E27, and one or more pharmaceutically acceptable carriers or diluents.

E29. A compound or a pharmaceutically acceptable salt thereof according to any one of embodiments E1 to E27 for use as a medicament.

E30. A compound, or a pharmaceutically acceptable salt thereof, or a pharmaceutical composition according to any one of embodiments E1 to E28 for use in the treatment of depression.

E31. The compound or a pharmaceutical composition according to embodiment E30, wherein the depression is selected of major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

E32. A compound, or a pharmaceutically acceptable salt thereof, or a pharmaceutical composition according to any one of embodiments E1 to E28 for use in the treatment of a condition selected from suicidal ideation, bipolar disorder (including bipolar depression), obsessive compulsive disorder and status epilepticus.

E33. A method for the treatment of depression comprising the administration of a therapeutically effective amount of a compound or a pharmaceutically acceptable salt thereof, or a pharmaceutical composition according to any one of embodiments E1 to E28 to a patient (e.g. a human patient) in need thereof.

E34. The method for the treatment of depression according to embodiment E33, wherein depression is selected from major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

E35. Use of a compound or a pharmaceutically acceptable salt thereof, or a pharmaceutical composition according to any one of embodiments E1 to E28 for the manufacture of a medicament for use in the treatment of depression.

E36. The use of a compound or pharmaceutical composition according to embodiment E35, wherein the depression is selected from the group consisting of major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

Reference to compounds encompassed by the invention includes the free substance of compounds of the invention, pharmaceutically acceptable salts of compounds of the invention, such as acid addition salts or base addition salts, and polymorphic and amorphic forms of compounds of the invention and of pharmaceutically acceptable salts thereof. Furthermore, the compounds of the invention and pharmaceutically acceptable salts thereof may potentially exist in unsolvated as well as in solvated forms with pharmaceutically acceptable solvents such as water, ethanol and the like. Both solvated and unsolvated forms are encompassed by the present invention.

Compound names can be assigned by using the Struct=Name naming algorithm as part of CHEMDRAW®.

It should be understood that the compounds of the invention may possess tautomeric forms, stereoisomers, geometric isomers, and that these also constitute embodiments of the invention.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention. Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

Included in this invention are also isotopically labelled compounds, which are similar to those claimed in formula I, wherein one or more atoms are represented by an atom of the same element having an atomic mass or mass number different from the atomic mass or mass number usually found in nature (e.g., $^2H$, $^3H$, $^{11}C$, $^{13}C$, $^{15}N$, $^{18}F$ and the like). Particular mention is made of $^2H$ substituted compounds i.e. compounds wherein one or more H atoms are represented by deuterium.

In one embodiment of the invention one or more of the hydrogen atoms of the compound of formula I are represented by deuterium. It is recognized that elements are present in natural isotopic abundances in most synthetic compounds, and result in inherent incorporation of deuterium. However, the natural isotopic abundance of hydrogen isotopes such as deuterium is immaterial (about 0.015%) relative to the degree of stable isotopic substitution of com-pounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan.

In one embodiment, designation of a position as "D" in a compound has a minimum deuterium incorporation of greater than about 60% at that position such as greater than about 70% at that position such as greater than about 80% at that position such as greater than about 85% at that position. In a further embodiment, designation of a position as "D" in a compound has a minimum deuterium incorporation of greater than about 90% at that position such as greater than about 95% at that position such as greater than about 97% at that position such as greater than about 99% at that position.

a. Pharmaceutically Acceptable Salts

The compounds of this invention (parent compounds and their respective prodrugs) are generally utilized as the free substance or as a pharmaceutically acceptable salt thereof. When a compound of the invention contains a free base such salts may be prepared in a conventional manner by treating a solution or suspension of a free base of a compound of the invention with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts.

The term "pharmaceutically acceptable salts" include salts formed with inorganic and/or organic acids on the nitrogen atoms in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin, and sulfonic acids such as methanesulfonic acid, ethanesulfonic acid, toluenesulfonic acid and benzenesulfonic acid.

In an embodiment of the invention, the pharmaceutically acceptable salt is a hydrogen chloride salt.

In an embodiment of the invention, the pharmaceutically acceptable salt is a hydrogen bromide salt.

The term pharmaceutically acceptable salts also include salts formed with inorganic and/or organic bases on the acidic groups of compounds of the invention. Said bases may be selected from for example alkali metal bases, such as sodium hydroxide, lithium hydroxide, potassium hydroxide, alkaline earth bases, such as calcium hydroxide and magnesium hydroxide, and organic bases, such as trimethylamine.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

3. Conditions for Treatment

The invention encompasses use of the compounds of the invention for treatment of all diseases and disorders listed above.

As described above the present invention may be useful in the treatment of depression and depressive disorders. Hence in one embodiment, a compound of the invention is used for the treatment of depression.

The diagnosis of depression usually follows a clinical evaluation by a psychiatrist or other mental health professionals. The two most recognized sets of diagnostic criteria for major depressive disorder and other depressive, or mood disorders, are outlined in the DSM, Diagnostic and Statistical Manual of Mental Disorders, Fourth Edition, (DSM IV) published by the American psychiatric association and the ICD (ICD-10: International Statistical Classification of Diseases and Related Health Problems-10th Revision, published periodically by the World Health Organization) or any other psychiatric classification system.

Signs and symptoms of depression are for example depressed mood, loss of interest (anhedonia), weight or appetite changes, sleep problems, psychomotor activity (objective or subjective), fatigability, worthlessness, concentration difficulty, suicidal ideation, loss of confidence, sexual dysfunction and self-reproach.

Thus in an embodiment of the invention, treatment with compounds of the invention prevent, alter, reduce or alleviate one or more signs or symptoms of depression selected from the group consisting of depressed mood, loss of interest (anhedonia), weight or appetite changes, sleep problems, psychomotor activity (objective or subjective), fatigability, worthlessness, concentration difficulty, suicidal ideation, loss of confidence, sexual dysfunction and self-reproach.

The skilled person is familiar with various test for measuring the improvement of depressive symptoms. Examples of test for measuring the improvements are but not limited to the HAM-D or MADRS scale.

In an embodiment the depression is major depressive disorder

In a further embodiment the depression is treatment-resistant depression.

In a further embodiment the depression is selected from major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

In an embodiment of the invention, compound of the invention is used in the treatment of pain [Expert Rev Clin Pharmacol. 2011 May 1; 4(3): 379-388].

In a further embodiment the pain is neuropathic pain.

Preclinical animal models has demonstrated pro-cognitive and antidepressant-like effects with the use of NDMA glycine site modulators[Peyrovian et al., Progress in Neuropsychopharmacology & Biological Psychiatry. 92 (2019) 387-404].

Hence, in an embodiment of the invention, a compound of formula I or a pharmaceutically acceptable salt thereof is used in the treatment of a condition selected from suicidal ideation, bipolar disorder (including bipolar depression), obsessive compulsive disorder and status epilepticus In a further embodiment, the condition is suicidal ideation.

In an embodiment of the invention, compound of the invention is used the treatment of a neurological disorder or neuropsychiatric disorder.

a. Combination Treatment

In one embodiment of the invention, the compounds of the invention are for use as stand-alone treatment as the sole active compound. In another embodiment of the invention, the compounds of the invention may be used in combination with other agents useful in the treatment of disorders such as depression. The terms "combined use", "in combination with" and "a combination of" and the like as used herein in the context of the method of the invention comprising the combined administration of therapeutically effective amounts of a compound of the invention, and another compound, which compound is useful in the treatment a neurodegenerative disease or disorder, is intended to mean the administration of a compound of the invention simultaneously or sequentially, in any order, together with said other compound.

The two compounds may be administered simultaneously or sequentially with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more other compounds useful in the treatment of depression when treatment with a compound of the invention initiated. In other instances, the patient may already be in treatment with a compound of the invention when treatment with one or more other compounds useful in the treatment of a depression or psychosis is initiated. In other instances, the treatment with a compound of the invention and treatment with one or more other compounds useful in the treatment of psychosis initiated at the same time.

b. Compounds for Combination Treatment

Examples of therapeutically active compounds which may advantageously be combined with compounds of the invention include sedatives or hypnotics, such as benzodiazepines; anticonvulsants, such as lamotrigine, valproic acid, topiramate, gabapentin, carbamazepine; mood stabilizers such as lithium; dopaminergic drugs, such as dopamine agonists and L-Dopa; drugs to treat ADHD, such as atomoxetine; psychostimulants, such as modafinil, ketamine, methylphenidate and amphetamine; other antidepressants, such as mirtazapine, mianserin, vortioxetine, cipralex, and buproprion; hormones, such as T3, estrogen, DHEA and testosterone; atypical antipsychotics, such as olanzapine, brexpiprazole and aripiprazole; typical antipsychotics, such as haloperidol; drugs to treat Alzheimer's diseases, such as cholinesterase inhibitors and memantine, folate; S-Adenosyl-Methionine; immunmodulators, such as interferons; opiates, such as buprenorphins; angiotensin II receptor 1 antagonists (AT1 antagonists); ACE inhibitors; statins; and alpha1 adrenergic antagonist, such as prazosin.

c. Administration Routes

The pharmaceutical compositions comprising a compound of the invention, either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route.

It will be appreciated that the route will depend on the general condition and age of the subject to be treated, the nature of the condition to be treated and the active ingredient.

d. Doses

In one embodiment, the compound of the present invention is administered in an amount from about 0.5 mg/kg body weight to about 50 mg/kg body weight per day. In particular, daily dosages may be in the range of 1 mg/kg body weight to about 30 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

In an embodiment the frequency of administration is 1, 2, 3, 4, or 5 times per day In an embodiment the frequency of administration is once weekly.

In an embodiment the frequency of administration is twice weekly.

A typical oral dosage for adults will be in the range of 500-3000 mg/day of a compound of the present invention, such as 700-2800 mg/day, such as 1000-2000 mg/day or 1200-1700 mg/day. Conveniently, the compounds of the invention are administered in a unit dosage form containing said compounds in an amount of about 100 to 1000 mg, such as 100 mg, 150 mg, 200 mg, 250 mg, 300 mg, 350 mg, 400 mg, 450 mg, 500 mg, 750 mg or up to 1000 mg of a compound of the present invention.

In an embodiment the frequency of administration is 1, 2, 3, 4, or 5 times per day.

In one embodiment the frequency of administration is once weekly.

In an embodiment the frequency of administration is twice weekly.

A typical IV dosage for adults will be in the range of 20-300 mg/day of a compound of the present invention, such as 50-200 mg/day, such as 70-150 mg/day or 75-125 mg/day.

Conveniently, the compounds of the invention are administered in a unit dosage form containing said compounds in an amount of about 10 to 300 mg, such as 10 mg, 20 mg, 50 mg, 100 mg, 150 mg, 200 mg, 250 mg, 300 mg of a compound of the present invention.

In an embodiment the frequency of administration is once weekly.

In an embodiment the frequency of administration is twice weekly.

4. Pharmaceutical Formulations and Excipients

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of the invention, such as one of the compounds disclosed in the Experimental Section herein. The present invention also provides a process for making a pharmaceutical composition comprising a compound of the invention. The pharmaceutical compositions according to the invention may be formulated with pharmaceutically acceptable excipients in accordance with conventional techniques such as those disclosed in Remington, "The Science and Practice of Pharmacy", 22$^{th}$ edition (2013), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an oral-dispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

5. Compounds of the Invention

TABLE 1

Exemplified parent compounds of the invention

| Example | Name | structure |
|---------|------|-----------|
| Compound 1a | (R)-2-amino-3-(7-(difluoromethyl)thieno[3,2-b]pyridine-2-carboxamido)propanoic acid | 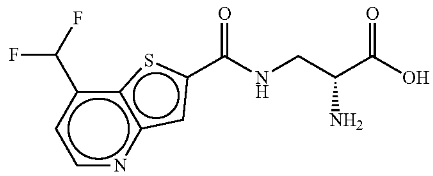 |
| Compound 1b | (R)-2-amino-3-(7-cyclopropylthieno[3,2-b]pyridine-2-carboxamido)propanoic acid | 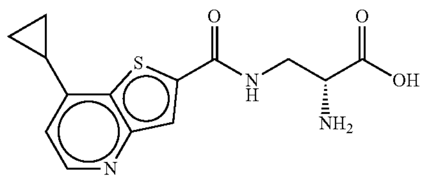 |
| Compound 1c | (R)-2-amino-3-(7-methylthieno[3,2-b]pyridine-2-carboxamido)propanoic acid | 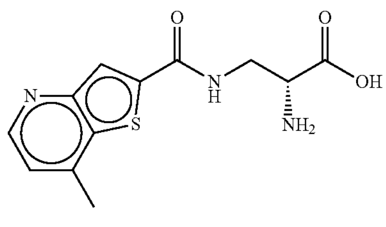 |
| Compound 1d | (R)-2-amino-3-(7-(2-ethylphenyl)thieno[3,2-b]pyridine-2-carboxamido)propanoic acid | 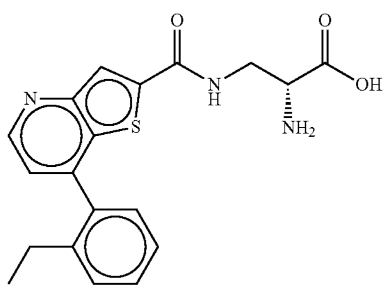 |
| Compound 1e | (R)-2-amino-3-(7-methoxythieno[3,2-b]pyridine-2-carboxamido)propanoic acid | 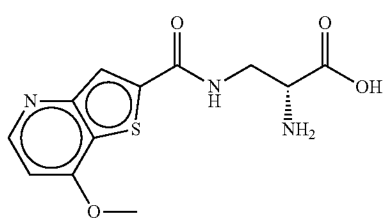 |
| Compound 1f | (R)-2-amino-3-(7-(trifluoromethyl)thieno[3,2-b]pyridine-2-carboxamido) propanoic acid | 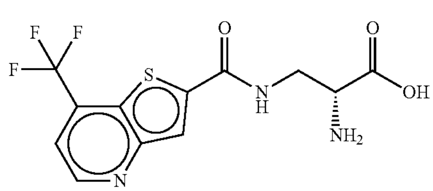 |

TABLE 1-continued

Exemplified parent compounds of the invention

| Example | Name | structure |
|---|---|---|
| Compound 1g | (R)-2-amino-3-[(7-isopropoxythieno[3,2-b]pyridine-2-carboxamido) propanoic acid | 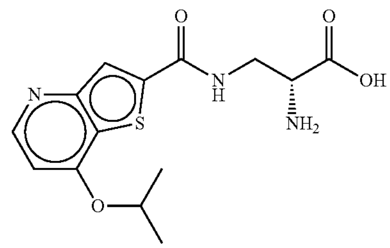 |
| Compound 1h | (R)-2-amino-3-[(7-bromothieno[3,2-b]pyridine-2-carboxamido) propanoic acid | 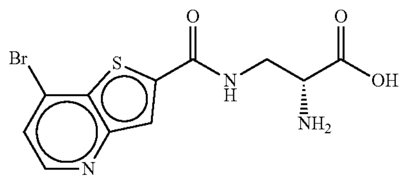 |
| Compound 1i | (R)-2-amino-3-[(7-hydroxymethylthieno[3,2-b]pyridine-2-carboxamido) propanoic acid | 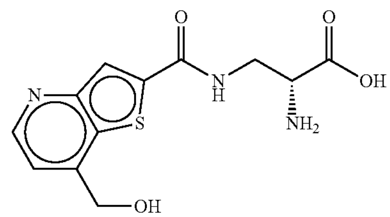 |
| Compound 1j | (R)-2-amino-3-[[7-(fluoromethyl)thieno[3,2-b]pyridine-2-carboxamido] propanoic acid | 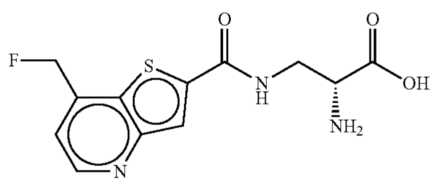 |
| Compound 1k | (R)-2-amino-3-[(6-fluoro-7-methyl-thieno[3,2-b]pyridine-2-carboxamido) propanoic acid | 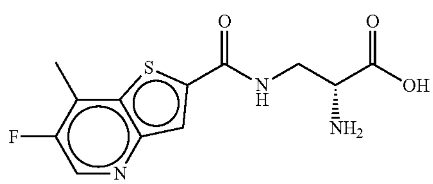 |
| Compound 1l | (R)-2-amino-3-[(6,7-dimethylthieno[3,2-b]pyridine-2-carboxamido) propanoic acid | 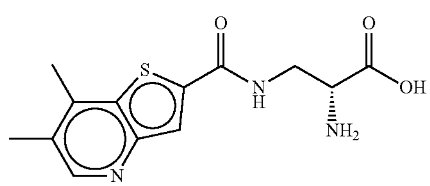 |

TABLE 2

Exemplified prodrugs of the invention

| Example | Name | Structure |
|---|---|---|
| Compound 2a | Methyl (R)-2-amino-3-(7-(difluoromethyl)thieno[3,2-b]pyridine-2-carboxamido)propanoate | 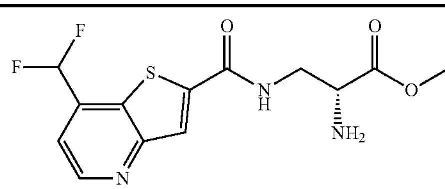 |

TABLE 2-continued

Exemplified prodrugs of the invention

| Example | Name | Structure |
|---|---|---|
| Compound 2b | Methyl (R)-2-amino-3-(7-cyclopropylthieno[3,2-b]pyridine-2-carboxamido)propanoate | 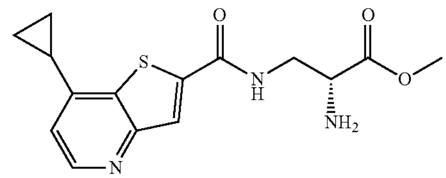 [SMILES: COC(=O)[C@H](N)CNC(=O)c1cc2nccc(C3CC3)c2s1] |
| Compound 2c | Methyl (R)-2-amino-3-(7-methylthieno[3,2-b]pyridine-2-carboxamido)propanoate | 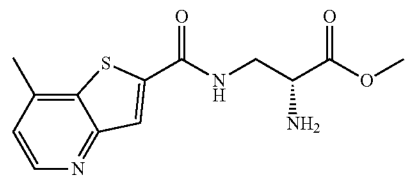 [SMILES: COC(=O)[C@H](N)CNC(=O)c1cc2nccc(C)c2s1] |
| Compound 2d | Ethyl (R)-2-amino-3-(7-methylthieno[3,2-b]pyridine-2-carboxamido)propanoate | 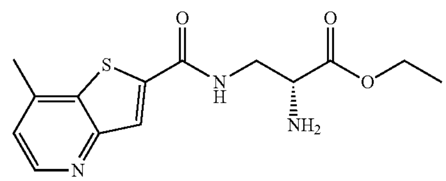 [SMILES: CCOC(=O)[C@H](N)CNC(=O)c1cc2nccc(C)c2s1] |
| Compound 2e | Propyl (R)-2-amino-3-(7-methylthieno[3,2-b]pyridine-2-carboxamido)propanoate | 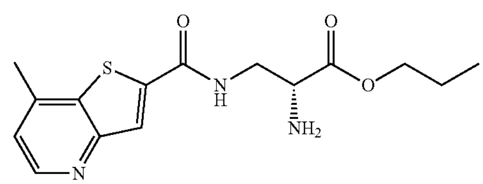 [SMILES: CCCOC(=O)[C@H](N)CNC(=O)c1cc2nccc(C)c2s1] |
| Compound 2f | Isopropyl (R)-2-amino-3-(7-methylthieno[3,2-b]pyridine-2-carboxamido)propanoate | 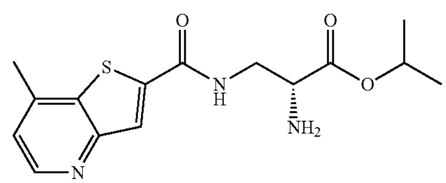 [SMILES: Cc1ccnc2cc(C(=O)NC[C@@H](N)C(=O)OC(C)C)sc12] |
| Compound 2g | Cyclopropyl (R)-2-amino-3-(7-methylthieno[3,2-b]pyridine-2-carboxamido)propanoate | 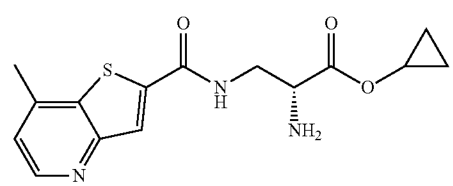 [SMILES: Cc1ccnc2cc(C(=O)NC[C@@H](N)C(=O)OC3CC3)sc12] |
| Compound 2h | Butyl (R)-2-amino-3-(7-methylthieno[3,2-b]pyridine-2-carboxamido)propanoate | 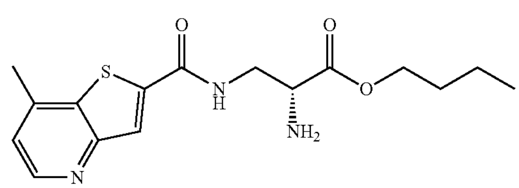 [SMILES: CCCCOC(=O)[C@H](N)CNC(=O)c1cc2nccc(C)c2s1] |
| Compound 2i | Isobutyl (R)-2-amino-3-(7-methylthieno[3,2-b]pyridine-2-carboxamido)propanoate | 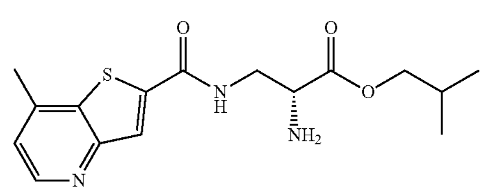 [SMILES: Cc1ccnc2cc(C(=O)NC[C@@H](N)C(=O)OCC(C)C)sc12] |

TABLE 2-continued

Exemplified prodrugs of the invention

| Example | Name | Structure |
|---|---|---|
| Compound 2j | Cyclopropylmethyl (R)-2-amino-3-(7-methylthieno[3,2-b]pyridine-2-carboxamido)propanoate | 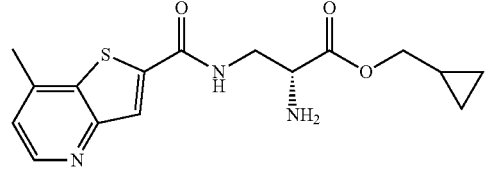 [SMILES: Cc1ccnc2cc(C(=O)NC[C@@H](N)C(=O)OCC3CC3)sc12] |
| Compound 2k | 2-Methoxyethyl (R)-2-amino-3-(7-methylthieno[3,2-b]pyridine-2-carboxamido)propanoate | 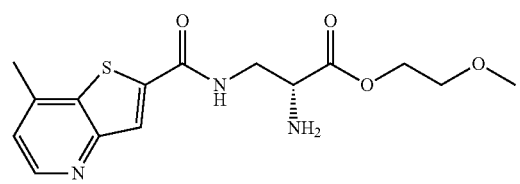 |
| Compound 2l | Isopentyl (R)-2-amino-3-(7-methylthieno[3,2-b]pyridine-2-carboxamido)propanoate | 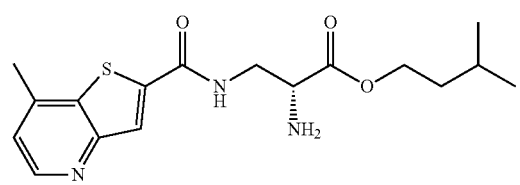 [SMILES: Cc1ccnc2cc(C(=O)NC[C@@H](N)C(=O)OCCC(C)C)sc12] |
| Compound 2m | Benzyl (R)-2-amino-3-(7-methylthieno[3,2-b]pyridine-2-carboxamido)propanoate | 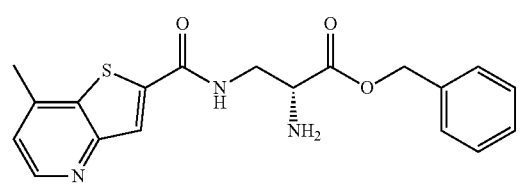 [SMILES: Cc1ccnc2cc(C(=O)NC[C@@H](N)C(=O)OCc3ccccc3)sc12] |
| Compound 2n | Cyclohexyl (R)-2-amino-3-(7-methylthieno[3,2-b]pyridine-2-carboxamido)propanoate | 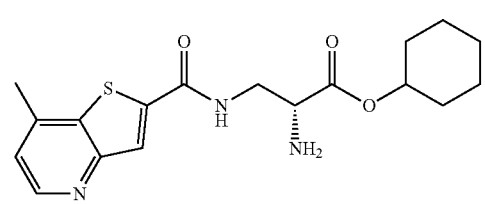 [SMILES: Cc1ccnc2cc(C(=O)NC[C@@H](N)C(=O)OC3CCCCC3)sc12] |
| Compound 2o | Phenyl (R)-2-amino-3-(7-methylthieno[3,2-b]pyridine-2-carboxamido)propanoate | 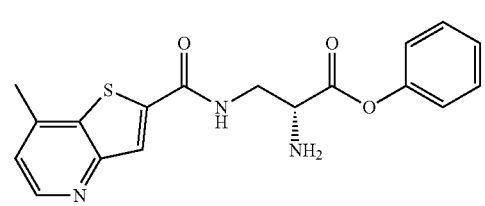 [SMILES: Cc1ccnc2cc(C(=O)NC[C@@H](N)C(=O)Oc3ccccc3)sc12] |
| Compound 2p | 2-Oxo-2-(pyrrolidin-1-yl)ethyl (R)-2-amino-3-(7-methylthieno[3,2-b]pyridine-2-carboxamido)propanoate | 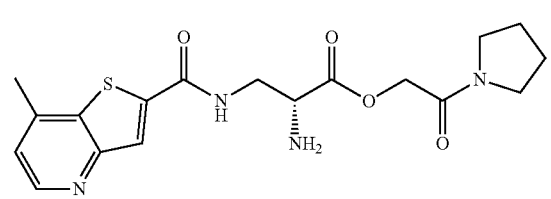 [SMILES: Cc1ccnc2cc(C(=O)NC[C@@H](N)C(=O)OCC(=O)N3CCCC3)sc12] |
| Compound 2q | Methyl (R)-2-amino-3-(7-(2-ethylphenyl)thieno[3,2-b]pyridine-2-carboxamido)propanoate | 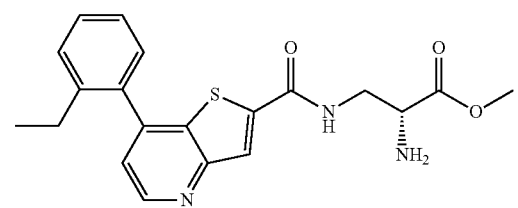 [SMILES: CCc1ccccc1-c1ccnc2cc(C(=O)NC[C@@H](N)C(=O)OC)sc12] |

TABLE 2-continued

Exemplified prodrugs of the invention

| Example | Name | Structure |
|---|---|---|
| Compound 2r | Methyl (R)-2-amino-3-(7-methoxythieno[3,2-b]pyridine-2-carboxamido)propanoate | 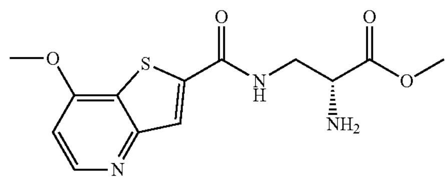 |
| Compound 2s | Methyl (R)-2-amino-3-(7-(trifluoromethyl)thieno[3,2-b]pyridine-2-carboxamido)propanoate | 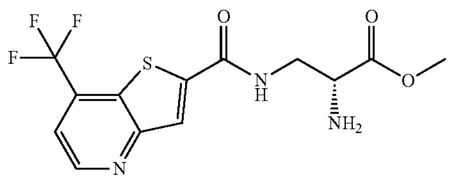 [SMILES: COC(=O)[C@H](N)CNC(=O)c1cc2nccc(C(F)(F)F)c2s1] |
| Compound 2t | Methyl (R)-2-amino-3-(7-isopropoxythieno[3,2-b]pyridine-2-carboxamido)propanoate | 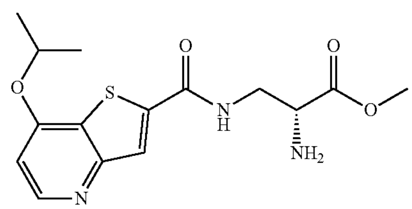 [SMILES: COC(=O)[C@H](N)CNC(=O)c1cc2nccc(OC(C)C)c2s1] |
| Compound 2u | Methyl (R)-2-amino-3-(7-bromothieno[3,2-b]pyridine-2-carboxamido)propanoate | 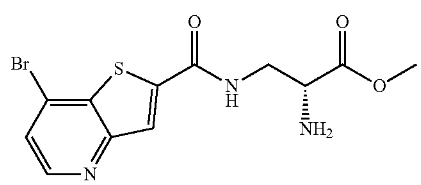 [SMILES: COC(=O)[C@H](N)CNC(=O)c1cc2nccc(Br)c2s1] |
| Compound 2v | Methyl (R)-2-amino-3-(7-(hydroxymethyl)thieno[3,2-b]pyridine-2-carboxamido)propanoate | 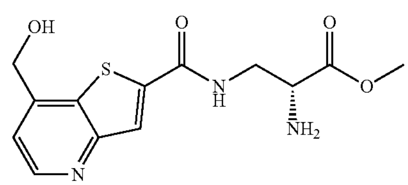 [SMILES: COC(=O)[C@H](N)CNC(=O)c1cc2nccc(CO)c2s1] |
| Compound 2w | Methyl (R)-2-amino-3-(7-(fluoromethyl)thieno[3,2-b]pyridine-2-carboxamido)propanoate | 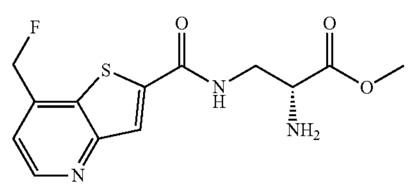 [SMILES: COC(=O)[C@H](N)CNC(=O)c1cc2nccc(CF)c2s1] |
| Compound 2x | Methyl (R)-2-amino-3-(6-fluoro-7-methyl-thieno[3,2-b]pyridine-2-carboxamido)propanoate | 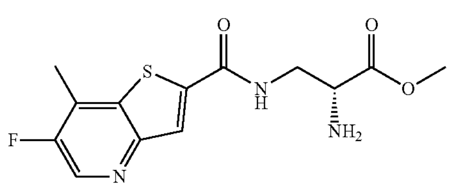 [SMILES: COC(=O)[C@H](N)CNC(=O)c1cc2ncc(F)c(C)c2s1] |
| Compound 2y | Methyl (R)-2-amino-3-(6,7-dimethylthieno[3,2-b]pyridine-2-carboxamido)propanoate | 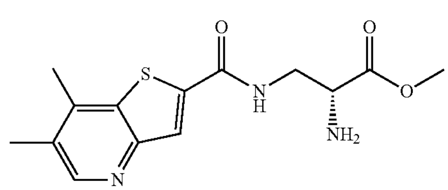 |

6. Experimental Section a. Preparation of the Compounds of the Invention

The compounds of the present invention of the general formula I, wherein $R^1$, $R^2$, $R^3$, $R^4$ and $R^5$ are as defined above can be prepared by the methods outlined in the following reaction Schemes 1-18 and in the examples. In the described methods, it impossible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

The schemes may involve the use of selective protecting groups during the synthesis of the compounds of the invention. One skilled in the art would be able to select the appropriate protecting group for a particular reaction. It may be necessary to incorporate protection and de-protection strategies for substituents such as amino, amido, carboxylic acid and hydroxyl groups in the synthetic methods described below to synthesize the compounds of Formula I. Methods for protection and de-protection of such groups are well known in the art, and may be found in T. Green, et al., Protective Groups in Organic Synthesis, 1991, 2nd Edition, John Wiley & Sons, New York.

The schemes in this section are representative of methods useful in synthesizing the compounds of the present invention. They are not intended to constrain the scope of the invention in anyway.

Scheme 1

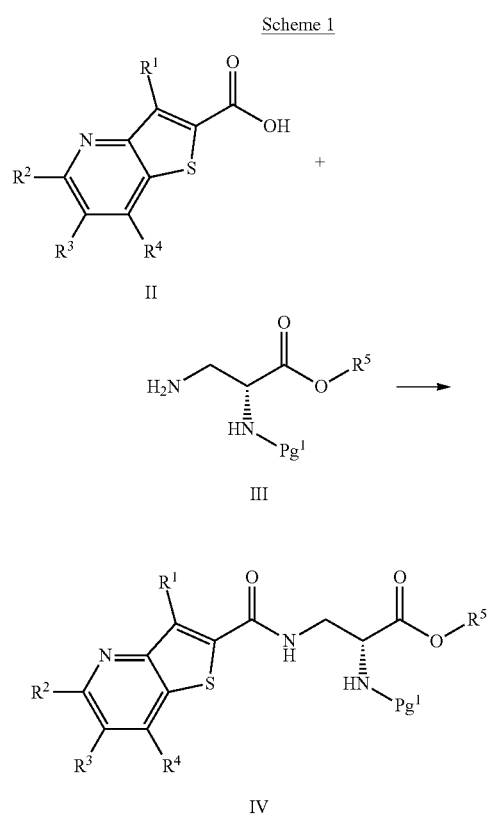

Compounds of general formula I (Scheme 1) may be prepared from compounds with general formula IV by standard de-protection procedures. As an example, compounds of general formula I (Scheme 1) may be prepared from compounds with general formula IV where $Pg^1$ is a N-Carbobenzyloxy group (Cbz) and $R^5$ is defined as in general formula I.

Compounds with general formula IV may be prepared by compounds of general formula III with carboxylic acids (or salt thereof) of general formula II by standard peptide coupling such as using O-(Benzotriazol-1-yl)-N,N,N',N'-tetramethyluronium tetrafluoroborate in the presence of a base such as N,N-diisopropylethylamine in a solvent such as N,N-dimethylformamide.

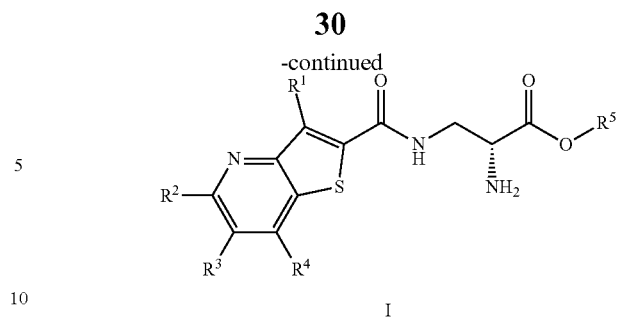

Scheme 2

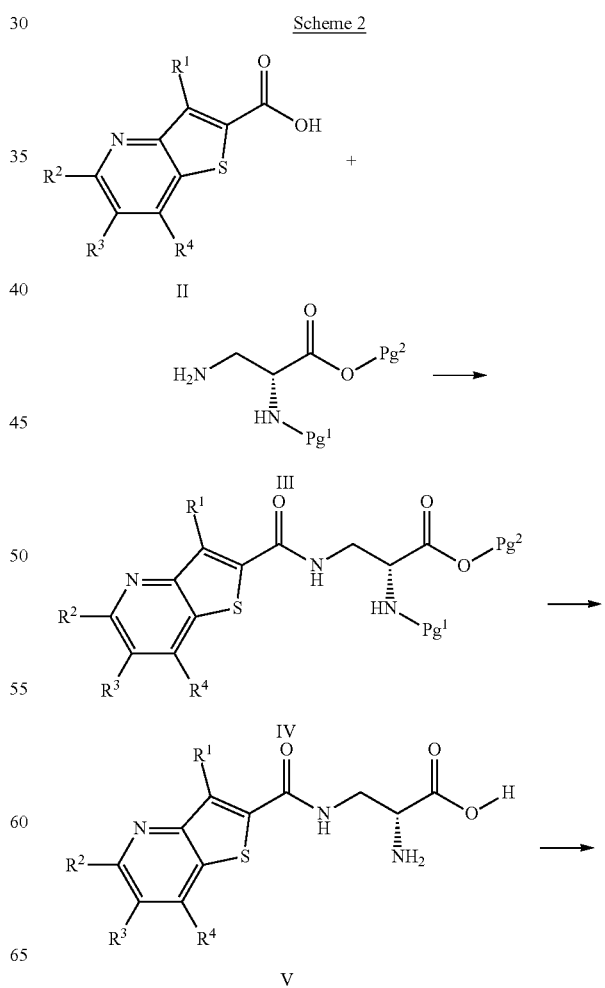

-continued

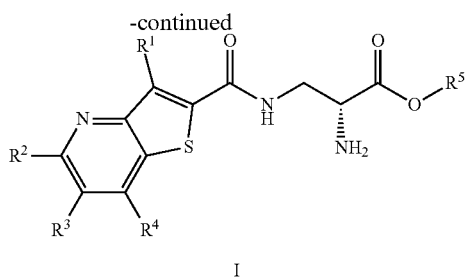

I

Compounds of general formula I (Scheme 2) may be prepared from compounds with general formula V by standard esterification procedures. As an example, compounds of general formula I (Scheme 2) may be prepared from compounds with general formula V by treatment with a reagent such as thionyl chloride in methanol ($R^5$=Me). Compounds of general formula V may be prepared from compounds with general formula IV by standard de-protection procedures. As an example, compounds of general formula V (Scheme 2) may be prepared from compounds with general formula IV where $Pg^1$ is Cbz and $Pg^2$ is benzyl using conditions such as HBr in acetic acid.

Compounds with general formula IV may be prepared by compounds of general formula III with carboxylic acids (or salt thereof) of general formula II by standard peptide coupling such as using O-(Benzotriazol-1-yl)-N,N,N',N'-tetramethyluronium tetrafluoroborate in the presence of a base such as N,N-diisopropylethylamine in a solvent such as N,N-dimethylformamide.

Scheme 3

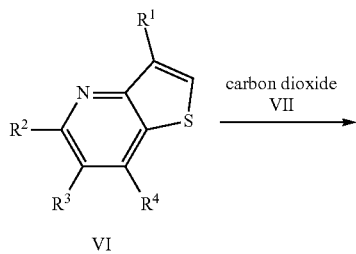

Thieno[3,2-b]pyridine-2-carboxylic acid (or salt thereof) of general formula II (Scheme 3), can be obtained from thieno[3,2-b]pyridine of general formula VI by deprotonation at low temperature using a base such as lithium diisopropylamide (LDA) in a solvent such as tetrahydrofuran (THF) followed by the addition of carbon dioxide VII and allowing the reaction mixture to reach room temperature.

Scheme 4

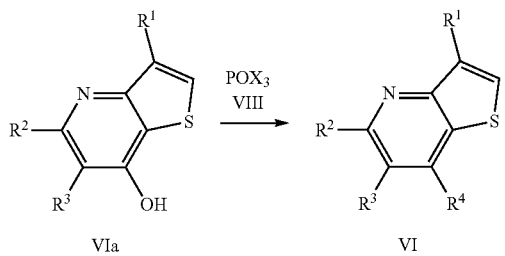

Thieno[3,2-b]pyridine of general formula VI where $R^4$ is Cl, is commercially available. Thieno[3,2-b]pyridine of general formula VI where $R^4$ is Br (Scheme 4) can be obtained by treatment of compound VIa with a reagent such as Phosphorus(V) oxybromide VIII at elevated temperature.

Scheme 5

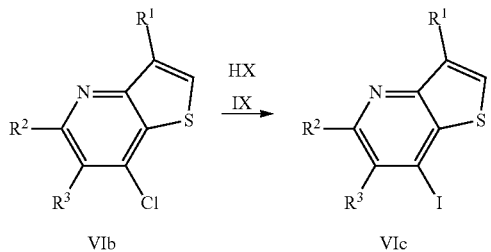

Thieno[3,2-b]pyridine of general formula VIc (Scheme 5), can be obtained by treatment of compound VIb under reaction conditions such as HI in water at elevated temperature.

Scheme 6

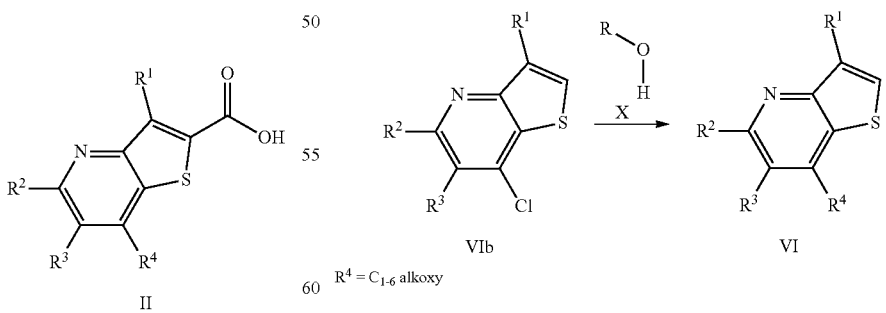

$R^4 = C_{1-6}$ alkoxy

Thieno[3,2-b]pyridine of general formula VI (Scheme 6) where $R^4$ is $C_{1-6}$ alkoxy can be obtained by treatment of compound VIb under reaction conditions such as in the presence of an alcohol ROH X, deprotonated by a base such as sodium, at elevated temperature.

Scheme 7

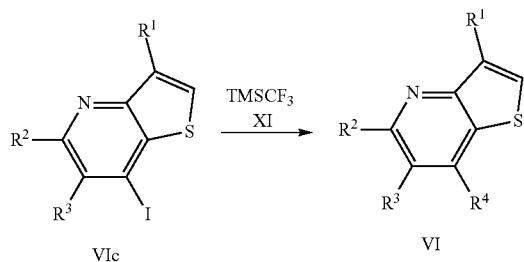

Thieno[3,2-b]pyridine of general formula VI (Scheme 7) where R⁴ can be trifluoromethyl as described in general Formula I can be obtained by treatment of compound VIc, under reaction conditions such as in the presence of metal catalyst such as copper iodide, a reagent such as potassium fluoride, and a perfluorinated precursor such as trimethyl (trifluoromethyl)silane (TMSCF₃) XI.

Scheme 8

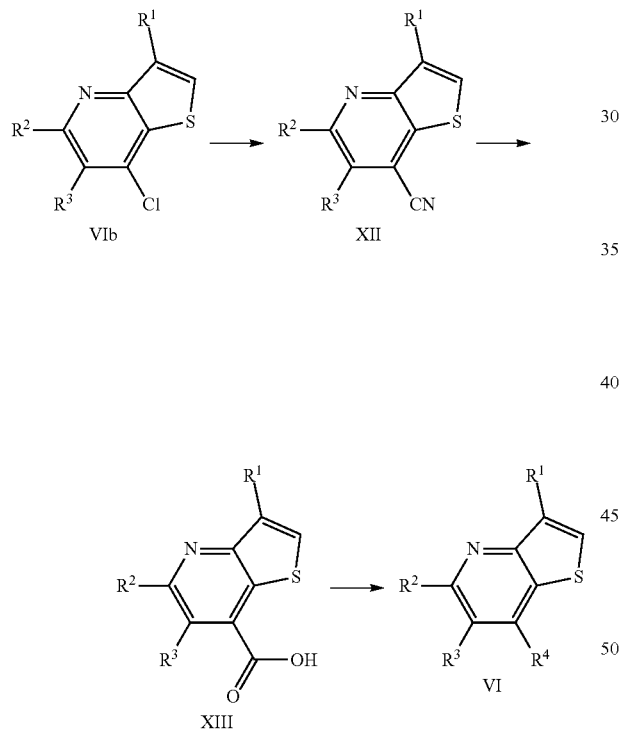

Thieno[3,2-b]pyridine of general formula VI (Scheme 8) where R⁴ can be —CH₂OH as described in general Formula I can be obtained from compound XIII, by treatment with a reducing agent such as sodium borohydride. Compound XIII can be obtained from compound XII in reaction conditions such as hydrochloric acid in methanol. Compound XII can be obtained from compound VIb using a reagent such as zinc cyanide in the presence of metal catalysts such as [1,1'-Bis(diphenylphosphino)ferrocene]dichloropalladium(II), complex with dichloromethane and bis(dibenzylideneacetone) palladium and zinc.

Scheme 9

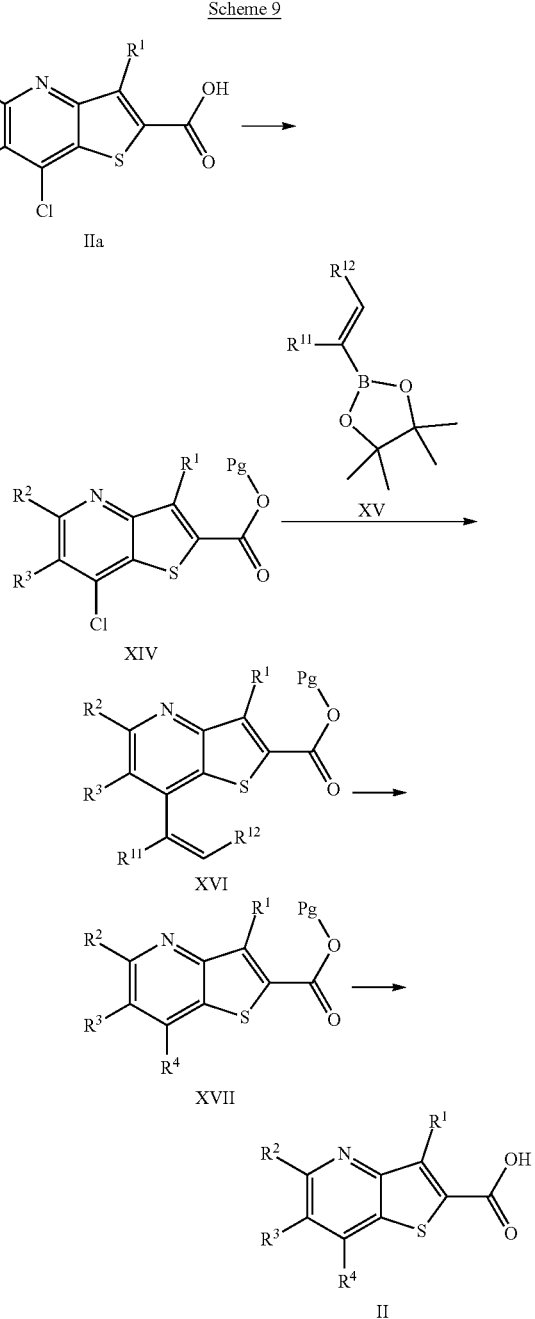

Thieno[3,2-b]pyridine-2-carboxylic acid of general formula II (or salt thereof), (Scheme 9) where R⁴ can be as described in general Formula I can be prepared from the corresponding ester where Pg can be methyl as in compounds of general formula XVII by hydrolysis under aqueous conditions in a variety of conditions known to chemists skilled in the art. Compounds of general formula XVII can be obtained from compounds of general formula XVI under reaction conditions such as hydrogenation in the presence of a catalyst such as palladium on carbon. Compounds of general formula XVI can be obtained by reacting compounds of general formula XIV with reagents of general formula XV under reaction conditions such as in the presence of a catalyst such as [1,1'-Bis(diphenylphosphino)

ferrocene]dichloropalladium(II), complex with dichloromethane and a base such as potassium carbonate. Compounds of general formula XIV where Pg is methyl can be obtained from compounds of general formula IIa by treatment with a reagent such as thionyl chloride in methanol as solvent.

Scheme 10

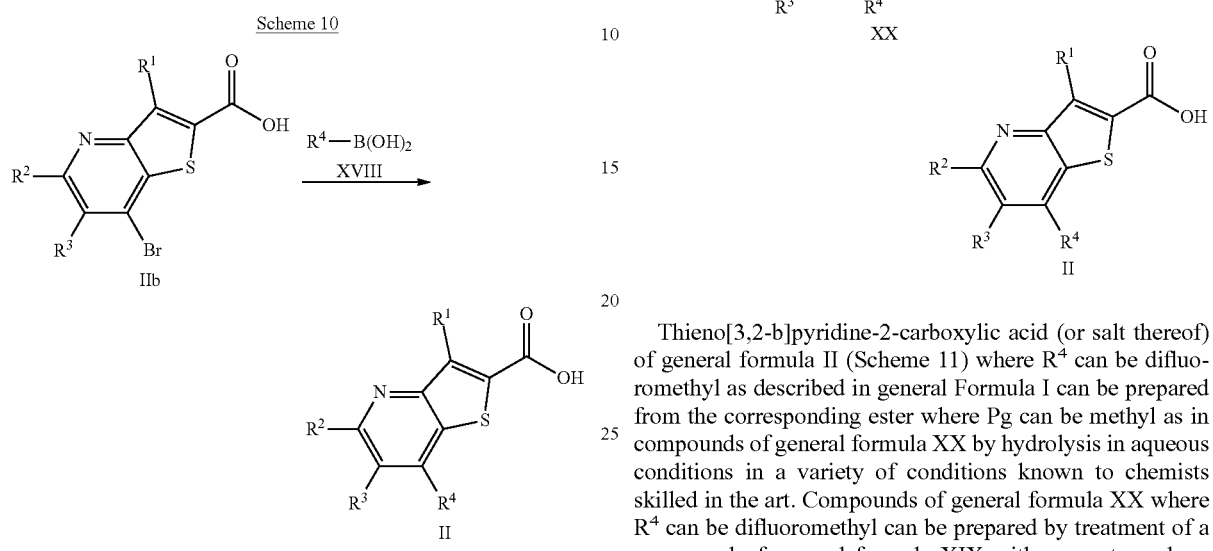

Compounds of general formula II (or salt thereof) where $R^4$ is as described for Formula I (Scheme 10) can be obtained reacting compounds of general formula IIb, with reagents of general formula XVIII in the presence of a catalyst such as [1,1'-Bis(diphenylphosphino)ferrocene]dichloropalladium(II), complex with dichloromethane or [1,1'-Bis(di-tert-butylphosphino)ferrocene]dichloropalladium(II) and a base such as sodium carbonate.

Scheme 11

Thieno[3,2-b]pyridine-2-carboxylic acid (or salt thereof) of general formula II (Scheme 11) where $R^4$ can be difluoromethyl as described in general Formula I can be prepared from the corresponding ester where Pg can be methyl as in compounds of general formula XX by hydrolysis in aqueous conditions in a variety of conditions known to chemists skilled in the art. Compounds of general formula XX where $R^4$ can be difluoromethyl can be prepared by treatment of a compound of general formula XIX with reagents such as (diethylamino)sulfur trifluoride. Compounds of general formula XIX can be prepared from compounds of general formula XVI, in the presence of ozone followed by treatment with a reagent such as triphenyl phosphine.

Scheme 12

Thieno[3,2-b]pyridine-2-carboxylic acid of general formula II, where $R^1$ is hydrogen (or salt thereof) (Scheme 12)

can be prepared from the corresponding ester where Pg can be methyl as in compounds of general formula XXIII by hydrolysis under aqueous conditions known to chemists skilled in the art. Compounds of general formula XXIII can be prepared by reaction of aldehydes of general formula XXI with a reagent of general formula XXII in the presence of a base such as triethylamine.

Scheme 13

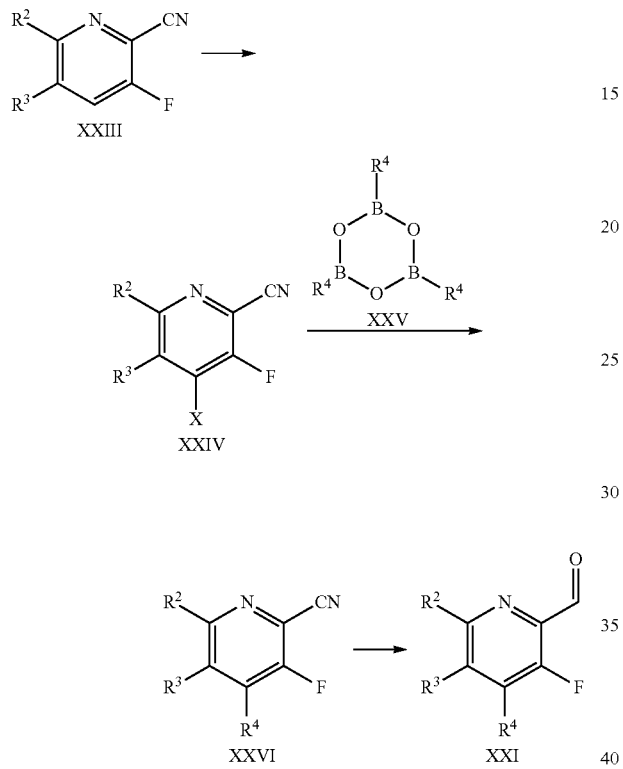

Aldehydes of general formula XXI (Scheme 13) can be prepared from compounds of general formula XXVI using a reducing reagent such as diisobutylaluminum hydride. Compounds of general formula XXVI can be prepared from compounds of general formula XXIV, where X is an halogen such as iodine, by reaction with a reagent such as XXV in the presence of a catalyst such as [1,1'-Bis(diphenylphosphino)ferrocene]dichloropalladium(II), complex with dichloromethane and a base such as potassium phosphate. Compounds of general formula XXIV can be prepared from compounds of general formula XXIII, via deprotonation using a base such as lithium diisopropylamide followed by the addition of an electrophilic halogen species, such as molecular iodine.

Scheme 14

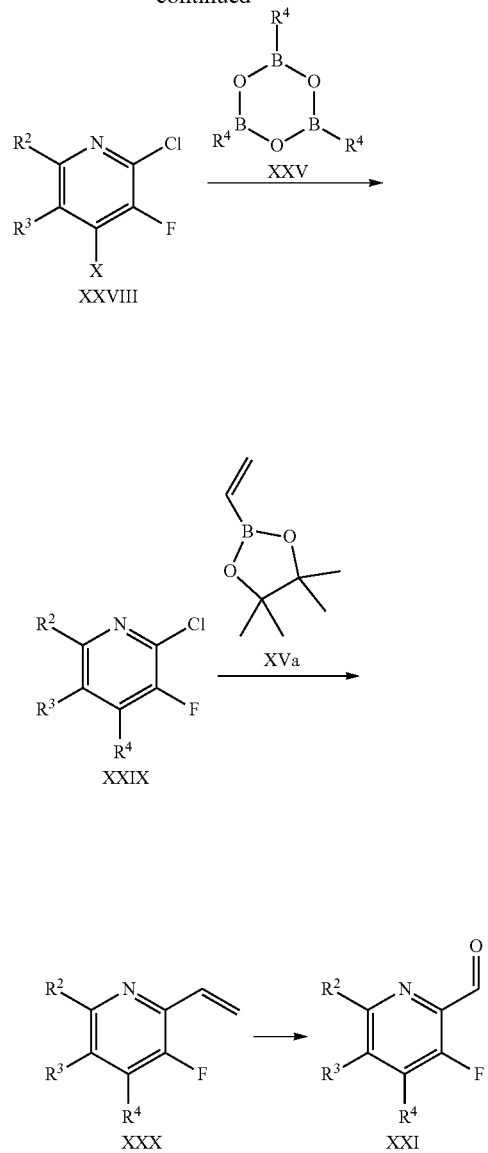

Aldehydes of general formula XXI (Scheme 14) can be prepared from compounds of general formula XXX, under reaction conditions such in the presence of ozone followed by treatment with reagent such as triphenyl phosphine. Compounds of general formula XXX can be obtained reacting compounds of general formula XXIX with reagents of general formula XVa, under reaction conditions such as in the presence of a catalyst such as [1,1'-Bis(diphenylphosphino)ferrocene]dichloropalladium(II), complex with dichloromethane and a base such as potassium carbonate. Compounds of general formula XXIX can be prepared from compounds of general formula XXVIII, where X is an halogen such as iodine, by reaction with a reagent such as XXV in the presence of a catalyst such as [1,1'-Bis(diphenylphosphino)ferrocene]dichloropalladium(II), complex with dichloromethane and a base such as potassium carbonate Compounds of general formula XXVIII can be prepared from compounds of general formula XXVII, via deprotonation using a base such as lithium diisopropylamide followed by the addition of an electrophilic halogen species such as molecular iodine.

Scheme 15

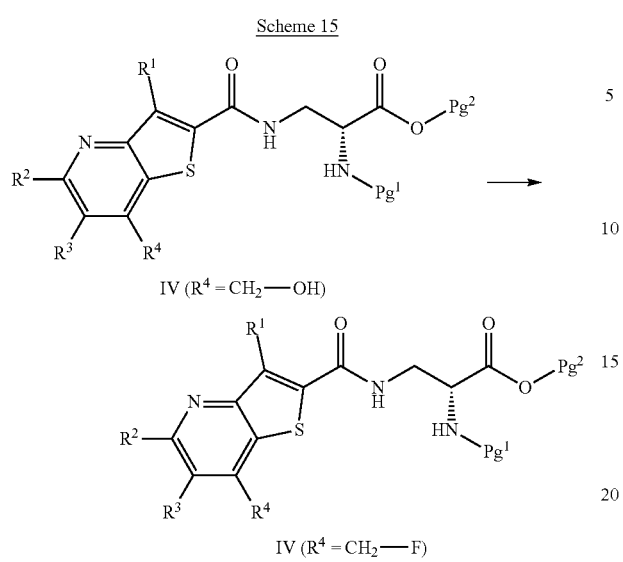

IV (R⁴ = CH₂—OH)

IV (R⁴ = CH₂—F)

Compounds of general formula IV (Scheme 15) where R⁴=—CH₂F may be prepared from compounds of general formula IV where R⁴=—CH₂OH using reagents such as (diethylamino)sulfur trifluoride.

Scheme 16

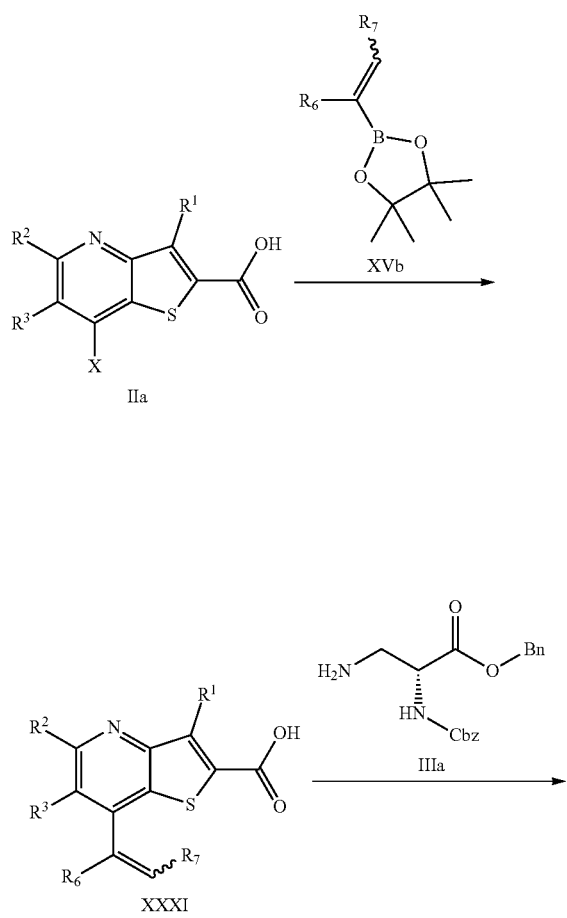

XXXII

V

Compounds of general formula V (Scheme 16) may be prepared from compounds with general formula XXXII under reaction conditions such as hydrogenation in the presence of a catalyst such as palladium on carbon. Compounds with general formula XXXII may be prepared by reacting protected amines such as IIIa with carboxylic acids of general formula XXXI by standard peptide coupling methods such as using O-(Benzotriazol-1-yl)-N,N,N',N'-tetramethyluronium tetrafluoroborate in the presence of a base such as N,N-diisopropylethylamine in a solvent such as N,N-dimethylformamide. Compounds of general formula XXXI can be obtained reacting compounds of general formula IIa where X is Cl or Br, with reagent of formula XVb under reaction conditions such as in the presence of a catalyst such as [1,1'-Bis(di-tert-butylphosphino)ferrocene]dichloropalladium(II) and a base such as potassium carbonate.

Scheme 17

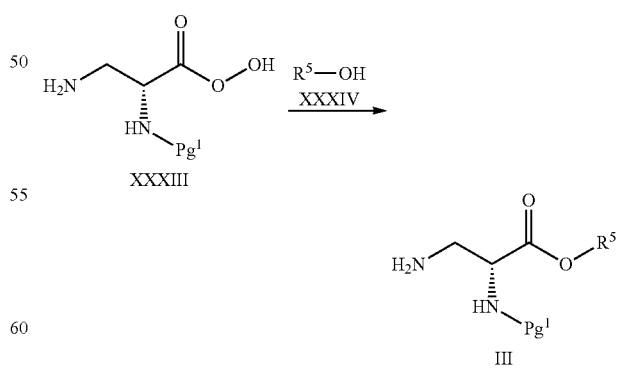

Compounds of general formula III where R⁵ is as defined herein (Scheme 17) may be prepared by reacting carboxylic acids of formula XXXIII with alcohols of formula XXXIV using standard esterification procedures.

Scheme 18

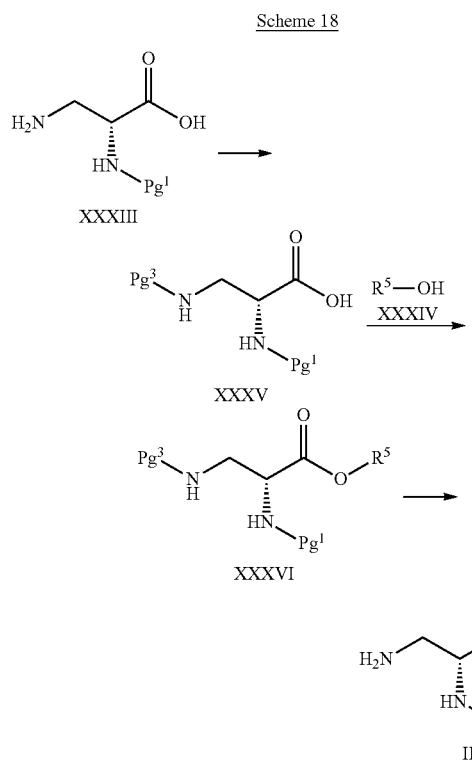

Compounds of general formula III where $R^5$ is as defined herein (Scheme 18) may be prepared by deprotection of compounds of general formula XXXVI where $Pg^3$ could be a tert-butyloxycarbonyl protecting group (Boc) and $Pg^1$ could be a benzyloxy carbamate (Cbz). Compounds of general formula XXXVI where $R^5$ is as in general formula I may be prepared by reacting carboxylic acids of formula XXXV with alcohols of formula XXXIV using standard esterification procedures. Compounds of general formula XXXV where $Pg^3$ could be a tert-butyloxycarbonyl protecting group (Boc) may be prepared by protection of compounds of general formula XXXIII using standard procedures.

b. General Methods

LC-MS Methods

Analytical LC-MS Data were obtained using one of the methods identified below.

Method AA: A Waters Acquity UPLC-MS was used. Column: Acquity UPLC BEH C18 1.7 µm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method BB: A Waters Acquity UPLC-MS was used. Column: Acquity UPLC BEH C18 1.7 µm; 2.1×50 mm; Column temperature: 60° C.; Solvent system: A=water/trifluoroacetic acid (99.5:0.5) and B=acetonitrile/water/trifluoroacetic acid (94.965:5:0.035); Method: Linear gradient elution with A:B=90:10 to 0:100 in 1.0 minutes and with a flow rate of 1.2 mL/min.

Preparative HPLC

Preparative-HPLC (Method A): Instrument: Gilson GX-281 Liquid Handler, SHIMADZU LC-8A LCMS2010; Column: YMC-Actus Triart C18 150*30 5 µm; Mobile Phase A: water (0.05% HCl v/v); Mobile phase B: MeCN; Gradient: B from 5% to 35% in 10 min then hold at 100% for 3 min; FlowRate (ml/min): 25; Column temperature: 35° C. and Wavelength: 220 nm 254 nm.

Preparative HPLC (Method B): Instrument: Gilson GX-215, Gilson 322 Pump, Gilson 156 UV Detector; Column: YMC-Actus Triart C18 150*30 5 µm; Mobile Phase A: water (0.05% HCl v/v); Mobile phase B: MeCN; Gradient: B from 0% to 28% in 10 min then hold at 100% for 3 min; FlowRate (ml/min): 25; Column temperature: 40° C. and Wavelength: 220 nm 254 nm.

Preparative HPLC (Method C): Instrument: Gilson GX-281 Liquid Handler, Gilson 322 Pump, Gilson 156 UV Detector; Column: Xtimate C18 150*25 mm*5 µm; Mobile Phase A: water (0.05% ammonia hydroxide v/v); Mobile phase B: MeCN; Gradient: from 42% to 72% in 10 min then hold at 100% for 2.5 min; Flow Rate (ml/min): 25; Column temperature: 25° C. and Wavelength: 220 nm 254 nm.

Preparative HPLC (Method D): Instrument: Gilson GX-281, Gilson 322 Pump, Gilson 156 UV Detector; Column: Gemini 150*25 mm*5 µm; Mobile Phase A: water (0.05% ammonia hydroxide v/v); Mobile phase B: MeCN; Gradient: B from 52% to 82% in 10 min then hold at 100% for 2 min; FlowRate (ml/min): 25; Column temperature: 30° C. and Wavelength: 220 nm 254 nm.

Preparative HPLC (Method E): Instrument: Gilson GX-215, Gilson 322 Pump, Gilson 156 UV Detector; Column: Venusil ASB Phenyl 250*50 10 µm; Mobile Phase A: water (0.05% HCl); Mobile phase B: MeCN; Gradient: B from 15% to 45% in 10 min then hold 100% B for 1 min; Flow Rate (mL/min): 25; Column temperature: 40° C.-, Wavelength: 220 nm 254 nm.

Preparative HPLC (Method F): Instrument: Gilson GX-281 Liquid Handler, Gilson 322 Pump, Gilson 156 UV Detector; Column: Venusil ASB Phenyl 250*50 mm*10 µm; Mobile Phase A: water (0.05% HCl); Mobile phase B: MeCN; Gradient: B from 18% to 48% in 10 min then hold at 100% for 1 min; Flow Rate (ml/min): 25; Column temperature: 40° C.; Wavelength: 220 nm, 254 nm.

Preparative HPLC (Method G): Instrument: Gilson GX-281 Liquid Handler, Gilson 322 Pump, Gilson 156 UV Detector; Column: Xtimate C18 150*25 mm*5 µm; Mobile Phase A: water (0.05% ammonia hydroxide v/v); Mobile phase B: MeCN; Gradient: B from 64% to 94% in 10 min then hold at 100% for 2.5 min; Flow Rate (ml/min): 25; Column temperature: 25° C. and Wavelength: 220 nm 254 nm.

Preparative HPLC (Method H): HPLC Instrument: Gilson GX-281 Liquid Handler, Gilson 322 Pump, Gilson 156 UV Detector; Column: Xtimate C18 150*25 mm*5 µm; Mobile Phase: A: water (0.05% ammonia hydroxide v/v); Mobile phase B: MeCN; Gradient: B from 34% to 64% in 10 min then hold at 100% for 2.5 min; FlowRate (ml/min): 25; Column temperature: 25° C.; Wavelength: 220 nm 254 nm.

Preparative HPLC (Method I): Instrument: Gilson GX-215, Gilson 322 Pump, Gilson 156 UV Detector; Column: Waters Xbridge 150*25 mm*5 µm; Mobile Phase: A: water (10 mM $NH_4HCO_3$); Mobile phase B: MeCN; Gradient: B from 21% to 51% in 10 min then hold at 100% for 2.5 min: FlowRate (ml/min): 25; Column temperature: 30° C.; Wavelength: 220 nm 254 nm.

Preparative HPLC (Method J): Instrument: Gilson GX-215 Liquid Handler, Gilson 322 Pump, Gilson 156 UV Detector; Column: DYA-5 C18 150*25 mm*5 µm; Mobile Phase A: water (0.05% HCl v/v); Mobile phase B: MeCN; Gradient: B from 6% to 36% in 10 min then hold at 100% for 3 min; Flow Rate (ml/min): 25; Column temperature: 35° C. and Wavelength: 220 nm 254 nm.

Preparative HPLC (Method K): Instrument: Gilson GX-281, Gilson 322 Pump, Gilson 156 UV Detector; Column: Phenomenex Gemini C18 250*50*10 μm; Mobile Phase A: water (10 mM NH$_4$HCO$_3$); Mobile phase B: MeCN; Gradient: B from 10% to 40% in 11.2 min holds at 100% for 2.5 min; FlowRate (ml/min): 22; Column temperature: 40° C. and Wavelength: 220 nm 254 nm.

Preparative HPLC (Method L): Instrument: Gilson GX-281 Liquid Handler, Gilson 322 Pump, Gilson 156 UV Detector; Column: Waters Xbridge 150*25 5 μm; Mobile Phase A: water (10 mM NH$_4$HCO$_3$); Mobile phase B: MeCN; Gradient: B from 25% to 55% in 10 min then hold at 100% for 1.5 min; FlowRate (ml/min): 25; Column temperature: 30° C.; Wavelength: 220 nm 254 nm.

Preparative HPLC (Method M): HPLC Instrument: Gilson GX-281 Liquid Handler, Gilson 322 Pump, Gilson 156 UV Detector; Column: Venusil ASB Phenyl 250*50 10 μm; Mobile Phase A: water (0.05% HCl); Mobile phase B: MeCN; Gradient: B from 0% to 20% in 10 min then hold at 100% for 3 min; FlowRate (ml/min): 25; Column temperature: 40° C.; Wavelength: 220 nm 254 nm.

Preparative HPLC (Method N): Instrument: Gilson GX-281 Liquid Handler, Gilson 322 Pump, Gilson 156 UV Detector; Column: Agela Durashell C18 150 mm×25 mm×5 μm; Mobile Phase A: water (0.225% FA, v/v); Mobile phase B: MeCN; Gradient: B from 32% to 62% in 10 min, hold 100% B for 2 min; Flow Rate (ml/min): 25; Column temperature: 40° C. and Wavelength: 220 nm 254 nm.

Preparative HPLC (Method O): Instrument: Gilson GX-281, Gilson 322 Pump, Gilson 156 UV Detector; Column: Waters Xbridge 150*25*5 μm; Mobile Phase A: water (10 mM NH$_4$HCO$_3$); Mobile phase B: MeCN; Gradient: B from 40% to 66% in 8.4 min then hold at 100% for 2 min; FlowRate (ml/min): 25: Column temperature: 30° C. and Wavelength: 220 nm 254 nm.

Preparative HPLC (Method P): Instrument: Gilson GX-281 Liquid Handler, Gilson 322 Pump, Gilson 156 UV Detector; Column: Agela ASB 150*25 mm*5 μm; Mobile Phase A: water (0.05% HCl); Mobile phase B: MeCN; Gradient: B from 0% to 30% in 8 min then hold at 100% for 0 min; FlowRate (ml/min): 25; Column temperature: 40° C.; Wavelength: 220 nm 254 nm.

Preparative HPLC (Method Q): Instrument: Gilson GX-281 Liquid Handler, Gilson 322 Pump, Gilson 156 UV Detector; Column: Agela ASB 150*25 mm*5 μm; Mobile Phase A: water (0.05% HCl); Mobile phase B: MeCN; Gradient: B from 0% to 25% in 8 min then hold at 100% for 0 min; Flow Rate (ml/min): 25; Column temperature: 40° C. and Wavelength: 220 nm 254 nm.

Preparative HPLC (Method R): Instrument: Gilson GX-281 Liquid Handler, Gilson 322 Pump, Gilson 156 UV Detector; Column: Agela ASB 150*25 mm*5 μm; Mobile Phase A: water (0.05% HCl); Mobile phase B: MeCN; Gradient: B from 0% to 25% in 8 min then hold at 100% for 0 min; Flow Rate (ml/min): 25; Column temperature: 40° C. and Wavelength: 220 nm 254 nm.

Preparative HPLC (Method S): Instrument: Gilson GX-281 Liquid Handler, Gilson 322 Pump, Gilson 156 UV Detector; Column: Agela Durashell C18 150 mm×25 mm×5 μm; Mobile Phase A: water (0.225% FA, v/v); Mobile phase B: MeCN; Gradient: B from 40% to 70% in 10 min, hold 100% B for 0 min; Flow Rate (ml/min): 25; Column temperature: 40° C. and Wavelength: 220 nm 254 nm.

Preparative SFC (Method SFC1): Instrument: Berger, MULTIGR AM-II; Column: DAICEL CHIRALPAK AS-H (250 mm*30 mm, 5 μm); Mobile phase: CO2/IPA (0.1% NH3 in H2O)=35/35; Flow Rate: 60 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm.

$^1$H NMR spectra were recorded at 300, 400, 500 or 600 MHz on Bruker Avance instruments. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Abbreviations are in accordance with to the ACS Style Guide: "The ACS Style guide—A manual for authors and editors" Janet S. Dodd, Ed. 1997, ISBN: 0841234620 c. Preparation of the Intermediates

Intermediate 1

(R)-3-(Benzyloxy)-2-(((benzyloxy)carbonyl)amino)-3-oxopropan-1-aminium chloride

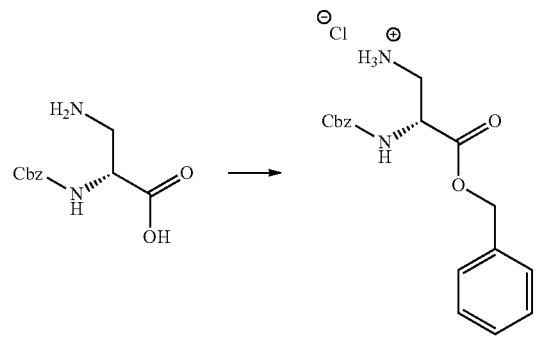 [SMILES: [Cl-] ; NC[C@@H](NC(=O)OCc1ccccc1)C(=O)O ; [NH3+]C[C@@H](NC(=O)OCc1ccccc1)C(=O)OCc1ccccc1]

To phenylmethanol (56.0 mL) was added thionyl chloride (2.1 g, 17.6 mmol) dropwise at 28° C. After completion of the addition, (R)-3-amino-2-(((benzyloxy)carbonyl)amino) propanoic acid (3.8 g, 15.9 mmol) was added in several portions and the reaction was stirred for 24 h at 28° C. LCMS showed the reaction was completed. The excess benzyl alcohol was removed at 80° C./0.02 bar and the residue was stirred in cyclohexane (35 mL) for 16 h. Filtration and trituration of the filter cake with methyl tert-butyl ether (50 mL) afforded the title compound (3.0 g, yield: 51.6%). LCMS (m/z) 329.2 [M+H+], $t_R$=(min, Method AA)=0.52.

Intermediate 2

(R)-2-(((benzyloxy)carbonyl)amino)-3-((tert-butoxycarbonyl)amino)propanoic acid

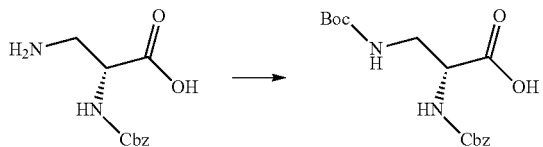 [SMILES: NC[C@@H](NC(=O)OCc1ccccc1)C(=O)O ; CC(C)(C)OC(=O)NC[C@@H](NC(=O)OCc1ccccc1)C(=O)O]

To a solution of (R)-3-amino-2-(((benzyloxy)carbonyl) amino)propanoic acid (4.5 g, 18.9 mmol) in 10% sodium carbonate aqueous solution (50 mL) were added dioxane (30 mL) and di-tert-butyl dicarbonate (6.18 g, 28.32 mmol) at 0° C. The reaction mixture was stirred at 20° C. for 16 h. The mixture was diluted with water (100 mL) and washed with methyl tert-butyl ether (50 mL×3). The aqueous layer was acidified with 2N HCl to pH to 56 and extracted with ethyl acetate (80 mL×3). The combined organic layers were dried over sodium sulfate, filtered and concentrated. The residue was slurried in diisopropyl ether (40 mL) and collected to give compound (R)-2-(((benzyloxy)carbonyl)amino)-3-((tert-butoxycarbonyl)amino)propanoic acid (5.5 g).

$^1$H NMR (400 MHz, DMSO-d$_6$) δ ppm 7.43-7.28 (m, 5H), 5.20-5.09 (m, 2H), 4.52-4.28 (m, 1H), 3.69-3.40 (m, 2H), 1.43 (s, 9H).

Intermediate 3

Methyl (R)-3-amino-2-(((benzyloxy)carbonyl)amino)propanoate

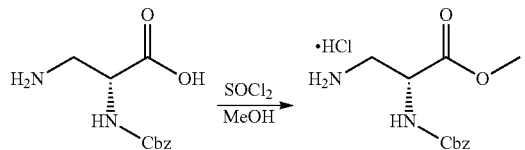

To a solution of (R)-3-amino-2-(((benzyloxy)carbonyl)amino)propanoic acid (200 g, 839 mmol) in methanol (1 L) was added dropwise thionyl chloride (656 g, 5.5 mol) at 0° C. The mixture was allowed to warm to 25° C. and stirred for 18 h. The reaction was concentrated and the residue washed with MTBE (500 mL×2) to give methyl (R)-3-amino-2-(((benzyloxy)carbonyl)amino)propanoate (240 g) as HCl salt.

$^1$H NMR (400 MHz, MeOD) δ 7.31-7.39 (m, 5H), 5.13 (s, 2H), 4.50-4.54 (m, 1H), 3.77 (s, 3H), 3.43-3.48 (m, 1H), 3.24-3.27 (m, 1H)

Intermediate 4

Ethyl(R)-3-amino-2-(((benzyloxy)carbonyl)amino)propanoate

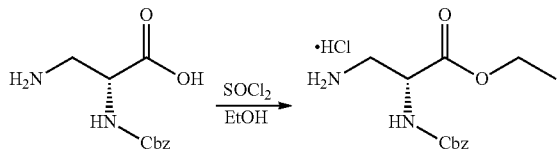

To a solution of (R)-3-amino-2-(((benzyloxy)carbonyl)amino)propanoic acid (5 g, 21 mmol) in ethanol (60 mL) was added dropwise thionyl chloride (4.99 g, 42 mmol). The mixture was stirred at 30° C. for 16 h. The reaction was concentrated to give ethyl (R)-3-amino-2-(((benzyloxy)carbonyl)amino)propanoate (6.0 g) as HCl salt.

$^1$H NMR (400 MHz, DMSO-d$_6$) δ 8.38 (br s, 3H), 7.94 (d, 1H), 7.41-7.30 (m, 5H), 5.07 (s, 2H), 4.46-4.37 (m, 1H), 4.12 (q, 2H), 3.25-3.15 (m, 1H), 3.11-2.99 (m, 1H), 1.18 (t, 3H).

Intermediate 5

(R)-propyl 3-amino-2-(((benzyloxy)carbonyl)amino)propanoate

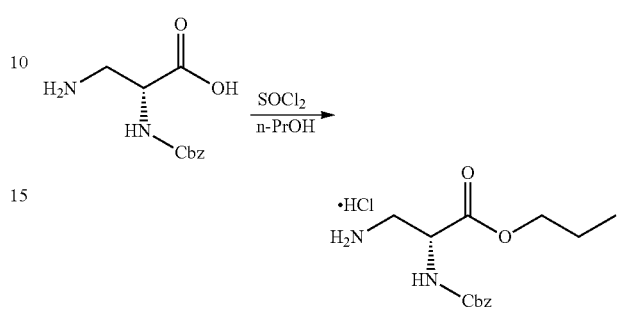

To a solution of (R)-3-amino-2-(((benzyloxy)carbonyl)amino)propanoic acid (2.0 g, 8.4 mmol) in n-PrOH (30 mL) was added thionyl chloride (2.0 g, 16.78 mmol) at 0° C. The mixture was stirred at 25° C. for 16 h. The reaction mixture was concentrated. The residue was treated with methyl tert-butyl ether (5 mL) and hexane (15 mL). The solid was collected by filtration and washed with hexane (15 mL×2) and dried to give (R)-propyl 3-amino-2-(((benzyloxy)carbonyl)amino)propanoate (2.2 g) as a HCl salt.

$^1$H NMR (400 MHz, DMSO-d$_6$) δ 8.12 (br s, 3H), 7.88 (br d, 1H), 7.40-7.32 (m, 5H), 5.11-5.03 (m, 2H), 4.42-4.36 (m, 1H), 4.04 (t, 2H), 3.28-3.22 (m, 1H), 3.13-3.01 (m, 1H), 1.61-1.54 (m, 2H), 0.87 (t, 3H).

Intermediate 6

Isopropyl (R)-3-amino-2-(((benzyloxy)carbonyl)amino)propanoate hydrochloride

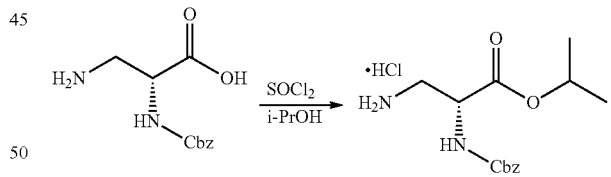

To a solution of (R)-3-amino-2-(((benzyloxy)carbonyl)amino)propanoic acid (5 g, 21 mmol) in i-PrOH (60 mL) was added drop wise thionyl chloride (5.0 g, 42 mmol). The mixture was stirred at 30° C. for 16 h. Then additional thionyl chloride (3 mL) was added, the reaction was then stirred at 30° C. for 24 h. The mixture was concentrated to give 10 g crude product. The crude product was treated with cyclohexane (30 mL) and stirred for 3 h. The solid was collected and dried to give isopropyl (R)-3-amino-2-(((benzyloxy)carbonyl)amino)propanoate (6.3 g) as HCl salt.

$^1$H NMR (400 MHz, DMSO-d$_6$) δ 8.38 (br, 3H), 7.92 (d, J=8.0 Hz, 1H), 7.39-7.29 (m, 5H), 5.06 (s, 2H), 4.95-4.86 (m, 1H), 4.39-4.31 (m, 1H), 3.22-3.12 (m, 1H), 3.10-2.99 (m, 1H), 1.17 (dd, J=9.2, 6.4 Hz, 6H).

Intermediate 7

Cyclopropyl (R)-2-(((benzyloxy)carbonyl)amino)-3-((tert-butoxycarbonyl)amino)propanoate

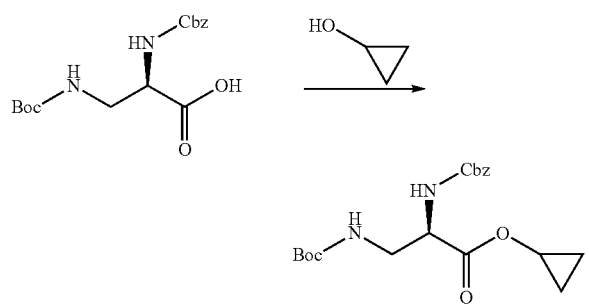

To a mixture of (R)-2-(((benzyloxy)carbonyl)amino)-3-((tert-butoxycarbonyl)amino)propanoic acid (1.1 g, 3.25 mmol) and cyclopropanol (208 mg, 3.58 mmol) in DMF (25 mL) was added N,N-diisopropylethylamine (1.26 g, 9.75 mmol) and HATU (1.85 g, 4.88 mmol). The reaction mixture was stirred at 50° C. for 16 h. The mixture was diluted with water (20 mL) and extracted with ethyl acetate (30 mL×3). The combined organic layers were washed with brine (30 mL×3) and concentrated. The residue was purified by Combi Flash on silica gel to give cyclopropyl (R)-2-(((benzyloxy)carbonyl)amino)-3-((tert-butoxycarbonyl)amino)propanoate (1.1 g).

$^1$H NMR (400 MHz, CDCl$_3$) δ 7.40-7.30 (m, 5H), 5.75 (br s, 1H), 5.12 (s, 2H), 4.80 (br s, 1H), 4.40-4.34 (m, 1H), 4.20-4.15 (m, 1H), 3.57-3.50 (m, 2H), 1.43 (s, 9H), 0.78-0.70 (m, 4H).

Intermediate 8

Cyclopropyl(R)-3-amino-2-(((benzyloxy)carbonyl)amino)propanoate

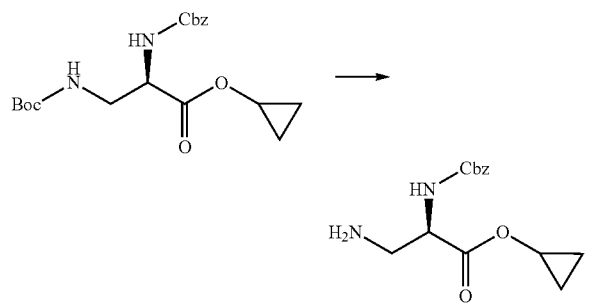

A mixture of (R)-cyclopropyl 2-(((benzyloxy)carbonyl)amino)-3-((tert-butoxycarbonyl)amino)propanoate (1.0 g, 2.64 mmol) in HCl/Ethyl acetate (15 mL) was stirred at 15° C. for 1 hour. The mixture was concentrated below 40° C. to give (R)-cyclopropyl 3-amino-2-(((benzyloxy)carbonyl)amino)propanoate (810 mg) as HCl salt.

$^1$H NMR (400 MHz, DMSO-d$_6$) δ 8.00 (br s, 3H), 7.86 (br d, J=8.4 Hz, 1H), 7.42-7.31 (m, 5H), 5.07 (s, 2H), 4.37-4.30 (m, 1H), 4.15-4.09 (m, 1H), 3.25-3.00 (m, 2H), 0.74-0.57 (m, 4H).

Intermediate 9

Butyl(R)-3-amino-2-(((benzyloxy)carbonyl)amino)propanoate

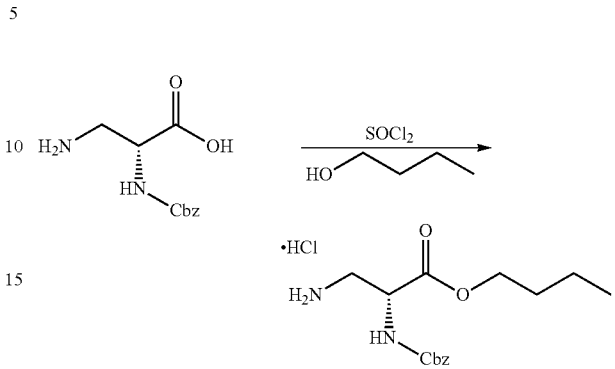

To a mixture of (R)-3-amino-2-(((benzyloxy)carbonyl)amino)propanoic acid (8 g, 33.6 mmol) and butan-1-ol (30 mL) was added thionyl chloride (12 g, 101 mmol) dropwise at 0° C. over 30 minutes. The resulting mixture was stirred at 30° C. for 15.5 h. The reaction was concentrated in vacuo. The residue was purified by washing with petroleum ether (50 mL) at 25° C. to give butyl (R)-3-amino-2-(((benzyloxy)carbonyl)amino)propanoate hydrochloride (11 g).

$^1$H NMR (400 MHz, DMSO-d$_6$) δ 8.37 (s, 3H), 7.92 (d, 1H), 7.30-7.38 (m, 5H), 5.04 (s, 2H), 4.36-4.43 (m, 1H), 4.05 (t, 2H), 3.18 (m, 1H), 3.04 (m, 1H), 1.47-1.55 (m, 2H), 1.23-1.32 (m, 2H), 0.82-0.87 (t, 3H).

Intermediate 10

Cyclohexyl(R)-2-(((benzyloxy)carbonyl)amino)-3-((tert-butoxycarbonyl)amino)propanoate

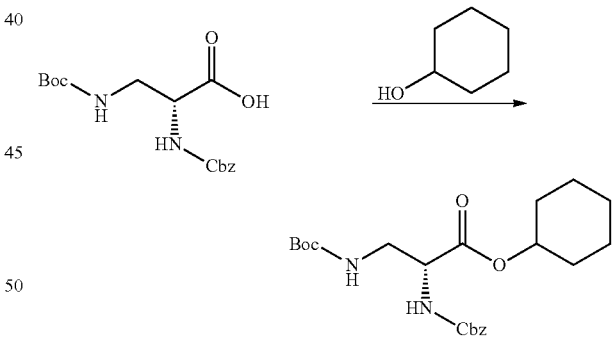

A mixture of (R)-2-(((benzyloxy)carbonyl)amino)-3-((tert-butoxycarbonyl)amino)propanoic acid (1 g, 2.96 mmol), HATU (1.69 g, 4.43 mmol) and N,N-diisopropylethylamine (1.15 g, 8.9 mmol) in DMF (25 mL) was stirred at 20° C. for 30 min, cyclohexanol (326 mg, 3.25 mmol) was added and the resulting mixture was stirred at 50° C. for 16 h. The mixture was diluted with water (25 mL) and extracted with ethyl acetate (50 mL×2). The combined organic phases were washed with brine (50 mL×2), dried over anhydrous sodium sulfate and concentrated. The residue was purified by Combi Flash (silica gel, from 0 to 30%, Ethyl acetate in petroleum ether) to give cyclohexyl (R)-2-(((benzyloxy)carbonyl)amino)-3-((tert-butoxycarbonyl)amino)propanoate (520 mg).

¹H NMR (400 MHz, CDCl₃) δ 7.41-7.28 (m, 5H), 5.89-5.65 (m, 1H), 4.92-4.70 (m, 2H), 4.49-4.33 (m, 1H), 3.68-3.47 (m, 2H), 1.91-1.73 (m, 4H), 1.61-1.34 (m, 15H).

Intermediate 11

Cyclohexyl (R)-3-amino-2-(((benzyloxy)carbonyl)amino)propanoate hydrochloride

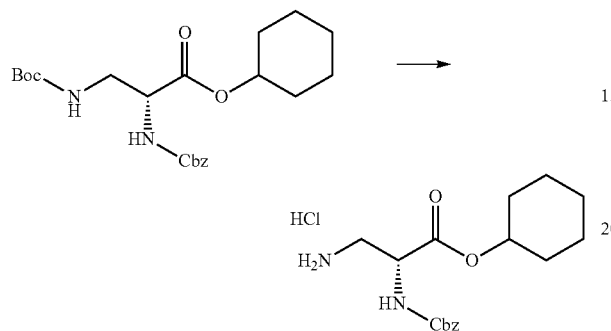

A solution of (R)-cyclohexyl 2-(((benzyloxy)carbonyl)amino)-3-((tert-butoxycarbonyl)amino)propanoate (520 mg, 1.24 mmol) in HCl/Ethyl acetate (4 mL, 4 M) was stirred at 20° C. for 1 hour. The mixture was concentrated to give cyclohexyl (R)-3-amino-2-(((benzyloxy)carbonyl)amino)propanoate (440 mg) as HCl salt.
¹H NMR (400 MHz, CDCl₃) δ 8.44-8.06 (m, 3H), 7.34-7.13 (m, 5H), 6.58 (br d, J=6.8 Hz, 1H), 5.03 (s, 2H), 4.78-4.33 (m, 2H), 3.59-3.23 (m, 2H), 1.89-1.19 (m, 10H).

Intermediate 12

Phenyl (R)-2-(((benzyloxy)carbonyl)amino)-3-((tert-butoxycarbonyl)amino)propanoate

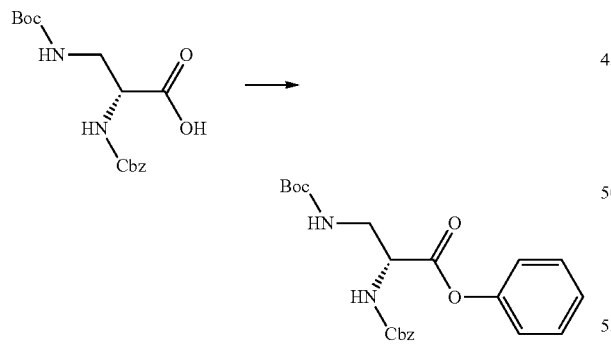

To a solution of (R)-2-(((benzyloxy)carbonyl)amino)-3-((tert-butoxycarbonyl)amino)propanoic acid (1 g, 2.9 mmol) in DMF (25 mL) was added HATU (1.69 g, 4.4 mmol), N,N-diisopropylethylamine (1.15 g, 8.9 mmol) and phenol (306 mg, 3.25 mmol). The mixture was stirred at 50° C. for 16 h. The mixture was diluted with water (10 mL) and extracted with ethyl acetate (20 mL×3). The combined organic layers were washed with brine (20 mL×3) and concentrated. The residue was purified by Combi Flash on silica gel (petroleum ether:ethyl acetate with ethyl acetate from 0 to 25%) to give compound phenyl (R)-2-(((benzyloxy)carbonyl)amino)-3-((tert-butoxycarbonyl)amino)propanoate (890 mg).
¹H NMR (400 MHz, CDCl₃) δ 7.42-7.32 (m, 7H), 7.27-7.21 (m, 1H), 7.19-7.09 (m, 2H), 5.91 (br s, 1H), 5.15 (s, 2H), 4.91 (br s, 1H), 4.72-4.62 (m, 1H), 3.88-3.76 (m, 1H), 3.74-3.63 (m, 1H), 1.44 (s, 9H).

Intermediate 13

Phenyl (R)-3-amino-2-(((benzyloxy)carbonyl)amino)propanoate

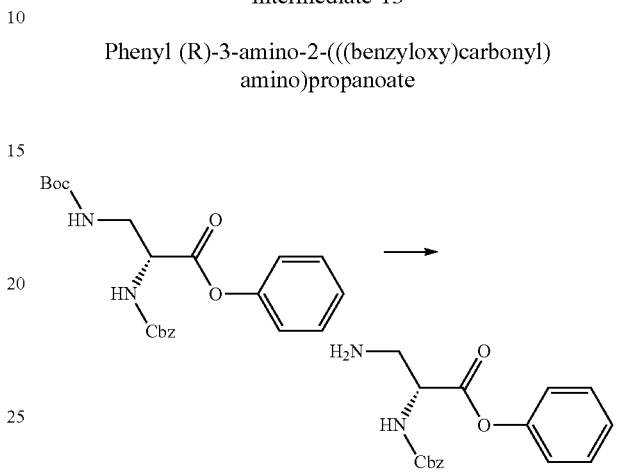

A mixture of (R)-phenyl 2-(((benzyloxy)carbonyl)amino)-3-((tert-butoxycarbonyl)amino)propanoate (890 mg, 2.15 mmol) in HCl/Ethyl acetate (4 M, 15 mL) was stirred at 15° C. for 1 hour. The mixture was concentrated below 40° C. to give compound phenyl (R)-3-amino-2-(((benzyloxy)carbonyl)amino)propanoate (870 mg) as HCl salt.
¹H NMR (400 MHz, DMSO-d₆) δ 8.35 (br s, 3H), 8.19 (br d, J=8.0 Hz, 1H), 7.46-7.27 (m, 8H), 7.11 (d, J=7.6 Hz, 2H), 5.22-5.03 (m, 2H), 4.74-4.62 (m, 1H), 3.30-3.14 (m, 1H).

Intermediate 14

2-Oxo-2-(pyrrolidin-1-yl)ethyl(R)-2-(((benzyloxy)carbonyl)amino)-3-((tert-butoxycarbonyl)amino)propanoate

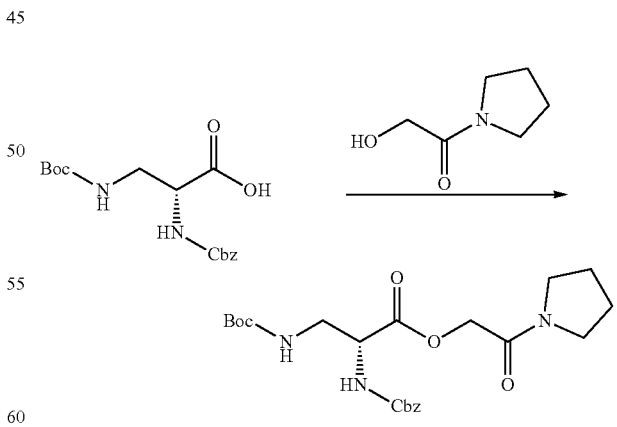

To a solution of (R)-2-(((benzyloxy)carbonyl)amino)-3-((tert-butoxycarbonyl)amino)propanoic acid (1 g, 2.96 mmol), HATU (1.69 g, 4.43 mmol) and N,N-diisopropylethylamine (1.15 g, 8.87 mmol) in DMF (15 mL) was added 2-hydroxy-1-(pyrrolidin-1-yl)ethanone (382 mg, 2.96 mmol). The mixture was stirred at 50° C. for 16 h. The mixture was diluted with water (20 mL) and extracted with ethyl acetate (20 mL×3). The combined organic layers were washed with brine (20 mL×3) and concentrated. The residue was purified by Combi Flash on silica gel (petroleum ether:ethyl acetate with ethyl acetate from 0 to 54%) to give 2-oxo-2-(pyrrolidin-1-yl)ethyl (R)-2-(((benzyloxy)carbonyl)amino)-3-((tert-butoxycarbonyl)amino)propanoate (700 mg).

$^1$H NMR (400 MHz, CDCl$_3$) δ 7.41-7.29 (m, 5H), 6.20 (br, 1H), 6.11 (d, J=6.8 Hz, 1H), 5.18-5.07 (m, 2H), 5.01 (d, J=14.4 Hz, 1H), 4.55-4.39 (m, 2H), 3.90-3.70 (m, 1H), 3.65-3.31 (m, 5H), 2.05-1.97 (m, 2H), 1.92-1.85 (m, 2H), 1.43 (s, 9H).

Intermediate 15

2-Oxo-2-(pyrrolidin-1-yl)ethyl (R)-3-amino-2-(((benzyloxy)carbonyl)amino)propanoate

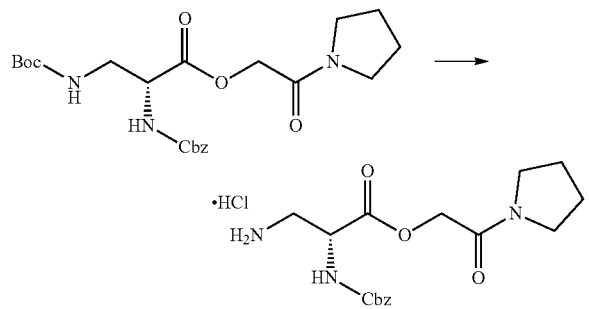

To a solution of (R)-2-oxo-2-(pyrrolidin-1-yl)ethyl 2-(((benzyloxy)carbonyl)amino)-3-((tert-butoxycarbonyl)amino)propanoate (700 mg, 1.56 mmol) in ethyl acetate (4 mL) was added HCl/Ethyl acetate (4 M, 10 mL). The mixture was stirred at 15° C. for 1 hour. The mixture was concentrated in vacuo to give 2-oxo-2-(pyrrolidin-1-yl)ethyl (R)-3-amino-2-(((benzyloxy)carbonyl)amino)propanoate (600 mg) as HCl salt.

$^1$H NMR (400 MHz, DMSO-d$_6$) δ 8.39 (br s, 3H), 8.03 (d, J=8.0 Hz, 1H), 7.39-7.32 (m, 5H), 5.07 (s, 2H), 4.98 (d, J=15.2 Hz, 1H), 4.76 (d, J=15.2 Hz, 1H), 4.60-4.51 (m, 1H), 3.39 (t, J=6.4 Hz, 2H), 3.30 (t, J=7.2 Hz, 2H), 3.26-3.14 (m, 2H), 1.92-1.86 (m, 2H), 1.81-1.72 (m, 2H).

Intermediate 16

Isopentyl(R)-3-amino-2-(((benzyloxy)carbonyl)amino)propanoate

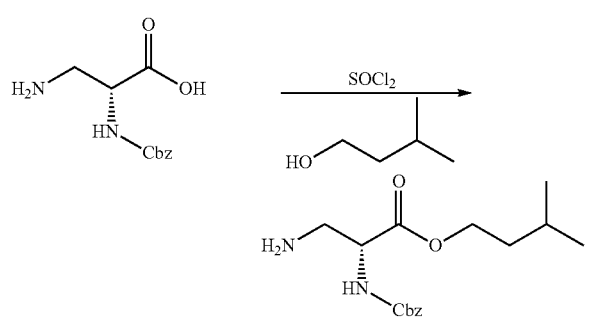

To a solution of (R)-3-amino-2-(((benzyloxy)carbonyl)amino)propanoic acid (5 g, 21 mmol) in 3-methylbutan-1-ol (50 mL) was added thionyl chloride (5 g, 42 mmol) at 0° C. The mixture was stirred at 25° C. for 16 h. The 3-methylbutan-1-ol was removed at 80° C./0.02 bar, the residue was dissolved in water (30 mL), and washed with ethyl acetate (20 mL×3). The aqueous layers were concentrated to give a isopentyl (R)-3-amino-2-(((benzyloxy)carbonyl)amino)propanoate hydrochloride (6 g).

$^1$H NMR (400 MHz, DMSO-d$_6$) δ 8.50 (br, 3H), 7.97 (d, 1H), 7.38-7.30 (m, 5H), 5.10-4.99 (m, 2H), 4.48-4.38 (m, 1H), 4.10 (t, 2H), 3.24-3.16 (m, 1H), 3.12-3.02 (m, 1H), 1.58-1.67 (m, 1H), 1.45 (q, 2H), 0.87-0.83 (m, 6H).

Intermediate 17

2-Methoxyethyl(R)-3-amino-2-(((benzyloxy)carbonyl)amino)propanoate

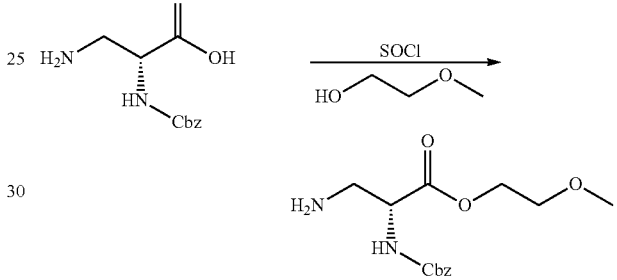

To a solution of (R)-3-amino-2-(((benzyloxy)carbonyl)amino)propanoic acid (5 g, 21 mmol) in 2-methoxyethanol (50 mL) was added thionyl chloride (5 g, 42 mmol). The mixture was stirred at 20° C. for 16 h. The mixture was concentrated to give 2-methoxyethyl (R)-3-amino-2-(((benzyloxy)carbonyl)amino)propanoate (7 g) as HCl salt.

$^1$H NMR (400 MHz, DMSO-d$_6$) δ 8.35 (br, 3H), 7.95 (d, 1H), 7.38-7.31 (m, 5H), 5.11-5.00 (m, 2H), 4.49-4.40 (m, 1H), 4.25-4.15 (m, 2H), 3.50 (m, 2H), 3.25 (m, 4H), 3.05 (m, 1H).

Intermediate 18

Lithium 7-chlorothieno[3,2-b]pyridine-2-carboxylate

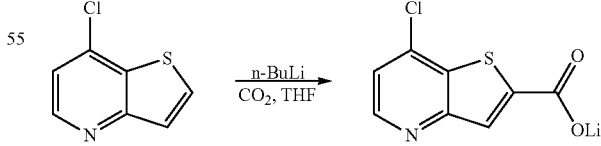

To a solution of 7-chlorothieno[3,2-b]pyridine (10.0 g, 58.9 mmol) in THF (150 mL) was added drop wise n-butyllithium (n-BuLi) (2.5 M in hexane, 23.6 mL) at −78° C. The mixture was stirred at −78° C. for 30 minutes. Then gaseous carbon dioxide (15 psi) was bubbled through the reaction solution and the mixture was allowed to warm to 20° C. over a period of 16 h. The mixture was diluted with THF (20 mL)

and filtered to give lithium 7-chlorothieno[3,2-b]pyridine-2-carboxylate (12 g).

d. Preparation of the Exemplified Compounds of the Invention

Compound 1a (R)-2-amino-3-(7-(difluoromethyl)thieno[3,2-b]pyridine-2-carboxamido)propanoic acid The overall synthesis scheme for the preparation of (R)-2-amino-3-(7-(difluoromethyl)thieno[3,2-b]pyridine-2-carboxamido)propanoic acid is shown below.

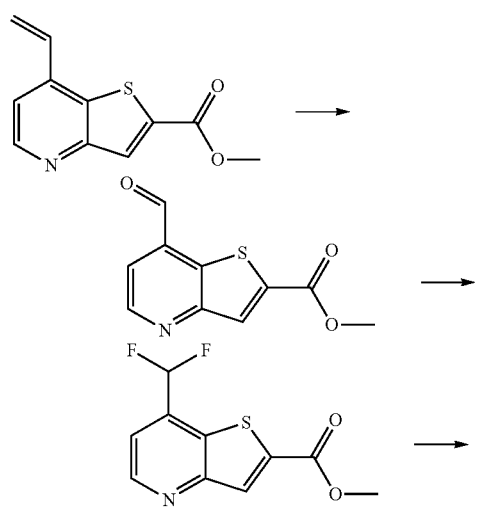

Step 1: Methyl 7-formylthieno[3,2-b]pyridine-2-carboxylate

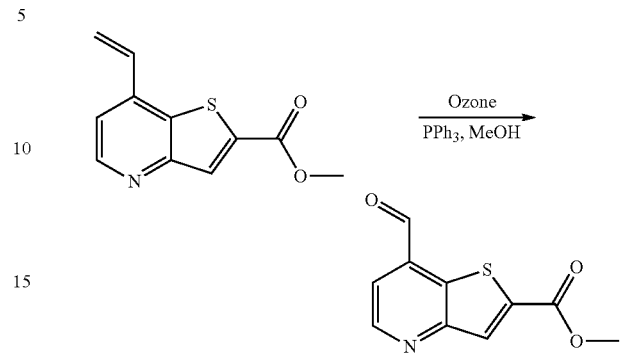

Ozone was bubbled through a solution of methyl 7-vinylthieno[3,2-b]pyridine-2-carboxylate (700 mg, 3.19 mmol) in MeOH (30 mL) at −78° C. for 10 min, then the mixture was warmed to 25° C. PPh$_3$ (1.26 g, 4.79 mmol) was added, and the mixture was stirred at 25° C. for 2 h. The mixture was concentrated under reduced pressure. The residue was purified by CombiFlash (petroleum ether:ethyl acetate with ethyl acetate from 0 to 30%) to give methyl 7-formylthieno[3,2-b]pyridine-2-carboxylate (550 mg).

$^1$H NMR (400 MHz, CDCl$_3$) δ 10.35 (s, 1H), 9.10 (d, J=4.4 Hz, 1H), 8.33 (s, 1H), 7.82 (d, J=4.4 Hz, 1H), 4.02 (s, 3H).

Step 2: Methyl 7-(difluoromethyl)thieno[3,2-b]pyridine-2-carboxylate

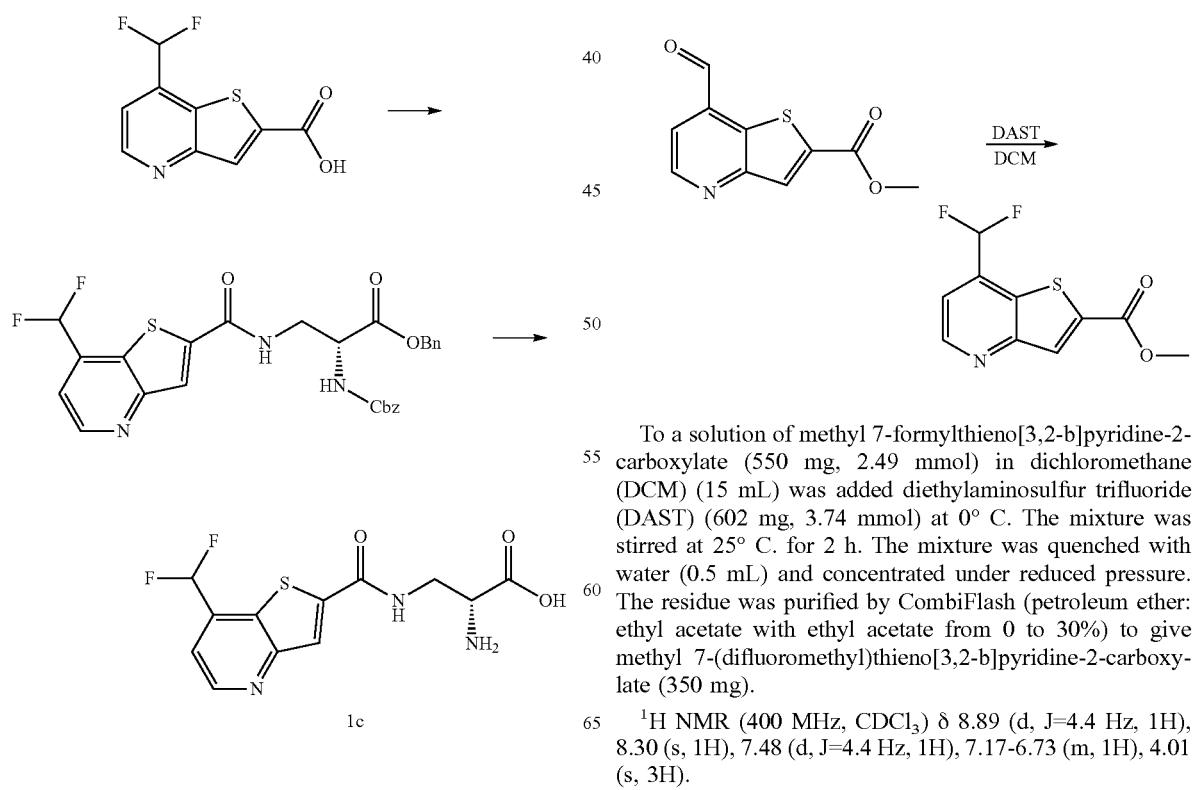

To a solution of methyl 7-formylthieno[3,2-b]pyridine-2-carboxylate (550 mg, 2.49 mmol) in dichloromethane (DCM) (15 mL) was added diethylaminosulfur trifluoride (DAST) (602 mg, 3.74 mmol) at 0° C. The mixture was stirred at 25° C. for 2 h. The mixture was quenched with water (0.5 mL) and concentrated under reduced pressure. The residue was purified by CombiFlash (petroleum ether: ethyl acetate with ethyl acetate from 0 to 30%) to give methyl 7-(difluoromethyl)thieno[3,2-b]pyridine-2-carboxylate (350 mg).

$^1$H NMR (400 MHz, CDCl$_3$) δ 8.89 (d, J=4.4 Hz, 1H), 8.30 (s, 1H), 7.48 (d, J=4.4 Hz, 1H), 7.17-6.73 (m, 1H), 4.01 (s, 3H).

Step 3: 7-(difluoromethyl)thieno[3,2-b]pyridine-2-carboxylic acid

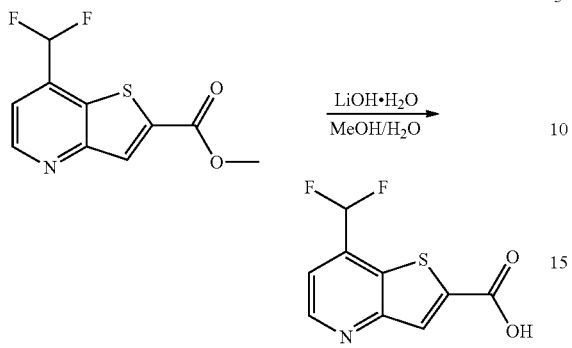

To a solution of methyl 7-(difluoromethyl)thieno[3,2-b]pyridine-2-carboxylate (440 mg, 1.81 mmol) in MeOH (10 mL) was added LiOH.H$_2$O (228 mg, 5.43 mmol) dissolved in water (1 mL). The mixture was stirred at 25° C. for 3 h. The mixture was concentrated under reduced pressure. The residue was dissolved in water (10 mL) and washed with ethyl acetate (10 mL). The aqueous layer was acidified by 2N HCl (2 mL) and the precipitate was collected to give 7-(difluoromethyl)thieno[3,2-b]pyridine-2-carboxylic acid (320 mg).
$^1$H NMR (400 MHz, DMSO-d$_6$) δ 8.94 (d, J=4.4 Hz, 1H), 8.22 (s, 1H), 7.73 (d, J=4.4 Hz, 1H), 7.63-7.32 (m, 1H).

Step 4: benzyl (R)-2-(((benzyloxy)carbonyl)amino)-3-(7-(difluoromethyl)thieno[3,2-b]pyridine-2-carboxamido)propanoate

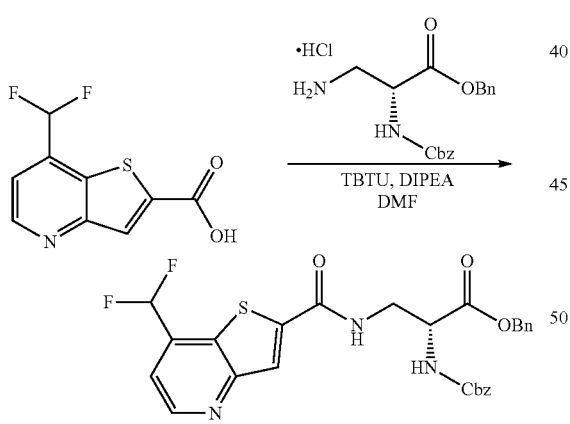

To a solution of 7-(difluoromethyl)thieno[3,2-b]pyridine-2-carboxylic acid (320 mg, 1.40 mmol) and benzyl (R)-3-amino-2-(((benzyloxy)carbonyl)amino)propanoate (511 mg, 1.40 mmol, HCl salt) in DMF (8 mL) was added O-(Benzotriazol-1-yl)-N,N,N',N'-tetramethyluronium tetrafluoroborate (674 mg, 2.10 mmol) and N,N-diisopropylethylamine (543 mg, 4.20 mmol). The mixture was stirred at 25° C. for 16 h. The mixture was diluted with water (10 mL) and extracted with ethyl acetate (10 mL×3). The combined organic layers were washed with water (20 mL) and brine (20 mL) and concentrated under reduced pressure. The residue was purified by Combi Flash (petroleum ether:ethyl acetate with ethyl acetate from 0 to 60%) to give benzyl (R)-2-(((benzyloxy)carbonyl)amino)-3-(7-(difluoromethyl)thieno[3,2-b]pyridine-2-carboxamido)propanoate (600 mg).
$^1$H NMR (400 MHz, CDCl$_3$) δ 8.85 (d, J=4.4 Hz, 1H), 7.90 (s, 1H), 7.46 (d, J=4.4 Hz, 1H), 7.39-7.27 (m, 10H), 7.06-6.76 (m, 1H), 6.05 (br d, 1H), 5.22 (s, 2H), 5.12 (s, 2H), 4.68-4.59 (m, 1H), 4.01-3.92 (m, 1H), 3.91-3.82 (m, 1H).

Step 5: Preparation of (R)-2-amino-3-(7-(difluoromethyl)thieno[3,2-b]pyridine-2-carboxamido)propanoic acid

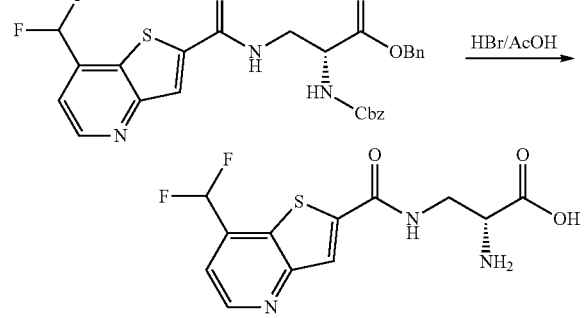

A mixture of benzyl (R)-2-(((benzyloxy)carbonyl)amino)-3-(7-(difluoromethyl)thieno[3,2-b]pyridine-2-carboxamido)propanoate (200 mg, 0.37 mmol) in 33% HBr in AcOH (4 mL) was stirred at 50° C. for 16 h. The mixture was concentrated under reduced pressure. The residue was purified by preparative HPLC (Method A) to give (R)-2-amino-3-(7-(difluoromethyl)thieno[3,2-b]pyridine-2-carboxamido)propanoic acid (86 mg) as HCl salt.
$^1$H NMR (400 MHz, DMSO-d$_6$) δ 9.58 (br t, J=6.0 Hz, 1H), 8.91 (d, J=4.8 Hz, 1H), 8.66-8.58 (m, 3H), 8.55 (s, 1H), 7.69 (d, J=4.8 Hz, 1H), 7.63-7.31 (m, 1H), 4.22-4.12 (m, 1H), 3.94-3.76 (m, 2H).
LCMS (MH+): m/z=316.2, t$_R$ (min, Method BB)=0.29.
[α]$^{20}$D=−6.5, (c=2 mg/mL, DMSO).

Compound 2a

Methyl (R)-2-amino-3-(7-(difluoromethyl)thieno[3,2-b]pyridine-2-carboxamido)propanoate

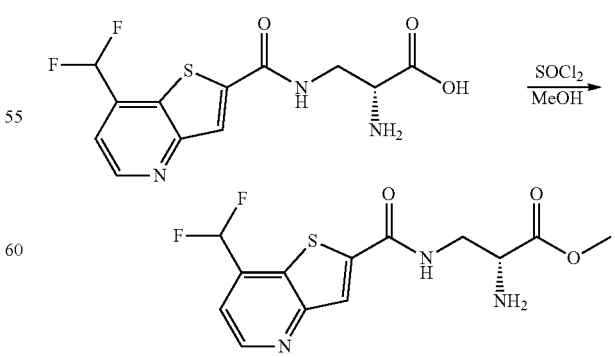

To a solution of (R)-2-amino-3-(7-(difluoromethyl)thieno[3,2-b]pyridine-2-carboxamido) propanoic acid (380 mg, 0.74 mmol, HBr salt) in MeOH (5 mL) was added thionyl chloride (263 mg, 2.21 mmol). The mixture was stirred at 50° C. for 16 h. The mixture was concentrated under reduced pressure. The residue was dissolved in water (5 mL) and adjusted to pH=8 with saturated aqueous sodium carbonate and extracted with ethyl acetate (10 mL×4). The combined organic layers were washed with brine (15 mL) and dried over anhydrous sodium sulfate, filtered and concentrated under reduced pressure. The residue was purified by Combi Flash (DCM: MeOH with MeOH from 0 to 15%) to give methyl (R)-2-amino-3-(7-(difluoromethyl)thieno[3,2-b]pyridine-2-carboxamido)propanoate (145 mg).

$^1$H NMR (400 MHz, CDCl$_3$) δ 8.86 (d, J=4.8 Hz, 1H), 8.00 (s, 1H), 7.46 (d, J=4.8 Hz, 1H), 7.08 (brs, 1H), 7.06-6.73 (t, 1H), 3.97-3.88 (m, 1H), 3.83-3.74 (m, 4H), 3.61-3.51 (m, 1H).

LCMS (MH+): m/z=330.2, $t_R$ (min, Method BB)=0.34 min.

$[α]^{20}$D=−39.7, (c=1 mg/mL, CH$_3$OH).

Compound 1b (R)-2-amino-3-(7-cyclopropylthieno[3,2-b]pyridine-2-carboxamido) propanoic acid The overall synthesis scheme for the preparation of (R)-2-amino-3-(7-cyclopropylthieno[3,2-b]pyridine-2-carboxamido) propanoic acid is shown below.

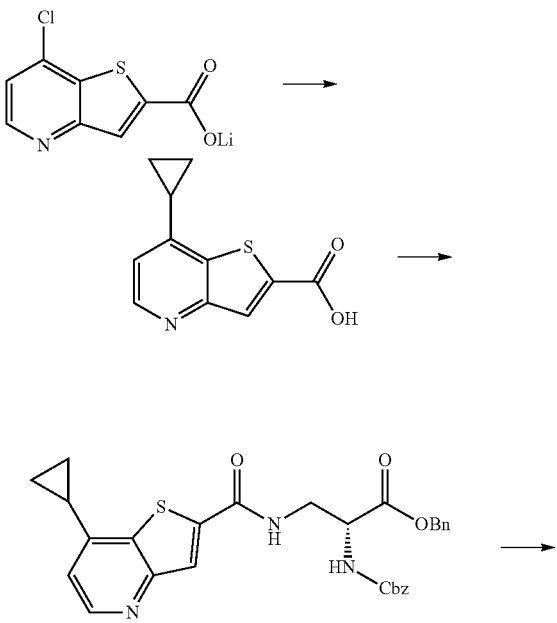

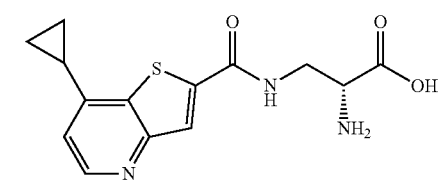

Step 1: 7-cyclopropylthieno[3,2-b]pyridine-2-carboxylic acid

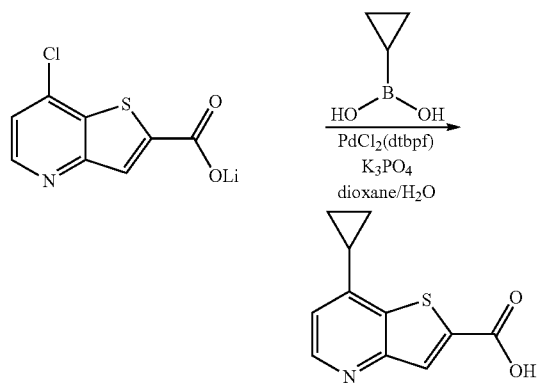

A mixture of lithium 7-chlorothieno[3,2-b]pyridine-2-carboxylate (500 mg, 2.46 mmol), cyclopropylboronic acid (423 mg, 4.92 mmol) and K$_3$PO$_4$ (1.04 g, 4.92 mmol) in dioxane (10 mL) and water (2 mL) was stirred under N$_2$. Then [1,1'-Bis(di-tert-butylphosphino)ferrocene]dichloropalladium(II) (PdCl$_2$(dtbpf)) (80 mg, 0.123 mmol) was added and the mixture was stirred at 110° C. for 16 h in a sealed tube. The mixture was poured into water (15 mL), extracted with ethyl acetate (20 mL). The aqueous was adjusted pH (45) by HCl aq. (3M) and concentrated to afford 7-cyclopropylthieno[3,2-b]pyridine-2-carboxylic acid (700 mg).

Step 2: benzyl (R)-2-(((benzyloxy)carbonyl)amino)-3-(7-cyclopropylthieno[3,2-b]pyridine-2-carboxamido)propanoate

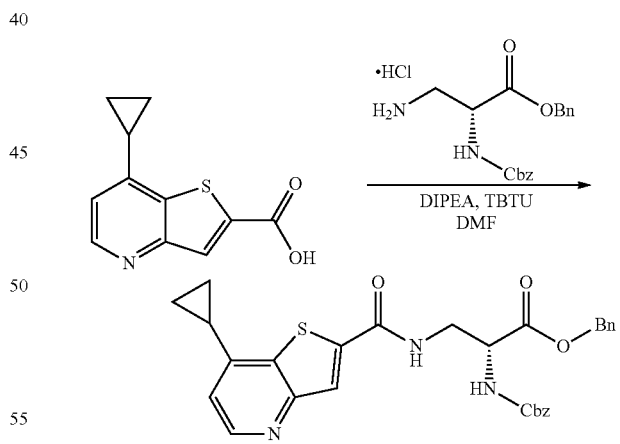

A mixture of crude 7-cyclopropylthieno[3,2-b]pyridine-2-carboxylic acid (650 mg, 2.89 mmol), benzyl (R)-3-amino-2-(((benzyloxy)carbonyl)amino)propanoate (1.05 g, 2.89 mmol, HCl salt), N,N-diisopropylethylamine (1.12 g, 8.67 mmol) and O-(Benzotriazol-1-yl)-N,N,N',N'-tetramethyluronium tetrafluoroborate (1.39 g, 4.34 mmol) in DMF (5 mL) was stirred at 30° C. for 16 h. The mixture was poured into water (20 mL) and extracted with ethyl acetate (20 mL×2). The combined organic phases were washed with brine (30 mL×3), dried over anhydrous sodium sulfate and concentrated. The residue was purified by combiFlash (Ethyl acetate:Petroleum ether=0~50%) to give benzyl (R)-2-(((benzyloxy)carbonyl)amino)-3-(7-cyclopropylthieno[3,2-b]pyridine-2-carboxamido)propanoate (260 mg).

¹H NMR (400 MHz, DMSO-d₆) δ 9.05 (br, 1H), 8.60 (d, 1H), 8.18 (s, 1H), 7.89 (br d, 1H), 7.36-7.22 (m, 10H), 7.04 (d, J=5.2 Hz, 1H), 5.11 (d, J=5.2 Hz, 2H), 5.06 (m, 2H), 4.47-4.42 (m, 1H), 3.77-3.65 (m 2H), 2.10-2.18 (m 1H), 1.24-1.17 (m 2H), 1.05-0.96 (m 2H).

Step 3: (R)-2-Amino-3-(7-cyclopropylthieno[3,2-b]pyridine-2-carboxamido) propanoic acid

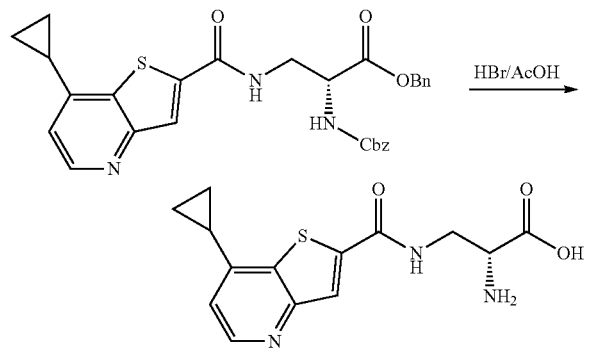

A mixture of benzyl (R)-2-(((benzyloxy)carbonyl)amino)-3-(7-cyclopropylthieno[3,2-b]pyridine-2-carboxamido)propanoate (80.0 mg, 0.15 mmol) and HBr/AcOH (3 mL, 33%) was stirred at 50° C. for 16 h. The mixture was concentrated on vacuo. The residue was purified by preparative-HPLC (Method B) to give (R)-2-amino-3-(7-cyclopropylthieno[3,2-b]pyridine-2-carboxamido)propanoic acid (15 mg) as HCl salt.

¹H NMR (400 MHz, D₂O) δ 8.59-8.52 (m, 1H), 8.09-8.02 (m, 1H), 7.24-7.14 (m, 1H), 4.21-4.12 (m, 1H), 3.95 (dd, 1H), 3.85 (dd, 1H), 2.26 (m, 1H), 1.45 (dd, 2H), 1.24-1.14 (m, 2H).

LCMS (MH+): m/z=306.2, tR (min, Method BB)=0.22.
[α]²⁰D=12.0 (c=0.25 mg/mL, CH₃OH).

Compound 2b

Methyl(R)-2-amino-3-(7-cyclopropylthieno[3,2-b]pyridine-2-carboxamido)propanoate The overall synthesis scheme for the preparation of methyl (R)-2-amino-3-(7-cyclopropylthieno[3,2-b]pyridine-2-carboxamido)propanoate is shown below.

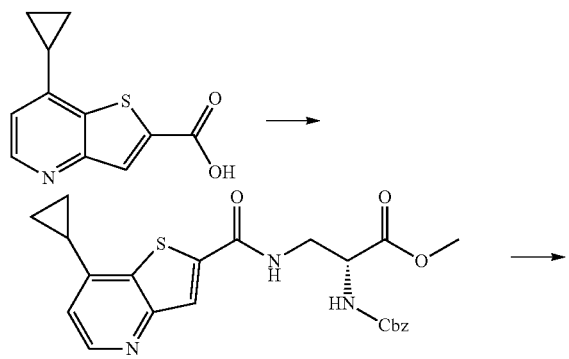

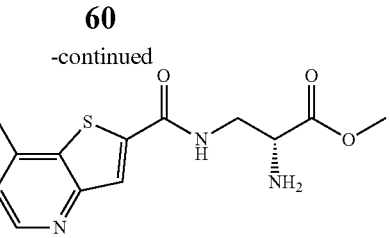

Step 1: Methyl (R)-2-(((benzyloxy)carbonyl)amino)-3-(7-cyclopropylthieno[3,2-b]pyridine-2-carboxamido)propanoate

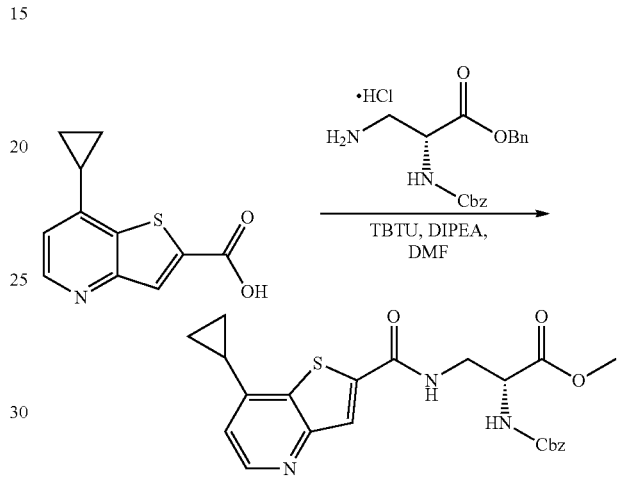

A mixture of 7-cyclopropylthieno[3,2-b]pyridine-2-carboxylic acid (980 mg, 4.47 mmol), (R)-methyl 3-amino-2-(((benzyloxy)carbonyl)amino)propanoate (1.29 g, 4.47 mmol, HCl salt), 2-(1H-Benzotriazole-1-yl)-1,1,3,3-tetramethylaminium tetrafluoroborate (TBTU) (2.15 g, 6.7 mmol) and N,N-diisopropylethylamine (2.89 g, 22.35 mmol) in DMF (20 mL) was stirred at 25° C. for 16 h. The mixture was diluted with water (30 mL) and extracted with ethyl acetate (10 mL×3). The organic phase was washed with brine (10 mL×2), dried over anhydrous sodium sulfate and concentrated. The residue was purified by CombiFlash (Petroleum ether: Ethyl acetate=0~80%) to give methyl (R)-2-(((benzyloxy)carbonyl)amino)-3-(7-cyclopropylthieno[3,2-b]pyridine-2-carboxamido)propanoate (600 mg).

¹H NMR (400 MHz, CDCl₃) δ 8.59 (d, J=4.8 Hz, 1H), 7.90 (s, 1H), 7.37-7.26 (m, 6H), 6.83 (d, J=4.8 Hz, 1H), 5.99 (br d, J=6.8 Hz, 1H), 5.12 (s, 2H), 4.66-4.52 (m, 1H), 3.99-3.83 (m, 2H), 3.80 (s, 3H), 2.18-2.04 (m, 1H), 1.25-1.16 (m, 2H), 1.01-0.93 (m, 2H).

Step 2: Methyl (R)-2-amino-3-(7-cyclopropylthieno[3,2-b]pyridine-2-carboxamido)propanoate

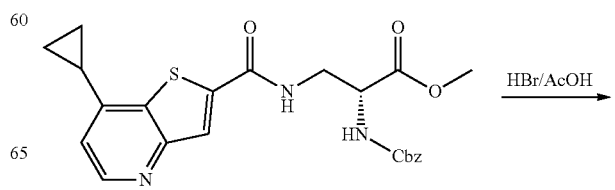

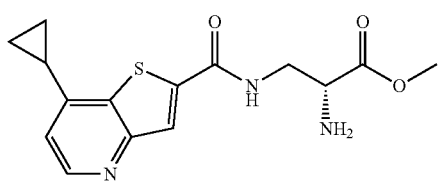

A mixture of methyl (R)-2-(((benzyloxy)carbonyl)amino)-3-(7-cyclopropylthieno[3,2-b]pyridine-2-carboxamido)propanoate (700 mg, 1.54 mmol) and HBr/AcOH (10 mL, 30%) was stirred at 25° C. for 16 h. The mixture was diluted with methyl tert-butyl ether (20 mL). The precipitate was filtered. The filter cake was dried to give the crude product. The crude product was washed with $CH_3OH$ (10 mL). The product was filtered to give methyl (R)-2-amino-3-(7-cyclopropylthieno[3,2-b]pyridine-2-carboxamido)propanoate (230 mg) as HBr salt.

$^1$H NMR (400 MHz, DMSO-$d_6$) δ 9.53 (br t, 1H), 8.84 (d, 1H), 8.55 (br s, 3H), 8.41 (s, 1H), 7.34 (d, 1H), 3.88-3.73 (m, 5H), 2.39-2.28 (m, 1H), 1.38 (m, 2H), 1.20 (br s, 2H).

LCMS (MH+): m/z=320.0, $t_R$ (min, Method BB)=0.31. $[α]^{20}D$=−1.0, (c=1.0 mg/mL, $CH_3OH$).

Compound 1c (R)-2-amino-3-(7-methylthieno[3,2-b]pyridine-2-carboxamido)propanoic acid The overall synthesis scheme for the preparation of (R)-2-amino-3-(7-methylthieno[3,2-b]pyridine-2-carboxamido)propanoic acid is shown below.

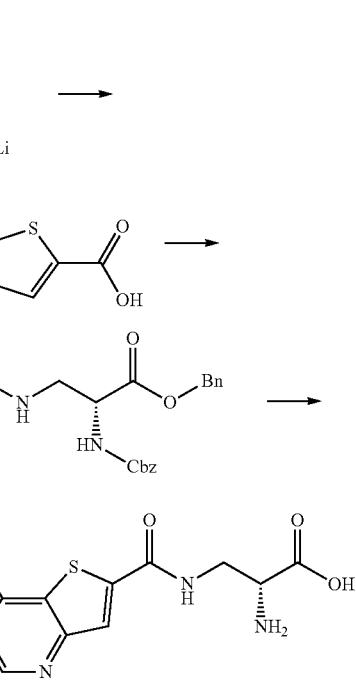

Step 1: 7-Methylthieno[3,2-b]pyridine-2-carboxylic acid

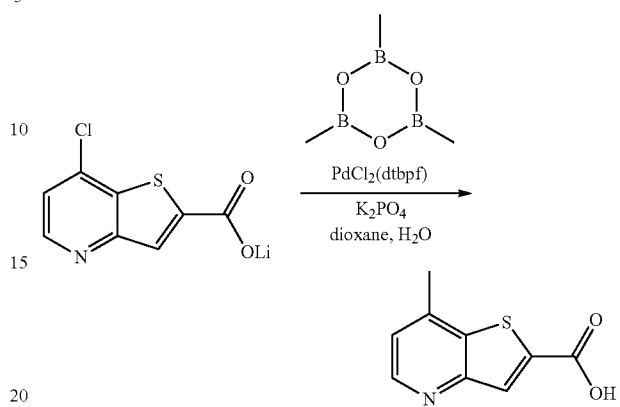

A mixture of lithium 7-chlorothieno[3,2-b]pyridine-2-carboxylate (300 mg, 1.37 mmol), 2,4,6-trimethyl-1,3,5,2,4,6-trioxatriborinane (344 mg, 2.74 mmol, 0.4 mL), $PdCl_2$(dtbpf) (90 mg, 0.14 mmol) and $K_3PO_4$ (727 mg, 3.43 mmol) in water (4 mL) and dioxane (12 mL) in a sealed tube was heated to 80° C. for 16 h under $N_2$. The mixture was filtered. The aqueous phase was adjusted to pH=34 with HCl (2M, 4 mL). The mixture was concentrated to give 7-methylthieno[3,2-b]pyridine-2-carboxylic acid (260 mg). The crude product was used for the next step without any further purification.

Step 2: benzyl (R)-2-(((benzyloxy)carbonyl)amino)-3-(7-methylthieno[3,2-b]pyridine-2-carboxamido)propanoate

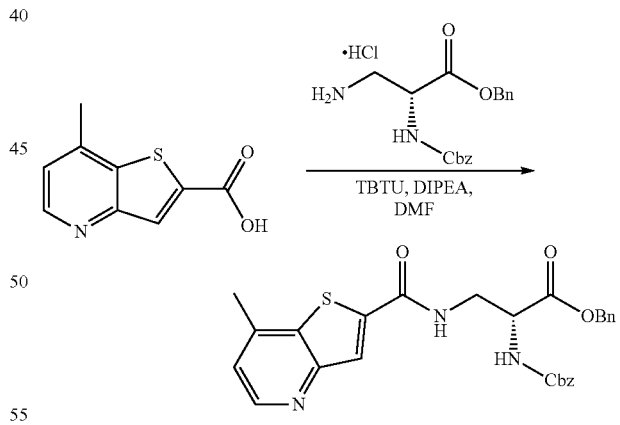

To a solution of 7-methylthieno[3,2-b]pyridine-2-carboxylic acid (300 mg, crude) in DMF (10 mL) was added TBTU (748 mg, 2.33 mmol), N,N-diisopropylethylamine (602 mg, 4.66 mmol) and benzyl (R)-3-amino-2-(((benzyloxy)carbonyl)amino)propanoate (566 mg, 1.55 mmol, HCl salt). The mixture was stirred at 20° C. for 15 h. The mixture was diluted with water (30 mL) and extracted with ethyl acetate (25 mL×3). The combined organic layers were washed with brine (30 mL) and concentrated. The residue was purified by Combi Flash on silica gel (petroleum ether:ethyl acetate with ethyl acetate from 0 to 100%) to give 390 mg crude product. The crude product was triturated with DCM (15 mL) and isolated by filtration and dried to give benzyl (R)-2-(((benzyloxy)carbonyl)amino)-3-(7-methylthieno[3,2-b]pyridine-2-carboxamido)propanoate (230 mg).

$^1$H NMR (400 MHz, DMSO-d$_6$) δ 9.04 (br t, J=5.6 Hz, 1H), 8.64 (d, J=4.8 Hz, 1H), 8.19 (s, 1H), 7.89 (br d, J=8.4 Hz, 1H), 7.37-7.22 (m, 11H), 5.17-5.00 (m, 4H), 4.48-4.39 (m, 1H), 3.76-3.62 (m, 2H), 2.57 (s, 3H).

Step 3: (R)-2-Amino-3-(7-methylthieno[3,2-b]pyridine-2-carboxamido)propanoic acid A mixture of benzyl (R)-2-(((benzyloxy)carbonyl)amino)-3-(7-methylthieno[3,2-b]pyridine-2-carboxamido)propanoate (100 mg, 0.20 mmol) and HBr/AcOH (3 mL, 33%) were stirred at 50° C. for 16 h. The mixture was diluted with methyl tert-butyl ether (3 mL) and water (3 mL). The aqueous phase was extracted with methyl tert-butyl ether (3 mL×2). The aqueous phase was lyophilized to give (R)-2-amino-3-(7-methylthieno[3,2-b]pyridine-2-carboxamido)propanoic acid (50 mg) as HBr salt.

$^1$H NMR (400 MHz, DMSO-d$_6$) δ 9.42 (br s, 1H), 8.91-8.80 (m, 1H), 8.54-8.32 (m, 4H), 7.61 (br s, 1H), 4.20-4.10 (m, 1H), 3.90-3.69 (m, 2H), 2.71 (s, 3H).

LCMS (MH+): m/z=280.1, t$_R$ (min, Method BB)=0.17. [α]$^{20}$D=−11.0, (c=1.0 mg/mL, CH$_3$OH).

Compound 2c

Methyl(R)-2-amino-3-(7-methylthieno[3,2-b]pyridine-2-carboxamido)propanoate

The overall synthesis scheme for the preparation of methyl (R)-2-amino-3-(7-methylthieno[3,2-b]pyridine-2-carboxamido)propanoate is shown below.

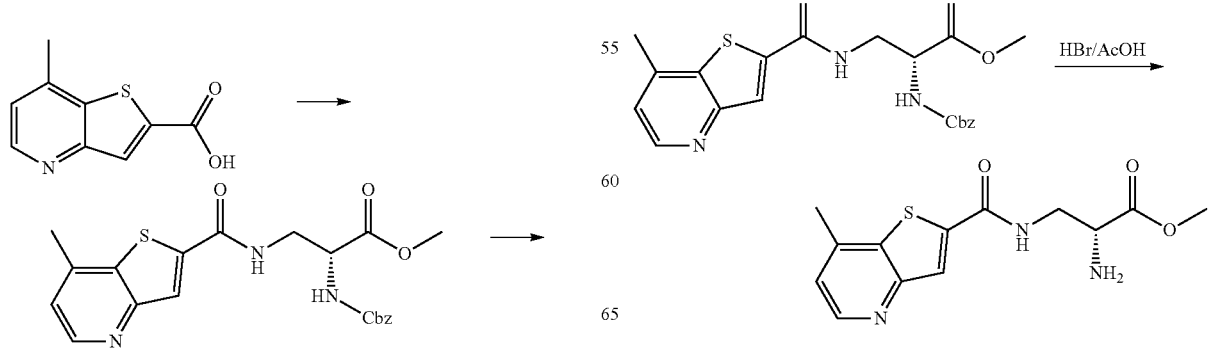

Step 1: Methyl (R)-2-(((benzyloxy)carbonyl)amino)-3-(7-methylthieno[3,2-b]pyridine-2-carboxamido)propanoate

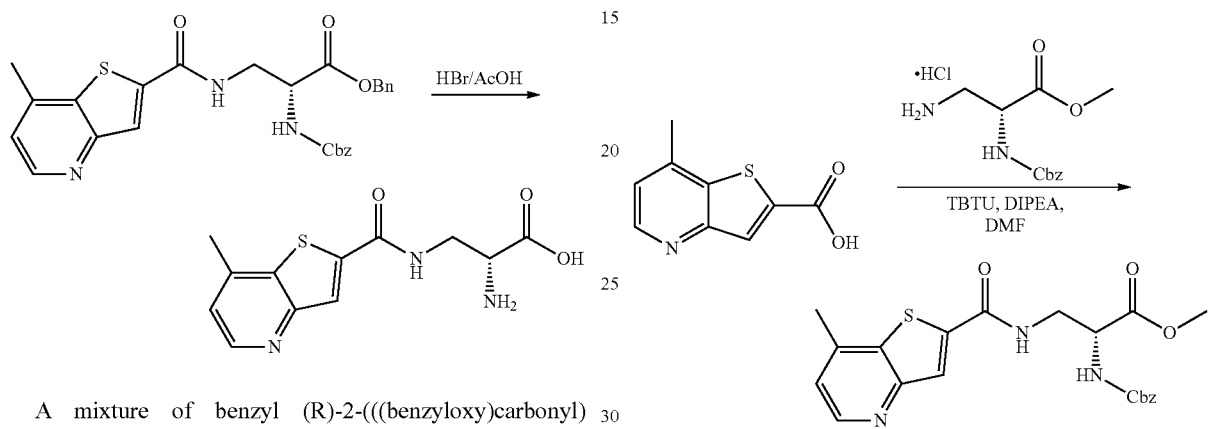

A mixture of 7-methylthieno[3,2-b]pyridine-2-carboxylic acid (800 mg, 4.14 mmol), (R)-methyl 3-amino-2-(((benzyloxy)carbonyl)amino)propanoate (1.2 g, 4.14 mmol, HCl salt), TBTU (1.99 g, 6.21 mmol) and N,N-diisopropylethylamine (2.68 g, 20.7 mmol, 3.6 mL) in DMF (20 mL) was stirred at 25° C. for 16 h. The mixture was diluted with water (90 mL) and extracted with ethyl acetate (20 mL×3). The organic phase was washed with brine (20 mL×2), dried over anhydrous sodium sulfate and concentrated. The residue was purified by CombiFlash (Petroleum ether: Ethyl acetate=0~90%) to give methyl (R)-2-amino-3-(7-methylthieno[3,2-b]pyridine-2-carboxamido)propanoate (1.1 g).

$^1$H NMR (400 MHz, CDCl$_3$) δ 8.61 (d, J=4.8 Hz, 1H), 7.91 (s, 1H), 7.40-7.25 (m, 6H), 7.13 (d, 4.4 Hz, 1H), 6.02 (br d, J=6.8 Hz, 1H), 5.11 (s, 2H), 4.63-4.55 (m, 1H), 3.98-3.83 (m, 2H), 3.79 (s, 3H), 2.58 (s, 3H).

Step 2: Methyl (R)-2-amino-3-(7-methylthieno[3,2-b]pyridine-2-carboxamido)propanoate A mixture of methyl (R)-2-amino-3-(7-methylthieno[3,2-b]pyridine-2-carboxamido)propanoate (600 mg, 1.4 mmol) and HBr/AcOH (6 mL, 33%) was stirred at 25° C. for 16 h. The mixture was diluted with methyl tert-butyl ether (6 mL). The precipitate was filtered and dried to give the crude product (0.6 g). The crude product was washed with MeOH (5 mL) and filtered. The filter cake was dried to give methyl (R)-2-amino-3-(7-methylthieno[3,2-b]pyridine-2-carboxamido) propanoate (400 mg) as HBr salt.

$^1$H NMR (400 MHz, CD$_3$OD) δ 8.91 (d, J=6.4 Hz, 1H), 8.45 (s, 1H), 7.91-7.86 (m, 1H), 4.39 (t, J=4.8 Hz, 1H), 4.10-4.03 (m, 1H), 3.97-3.91 (m, 1H), 3.90 (s, 3H), 2.93 (s, 3H).

LCMS (MH+): m/z=294.4, t$_R$ (min, Method BB)=0.27.

[α]$^{20}$D=−2.0, (c=1.0 mg/mL, CH$_3$OH).

Compound 2d

Ethyl (R)-2-amino-3-(7-methylthieno[3,2-b]pyridine-2-carboxamido)propanoate

The overall synthesis scheme for the preparation of ethyl (R)-2-amino-3-(7-methylthieno[3,2-b]pyridine-2-carboxamido)propanoate is shown below.

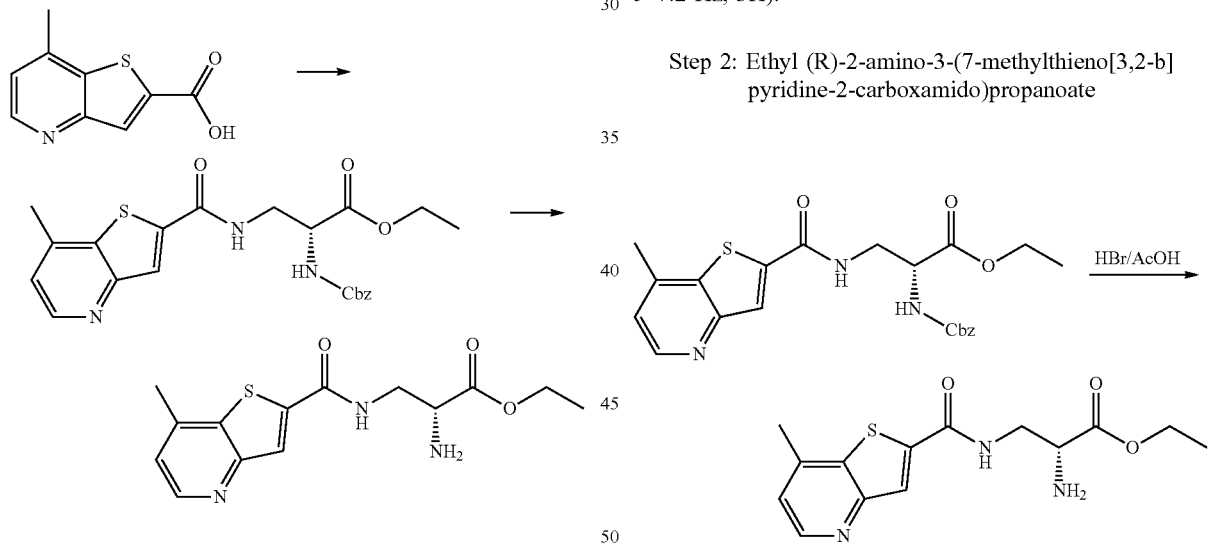

Step 1: Ethyl (R)-2-(((benzyloxy)carbonyl)amino)-3-(7-methylthieno[3,2-b]pyridine-2-carboxamido)propanoate

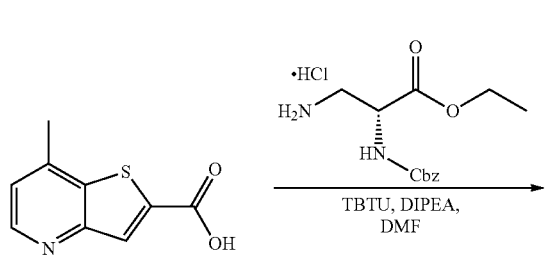

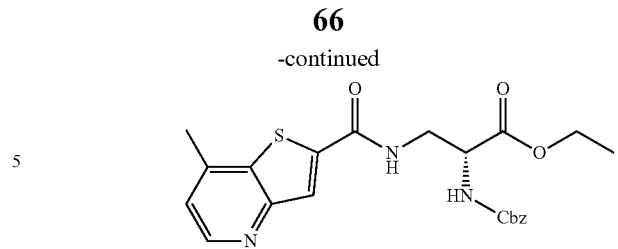

To a solution of 7-methylthieno[3,2-b]pyridine-2-carboxylic acid (2.5 g, crude) in DMF (30 mL) was added TBTU (6.23 g, 19.4 mmol), N,N-diisopropylethylamine (5.02 g, 38.8 mmol) and (R)-ethyl 3-amino-2-(((benzyloxy)carbonyl)amino)propanoate (3.45 g, 11.38 mmol, HCl salt). The mixture was stirred at 20° C. for 16 h. The mixture was diluted with water (50 mL) and extracted with ethyl acetate (40 mL×3). The combined organic layer was washed with water (50 mL×2) and brine (50 mL×2), dried over anhydrous sodium sulfate, filtered and concentrated. The residue was purified by Combi Flash on silica gel (petroleum ether:ethyl acetate with ethyl acetate from 0 to 100%) twice to give ethyl (R)-2-(((benzyloxy)carbonyl)amino)-3-(7-methylthieno[3,2-b]pyridine-2-carboxamido)propanoate (2.6 g). $^1$H NMR (400 MHz, CDCl$_3$) δ 8.62 (d, J=4.8 Hz, 1H), 7.93 (s, 1H), 7.49 (br s, 1H), 7.36-7.24 (m, 5H), 7.14 (d, J=4.8 Hz, 1H), 6.06 (br d, J=6.4 Hz, 1H), 5.12 (s, 2H), 4.63-4.55 (m, 1H), 4.25 (m, 2H), 4.00-3.82 (m, 2H), 2.59 (s, 3H), 1.29 (t, J=7.2 Hz, 3H).

Step 2: Ethyl (R)-2-amino-3-(7-methylthieno[3,2-b]pyridine-2-carboxamido)propanoate

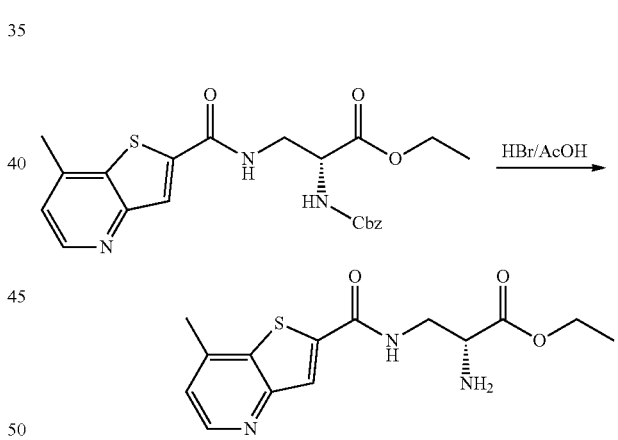

A mixture of ethyl (R)-2-(((benzyloxy)carbonyl)amino)-3-(7-methylthieno[3,2-b]pyridine-2-carboxamido)propanoate (1.6 g, 3.62 mmol) in 30% HBr in AcOH (20 mL) was stirred at 20° C. for 3 h. The mixture was concentrated. To the residue was added water (35 mL) and washed with methyl tert-butyl ether (30 mL). The aqueous layer was lyophilized to give ethyl (R)-2-amino-3-(7-methylthieno[3,2-b]pyridine-2-carboxamido)propanoate (1.55 g) as 2HBr salt. $^1$H NMR (400 MHz, DMSO-d$_6$) δ 9.47 (br s, 1H), 8.86 (d, J=4.8 Hz, 1H), 8.54 (br s, 3H), 8.41 (s, 1H), 7.64 (m, 1H), 4.28-4.22 (m, 1H), 4.18 (q, J=7.2 Hz, 2H), 3.85-3.72 (m, 2H), 2.71 (s, 3H), 1.18 (t, J=7.2 Hz, 3H).

LCMS (MH+): m/z=308.4, t$_R$ (min, Method BB)=0.30.

[α]$^{20}$D=2.1, (c=7.6 mg/mL, MeOH).

Compound 2e

Propyl(R)-2-amino-3-(7-methylthieno[3,2-b]pyridine-2-carboxamido)propanoate

The overall synthesis scheme for the preparation of propyl (R)-2-amino-3-(7-methylthieno[3,2-b]pyridine-2-carboxamido)propanoate is shown below.

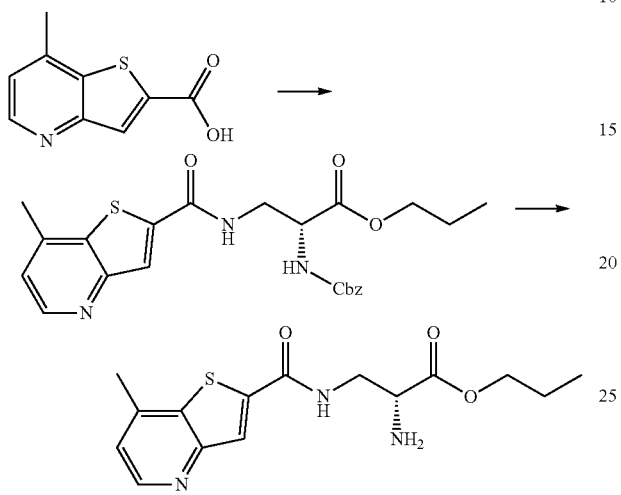

Step 1: Propyl (R)-2-(((benzyloxy)carbonyl)amino)-3-(7-methylthieno[3,2-b]pyridine-2-carboxamido)propanoate

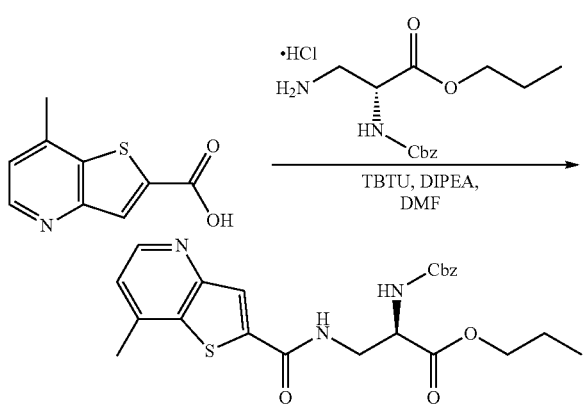

To a mixture of 7-methylthieno[3,2-b]pyridine-2-carboxylic acid (300 mg, crude), TBTU (748 mg, 2.33 mmol) and N,N-diisopropylethylamine (602 mg, 4.66 mmol) in DMF (6 mL) was added (R)-propyl 3-amino-2-(((benzyloxy)carbonyl)amino)propanoate (479 mg, 1.71 mmol, HCl salt). The mixture was stirred at 20° C. for 14 h. The reaction mixture was added water (10 mL), extracted with ethyl acetate (10 mL×3). The combined organic layers were washed with brine (10 mL×3), dried over anhydrous sodium sulfate and concentrated. The residue was purified by Combi Flash on silica gel (petroleum ether/ethyl acetate with ethyl acetate from 0% to 80%) twice to give propyl (R)-2-(((benzyloxy)carbonyl)amino)-3-(7-methylthieno[3,2-b]pyridine-2-carboxamido)propanoate (140 mg).

$^1$H NMR (400 MHz, CDCl$_3$) δ 8.64 (d, J=4.8 Hz, 1H), 7.93 (s, 1H), 7.36-7.27 (m, 6H), 7.15 (d, J=4.8 Hz, 1H), 5.96 (br d, J=5.6 Hz, 1H), 5.14 (s, 2H), 4.64-4.55 (m, 1H), 4.16 (m, 2H), 4.03-3.78 (m, 2H), 2.61 (s, 3H), 1.75-1.68 (m, 2H), 0.95 (t, J=7.2 Hz, 3H).

Step 2: Propyl (R)-2-amino-3-(7-methylthieno[3,2-b]pyridine-2-carboxamido)propanoate

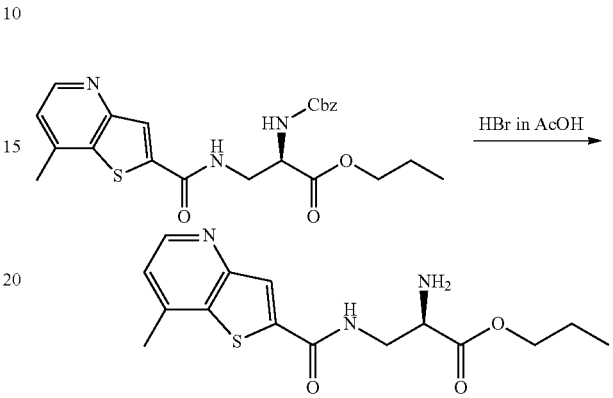

A mixture of propyl (R)-2-(((benzyloxy)carbonyl)amino)-3-(7-methylthieno[3,2-b]pyridine-2-carboxamido)propanoate (140 mg, 0.31 mmol) in 30% HBr in AcOH (6 mL) was stirred at 20° C. for 1 hour. The reaction mixture was concentrated. The residue was added MeCN (2 mL) and washed with methyl tert-butyl ether (10 mL×3). The solid was collected by filtration, added water (10 mL) and lyophilized to give propyl (R)-2-amino-3-(7-methylthieno[3,2-b]pyridine-2-carboxamido)propanoate (98 mg) as HBr salt.

$^1$H NMR (400 MHz, DMSO-d$_6$) δ 9.32 (br t, J=6.0 Hz, 1H), 8.76 (d, J=5.2 Hz, 1H), 8.50 (m, 3H), 8.32 (s, 1H), 7.50 (d, J=4.8 Hz, 1H), 4.30-4.21 (m, 1H), 4.18-4.05 (m, 2H), 2.65 (s, 3H), 1.64-1.54 (m, 2H), 0.85 (t, J=7.2 Hz, 3H).

LCMS (MH+): m/z=322.1, t$_R$ (min, Method BB)=0.36.

[α]$^{20}$D=−0.57 (c=4.6 mg/mL, CH$_3$OH).

Compound 2f

Isopropyl(R)-2-amino-3-(7-methylthieno[3,2-b]pyridine-2-carboxamido)propanoate

The overall synthesis scheme for the preparation of isopropyl (R)-2-amino-3-(7-methylthieno[3,2-b]pyridine-2-carboxamido)propanoate is shown below.

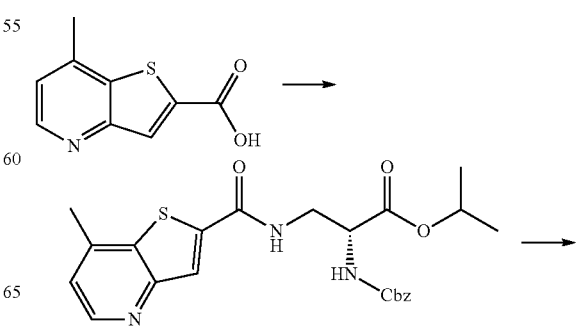

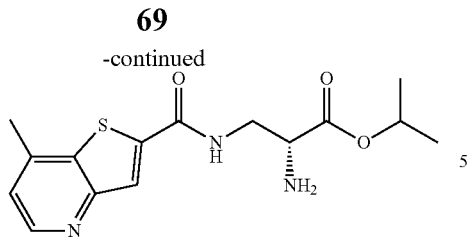
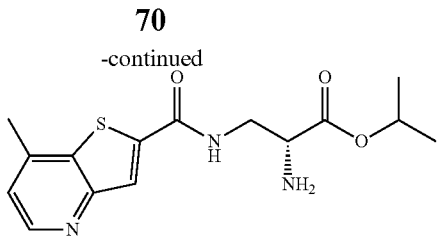

Step 1: Isopropyl (R)-2-(((benzyloxy)carbonyl) amino)-3-(7-methylthieno[3,2-b]pyridine-2-carboxamido)propanoate

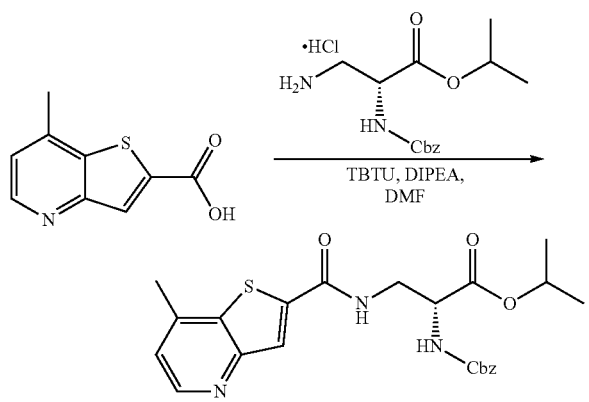

To a solution of 7-methylthieno[3,2-b]pyridine-2-carboxylic acid (2.5 g, crude) in DMF (30 mL) was added TBTU (6.23 g, 19.41 mmol), N,N-diisopropylethylamine (5.02 g, 38.82 mmol) and isopropyl (R)-3-amino-2-(((benzyloxy)carbonyl)amino)propanoate (3.5 g, 11.0 mmol, HCl salt). The mixture was stirred at 20° C. for 16 h. The mixture was diluted with water (50 mL) and extracted with ethyl acetate (40 mL×3). The combined organic layer was washed with water (50 mL×2) and brine (50 mL×2), dried over anhydrous sodium sulfate, filtered and concentrated. The residue was purified by Combi Flash on silica gel (petroleum ether:ethyl acetate with ethyl acetate from 0 to 100%) twice to give isopropyl (R)-2-(((benzyloxy)carbonyl)amino)-3-(7-methylthieno[3,2-b]pyridine-2-carboxamido)propanoate (2.4 g).

$^1$H NMR (400 MHz, CDCl$_3$) δ 8.62 (d, J=4.8 Hz, 1H), 7.93 (s, 1H), 7.48 (br s, 1H), 7.36-7.24 (m, 5H), 7.14 (d, J=4.8 Hz, 1H), 6.03 (br d, J=6.8 Hz, 1H), 5.15-5.05 (m, 3H), 4.61-4.51 (m, 1H), 3.97-3.82 (m, 2H), 2.60 (s, 3H), 1.27 (d, J=6.0 Hz, 6H).

Step 2: Isopropyl(R)-2-amino-3-(7-methylthieno[3,2-b]pyridine-2-carboxamido)propanoate

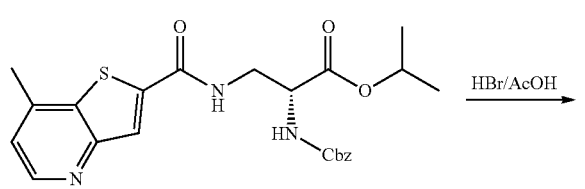

Isopropyl (R)-2-(((benzyloxy)carbonyl)amino)-3-(7-methylthieno[3,2-b]pyridine-2-carboxamido)propanoate (1.6 g, 3.51 mmol) in 30% HBr in AcOH (15 mL) was stirred at 20° C. for 2 h. The mixture was concentrated. The residue was added water (35 mL) and washed with methyl tert-butyl ether (30 mL). The aqueous layer was lyophilized to give compound Isopropyl (R)-2-(((benzyloxy)carbonyl)amino)-3-(7-methylthieno[3,2-b]pyridine-2-carboxamido)propanoate (1.6 g) as HBr salt.

$^1$H NMR (400 MHz, DMSO-d$_6$) δ 9.36 (m, 1H), 8.79 (d, J=5.2 Hz, 1H), 8.55-8.40 (m, 3H), 8.35 (s, 1H), 7.55 (d, J=5.2 Hz, 1H), 5.04-4.93 (m, 1H), 4.24-4.15 (m, 1H), 3.80-3.70 (m, 2H), 2.68 (s, 3H), 1.20 (dd, J=15.6, 6.0 Hz, 6H).

LCMS (MH+): m/z=322.4, t$_R$ (min, Method BB)=0.34. [α]$^{20}$D=1.8, (c=7.0 mg/mL, MeOH).

Compound 2g

Cyclopropyl (R)-2-amino-3-(7-methylthieno[3,2-b]pyridine-2-carboxamido)propanoate The overall synthesis scheme for the preparation of cyclopropyl (R)-2-amino-3-(7-methylthieno[3,2-b]pyridine-2-carboxamido)propanoate is shown below.

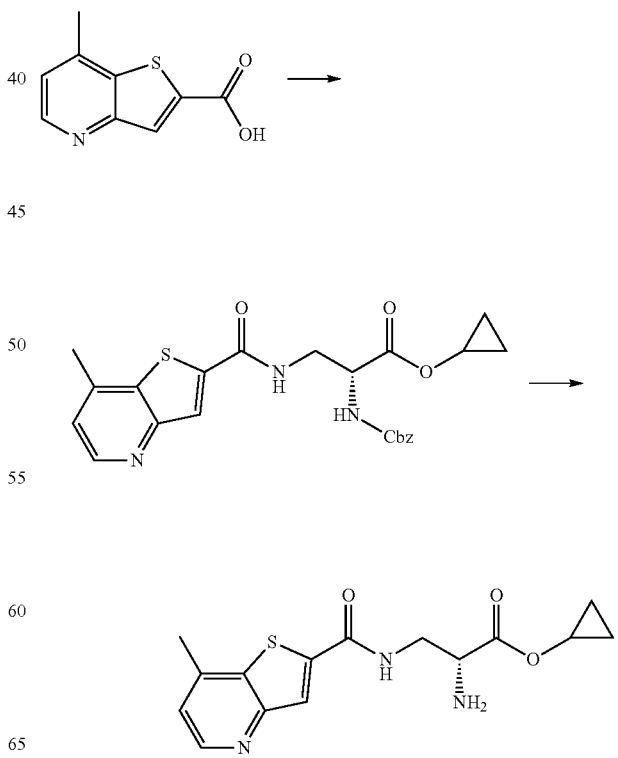

Step 1: Cyclopropyl(R)-2-(((benzyloxy)carbonyl)amino)-3-(7-methylthieno[3,2-b]pyridine-2-carboxamido)propanoate

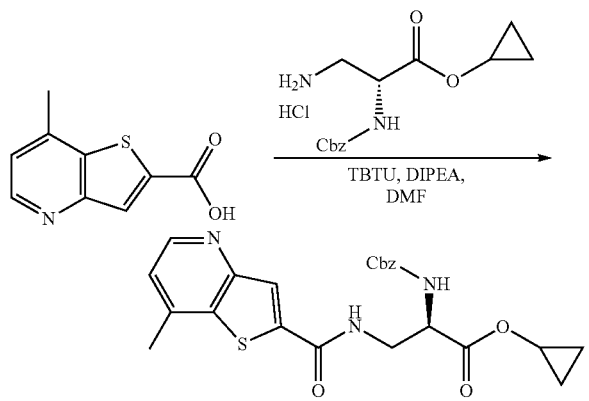

To a solution of 7-methylthieno[3,2-b]pyridine-2-carboxylic acid (200 mg, crude) in DMF (3 mL) was added cyclopropyl (R)-3-amino-2-(((benzyloxy)carbonyl)amino)propanoate (326 mg, 1.04 mmol, HCl salt), TBTU (499 mg, 1.55 mmol) and N,N-diisopropylethylamine (401 mg, 3.11 mmol). The reaction mixture was stirred at 10° C. for 3 h. The reaction mixture was added water (10 mL), extracted with ethyl acetate (10 mL×3). The combined organic layers were washed with brine (10 mL×3), dried over anhydrous sodium sulfate and concentrated. The residue was purified by column chromatography on silica gel (petroleum ether/ethyl acetate with ethyl acetate from 70% to 80%) to give cyclopropyl (R)-2-(((benzyloxy)carbonyl)amino)-3-(7-methylthieno[3,2-b]pyridine-2-carboxamido)propanoate (150 mg).

$^1$H NMR (400 MHz, DMSO-$d_6$) δ 8.97 (br t, J=5.6 Hz, 1H), 8.60 (d, J=4.8 Hz, 1H), 8.16 (s, 1H), 7.79 (d, J=8.0 Hz, 1H), 7.33-7.21 (m, 6H), 5.07-4.97 (m, 2H), 4.35-4.24 (m, 1H), 4.02-3.99 (m, 1H), 3.66-3.53 (m, 2H), 2.54 (s, 3H), 0.65-0.46 (m, 4H).

Step 2: Cyclopropyl (R)-2-amino-3-(7-methylthieno[3,2-b]pyridine-2-carboxamido)propanoate

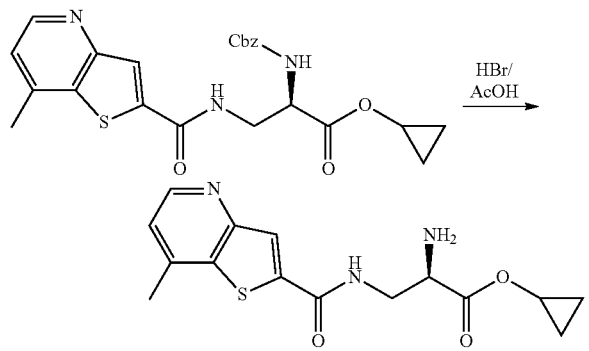

A solution of cyclopropyl (R)-2-(((benzyloxy)carbonyl)amino)-3-(7-methylthieno[3,2-b]pyridine-2-carboxamido)propanoate (120 mg, 0.26 mmol) in AcOH (5 mL) were added 30% HBr in AcOH (0.5 mL). The reaction mixture was stirred at 10° C. for 2 h. The mixture was added methyl tert-butyl ether (6 mL) and stirred for 5 minutes and then allowed to stand for 5 minutes and then the organic solvent was discarded. The residue was concentrated. The residue was then washed with methyl tert-butyl ether (5 mL×2) to give cyclopropyl (R)-2-amino-3-(7-methylthieno[3,2-b]pyridine-2-carboxamido)propanoate (100 mg) as HBr salt.

$^1$H NMR (400 MHz, DMSO-$d_6$) δ 9.36 (br t, J=5.6 Hz, 1H), 8.80 (d, J=5.2 Hz, 1H), 8.52 (br s, 3H), 8.34 (s, 1H), 7.55 (d, J=4.8 Hz, 1H), 4.28-4.21 (m, 1H), 4.20-4.14 (m, 1H), 3.80-3.75 (m, 2H), 2.68 (s, 3H), 0.75-0.61 (m, 4H).

LCMS (MH+): m/z=319.8, $t_R$ (min, Method BB)=0.32. [α]$^{20}$D=2 (c=1 mg/mL, MeOH).

Compound 2h

Butyl (R)-2-amino-3-(7-methylthieno[3,2-b]pyridine-2-carboxamido)propanoate

The overall synthesis scheme for the preparation of cyclopropyl (R)-2-amino-3-(7-methylthieno[3,2-b]pyridine-2-carboxamido)propanoate is shown below.

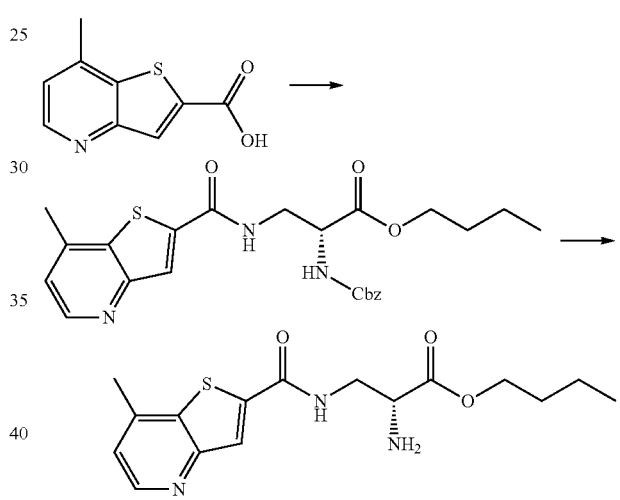

Step 1: Butyl (R)-2-(((benzyloxy)carbonyl)amino)-3-(7-methylthieno[3,2-b]pyridine-2-carboxamido)propanoate

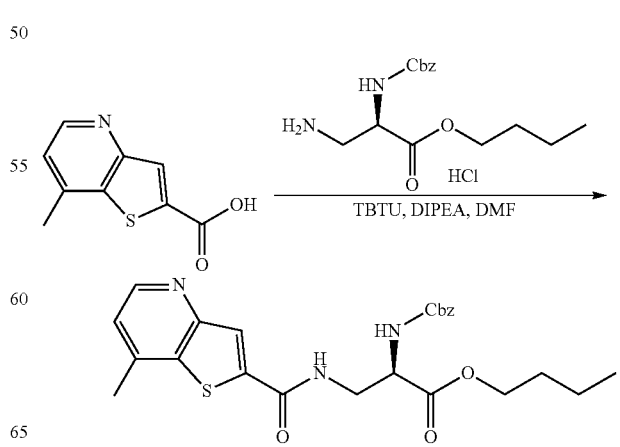

To a solution of butyl (R)-3-amino-2-(((benzyloxy)carbonyl)amino)propanoate (428 mg, 1.29 mmol, HCl salt), N,N-diisopropylethylamine (502 mg, 3.88 mmol) and 7-methylthieno[3,2-b]pyridine-2-carboxylic acid (250 mg, crude) in DMF (50 mL) was added TBTU (623 mg, 1.94 mmol) under N₂. The mixture was stirred at 20° C. for 16 h. The reaction was added water (100 ml) and extracted with ethyl acetate (30 mL×3). The organic layers were concentrated. The residue was purified by Combi Flash (silica gel, Petroleum ether: Ethyl acetate, Ethyl acetate from 0% to 70%) to give butyl (R)-2-(((benzyloxy)carbonyl)amino)-3-(7-methylthieno[3,2-b]pyridine-2-carboxamido)propanoate (120 mg).

¹H NMR (400 MHz, CDCl₃) δ 8.63 (d, J=4.8 Hz, 1H), 7.92 (s, 1H), 7.41-7.27 (m, 6H), 7.15 (d, J=4.8 Hz, 1H), 5.96 (br d, J=6.8 Hz, 1H), 5.13 (s, 2H), 4.65-4.51 (m, 1H), 4.26-4.13 (m, 2H), 4.04-3.89 (m, 1H), 3.88-3.77 (m, 1H), 2.60 (s, 3H), 1.66-1.55 (m, 2H), 1.42-1.32 (m, 2H), 0.92 (t, J=7.2 Hz, 3H).

Step 2: Butyl (R)-2-amino-3-(7-methylthieno[3,2-b]pyridine-2-carboxamido)propanoate

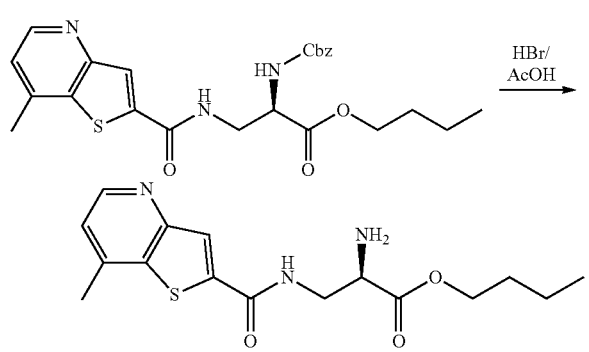

A solution of butyl (R)-2-(((benzyloxy)carbonyl)amino)-3-(7-methylthieno[3,2-b]pyridine-2-carboxamido)propanoate (120 mg, 0.26 mmol) in 30% HBr in AcOH (10 mL) was stirred at 20° C. for 2 h. The reaction was concentrated. The residue was added MeCN (1 mL) and methyl tert-butyl ether (20 mL) and stirred at 20° C. for 1 hour, filtered and dried to give butyl (R)-2-amino-3-(7-methylthieno[3,2-b]pyridine-2-carboxamido)propanoate (95 mg) as HBr salt.

¹H NMR (400 MHz, DMSO-d₆) δ 9.43 (br t, J=5.6 Hz, 1H), 8.84 (d, J=5.6 Hz, 1H), 8.53 (br s, 3H), 8.39 (s, 1H), 7.61 (d, J=5.2 Hz, 1H), 4.26-4.24 (m, 1H), 4.20-4.08 (m, 2H), 3.84-3.76 (m, 2H), 2.71 (s, 3H), 1.59-1.47 (m, 2H), 1.35-1.22 (m, 2H), 0.78 (t, J=7.2 Hz, 3H).

LCMS (MH+): m/z=336.1, t_R (min, Method BB)=0.41.

[α]²⁰D=3 (c=2 mg/mL, MeOH).

Compound 2i

Isobutyl (R)-2-amino-3-(7-methylthieno[3,2-b]pyridine-2-carboxamido)propanoate

The overall synthesis scheme for the preparation of isobutyl (R)-2-amino-3-(7-methylthieno[3,2-b]pyridine-2-carboxamido)propanoate is shown below.

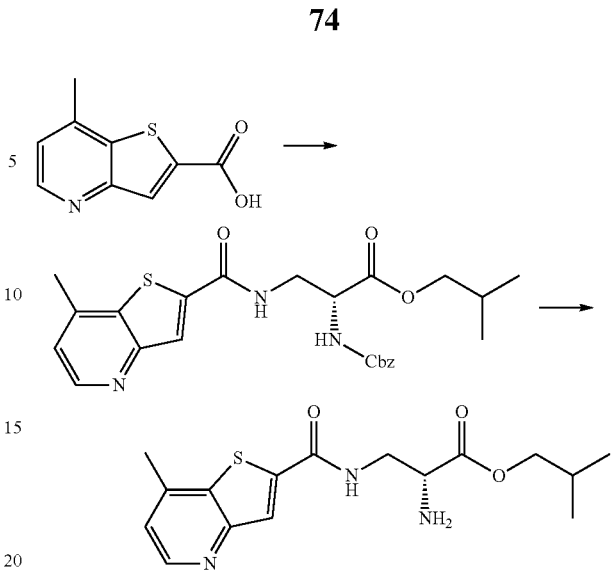

Step 1: Isobutyl (R)-2-(((benzyloxy)carbonyl)amino)-3-(7-methylthieno[3,2-b]pyridine-2-carboxamido)propanoate

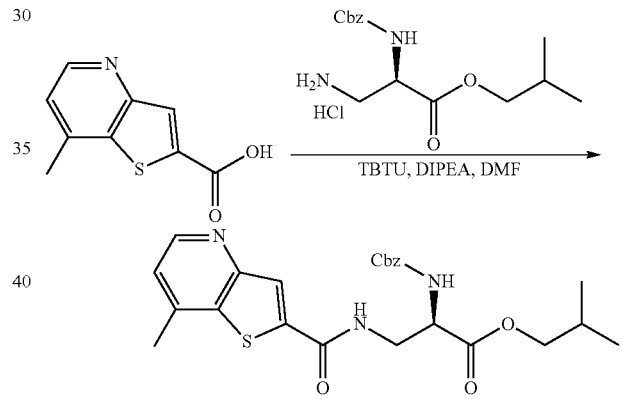

To a solution of 7-methylthieno[3,2-b]pyridine-2-carboxylic acid (200 mg, crude) in DMF (3 mL) were added isobutyl (R)-3-amino-2-(((benzyloxy)carbonyl)amino)propanoate (377 mg, 1.14 mmol, HCl salt), TBTU (499 mg, 1.55 mmol) and N,N-diisopropylethylamine (401 mg, 3.11 mmol). The reaction mixture was stirred at 15° C. for 2 h. The reaction mixture was added water (10 mL), and was extracted with ethyl acetate (10 mL×3). The combined organic layers were washed with brine (10 mL×3), dried over anhydrous sodium sulfate and concentrated. The residue was purified by column chromatography on silica gel (petroleum ether/ethyl acetate with ethyl acetate from 50% to 60%) to give isobutyl (R)-2-(((benzyloxy)carbonyl)amino)-3-(7-methylthieno[3,2-b]pyridine-2-carboxamido)propanoate (130 mg).

¹H NMR (400 MHz, CDCl₃) δ 8.64 (d, J=4.8 Hz, 1H), 7.92 (s, 1H), 7.39-7.27 (m, 6H), 7.15 (d, J=4.0 Hz, 1H), 5.95 (d, J=6.4 Hz, 1H), 5.13 (s, 2H), 4.65-4.55 (m, 1H), 4.06-3.92 (m, 3H), 3.87-3.80 (m, 1H), 2.60 (s, 3H), 2.00-1.90 (m, 1H), 0.94 (d, J=6.8 Hz, 6H).

Step 2: Isobutyl (R)-2-amino-3-(7-methylthieno[3,2-b]pyridine-2-carboxamido)propanoate

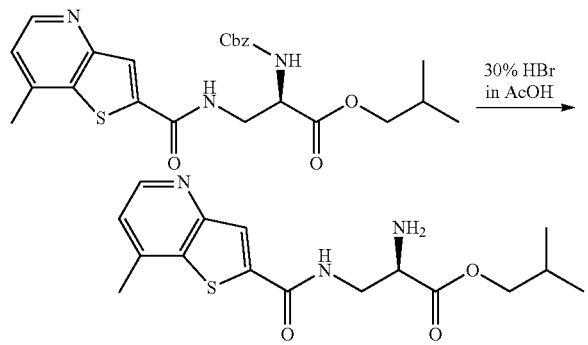

A solution of isobutyl (R)-2-(((benzyloxy)carbonyl)amino)-3-(7-methylthieno[3,2-b]pyridine-2-carboxamido)propanoate (120 mg, 0.26 mmol) in 30% HBr in AcOH (3 mL) was stirred at 10° C. for 1 hour. The solvent was removed. The residue was washed with a mixture of MeCN (1 mL) and methyl tert-butyl ether (5 mL). The organic layer was decanted, then the residue was lyophilized to give isobutyl (R)-2-amino-3-(7-methylthieno[3,2-b]pyridine-2-carboxamido)propanoate (110 mg) as HBr salt.

$^1$H NMR (400 MHz, DMSO-$d_6$) δ 9.32 (br s, 1H), 8.78 (br s, 1H), 8.51 (br s, 3H), 8.35 (br s, 1H), 7.53 (br s, 1H), 4.35-4.25 (m, 1H), 4.03-3.89 (m, 2H), 3.81 (t, J=5.6 Hz, 2H), 2.67 (s, 3H), 1.97-1.82 (m, 1H), 0.88 (dd, J=2.0, 6.8 Hz, 6H).

LCMS (MH+): m/z=336.1, $t_R$ (min, Method BB)=0.41. [α]$^{20}$D=2 (c=1 mg/mL, MeOH).

Compound 2J

Cyclopropylmethyl (R)-2-amino-3-(7-methylthieno[3,2-b]pyridine-2-carboxamido)propanoate

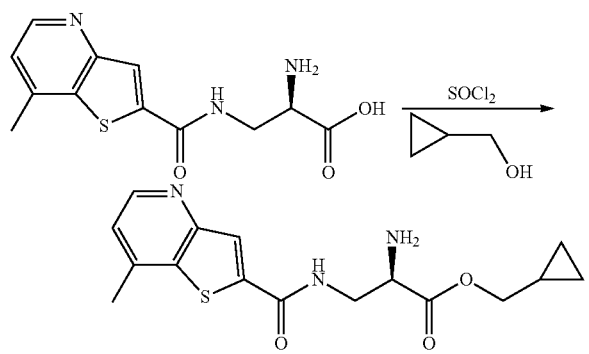

To a solution of (R)-2-amino-3-(7-methylthieno[3,2-b]pyridine-2-carboxamido)propanoic acid (150 mg, 0.42 mmol, HBr salt) in cyclopropylmethanol (5 mL) was added thionyl chloride (99 mg, 0.83 mmol). The mixture was stirred at 40° C. for 16 h. The reaction mixture was concentrated. The residue was washed with methyl tert-butyl ether (10 mL×3). The solid was collected by filtration and dried. The product was purified by preparative HPLC (Method E) and lyophilized to give cyclopropylmethyl (R)-2-amino-3-(7-methylthieno[3,2-b]pyridine-2-carboxamido)propanoate (49 mg) as HCl salt.

$^1$H NMR (400 MHz, MeOD) δ 8.91 (d, J=5.6 Hz, 1H), 8.46 (s, 1H), 7.87 (d, J=5.6 Hz, 1H), 4.39 (t, J=5.6 Hz, 1H), 4.20-3.95 (m, 4H), 2.93 (s, 3H), 1.34-1.09 (m, 1H), 0.63-0.54 (m, 2H), 0.40-0.31 (m, 2H).

LCMS (MH+): m/z=333.8, $t_R$ (min, Method BB)=0.37. [α]$^{20}$D=4.1 (c=7.8 mg/mL, CH$_3$OH).

Compound 2k 2-methoxyethyl (R)-2-amino-3-(7-methylthieno[3,2-b]pyridine-2-carboxamido)propanoate The overall synthesis scheme for the preparation of 2-methoxyethyl (R)-2-amino-3-(7-methylthieno[3,2-b]pyridine-2-carboxamido)propanoate is shown below.

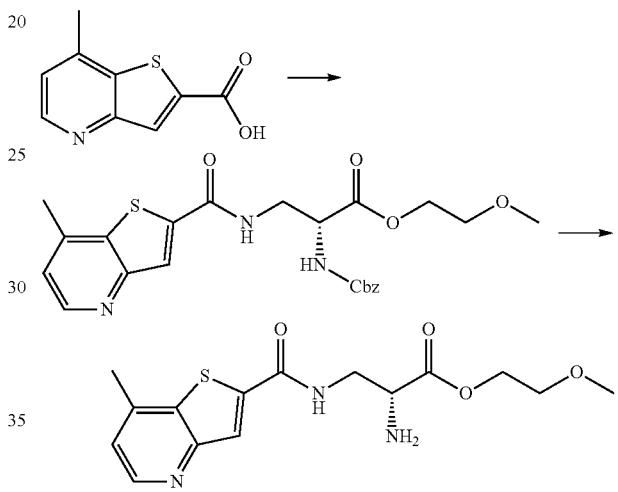

Step 1: 2-methoxyethyl (R)-2-(((benzyloxy)carbonyl)amino)-3-(7-methylthieno[3,2-b]pyridine-2-carboxamido)propanoate

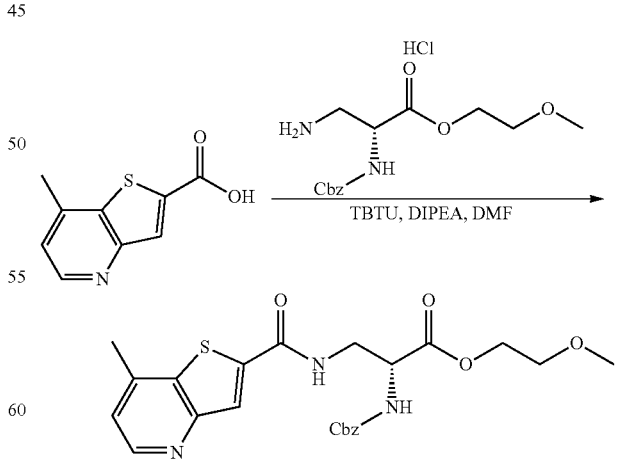

To a solution of 7-methylthieno[3,2-b]pyridine-2-carboxylic acid (800 mg, 4.14 mmol) and 2-methoxyethyl (R)-3-amino-2-(((benzyloxy)carbonyl)amino)propanoate (2.07 g, 6.21 mmol, HCl salt) in DMF (20 mL) was added TBTU (1.60 g, 4.97 mmol) and N,N-diisopropylethylamine (1.61 g, 12.42 mmol). The mixture was stirred at 20° C. for 16 h. The reaction mixture was quenched with water (10 mL), and extracted with ethyl acetate (20 mL×3). The combined organic layers were washed with brine (10 mL×3), dried over anhydrous sodium sulfate and concentrated. The residue was purified by Combi Flash on silica gel (ethyl acetate/Petroleum ether with ethyl acetate from 0% to 100%) to give 2-methoxyethyl (R)-2-(((benzyloxy)carbonyl)amino)-3-(7-methylthieno[3,2-b]pyridine-2-carboxamido)propanoate (800 mg).

$^1$H NMR (400 MHz, DMSO-d$_6$) δ 9.01 (t, J=5.6 Hz, 1H), 8.63 (d, J=4.8 Hz, 1H), 8.20 (s, 1H), 7.83 (d, J=8.0 Hz, 1H), 7.37-7.24 (m, 6H), 5.09-4.99 (m, 2H), 4.42-4.34 (m, 1H), 4.20-4.12 (m, 2H), 3.74-3.57 (m, 2H), 3.50-3.42 (m, 2H), 3.17 (s, 3H), 2.57 (s, 3H).

Step 2: 2-methoxyethyl (R)-2-amino-3-(7-methylthieno[3,2-b]pyridine-2-carboxamido)propanoate

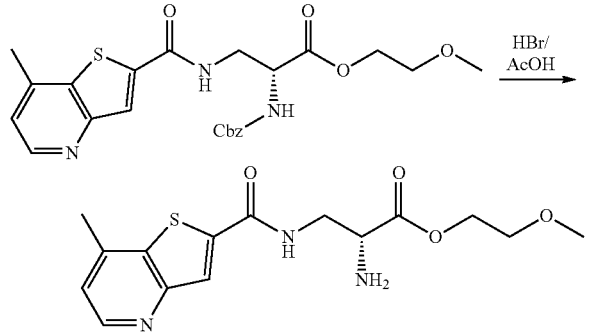

To a solution of 2-methoxyethyl (R)-2-(((benzyloxy)carbonyl)amino)-3-(7-methylthieno[3,2-b]pyridine-2-carboxamido)propanoate (400 mg, 0.85 mmol) in AcOH (10 mL) was added 30% HBr in AcOH (1 mL), the mixture was stirred at 20° C. for 16 h. The mixture was concentrated. The residue was purified by preparative HPLC (Method E) to give 2-methoxyethyl (R)-2-amino-3-(7-methylthieno[3,2-b]pyridine-2-carboxamido)propanoate (170 mg) as HCl salt.

$^1$H NMR (400 MHz, DMSO-d$_6$) δ 9.72 (t, J=5.6 Hz, 1H), 8.88-8.74 (m, 4H), 8.54 (s, 1H), 7.60 (d, J=5.2 Hz, 1H), 4.33-4.18 (m, 3H), 3.54-3.48 (m, 2H), 3.17 (s, 3H), 2.70 (s, 3H).

LCMS (MH+): m/z=338.1, t$_R$ (min, Method BB)=0.3. [α]$^{20}$D=−14 (c=3 mg/mL, DMSO).

Compound 21

Isopentyl(R)-2-amino-3-(7-methylthieno[3,2-b]pyridine-2-carboxamido)propanoate

The overall synthesis scheme for the preparation of isopentyl (R)-2-amino-3-(7-methylthieno[3,2-b]pyridine-2-carboxamido)propanoate is shown below.

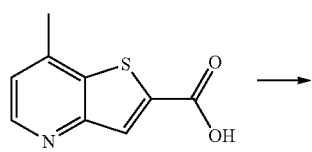

Step 1: Isopentyl (R)-2-(((benzyloxy)carbonyl)amino)-3-(7-methylthieno[3,2-b]pyridine-2-carboxamido)propanoate

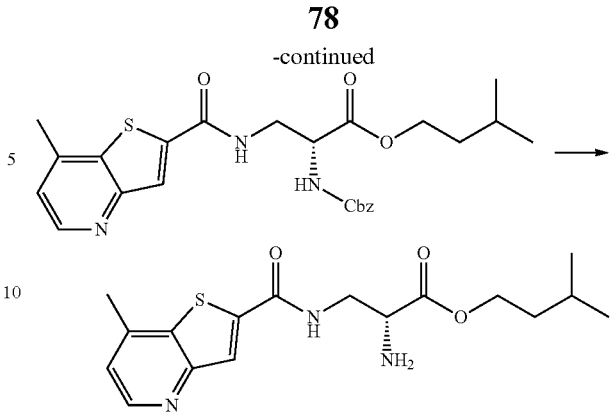

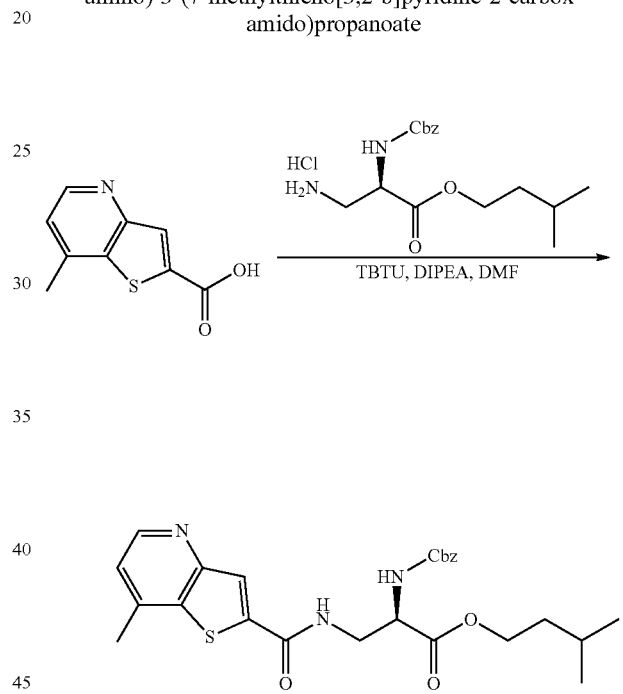

To a mixture of 7-methylthieno[3,2-b]pyridine-2-carboxylic acid (200 mg, crude) and isopentyl (R)-3-amino-2-(((benzyloxy)carbonyl)amino)propanoate (393 mg, 1.14 mmol, HCl salt) in DMF (5 mL) was added TBTU (499 mg, 1.55 mmol) and N,N-diisopropylethylamine (401 mg, 3.11 mmol), the mixture was stirred at 20° C. for 1 hour. The mixture was added water (10 mL) and extracted with ethyl acetate (20 mL×3), the organic layers were washed with brine (20 mL×3), dried over anhydrous sodium sulfate, filtered and concentrated. The residue was purified by Combi Flash on silica gel chromatography (Petroleum ether: Ethyl acetate, Ethyl acetate from 0% to 70%) twice to give isopentyl (R)-2-(((benzyloxy)carbonyl)amino)-3-(7-methylthieno[3,2-b]pyridine-2-carboxamido)propanoate (250 mg).

$^1$H NMR (400 MHz, CDCl$_3$) δ 8.65 (d, J=4.8 Hz, 1H), 7.92 (s, 1H), 7.38-7.28 (m, 6H), 7.16 (d, J=4.4 Hz, 1H), 5.92 (br d, J=6.4 Hz, 1H), 5.14 (s, 2H), 4.64-4.55 (m, 1H), 4.29-4.19 (m, 2H), 4.01-3.79 (m, 2H), 2.61 (s, 3H), 1.73-1.65 (m, 1H), 1.59-1.52 (m, 2H), 0.92 (d, J=6.4 Hz, 6H).

Step 2: Isopentyl(R)-2-amino-3-(7-methylthieno[3,2-b]pyridine-2-carboxamido)propanoate Step 1: Benzyl (R)-2-(((benzyloxy)carbonyl)amino)-3-(7-methylthieno[3,2-b]pyridine-2-carboxamido)propanoate

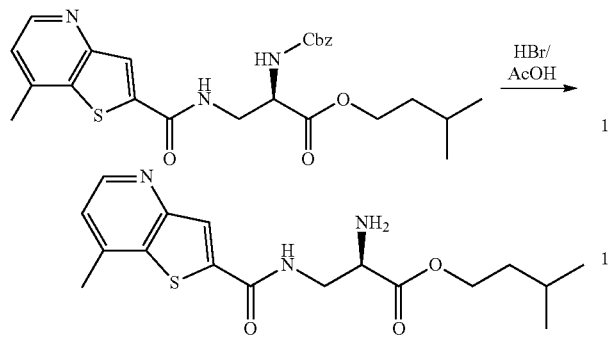

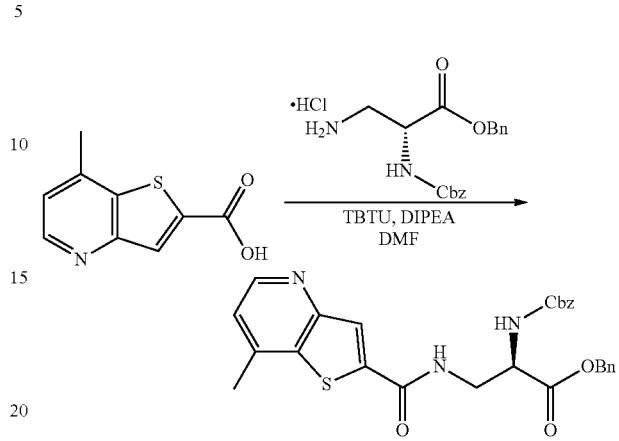

A solution of isopentyl (R)-2-(((benzyloxy)carbonyl)amino)-3-(7-methylthieno[3,2-b]pyridine-2-carboxamido)propanoate (200 mg, 0.41 mmol) in 30% HBr in AcOH (6 mL) was stirred at 20° C. for 1 hour. The sample was added water (15 mL) and lyophilized. The obtained solid was further purified by preparative-HPLC (Method F) to give isopentyl (R)-2-amino-3-(7-methylthieno[3,2-b]pyridine-2-carboxamido)propanoate (105 mg) as HCl salt.

$^1$H NMR (400 MHz, DMSO-d$_6$) δ 9.66 (br t, J=5.6 Hz, 1H), 8.82-8.75 (m, 4H), 8.52 (s, 1H), 7.54 (d, J=4.8 Hz, 1H), 4.15-4.12 (t, 2H), 3.92-3.73 (m, 2H), 2.67 (s, 3H), 1.65-1.54 (m, 1H), 1.45-1.38 (m, 2H), 0.77 (t, J=6.8 Hz, 6H).

LCMS (MH+): m/z=349.8, t$_R$ (min, Method BB)=0.45.

[α]$^{20}$D=+2.5 (c=4.0 mg/mL, CH$_3$OH).

Compound 2m

Benzyl(R)-2-amino-3-(7-methylthieno[3,2-b]pyridine-2-carboxamido)propanoate

The overall synthesis scheme for the preparation of benzyl (R)-2-amino-3-(7-methylthieno[3,2-b]pyridine-2-carboxamido)propanoate is shown below.

To a solution of 7-methylthieno[3,2-b]pyridine-2-carboxylic acid (300 mg, crude) in DMF (10 mL) was added TBTU (748 mg, 2.33 mmol), N,N-diisopropylethylamine (602 mg, 4.66 mmol) and benzyl (R)-3-amino-2-(((benzyloxy)carbonyl)amino)propanoate (566 mg, 1.55 mmol, HCl salt). The mixture was stirred at 20° C. for 15 h. The mixture was diluted with water (30 mL) and extracted with ethyl acetate (25 mL×3). The combined organic layers were washed with brine (30 mL) and concentrated. The residue was purified by Combi Flash on silica gel (petroleum ether:ethyl acetate with ethyl acetate from 0 to 100%) to give 390 mg crude product. The crude product was triturated with DCM (15 mL) and the solid was collected and dried to give benzyl (R)-2-(((benzyloxy)carbonyl)amino)-3-(7-methylthieno[3,2-b]pyridine-2-carboxamido)propanoate (230 mg).

$^1$H NMR (400 MHz, DMSO-d$_6$) δ 9.04 (br t, J=5.6 Hz, 1H), 8.64 (d, J=4.8 Hz, 1H), 8.19 (s, 1H), 7.89 (br d, J=8.4 Hz, 1H), 7.37-7.22 (m, 11H), 5.17-5.00 (m, 4H), 4.48-4.39 (m, 1H), 3.76-3.62 (m, 2H), 2.57 (s, 3H).

Step 2: Benzyl (R)-2-amino-3-(7-methylthieno[3,2-b]pyridine-2-carboxamido)propanoate

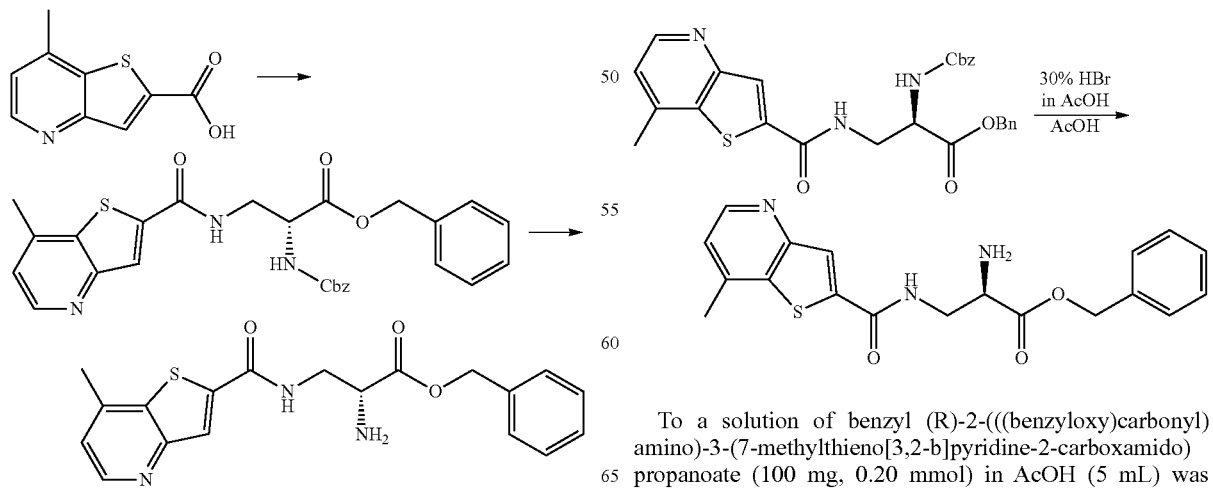

To a solution of benzyl (R)-2-(((benzyloxy)carbonyl)amino)-3-(7-methylthieno[3,2-b]pyridine-2-carboxamido)propanoate (100 mg, 0.20 mmol) in AcOH (5 mL) was added 30% HBr in AcOH (0.5 mL). The mixture was stirred at 20° C. for 1 hour 40 min. The mixture was diluted with methyl tert-butyl ether (6 mL) and a precipitate was formed. The organic layer was discarded and the precipitate was collected. The residue was washed with MeCN (5 mL) and dried to give benzyl (R)-2-amino-3-(7-methylthieno[3,2-b]pyridine-2-carboxamido)propanoate (82 mg) as HBr salt.

$^1$H NMR (400 MHz, CD$_3$OD) δ 8.92 (d, J=6.0 Hz, 1H), 8.33 (s, 1H), 7.88 (d, J=5.6 Hz, 1H), 7.44-7.37 (m, 2H), 7.29-7.15 (m, 3H), 5.38-5.32 (m, 1H), 5.30-5.24 (m, 1H), 4.44 (t, J=5.6 Hz, 1H), 4.09-4.01 (m, 1H), 3.99-3.90 (m, 1H), 2.93 (s, 3H).

LCMS (MH+): m/z=370, $t_R$ (min, Method BB)=0.42.
[α]$^{20}$D=8.6 (c=3.2 mg/mL, CH3OH).

Compound 2n

Cyclohexyl (R)-2-amino-3-(7-methylthieno[3,2-b]pyridine-2-carboxamido)propanoate The overall synthesis scheme for the preparation of cyclohexyl (R)-2-amino-3-(7-methylthieno[3,2-b]pyridine-2-carboxamido)propanoate is shown below.

A mixture of 7-methylthieno[3,2-b]pyridine-2-carboxylic acid (300 mg, 1.55 mmol), cyclohexyl (R)-3-amino-2-(((benzyloxy)carbonyl)amino)propanoate (590 mg, 1.65 mmol, HCl salt), TBTU (747.77 mg, 2.33 mmol) and N,N-diisopropylethylamine (602 mg, 4.66 mmol) in DMF (10 mL) was stirred at 20° C. for 16 h. The mixture was diluted with water (10 mL) and extracted with ethyl acetate (10 mL×2). The organic phase was washed with brine (10 mL×2), dried over anhydrous sodium sulfate and concentrated. The residue was purified by Combi Flash (silica gel, from 0 to 60%, Ethyl acetate in petroleum ether) to give 350 mg of the crude product. The compound was purified by SFC separation (Method SFC1) to give cyclohexyl (R)-2-(((benzyloxy)carbonyl)amino)-3-(7-methylthieno[3,2-b]pyridine-2-carboxamido)propanoate (270 mg).

$^1$H NMR (400 MHz, CDCl$_3$) δ 8.63 (d, J=4.8 Hz, 1H), 7.94 (s, 1H), 7.51-7.41 (m, 1H), 7.37-7.27 (m, 5H), 7.14 (d, J=4.4 Hz, 1H), 6.03 (d, J=6.8 Hz, 1H), 5.12 (s, 2H), 4.90-4.81 (m, 1H), 4.62-4.50 (m, 1H), 4.00-3.77 (m, 2H), 2.60 (s, 3H), 1.91-1.64 (m, 4H), 1.57-1.28 (m, 6H).

Step 2: cyclohexyl (R)-2-amino-3-(7-methylthieno[3,2-b]pyridine-2-carboxamido)propanoate

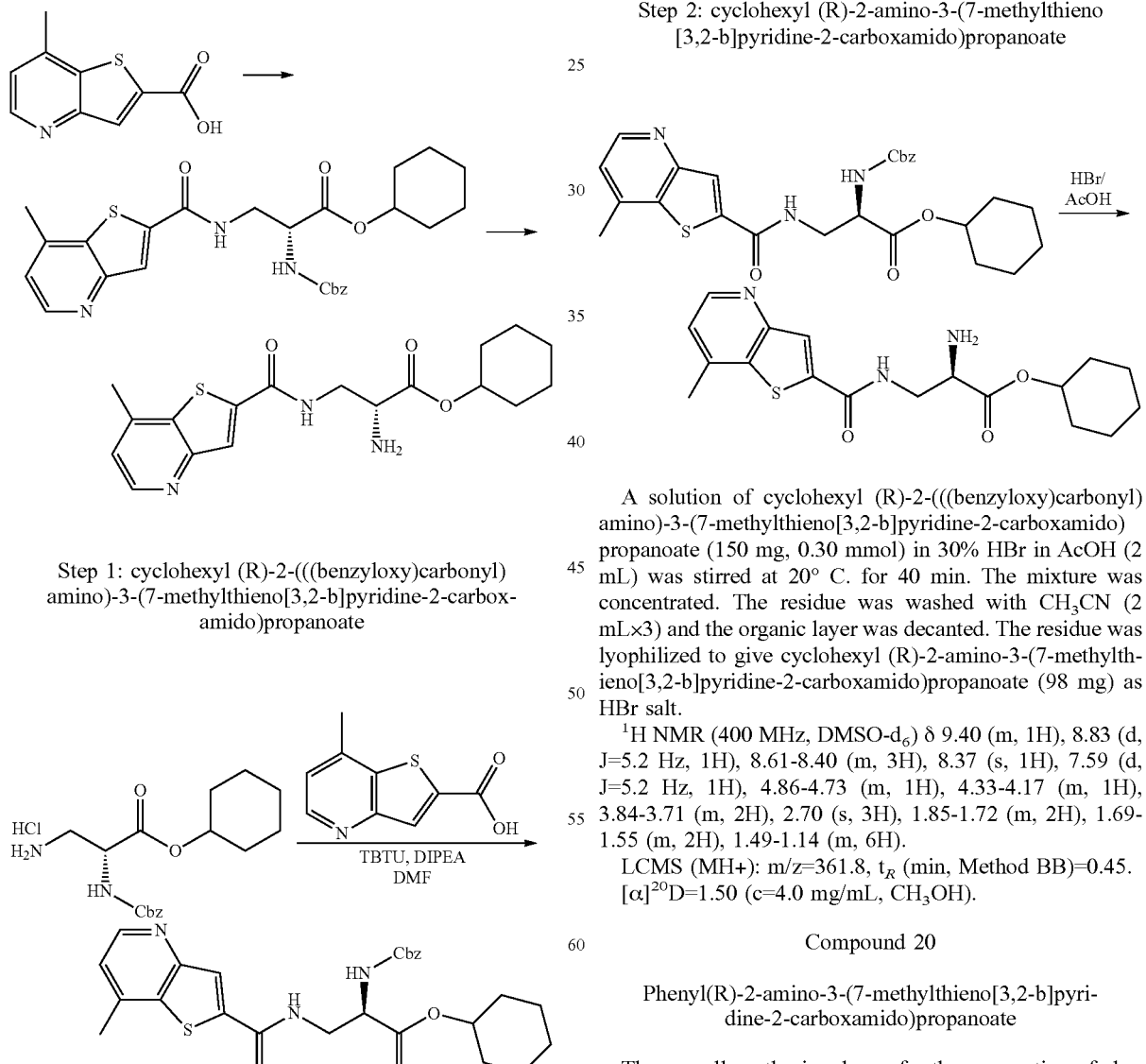

Step 1: cyclohexyl (R)-2-(((benzyloxy)carbonyl)amino)-3-(7-methylthieno[3,2-b]pyridine-2-carboxamido)propanoate A solution of cyclohexyl (R)-2-(((benzyloxy)carbonyl)amino)-3-(7-methylthieno[3,2-b]pyridine-2-carboxamido)propanoate (150 mg, 0.30 mmol) in 30% HBr in AcOH (2 mL) was stirred at 20° C. for 40 min. The mixture was concentrated. The residue was washed with CH$_3$CN (2 mL×3) and the organic layer was decanted. The residue was lyophilized to give cyclohexyl (R)-2-amino-3-(7-methylthieno[3,2-b]pyridine-2-carboxamido)propanoate (98 mg) as HBr salt.

$^1$H NMR (400 MHz, DMSO-d$_6$) δ 9.40 (m, 1H), 8.83 (d, J=5.2 Hz, 1H), 8.61-8.40 (m, 3H), 8.37 (s, 1H), 7.59 (d, J=5.2 Hz, 1H), 4.86-4.73 (m, 1H), 4.33-4.17 (m, 1H), 3.84-3.71 (m, 2H), 2.70 (s, 3H), 1.85-1.72 (m, 2H), 1.69-1.55 (m, 2H), 1.49-1.14 (m, 6H).

LCMS (MH+): m/z=361.8, $t_R$ (min, Method BB)=0.45.
[α]$^{20}$D=1.50 (c=4.0 mg/mL, CH$_3$OH).

Compound 2o

Phenyl(R)-2-amino-3-(7-methylthieno[3,2-b]pyridine-2-carboxamido)propanoate

The overall synthesis scheme for the preparation of phenyl (R)-2-amino-3-(7-methylthieno[3,2-b]pyridine-2-carboxamido)propanoate is shown below.

83

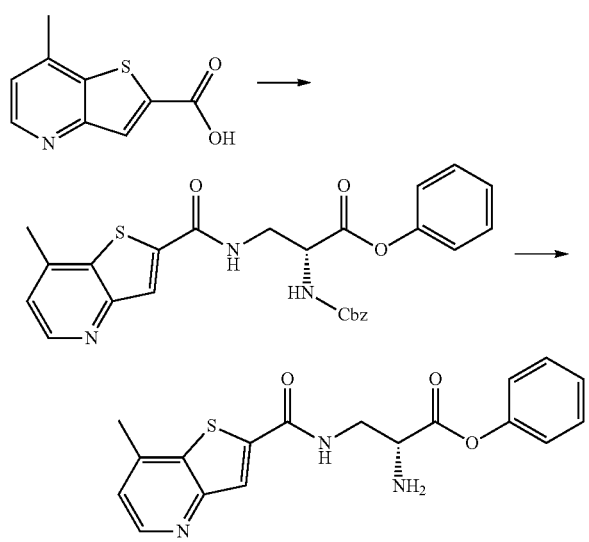

Step 1: Phenyl (R)-2-(((benzyloxy)carbonyl)amino)-
3-(7-methylthieno[3,2-b]pyridine-2-carboxamido)
propanoate

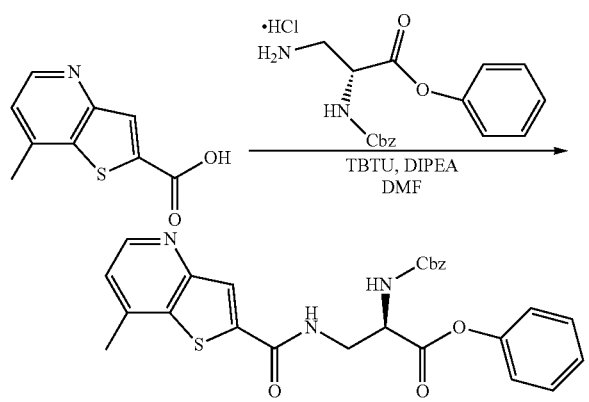

To a solution of 7-methylthieno[3,2-b]pyridine-2-carboxylic acid (150 mg, crude) in DMF (5 mL) was added TBTU (374 mg, 1.16 mmol), N,N-diisopropylethylamine (301 mg, 2.33 mmol) and phenyl (R)-3-amino-2-(((benzyloxy)carbonyl)amino)propanoate (272 mg, crude, HCl). The mixture was stirred at 15° C. for 16 h. The mixture was diluted with water (15 mL) and extracted with ethyl acetate (20 mL×3). The combined organic layers were washed with brine (20 mL×3) and concentrated. The residue was purified by Combi Flash on silica gel (petroleum ether: ethyl acetate with ethyl acetate from 0 to 100%) to give 240 mg of the product. The product was further triturated with DCM (3 mL). The solid was collected by filtration to give compound phenyl (R)-2-(((benzyloxy)carbonyl)amino)-3-(7-methylthieno[3,2-b]pyridine-2-carboxamido)propanoate (100 mg).

$^1$H NMR (400 MHz, DMSO-$d_6$) δ 9.16 (br t, J=5.6 Hz, 1H), 8.63 (d, J=4.8 Hz, 1H), 8.24 (s, 1H), 8.06 (d, J=7.6 Hz, 1H), 7.44-7.26 (m, 9H), 7.09 (d, J=7.6 Hz, 2H), 5.16-5.05 (m, 2H), 4.65-4.54 (m, 1H), 3.88-3.78 (m, 2H), 2.57 (s, 3H).

84

Step 2: Phenyl (R)-2-amino-3-(7-methylthieno[3,2-b]pyridine-2-carboxamido)propanoate

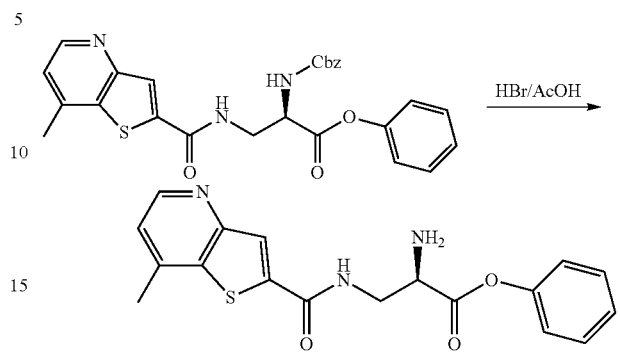

A mixture of phenyl(R)-2-(((benzyloxy)carbonyl)amino)-3-(7-methylthieno[3,2-b]pyridine-2-carboxamido)propanoate (90 mg, 0.18 mmol) and 30% HBr in AcOH (3 mL) was stirred at 15° C. for 1 hour. The mixture was concentrated. The residue was triturated with MeCN (2 mL) and methyl tert-butyl ether (5 mL). The solid was collected and dried to give phenyl (R)-2-amino-3-(7-methylthieno[3,2-b]pyridine-2-carboxamido)propanoate (65 mg) as HBr salt.

$^1$H NMR (400 MHz, CD$_3$OD) δ 8.91 (d, J=5.6 Hz, 1H), 8.45 (s, 1H), 7.88 (d, J=5.6 Hz, 1H), 7.48-7.42 (m, 2H), 7.35-7.27 (m, 3H), 4.68 (t, J=5.2 Hz, 1H), 4.21-4.15 (m, 2H), 2.94 (s, 3H).

LCMS (MH+): m/z=355.8, $t_R$ (min, Method BB)=0.41.
[α]$^{20}$D=−9.3 (c=2.5 mg/mL, CH$_3$OH).

Compound 2p

2-Oxo-2-(pyrrolidin-1-yl)ethyl (R)-2-amino-3-(7-methylthieno[3,2-b]pyridine-2-carboxamido)propanoate The overall synthesis scheme for the preparation of 2-Oxo-2-(pyrrolidin-1-yl)ethyl (R)-2-amino-3-(7-methylthieno[3,2-b]pyridine-2-carboxamido)propanoate is shown below.

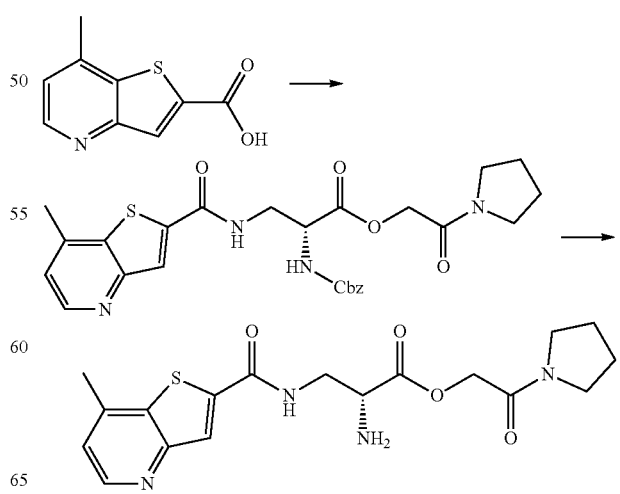

Step 1: 2-Oxo-2-(pyrrolidin-1-yl)ethyl (R)-2-(((benzyloxy)carbonyl)amino)-3-(7-methylthieno[3,2-b]pyridine-2-carboxamido)propanoate

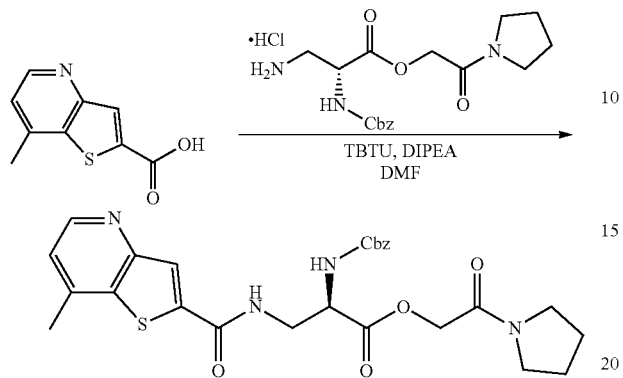

To a solution of 7-methylthieno[3,2-b]pyridine-2-carboxylic acid (150 mg, crude) in DMF (10 mL) was added TBTU (374 mg, 1.16 mmol), N,N-diisopropylethylamine (301 mg, 2.33 mmol) and 2-oxo-2-(pyrrolidin-1-yl)ethyl (R)-3-amino-2-(((benzyloxy)carbonyl)amino)propanoate (300 mg, crude, HCl salt). The mixture was stirred at 15° C. for 16 h. The mixture was diluted with water (15 mL) and extracted with ethyl acetate (20 mL×3). The combined organic layers were washed with brine (20 mL×3) and concentrated. The residue was purified by Combi Flash on silica gel (petroleum ether:ethyl acetate with ethyl acetate from 0 to 100% then MeOH: ethyl acetate with MeOH from 0% to 15%) twice to give 2-oxo-2-(pyrrolidin-1-yl)ethyl (R)-2-(((benzyloxy)carbonyl)amino)-3-(7-methylthieno[3,2-b]pyridine-2-carboxamido)propanoate (170 mg).

$^1$H NMR (400 MHz, CDCl$_3$) δ 9.18-9.07 (m, 1H), 8.60 (d, J=4.8 Hz, 1H), 8.20 (s, 1H), 7.40-7.31 (m, 5H), 7.11 (d, J=4.8 Hz, 1H), 6.12 (br d, J=6.8 Hz, 1H), 5.19-5.06 (m, 3H), 4.67-4.61 (m, 1H), 4.53 (d, J=14.8 Hz, 1H), 4.42-4.31 (m, 1H), 3.85-3.77 (m, 1H), 3.71-3.59 (m, 2H), 3.46-3.37 (m, 2H), 2.60 (s, 3H), 2.07-2.02 (m, 2H), 1.96-1.88 (m, 2H).

Step 2: 2-Oxo-2-(pyrrolidin-1-yl)ethyl (R)-2-amino-3-(7-methylthieno[3,2-b]pyridine-2-carboxamido)propanoate

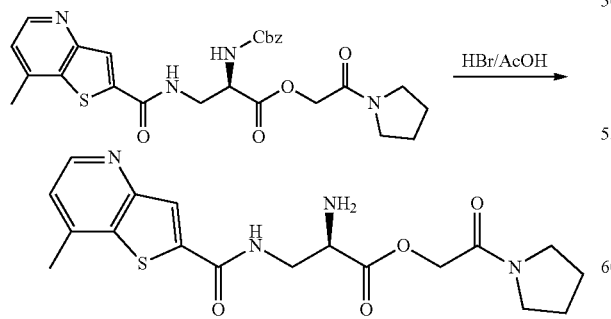

To a solution of 2-oxo-2-(pyrrolidin-1-yl)ethyl (R)-2-(((benzyloxy)carbonyl)amino)-3-(7-methylthieno[3,2-b]pyridine-2-carboxamido)propanoate (120 mg, 0.23 mmol) in AcOH (5 mL) was added 30% HBr in AcOH (0.5 mL). The mixture was stirred at 15° C. for 2 h. The mixture was added methyl tert-butyl ether (6 mL) and stirred for 5 min and allowed to stand for 5 min and then the organic solvent was decanted. The residue was concentrated. The residue was then washed with methyl tert-butyl ether (5 mL×2) to give compound 2-oxo-2-(pyrrolidin-1-yl)ethyl (R)-2-amino-3-(7-methylthieno[3,2-b]pyridine-2-carboxamido)propanoate (102 mg) as HBr salt.

$^1$H NMR (400 MHz, DMSO-d$_6$) δ 9.40 (br t, J=5.6 Hz, 1H), 8.81 (d, J=5.2 Hz, 1H), 8.62 (br s, 3H), 8.35 (s, 1H), 7.57 (d, J=4.8 Hz, 1H), 5.09 (d, J=15.2 Hz, 1H), 4.92 (d, J=15.2 Hz, 1H), 4.55-4.46 (m, 1H), 3.48-3.36 (m, 4H), 2.69 (s, 3H), 1.96-1.88 (m, 2H), 1.86-1.78 (m, 2H).

LCMS (MH+): m/z=390.8, t$_R$ (min. Method BB)=0.34 min.

[α]$^{20}$D=14.5 (c=4.6 mg/mL, CH$_3$OH).

Compound 1d (R)-2-Amino-3-(7-(2-ethylphenyl)thieno[3,2-b]pyridine-2-carboxamido)propanoic acid The overall synthesis scheme for the preparation of (R)-2-Amino-3-(7-(2-ethylphenyl)thieno[3,2-b]pyridine-2-carboxamido)propanoic acid is shown below.

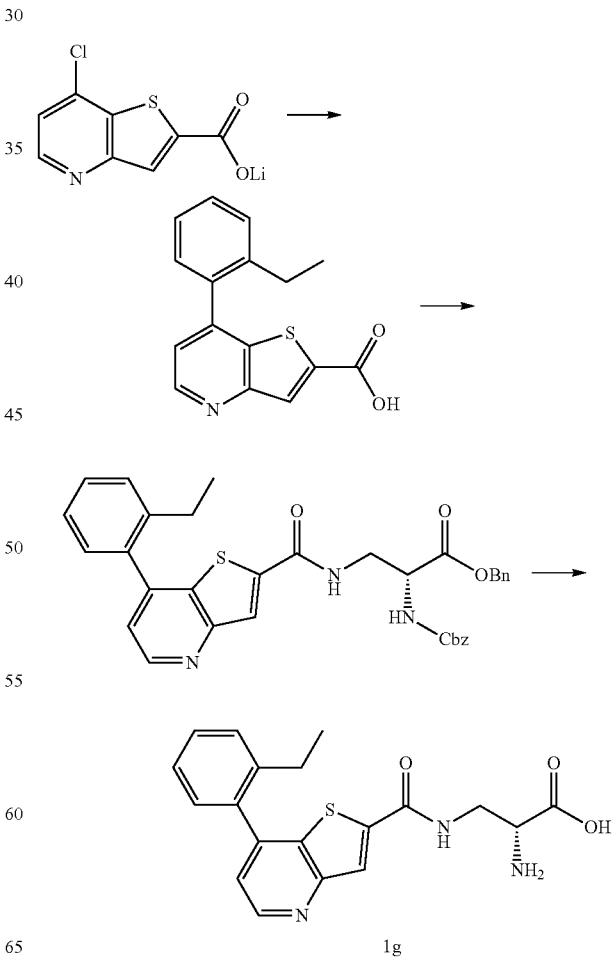

1g

Step 1: 7-(2-Ethylphenyl)thieno[3,2-b]pyridine-2-carboxylic acid

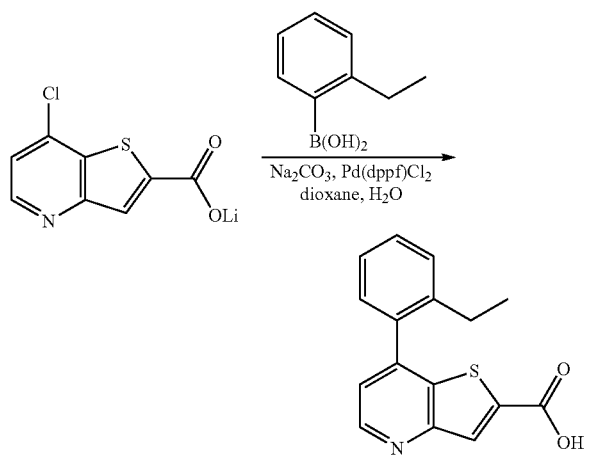

Lithium 7-chlorothieno[3,2-b]pyridine-2-carboxylate (1.0 g, 4.55 mmol), (2-ethylphenyl)boronic acid (1.16 g, 7.74 mmol), Na$_2$CO$_3$ (1.45 g, 13.6 mmol) and Pd(dppf)Cl$_2$ (333 mg, 0.46 mmol) in water (10 mL) and dioxane (20 mL) was de-gassed and then heated to 110° C. for 16 h under N$_2$. The mixture was concentrated, and the residue was diluted with water (10 mL), and extracted with ethyl acetate (10 mL×2). The aqueous phase was adjusted to pH=34 with HCl (2M, 5 mL). The precipitate was filtered and dried to give 7-(2-ethylphenyl)thieno[3,2-b]pyridine-2-carboxylic acid (700 mg).

$^1$H NMR (400 MHz, DMSO-d$_6$) δ 8.86 (d, 1H), 8.18 (s, 1H), 7.51-7.47 (m, 2H), 7.45 (d, 1H), 7.40-7.36 (m, 1H), 7.35-7.32 (m, 1H), 2.45-2.43 (m, 2H), 0.97 (t, 3H)

Step 2: Benzyl (R)-2-(((benzyloxy)carbonyl)amino)-3-(7-(2-ethylphenyl)thieno[3,2-b]pyridine-2-carboxamido)propanoate

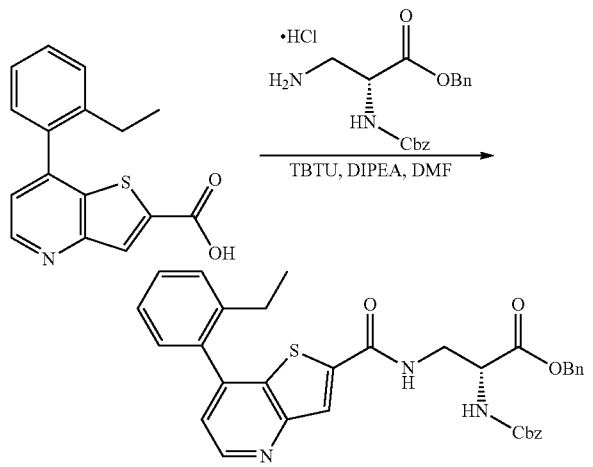

A mixture of 7-(2-ethylphenyl)thieno[3,2-b]pyridine-2-carboxylic acid (200 mg, 0.71 mmol), benzyl (R)-3-amino-2-(((benzyloxy)carbonyl)amino)propanoate (258 mg, 0.71 mmol, HCl salt), O-(Benzotriazol-1-yl)-N,N,N′,N′-tetramethyluronium tetrafluoroborate (340 mg, 1.06 mmol) and N,N-diisopropylethylamine (456 mg, 3.53 mmol) in DMF (10 mL) was stirred at 25° C. for 16 h. The mixture was diluted with water (30 mL) and extracted with ethyl acetate (10 mL×3). The organic phase was washed with brine (10 mL×2), dried over anhydrous sodium sulfate and concentrated. The residue was purified by preparative-HPLC (Method G) to give benzyl (R)-2-(((benzyloxy)carbonyl)amino)-3-(7-(2-ethylphenyl)thieno[3,2-b]pyridine-2-carboxamido)propanoate (200 mg).

$^1$H NMR (400 MHz, CDCl$_3$) δ 8.78 (d, 1H), 7.89 (s, 1H), 7.47-7.38 (m, 2H), 7.36-7.25 (m, 12H), 7.22 (d, 1H), 7.08 (br s, 1H), 5.97 (br s, 1H), 5.19 (s, 2H), 5.10 (s, 2H), 4.60-4.59 (m, 1H), 3.98-3.78 (m, 2H), 2.55-2.42 (m, 2H), 1.04 (t, 3H).

Step 3: (R)-2-Amino-3-(7-(2-ethylphenyl)thieno[3,2-b]pyridine-2-carboxamido)propanoic acid

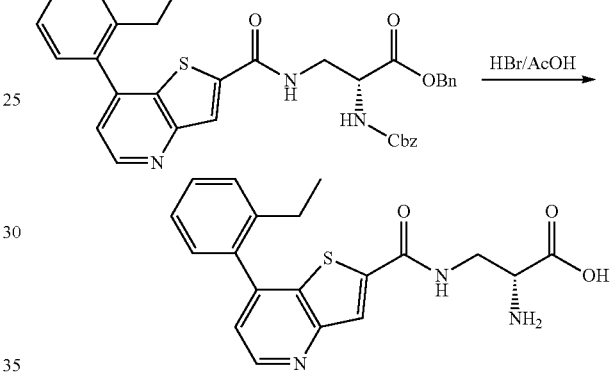

A mixture of benzyl (R)-2-(((benzyloxy)carbonyl)amino)-3-(7-(2-ethylphenyl)thieno[3,2-b]pyridine-2-carboxamido)propanoate (60 mg, 0.10 mmol) and HBr/AcOH (3 mL, 33%) were stirred at 50° C. for 16 h. The mixture was diluted with MTBE (3 mL), filtered and washed with MTBE (3×3 mL). The filter cake was dried to give (R)-2-amino-3-(7-(2-ethylphenyl)thieno[3,2-b]pyridine-2-carboxamido)propanoic acid (43 mg) as HBr salt.

$^1$H NMR (400 MHz, DMSO-d$_6$) δ 69.24-9.22 (m, 1H), 8.87 (d, 1H), 8.41-8.26 (m, 4H), 7.54-7.44 (m, 3H), 7.41-7.36 (m, 1H), 7.35-7.30 (m, 1H), 4.24-4.07 (m, 1H), 3.82-3.77 (m, 1H), 3.74-3.69 (m 1H), 2.45-2.43 (m 2H), 0.96 (t, 3H).

LCMS (MH+): m/z=370.1, t$_R$ (min, Method BB)=0.46. [α]$^{20}$D=−6.67, (c=1.5 mg/mL, CH$_3$OH).

Compound 2q

Methyl (R)-2-amino-3-(7-(2-ethylphenyl)thieno[3,2-b]pyridine-2-carboxamido)propanoate

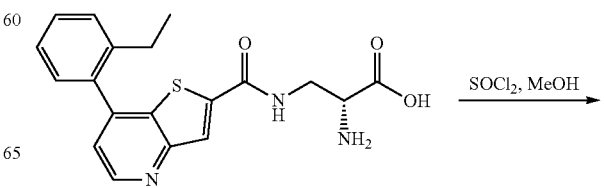

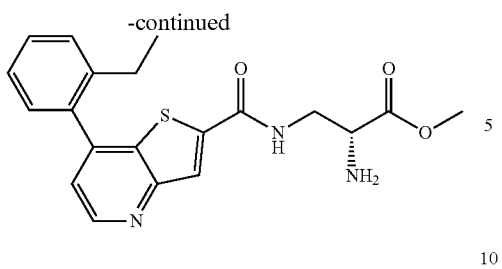

To a mixture of (R)-2-amino-3-(7-(2-ethylphenyl)thieno[3,2-b]pyridine-2-carboxamido) propanoic acid (295 mg, 555.28 mmol, HBr salt) in MeOH (10 mL) was added thionyl chloride (199 mg, 1.67 mmol) dropwise at 0° C. After completion of the addition, the reaction stirred for 42 hr at 30° C. The mixture was concentrated. The residue was purified by Preparative-HPLC (Method H) to give the crude product (0.2 g). The crude product was purified by Preparative-HPLC (Method I) to give methyl (R)-2-amino-3-(7-(2-ethylphenyl)thieno[3,2-b]pyridine-2-carboxamido)propanoate (45 mg).

$^1$H NMR (400 MHz, DMSO-d$_6$) δ 8.99 (br s, 1H), 8.81 (d, J=4.8 Hz, 1H), 8.31 (s, 1H), 7.54-7.26 (m, 5H), 3.61 (s, 3H), 3.57-3.52 (m, 1H), 3.49-3.42 (m, 2H), 2.44-2.42 (m, 2H), 0.96 (t, J=7.6 Hz, 3H).

LCMS (MH+): m/z=384.4, t$_R$ (min, Method BB)=0.49 min.

$[\alpha]^{20}$D=−12.0, (c=0.5 mg/mL, CH3OH).

Compound 1e (R)-2-amino-3-(7-methoxythieno[3,2-b]pyridine-2-carboxamido)propanoic acid The overall synthesis scheme for the preparation of (R)-2-amino-3-(7-methoxythieno[3,2-b]pyridine-2-carboxamido)propanoic acid is shown below.

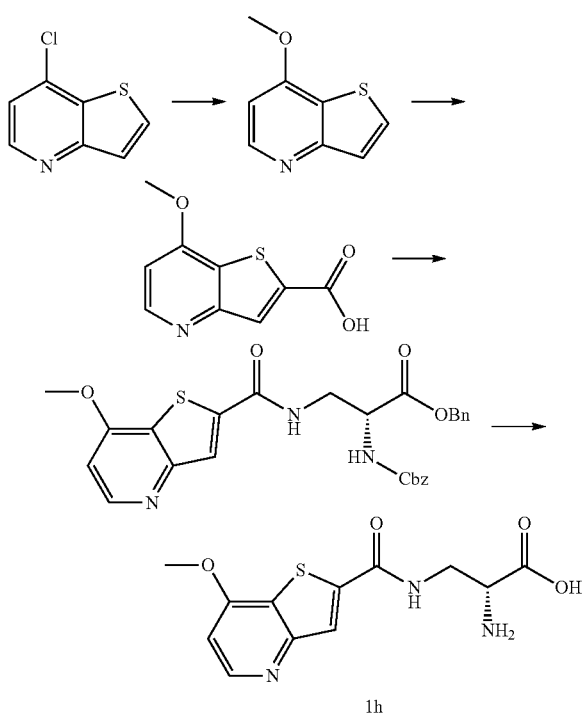

1h

Step 1: 7-methoxythieno[3,2-b]pyridine

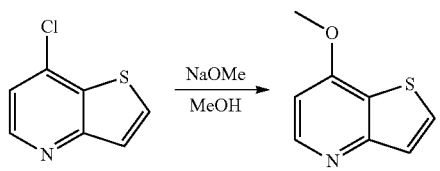

To MeOH (5.0 mL) was added Na (135 mg, 0.59 mmol). The mixture was stirred at room temperature for 1 hour, and 7-chlorothieno[3,2-b]pyridine (200 mg, 1.18 mmol) was added. The mixture was stirred at 110-120° C. for another 15 h. The reaction mixture was concentrated under reduced pressure to give 7-methoxythieno[3,2-b]pyridine (160 mg).

$^1$H NMR (400 MHz, CDCl$_3$) δ 8.57 (d, 1H), 7.67 (d, 1H), 7.50 (d, 1H), 6.70 (d, 1H), 4.04 (s, 3H).

Step 2: 7-methoxythieno[3,2-b]pyridine-2-carboxylic acid

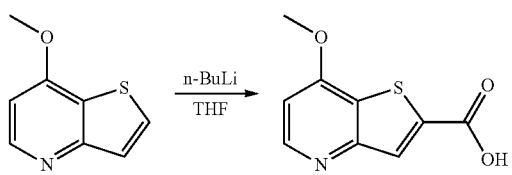

To a solution of 7-methoxythieno[3,2-b]pyridine (150 mg, 0.90 mmol) in THF (15 mL) was added n-BuLi (2.5 M in hexane, 0.5 mL) at −78° C. The mixture was stirred at −78° C. for 0.5 hour. CO$_2$ was bubbled into the solution for 0.5 hour. The mixture was warmed to room temperature and stirred for another 15 h. The reaction mixture was concentrated under reduced pressure to remove the solvent. The residue was diluted with water (20 mL) and HCl (2M, to pH~5), filtered and dried to give 7-methoxythieno[3,2-b]pyridine-2-carboxylic acid (120 mg).

$^1$H NMR (400 MHz, DMSO-d$_6$) δ 8.56 (br, 1H), 7.86 (s, 1H), 7.04 (br, 1H), 4.01 (s, 3H).

Step 3: Benzyl (R)-2-(((benzyloxy)carbonyl)amino)-3-(7-methoxythieno[3,2-b]pyridine-2-carboxamido)propanoate

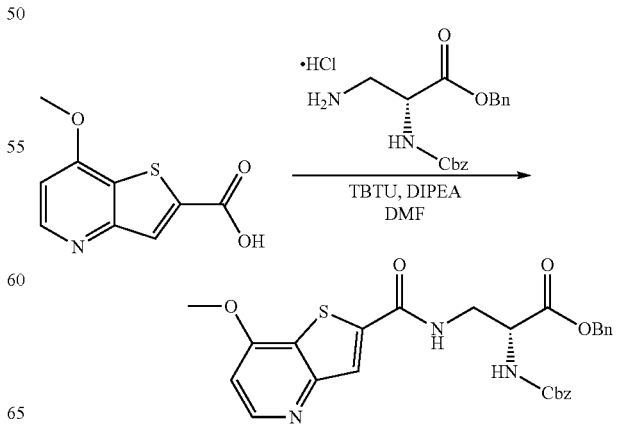

To a solution of 7-methoxythieno[3,2-b]pyridine-2-carboxylic acid (120 mg, 0.57 mmol) and benzyl (R)-3-amino-2-(((benzyloxy)carbonyl)amino) propanoate (207 mg, 0.63 mmol, HCl salt) in DMF (5 mL) was added O-(Benzotriazol-1-yl)-N,N,N',N'-tetramethyluronium tetrafluoroborate (276 mg, 0.86 mmol) and N,N-diisopropylethylamine (370 mg, 2.87 mmol). The mixture was stirred at 20-30° C. for 16 h. The residue was diluted with water (20 mL) and extracted with ethyl acetate (20 mL×2). The combined organic layers were washed with brine (10 mL), dried over MgSO₄, filtered and concentrated under reduced pressure to give a residue. The residue was purified by flash silica gel chromatography (Eluent of 0100% Ethyl acetate/Petroleum ether) to give benzyl (R)-2-(((benzyloxy)carbonyl)amino)-3-(7-methoxythieno[3,2-b]pyridine-2-carboxamido)propanoate (48 mg).

Step 4: (R)-2-amino-3-(7-methoxythieno[3,2-b]pyridine-2-carboxamido)propanoic acid

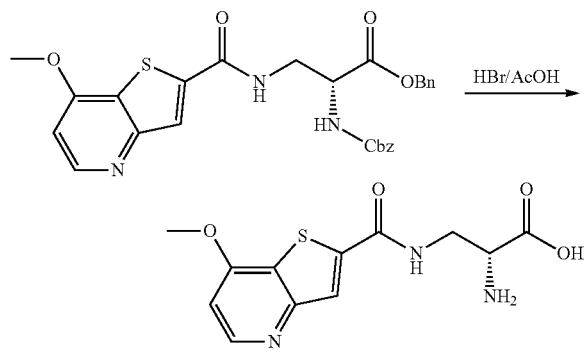

A solution of benzyl(R)-2-(((benzyloxy)carbonyl)amino)-3-(7-methoxythieno[3,2-b]pyridine-2-carboxamido)propanoate (125 mg, 0.24 mol) in HBr/AcOH (5 mL, 33%) was stirred at 50° C. for 16 h. The reaction mixture was concentrated under reduced pressure to give (R)-2-amino-3-(7-methoxythieno[3,2-b]pyridine-2-carboxamido) propanoic acid (100 mg) as HBr salt.

¹H NMR (400 MHz, DMSO-d₆) δ 9.52 (t, Hz, 1H), 9.00 (d, 1H), 8.40-8.30 (m, 4H), 7.52 (d, 1H), 4.22 (s, 3H), 4.15-4.13 (m, 1H), 3.84-3.72 (m, 2H).

LCMS (MH+): m/z=296.2, t_R (min, Method BB)=0.28.
[α]²⁰D=−1.45, (c=2.75 g/mL, CH₃OH).

Compound 2r

Methyl (R)-2-amino-3-(7-methoxythieno[3,2-b]pyridine-2-carboxamido) propanoate

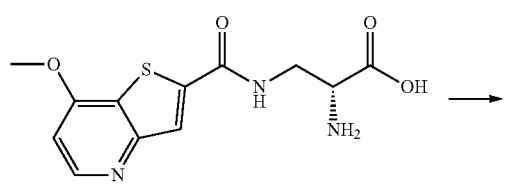

-continued

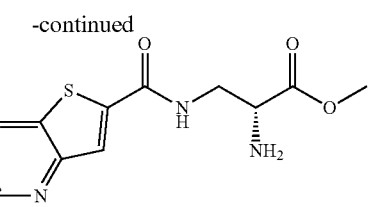

To a solution of (R)-2-amino-3-(7-methoxythieno[3,2-b]pyridine-2-carboxamido) propanoic acid (35 mg, 0.12 mmol) in MeOH (15 mL) was added thionyl chloride (1 mL) at 0° C. and stirred at 15-30° C. for 16 h. The reaction mixture was concentrated under reduced pressure to remove solvent. The residue was diluted with t-BuOMe/MeOH (15 mL V: V=15:1) and filtered and the filter cake was dried under reduced pressure to give a residue. The residue was diluted with water (15 mL) and sodium carbonate (sat. aq) to pH~9 extracted with ethyl acetate (15 mL×3). The combined organic layers were washed with brine (10 mL), dried over magnesium sulfate, filtered and concentrated under reduced pressure to give a residue. The residue was diluted with water (15 mL) and HCl (2M) to pH~4 and was freeze-dried to give methyl (R)-2-amino-3-(7-methoxythieno[3,2-b]pyridine-2-carboxamido)propanoate (35 mg) as HCl salt.

¹H NMR (400 MHz, D₂O) δ 8.74 (d, J=6.8 Hz, 1H), 8.09 (s, 1H), 7.41 (d, J=6.8 Hz, 1H), 4.42 (t, J=5.2 Hz, 1H), 4.40 (s, 3H). 4.25-3.99 (m, 2H), 3.94 (s, 3H)

LCMS (MH+): m/z=310.2, t_R (min, Method BB)=0.31.
[α]²⁰D=4 (c=1 mg/mL, CH₃OH).

Compound 1f (R)-2-amino-3-(7-(trifluoromethyl)thieno[3,2-b]pyridine-2-carboxamido)propanoic acid The overall synthesis scheme for the preparation of (R)-2-amino-3-(7-(trifluoromethyl)thieno[3,2-b]pyridine-2-carboxamido) propanoic acid is shown below.

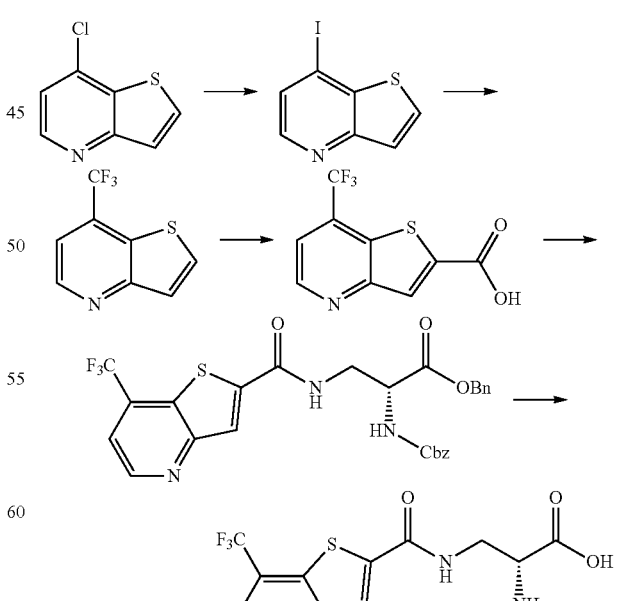

Step 1: 7-Iodothieno[3,2-b]pyridine

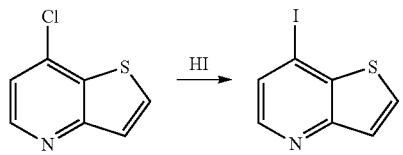

A solution of 7-chlorothieno[3,2-b]pyridine (1.00 g, 5.90 mmol) in HI (10 mL, 45% in water) was stirred at 130° C. for 16 h. The reaction mixture was cooled to room temperature, carefully quenched with sat.aq. $Na_2CO_3$ to pH=67, and extracted with ethyl acetate (3×10 mL). The combined organic layers were washed with brine (3×10 mL), dried over anhydrous sodium sulfate and concentrated. The residue was purified by CombiFlash (petroleum ether/ethyl acetate with ethyl acetate from 5% to 10%) to give 7-iodothieno[3,2-b]pyridine (1.2 g).

$^1$H NMR (400 MHz, $CDCl_3$) δ 8.32 (d, J=4.8 Hz, 1H), 7.85-7.77 (m, 2H), 7.66 (d, J=5.2 Hz, 1H).

Step 2: 7-(Trifluoromethyl)thieno[3,2-b]pyridine

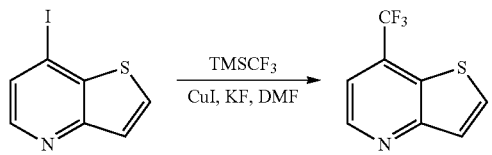 [SMILES: "TMSCF3" ; Ic1ccnc2ccsc12 ; FC(F)(F)c1ccnc2ccsc12]

To a solution of 7-iodothieno[3,2-b]pyridine (500 mg, 1.92 mmol) in DMF (5 mL) were added CuI (401 mg, 2.11 mmol), KF (334 mg, 5.75 mmol) and $TMSCF_3$ (327 mg, 2.30 mmol). The reaction mixture was stirred at 80° C. for 16 h. The reaction mixture was quenched with water (10 mL), and extracted with ethyl acetate (3×10 mL). The combined organic layers were washed with brine (3×10 mL), dried over anhydrous sodium sulfate and concentrated. The residue was purified by CombiFlash (petroleum ether/ethyl acetate with ethyl acetate from 0% to 3%) to give 7-(trifluoromethyl)thieno[3,2-b]pyridine (140 mg).

$^1$H NMR (400 MHz, $CDCl_3$) δ 8.87 (d, J=4.4 Hz, 1H), 7.90 (d, J=5.6 Hz, 1H), 7.68 (d, J=5.6 Hz, 1H), 7.52 (d, J=4.8 Hz, 1H).

Step 3: 7-(Trifluoromethyl)thieno[3,2-b]pyridine-2-carboxylic acid

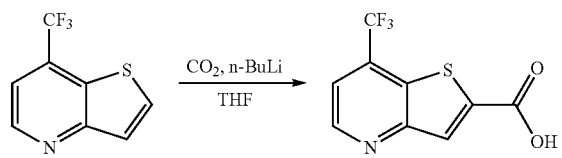

A solution of 7-(trifluoromethyl)thieno[3,2-b]pyridine (120 mg, 0.59 mmol) in THF (2 mL) was cooled to −78° C. and treated dropwise with n-BuLi (2.5 M solution in hexanes, 0.5 ml, 1.25 mmol) and stirred at −78° C. for 30 minutes. The reaction mixture was bubbled with $CO_2$ (15 psi) and stirred at −78° C. for 1 hr. The reaction mixture was quenched with water (10 mL), and extracted with ethyl acetate (3×10 mL). The combined organic layers were washed with brine (3×10 mL), dried over anhydrous sodium sulfate and concentrated to give 7-(trifluoromethyl)thieno[3,2-b]pyridine-2-carboxylic acid (70 mg).

LCMS (MH+): m/z=247.9, $t_R$=0.709 min.

Step 4: benzyl (R)-2-(((benzyloxy)carbonyl)amino)-3-(7-(trifluoromethyl)thieno[3,2-b]pyridine-2-carboxamido)propanoate

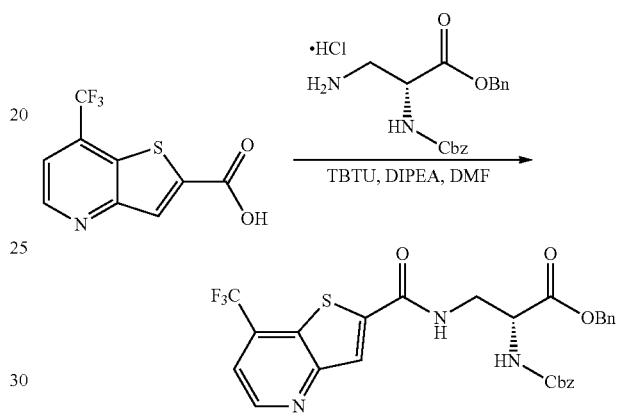

To a solution of 7-(trifluoromethyl)thieno[3,2-b]pyridine-2-carboxylic acid (130 mg, 0.52 mmol) in DMF (5 mL) were added benzyl (R)-3-amino-2-(((benzyloxy)carbonyl) amino) propanoate (192 mg, 0.52 mmol HCl salt), O-(Benzotriazol-1-yl)-N,N,N',N'-tetramethyluronium tetrafluoroborate (253 mg, 0.79 mmol) and N,N-diisopropylethylamine (203 mg, 1.58 mmol). The reaction mixture was stirred at 25° C. for 16 h. The reaction mixture was quenched with water (10 mL), and extracted with ethyl acetate (3×10 mL). The combined organic layers were washed with brine (3×10 mL), dried over anhydrous sodium sulfate and concentrated. The residue was further purified by Preparative HPLC (Method F) to give benzyl (R)-2-(((benzyloxy)carbonyl) amino)-3-(7-(trifluoromethyl)thieno[3,2-b]pyridine-2-carboxamido)propanoate (50 mg).

$^1$H NMR (400 MHz, $CDCl_3$) δ 8.91 (d, J=4.8 Hz, 1H), 7.88 (s, 1H), 7.58 (d, J=4.4 Hz, 1H), 7.40-7.28 (m, 10H), 5.93 (d, J=6.8 Hz, 1H), 5.27 (s, 2H), 5.13 (s, 2H), 4.66-4.60 (m, 1H), 4.05-3.92 (m, 1H), 3.88-3.77 (m, 1H).

Step 5: (R)-2-Amino-3-(7-(trifluoromethyl)thieno[3,2-b]pyridine-2-carboxamido) propanoic acid

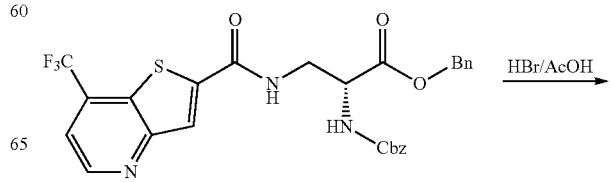

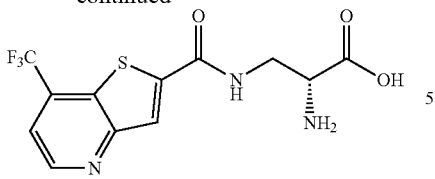

A solution of benzyl (R)-2-(((benzyloxy)carbonyl)amino)-3-(7-(trifluoromethyl)thieno[3,2-b]pyridine-2-carboxamido)propanoate (50 mg, 0.90 mmol) in HBr/AcOH (2 mL, 33%) was stirred at 50° C. for 16 h. The solvent was removed. The residue was purified by Preparative HPLC (Method J) to give (R)-2-amino-3-(7-(trifluoromethyl)thieno[3,2-b]pyridine-2-carboxamido) propanoic acid (8 mg) as HBr salt.

$^1$H NMR (400 MHz, DMSO-d$_6$) δ 9.69 (br, 1H), 9.02 (d, J=3.6 Hz, 1H), 8.63 (br, 4H), 7.93 (d, J=4.0 Hz, 1H), 4.20-4.10 (m, 1H), 3.79-3.77 (m, 2H).

LCMS (MH+): m/z=334.1, t$_R$ (min, Method BB)=0.36.

[α]$^{20}$D=−10.0 (c=1.0 mg/mL, CH$_3$OH).

Compound 2s

Methyl (R)-2-amino-3-(7-(trifluoromethyl)thieno[3,2-b]pyridine-2-carboxamido)propanoate The overall synthesis scheme for the preparation of methyl (R)-2-amino-3-(7-(trifluoromethyl)thieno[3,2-b]pyridine-2-carboxamido)propanoate is shown below.

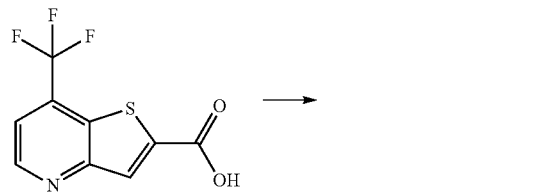

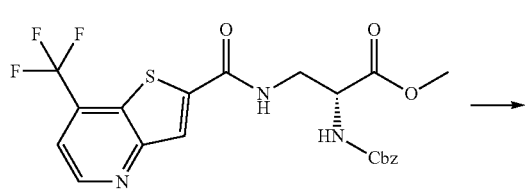

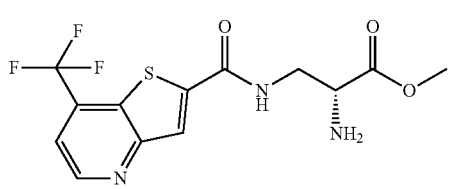

Step 1: Methyl (R)-2-(((benzyloxy)carbonyl)amino)-3-(7-(trifluoromethyl)thieno[3,2-b]pyridine-2-carboxamido)propanoate

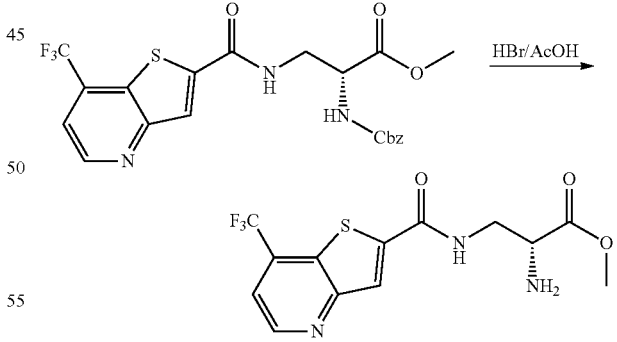

To a solution of 7-(trifluoromethyl)thieno[3,2-b]pyridine-2-carboxylic acid (1.00 g, 4.05 mmol) in DMF (10 mL) were added methyl (R)-3-amino-2-(((benzyloxy)carbonyl)amino) propanoate (1.40 g, 4.86 mmol, HCl salt), TBTU (1.95 g, 6.07 mmol) and N,N-diisopropylethylamine (1.57 g, 12.15 mmol). The reaction mixture was stirred at 25° C. for 16 h. The reaction mixture was quenched with water (10 mL), and extracted with ethyl acetate (3×10 mL). The combined organic layers were washed with brine (3×10 mL), dried over anhydrous sodium sulfate and concentrated. The residue was purified by CombiFlash (petroleum ether/ethyl acetate with ethyl acetate from 80% to 90%) to give methyl (R)-2-(((benzyloxy)carbonyl)amino)-3-(7-(trifluoromethyl)thieno[3,2-b]pyridine-2-carboxamido)propanoate (500 mg).

Step 2: methyl (R)-2-amino-3-(7-(trifluoromethyl)thieno[3,2-b]pyridine-2-carboxamido)propanoate A solution of methyl (R)-2-(((benzyloxy)carbonyl)amino)-3-(7-(trifluoromethyl)thieno[3,2-b]pyridine-2-carboxamido)propanoate (500 mg, 1.04 mmol) in HBr/AcOH (10 mL, 33%) was stirred at 15° C. for 16 h. The solvent was moved. The residue was washed with AcOH (2 mL). The reaction mixture was filtered, the filtration cake was washed with AcOH (1 ml) and filtration cake was collected to give methyl (R)-2-amino-3-(7-(trifluoromethyl)thieno[3,2-b]pyridine-2-carboxamido)propanoate (220 mg) as HBr salt.

¹H NMR (400 MHz, DMSO-d₆) δ 9.36 (t, J=6.0 Hz, 1H), 9.04 (d, J=4.8 Hz, 1H), 8.56-8.45 (m, 3H), 8.43 (s, 1H), 7.95 (d, J=4.4 Hz, 1H), 4.29-4.25 (m, 1H), 3.84-3.70 (m, 5H). LCMS (MH+): m/z=348.2, $t_R$ (min, Method BB)=0.42. [α]²⁰D=+2.0 (c=1.0 mg/mL, CH₃OH).

Compound 1g (R)-2-amino-3-(7-isopropoxythieno[3,2-b]pyridine-2-carboxamido)propanoic acid The overall synthesis scheme for the preparation of (R)-2-amino-3-(7-isopropoxythieno[3,2-b]pyridine-2-carboxamido)propanoic acid is shown below.

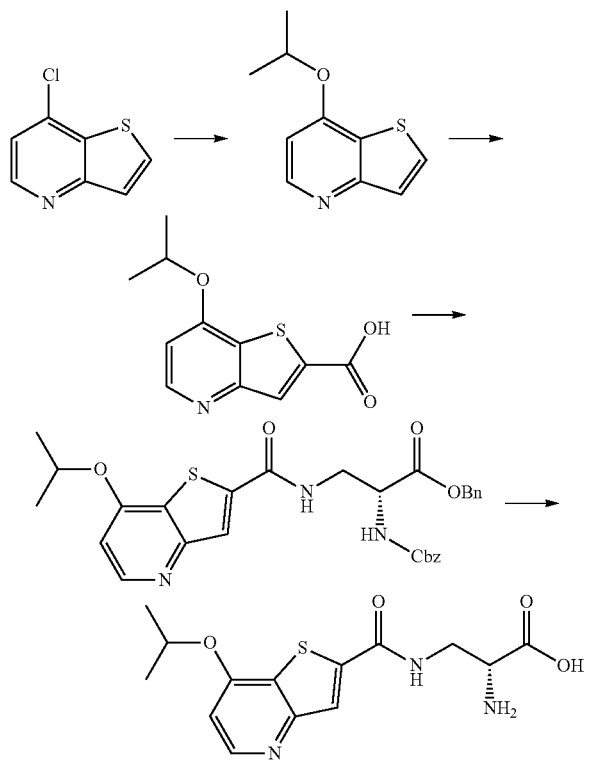

Step 1: 7-isopropoxythieno[3,2-b]pyridine

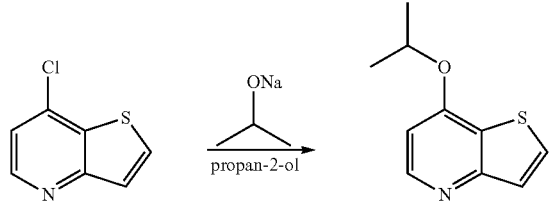

To propan-2-ol (15 mL) was added Na (339 mg, 15 mmol). The mixture was stirred at 50° C. for 1 hour and 7-chlorothieno[3,2-b]pyridine (500 mg, 2.95 mmol) was added. The mixture was stirred at 110-120° C. for another 15 h. The reaction mixture was concentrated under reduced pressure to remove solvent to give 7-isopropoxythieno[3,2-b]pyridine (320 mg).

¹H NMR (400 MHz, DMSO-d₆) δ 8.51 (d, J=5.6 Hz, 1H), 7.66 (d, J=5.6 Hz, 1H), 7.49 (d, J=5.6 Hz, 1H), 6.70 (d, J=5.6 Hz, 1H), 4.84-4.81 (m, 1H), 1.37 (d, J=6.0 Hz, 6H).

Step 2: 7-isopropoxythieno[3,2-b]pyridine-2-carboxylic acid

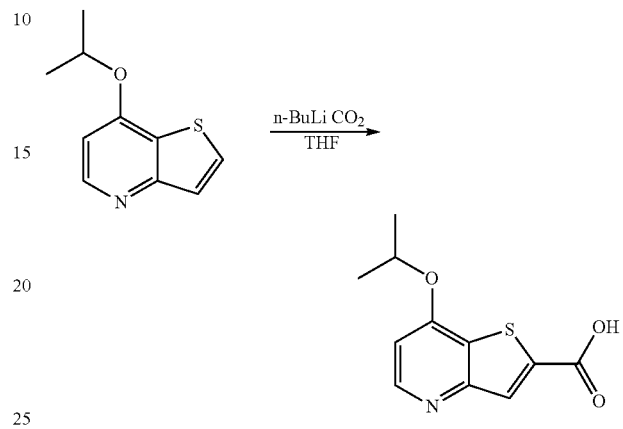

To a solution of 7-isopropoxythieno[3,2-b]pyridine (320 mg, 1.7 mmol), in THF (15 mL) was added n-BuLi (2.5 M in hexane, 0.9 mL) at −78° C. The mixture was stirred at −78° C. for 0.5 hour. CO₂ was bubbled into the solution for 0.5 h. The mixture was stirred at 20-30° C. for another 15 h. The reaction mixture was concentrated under reduced pressure to remove solvent. The residue was diluted with water (20 mL) and HCl (2M) to pH∼5, filtered, and the filter cake was dried under reduced pressure to give 7-isopropoxythieno[3,2-b]pyridine-2-carboxylic acid (210 mg).

¹H NMR (400 MHz, DMSO-d₆) δ 8.58 (d, J=5.4 Hz, 1H), 8.00 (s, 1H), 7.11 (d, J=5.4 Hz, 1H), 4.93-4.99 (m, 1H), 1.37 (d, J=6.0 Hz, 6H).

Step 3: Preparation of benzyl (R)-2-(((benzyloxy)carbonyl)amino)-3-(7-isopropoxythieno[3,2-b]pyridine-2-carboxamido)propanoate

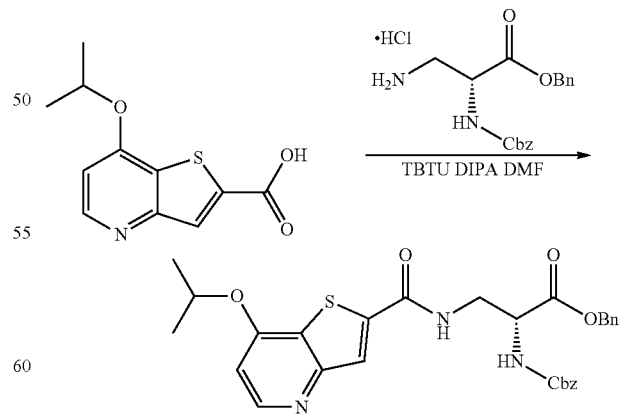

To a solution of 7-isopropoxythieno[3,2-b]pyridine-2-carboxylic acid (200 mg, 0.84 mmol) and benzyl (R)-3-amino-2-(((benzyloxy)carbonyl)amino) propanoate (304 mg, 0.93 mmol, HCl salt) in DMF (10 mL) was added O-(Benzotriazol-1-yl)-N,N,N',N'-tetramethyluronium tetrafluoroborate (406 mg, 1.3 mmol) and N,N-diisopropylethylamine (545 mg, 4.2 mmol). The mixture was stirred at 20-30° C. for 16 h. The residue was diluted with water (20 mL) and extracted with ethyl acetate (20 mL×2). The combined organic layers were washed with brine (15 mL), dried over MgSO$_4$, filtered and concentrated under reduced pressure. The residue was purified by flash silica gel chromatography (Eluent of 090% Ethyl acetate/Petroleum ether) to give compound benzyl (R)-2-(((benzyloxy)carbonyl)amino)-3-(7-isopropoxythieno[3,2-b]pyridine-2-carboxamido)propanoate (86 mg).

$^1$H NMR (400 MHz, CDCl$_3$) δ 8.56 (d, J=5.2 Hz, 1H), 7.76 (s, 1H), 7.38-7.27 (m, 10H), 7.09 (br, 1H), 6.72 (d, J=5.6 Hz, 1H), 5.99 (d, J=7.2 Hz, 1H), 5.20 (s, 2H), 5.11 (s, 2H), 4.85-4.85 (m, 1H), 4.65-4.55 (m, 1H), 3.97-3.80 (m, 2H), 1.47 (d, J=5.6 Hz, 6H).

Step 4: (R)-2-amino-3-(7-isopropoxythieno[3,2-b]pyridine-2-carboxamido)propanoic acid

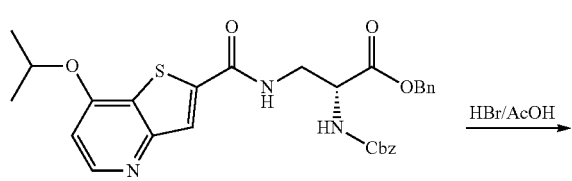

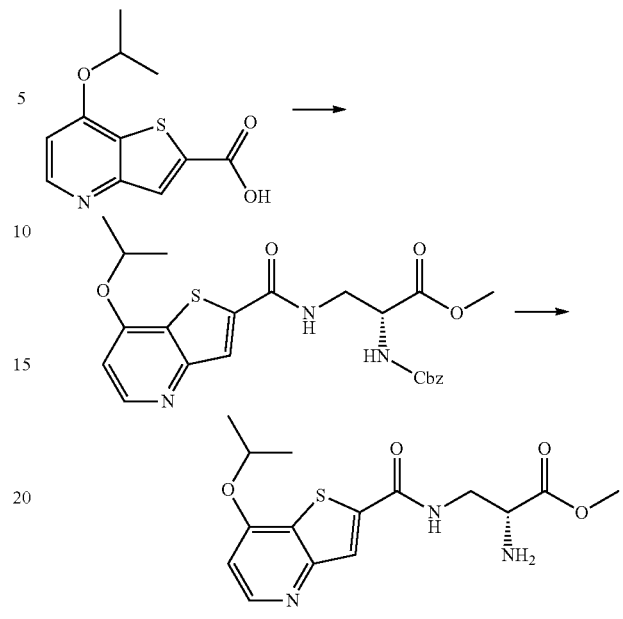

Step 1: methyl (R)-2-(((benzyloxy)carbonyl)amino)-3-(7-isopropoxythieno[3,2-b]pyridine-2-carboxamido)propanoate A solution of benzyl (R)-2-(((benzyloxy)carbonyl)amino)-3-(7-isopropoxythieno[3,2-b]pyridine-2-carboxamido)propanoate (80 mg, 0.15 mmol) in HBr/AcOH (10 mL, 33%) was stirred at 50° C. for 16 h. The reaction mixture was concentrated under reduced pressure to remove solvent. The residue was purified by Preparative-HPLC (Method K) to give (R)-2-amino-3-(7-isopropoxythieno[3,2-b]pyridine-2-carboxamido)propanoic acid (26 mg).

$^1$H NMR (400 MHz, DMSO-d$_6$) δ 9.06 (br, 1H), 8.54 (d, J=5.2 Hz, 1H), 8.10 (s, 1H), 7.57 (br, 2H), 7.08 (d, J=5.2 Hz, 1H), 5.02-4.90 (m, 1H), 3.69-3.65 (m, 1H), 3.55-3.40 (m, 2H), 1.36 (d, J=6.0 Hz, 1H).

LCMS (MH+): m/z=324.2, $t_R$ (min, Method BB)=0.24.

[α]$^{20}$D=18 (c=1 mg/mL, CH$_3$OH).

Compound 2t

Methyl (R)-2-amino-3-(7-isopropoxythieno[3,2-b]pyridine-2-carboxamido)propanoate The overall synthesis scheme for the preparation of methyl (R)-2-amino-3-(7-isopropoxythieno[3,2-b]pyridine-2-carboxamido)propanoate is shown below.

To a solution of 7-isopropoxythieno[3,2-b]pyridine-2-carboxylic acid (500 mg, 2.11 mmol) and methyl (R)-3-amino-2-(((benzyloxy)carbonyl)amino)propanoate (670 mg, 2.32 mmol, HCl salt) in DMF (20 mL) was added TBTU (1.0 g, 3.17 mmol) and N,N-diisopropylethylamine (1.36 g, 10.55 mmol). The mixture was stirred at 20-30° C. for 2 h. The residue was diluted with water (40 mL) and extracted with ethyl acetate (50 mL×2). The combined organic layers were washed with brine (15 mL), dried over MgSO4, filtered and concentrated under reduced pressure. The residue was purified by flash silica gel chromatography (Eluent of 0100% Ethyl acetate/Petroleum ether) to give methyl (R)-2-(((benzyloxy)carbonyl)amino)-3-(7-isopropoxythieno[3,2-b]pyridine-2-carboxamido)propanoate (510 mg) $^1$H NMR (400 MHz, CDCl$_3$) δ 8.55 (d, J=5.6 Hz, 1H), 7.88 (s, 1H), 7.43 (br s, 1H), 7.34-7.22 (m, 5H), 6.71 (d, J=6.4 Hz, 1H), 6.05 (d, J=6.8 Hz, 1H), 5.10 (s, 2H), 4.85-4.79 (m, 1H), 4.60-4.50 (m, 1H), 3.94-3.80 (m, 2H), 3.76 (s, 3H), 1.46 (d, J=6.0 Hz, 6H).

Step 2: methyl (R)-2-amino-3-(7-isopropoxythieno[3,2-b]pyridine-2-carboxamido)propanoate

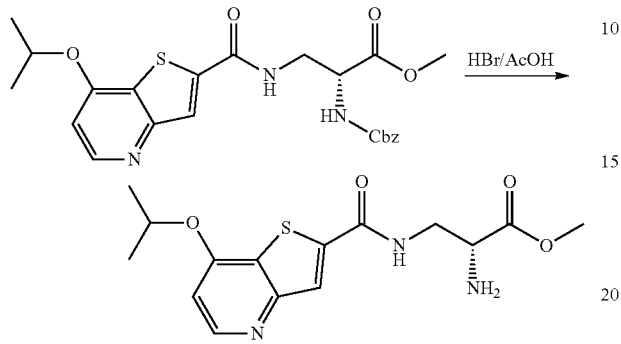

A solution of methyl (R)-2-(((benzyloxy)carbonyl)amino)-3-(7-isopropoxythieno[3,2-b]pyridine-2-carboxamido)propanoate (260 mg, 0.55 mmol) in HBr/AcOH (4 mL, 30%) was stirred at 10-20° C. for 16 h. The reaction mixture was diluted with methyl tert-butyl ether (10 mL) and filtered, washed with methyl tert-butyl ether (10 mL×3) and dried to give compound methyl (R)-2-amino-3-(7-isopropoxythieno[3,2-b]pyridine-2-carboxamido) propanoate (175 mg) as HBr salt.

$^1$HNMR (400 MHz, DMSO-d$_6$) δ 9.52 (br, 1H), 8.94 (d, J=6.4 Hz, 1H), 8.52 (br, 3H), 8.35 (s, 1H), 7.56 (d, J=6.4 Hz, 1H), 5.25-5.19 (m, 1H), 4.25-4.20 (m, 1H), 3.85-3.66 (m, 5H), 1.42 (d, J=6.0 Hz, 6H).

LCMS (MH+): m/z=338.2, t$_R$ (min, Method BB)=0.29.

[α]$^{20}$D=1.3 (c=2 mg/mL, CH3OH).

Compound 1h (R)-2-amino-3-(7-bromothieno[3,2-b]pyridine-2-carboxamido)propanoic acid The overall synthesis scheme for the preparation of (R)-2-amino-3-(7-bromothieno[3,2-b]pyridine-2-carboxamido) propanoic acid is shown below.

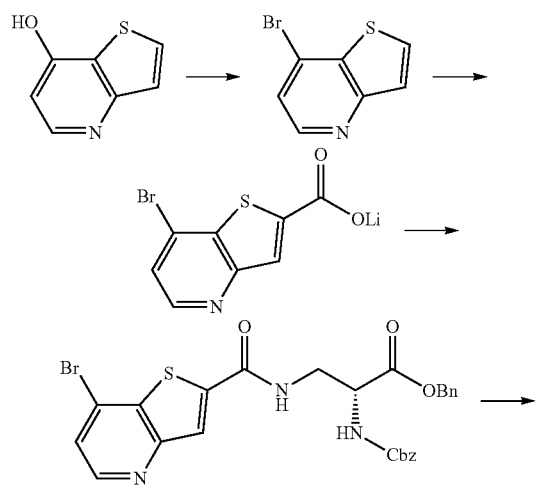

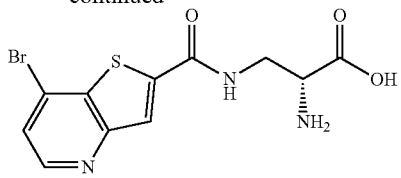

Step 1: 7-bromothieno[3,2-b]pyridine

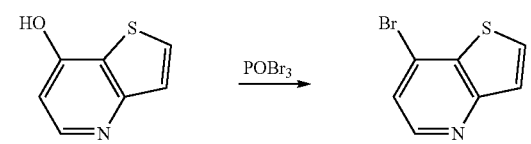

A mixture of thieno[3,2-b]pyridin-7-ol (2 g, 13 mmol) and POBr$_3$ (25 g, 8 mmol) was heated at 110° C. for 2 h. The mixture was cooled and was poured into ice water (100 mL) and then added 2M NaOH solution to adjust pH to 8. The mixture was extracted with ethyl acetate (40 mL×3). The organic layer was dried over anhydrous sodium sulfate, filtered and concentrated. The residue was purified by Combi Flash on silica gel (petroleum ether:ethyl acetate with ethyl acetate from 0 to 30%) to give 7-bromothieno[3,2-b]pyridine (2.5 g).

$^1$H NMR (400 MHz, CDCl$_3$) δ 8.51 (d, J=4.8 Hz, 1H), 7.82 (d, J=6.0 Hz, 1H), 7.66 (d, J=5.6 Hz, 1H), 7.46 (d, J=5.2 Hz, 1H).

Step 2: Lithium 7-bromothieno[3,2-b]pyridine-2-carboxylate

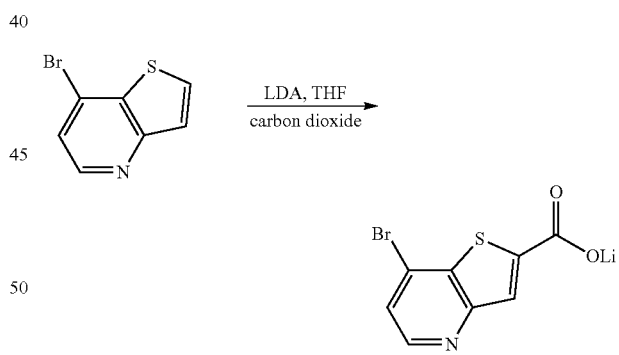

To a solution of diisopropylamine (473 mg, 4.67 mmol) in THF (20 mL) was added n-BuLi (2.5 M in hexane, 1.87 mL) dropwise at −70° C. and stirred at −70° C. for 30 min. Then 7-bromothieno[3,2-b]pyridine (1 g, 4.67 mmol) dissolved in THF (5 mL) was added dropwise and stirred at −70° C. for 30 min. Then gaseous carbon dioxide was bubbled through the reaction mixture and the mixture was allowed to warm to 25° C. over a period of 2 h. The mixture was filtered and the filter cake was washed with THF (10 mL×2). The solid was collected and dried to give lithium 7-bromothieno[3,2-b]pyridine-2-carboxylate (800 mg).

$^1$H NMR (400 MHz, DMSO-d$_6$) δ 8.47 (d, J=5.2 Hz, 1H), 7.68 (s, 1H), 7.62 (d, J=5.2 Hz, 1H).

Step 3: benzyl (R)-2-(((benzyloxy)carbonyl)amino)-3-(7-bromothieno[3,2-b]pyridine-2-carboxamido)propanoate

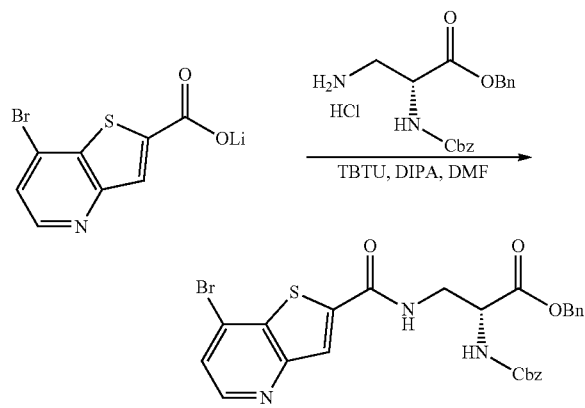

To a solution of lithium 7-bromothieno[3,2-b]pyridine-2-carboxylate (200 mg, 0.76 mmol) in DMF (5 mL) was added O-(Benzotriazol-1-yl)-N,N,N',N'-tetramethyluronium tetrafluoroborate (268 mg, 0.83 mmol), N,N-diisopropylethylamine (196 mg, 1.52 mmol) and benzyl (R)-3-amino-2-(((benzyloxy)carbonyl)amino)propanoate (276 mg, 0.76 mmol, HCl salt). The mixture was stirred at 25° C. for 2 h. The mixture was diluted with water (15 mL) and extracted with ethyl acetate (20 mL×3). The combined organic layers were washed with brine (20 mL×3), dried over anhydrous sodium sulfate, filtered and concentrated. The residue was purified by Combi Flash on silica gel (petroleum ether:ethyl acetate with ethyl acetate from 0 to 80%) twice to give compound benzyl (R)-2-(((benzyloxy)carbonyl)amino)-3-(7-bromothieno[3,2-b]pyridine-2-carboxamido)propanoate (190 mg).

$^1$H NMR (400 MHz, CDCl$_3$) δ 8.54 (d, J=4.8 Hz, 1H), 7.88 (s, 1H), 7.51 (d, J=5.2 Hz, 1H), 7.38-7.24 (m, 11H), 6.05 (br d, J=6.8 Hz, 1H), 5.22 (s, 2H), 5.16-5.08 (m, 2H), 4.68-4.57 (m, 1H), 4.00-3.82 (m, 2H).

Step 4: (R)-2-amino-3-(7-bromothieno[3,2-b]pyridine-2-carboxamido)propanoic acid

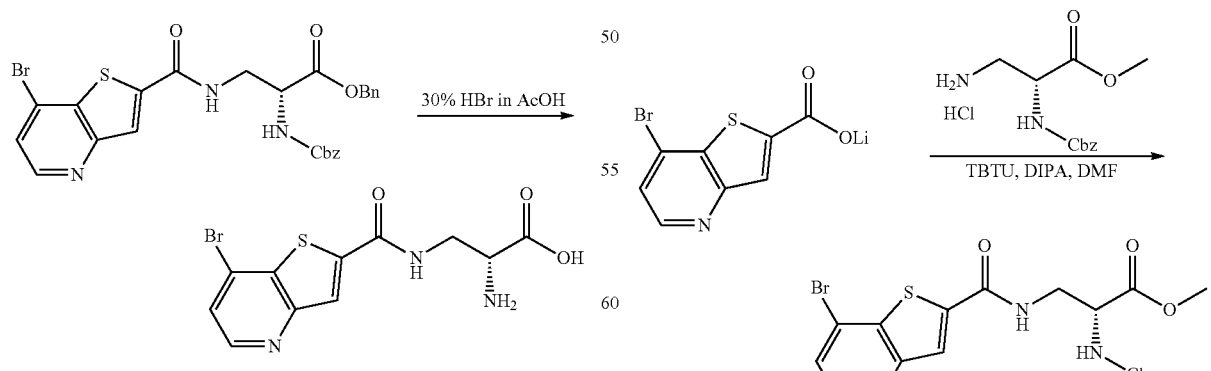

A mixture of benzyl (R)-2-(((benzyloxy)carbonyl)amino)-3-(7-bromothieno[3,2-b]pyridine-2-carboxamido)propanoate (100 mg, 0.18 mmol) and 30% HBr in AcOH (3 mL) was stirred at 25° C. for 16 h. The mixture was concentrated. The residue was added water (5 mL) and washed with methyl tert-butyl ether (5 mL×2). The aqueous layer was lyophilized to give (R)-2-amino-3-(7-bromothieno[3,2-b]pyridine-2-carboxamido)propanoic acid (75 mg) as HBr salt.

$^1$H NMR (400 MHz, DMSO-d$_6$) δ 9.28 (t, J=5.6 Hz, 1H), 8.64 (d, J=4.8 Hz, 1H), 8.41 (s, 1H), 8.36 (br d, J=4.0 Hz, 3H), 7.84 (d, J=4.8 Hz, 1H), 4.19-4.12 (m, 1H), 3.88-3.80 (m, 1H), 3.77-3.69 (m, 1H).

LCMS (MH+): m/z=343.9, t$_R$ (min, Method BB)=0.34. [α]$^{20}$D=−4.8 (c=3.2 mg/mL, CH$_3$OH).

Compound 2u

Methyl (R)-2-amino-3-(7-bromothieno[3,2-b]pyridine-2-carboxamido)propanoate

The overall synthesis scheme for the preparation of methyl (R)-2-amino-3-(7-bromothieno[3,2-b]pyridine-2-carboxamido)propanoate is shown below.

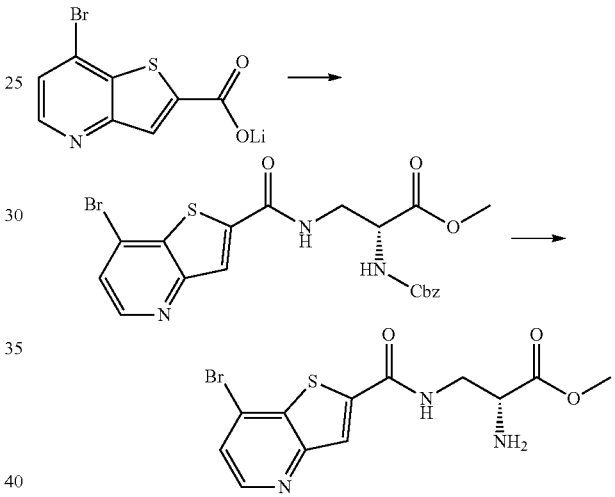

Step 1: Methyl (R)-2-(((benzyloxy)carbonyl)amino)-3-(7-bromothieno[3,2-b]pyridine-2-carboxamido)propanoate To a solution of lithium 7-bromothieno[3,2-b]pyridine-2-carboxylate (400 mg, 1.52 mmol) in DMF (10 mL) was added TBTU (730 mg, 2.27 mmol), N,N-diisopropylethylamine (392 mg, 3.03 mmol) and methyl (R)-3-amino-2-(((benzyloxy)carbonyl)amino)propanoate (437 mg, 1.52 mmol, HCl salt). The mixture was stirred at 25° C. for 3 h. The mixture was diluted with water (15 mL) and extracted with ethyl acetate (20 mL×3). The combined organic layers were washed with brine (20 mL×3), dried over anhydrous sodium sulfate, filtered and concentrated. The residue was purified by Combi Flash on silica gel (petroleum ether:ethyl acetate with ethyl acetate from 0 to 80%) three times to give compound methyl (R)-2-(((benzyloxy)carbonyl)amino)-3-(7-bromothieno[3,2-b]pyridine-2-carboxamido)propanoate (350 mg).

$^1$H NMR (400 MHz, DMSO-$d_6$) δ 9.12 (br t, J=5.6 Hz, 1H), 8.63 (d, J=4.8 Hz, 1H), 8.34 (s, 1H), 7.87-7.78 (m, 2H), 7.37-7.23 (m, 5H), 5.09-4.99 (m, 2H), 4.42-4.34 (m, 1H), 3.75-3.58 (m, 5H).

Step 2: methyl (R)-2-amino-3-(7-bromothieno[3,2-b]pyridine-2-carboxamido)propanoate

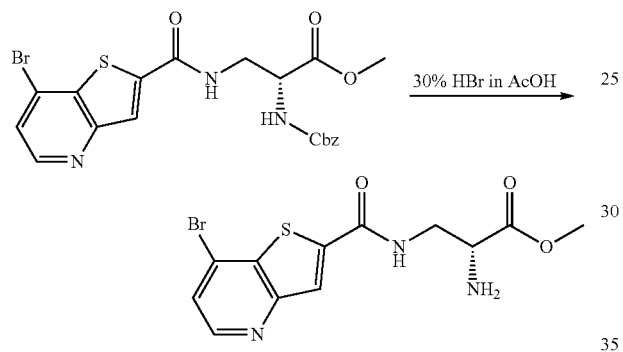

A mixture of methyl (R)-2-(((benzyloxy)carbonyl)amino)-3-(7-bromothieno[3,2-b]pyridine-2-carboxamido)propanoate (340 mg, 0.69 mmol) in 30% HBr in AcOH (5 mL) was stirred at 25° C. for 1 hour. The mixture was concentrated. The residue was added MeOH (2 mL) and then methyl tert-butyl ether (6 mL). The mixture was filtered and the solid was collected and dried to give methyl (R)-2-amino-3-(7-bromothieno[3,2-b]pyridine-2-carboxamido)propanoate (230 mg) as HBr salt.

$^1$H NMR (400 MHz, DMSO-$d_6$) δ 9.28 (t, J=5.6 Hz, 1H), 8.64 (d, J=5.2 Hz, 1H), 8.49 (br s, 3H), 8.40 (s, 1H), 7.84 (d, J=4.8 Hz, 1H), 4.31-421 (m, 1H), 3.86-3.71 (m, 5H).

LCMS (MH+): m/z=358, $t_R$ (min, Method BB)=0.39.
[α]$^{20}$D=2.9 (c=3.5 mg/mL, CH$_3$OH).

Compound 1i (R)-2-amino-3-(7-(hydroxymethyl)thieno[3,2-b]pyridine-2-carboxamido)propanoic acid The overall synthesis scheme for the preparation of (R)-2-amino-3-(7-(hydroxymethyl)thieno[3,2-b]pyridine-2-carboxamido)propanoic acid is shown below.

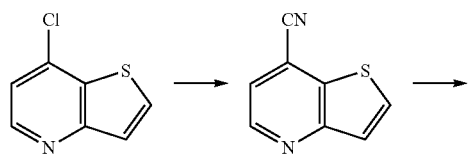

Step 1: thieno[3,2-b]pyridine-7-carbonitrile

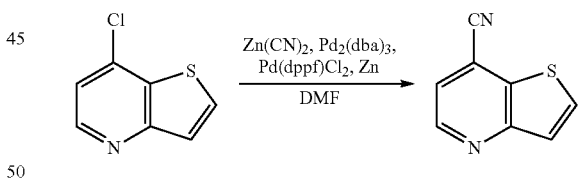

To a solution of 7-chlorothieno[3,2-b]pyridine (5 g, 29.48 mmol) and Zn(CN)$_2$ (3.77 g, 32.1 mmol) in DMF (50 mL) was added Pd$_2$(dba)$_3$ (2.70 g, 2.95 mmol), Pd(dppf)Cl$_2$ (2.16 g, 2.95 mmol) and Zn power (385 mg, 5.90 mmol) under N$_2$ atmosphere. The mixture was stirred at 120° C. for 2 h. The mixture was diluted with ethyl acetate (80 mL) and water (50 mL) and filtered through Celite. The filtrate was extracted with ethyl acetate (60 mL×2). The combined organic layers were washed with brine (50 mL×3) and concentrated. The residue was purified by Combi Flash on silica gel (petroleum ether:ethyl acetate with ethyl acetate from 0 to 20%) to give thieno[3,2-b]pyridine-7-carbonitrile (2.8 g).

$^1$H NMR (400 MHz, CDCl$_3$) δ 8.85 (d, J=4.8 Hz, 1H), 7.94 (d, J=5.6 Hz, 1H), 7.68 (d, J=5.6 Hz, 1H), 7.54 (d, J=4.8 Hz, 1H).

Step 2: methyl thieno[3,2-b]pyridine-7-carboxylate

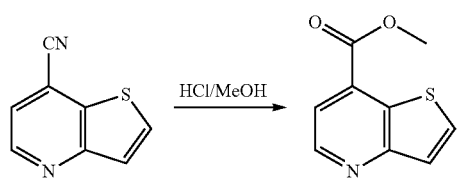

A mixture of thieno[3,2-b]pyridine-7-carbonitrile (2.8 g, 17.5 mmol) and HCl/MeOH (4 M, 50 mL) was stirred at 70° C. for 16 h. The mixture was concentrated. The residue was added water (10 mL) and pH adjusted to 8 with aqueous 2N NaOH solution. The mixture was extracted with ethyl acetate (30 mL×3). The organic layer was dried over anhydrous sodium sulfate, filtered and concentrated. The residue was purified by Combi Flash on silica gel (petroleum ether:ethyl acetate with ethyl acetate from 0 to 35%) to give compound methyl thieno[3,2-b]pyridine-7-carboxylate (2.7 g).
$^1$H NMR (400 MHz, CDCl$_3$) δ 8.84 (d, J=4.8 Hz, 1H), 7.89 (d, J=5.6 Hz, 1H), 7.86 (d, J=4.8 Hz, 1H), 7.63 (d, J=5.6 Hz, 1H), 4.07 (s, 3H).

Step 3: thieno[3,2-b]pyridin-7-ylmethanol

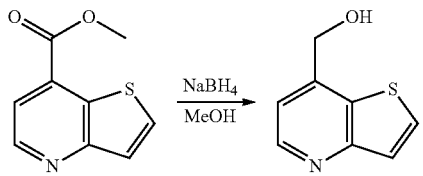

To a solution of methyl thieno[3,2-b]pyridine-7-carboxylate (2.7 g, 14 mmol) in MeOH (30 mL) was added NaBH$_4$ (793 mg, 21 mmol). The mixture was stirred at 25° C. for 3 h. The mixture was concentrated. The residue was added water (20 mL) and extracted with ethyl acetate (20 mL×3). The combined organic layers were dried over anhydrous sodium sulfate, filtered and concentrated to give thieno[3,2-b]pyridin-7-ylmethanol (2.1 g).
$^1$H NMR (400 MHz, DMSO-d$_6$) δ 8.62 (d, J=4.4 Hz, 1H), 8.10 (d, J=5.6 Hz, 1H), 7.57 (d, J=6.0 Hz, 1H), 7.32 (d, J=4.8 Hz, 1H), 5.77 (t, J=5.6 Hz, 1H), 4.82 (d, J=5.6 Hz, 2H).

Step 4: lithium 7-(hydroxymethyl)thieno[3,2-b]pyridine-2-carboxylate

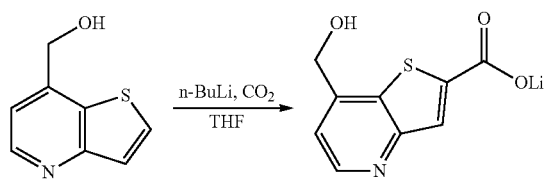

To a solution of thieno[3,2-b]pyridin-7-ylmethanol (500 mg, 3.03 mmol) in THF (20 mL) was added n-BuLi (2.5 M in hexane, 2.4 mL) dropwise at −70° C. and stirred at −70° C. for 30 min. Then gaseous carbon dioxide (15 psi) was bubbled through the reaction solution for 30 min and the mixture was allowed to warm to 25° C. over a period of 2 h. The mixture was filtered and the filter cake was washed with THF (10 mL×2). The solid was collected and dried to give compound lithium 7-(hydroxymethyl)thieno[3,2-b]pyridine-2-carboxylate (700 mg).

Step 5: benzyl (R)-2-(((benzyloxy)carbonyl)amino)-3-(7-(hydroxymethyl)thieno[3,2-b]pyridine-2-carboxamido)propanoate

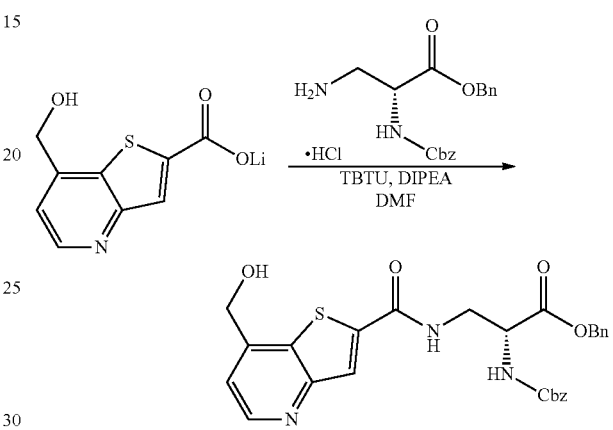

To a solution of lithium 7-(hydroxymethyl)thieno[3,2-b]pyridine-2-carboxylate (200 mg, crude) in DMF (10 mL) was added O-(Benzotriazol-1-yl)-N,N,N',N'-tetramethyluronium tetrafluoroborate (448 mg, 1.39 mmol), N,N-diisopropylethylamine (360 mg, 2.79 mmol) and benzyl (R)-3-amino-2-(((benzyloxy)carbonyl)amino)propanoate (339 mg, 0.93 mmol, HCl salt). The mixture was stirred at 25° C. for 2 h. The mixture was diluted with water (15 mL) and extracted with ethyl acetate (20 mL×3). The combined organic layers were washed with brine (20 mL×3), dried over anhydrous sodium sulfate, filtered and concentrated. The residue was purified by Combi Flash on silica gel (DCM: MeOH with MeOH from 0 to 10%) to give 200 mg crude product. The crude product was further purified by preparative-HPLC (Method O) to give compound benzyl (R)-2-(((benzyloxy)carbonyl)amino)-3-(7-(hydroxymethyl)thieno[3,2-b]pyridine-2-carboxamido)propanoate (100 mg).
$^1$H NMR (400 MHz, DMSO-d$_6$) δ 9.01 (br t, J=5.6 Hz, 1H), 8.69 (d, J=4.8 Hz, 1H), 8.16 (s, 1H), 7.88 (d, J=8.0 Hz, 1H), 7.39 (d, J=4.8 Hz, 1H), 7.36-7.22 (m, 10H), 5.86 (t, J=5.6 Hz, 1H), 5.15-5.00 (m, 4H), 4.83 (d, J=5.2 Hz, 2H), 4.48-4.37 (m, 1H), 3.76-3.58 (m, 2H).

Step 6: (R)-2-amino-3-(7-(hydroxymethyl)thieno[3,2-b]pyridine-2-carboxamido)propanoic acid

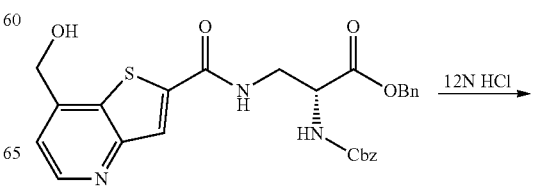

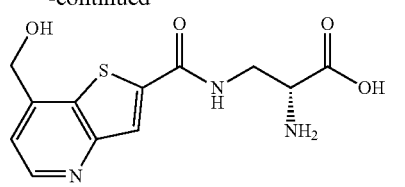

A mixture of benzyl (R)-2-(((benzyloxy)carbonyl)amino)-3-(7-(hydroxymethyl)thieno[3,2-b]pyridine-2-carboxamido)propanoate (60 mg, 0.12 mmol) and 12M aq. HCl (12 M, 4 mL) was stirred at 80° C. for 2 h. The residue was purified by preparative-HPLC (Method Q) to give compound (R)-2-amino-3-(7-(hydroxymethyl)thieno[3,2-b]pyridine-2-carboxamido)propanoic acid (18 mg) as HCl salt.

$^1$H NMR (400 MHz, D$_2$O) δ 8.82 (d, J=6.0 Hz, 1H), 8.20 (s, 1H), 7.85 (d, J=6.0 Hz, 1H), 5.22 (s, 2H), 4.18-4.14 (m, 1H), 4.06-3.99 (m, 1H), 3.94-3.86 (m, 1H).

LCMS (MH+): m/z=296.1, t$_R$ (min, Method BB)=0.26.

[α]$^{20}$D=5.0 (c=1.2 mg/mL, CH$_3$OH).

Compound 2v

Methyl (R)-2-amino-3-(7-(hydroxymethyl)thieno[3,2-b]pyridine-2-carboxamido) propanoate The overall synthesis scheme for the preparation of methyl (R)-2-amino-3-(7-(hydroxymethyl)thieno[3,2-b]pyridine-2-carboxamido) propanoate is shown below.

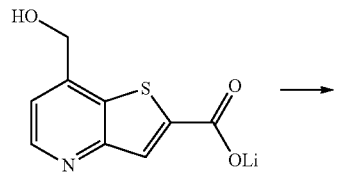

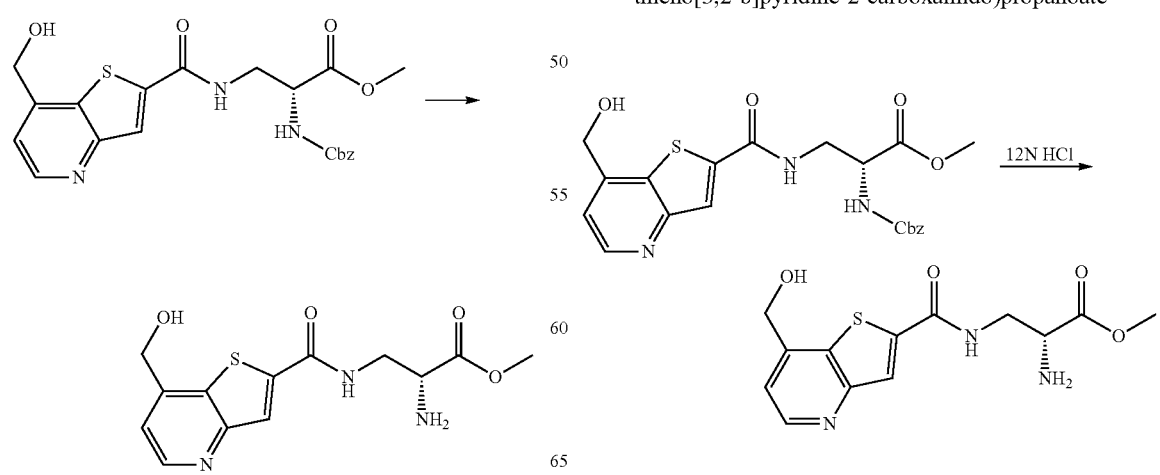

Step 1: Methyl (R)-2-(((benzyloxy)carbonyl)amino)-3-(7-(hydroxymethyl)thieno[3,2-b]pyridine-2-carboxamido)propanoate

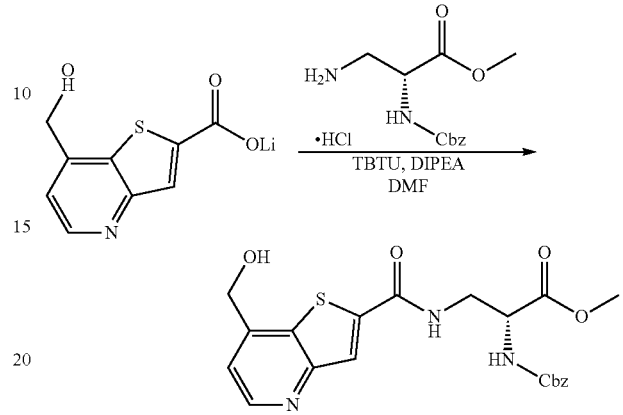

To a solution of lithium 7-(hydroxymethyl)thieno[3,2-b]pyridine-2-carboxylate (600 mg, crude) in DMF (15 mL) was added TBTU (1.07 g, 3.35 mmol), N,N-diisopropylethylamine (1.08 g, 8.37 mmol) and methyl (R)-3-amino-2-(((benzyloxy)carbonyl)amino)propanoate (806 mg, 2.79 mmol, HCl salt). The mixture was stirred at 25° C. for 2 h. The mixture was diluted with water (20 mL) and extracted with ethyl acetate (25 mL×3). The combined organic layers were washed with brine (20 mL×3), dried over anhydrous sodium sulfate, filtered and concentrated. The mixture was purified by Combi Flash on silica gel (DCM: MeOH with MeOH from 0 to 10%) to give 600 mg crude product. The crude product was further purified by preparative-HPLC (Method M) to give compound methyl (R)-2-(((benzyloxy)carbonyl)amino)-3-(7-(hydroxymethyl)thieno[3,2-b]pyridine-2-carboxamido)propanoate (200 mg).

$^1$H NMR (400 MHz, DMSO-d$_6$) δ 9.00 (br t, J=6.0 Hz, 1H), 8.68 (d, J=4.8 Hz, 1H), 8.18 (s, 1H), 7.81 (d, J=8.0 Hz, 1H), 7.39 (d, J=4.8 Hz, 1H), 7.36-7.20 (m, 5H), 5.86 (t, J=5.6 Hz, 1H), 5.11-4.96 (m, 2H), 4.83 (d, J=5.2 Hz, 2H), 4.41-4.31 (m, 1H), 3.72-3.54 (m, 5H).

Step 2: Methyl (R)-2-amino-3-(7-(hydroxymethyl)thieno[3,2-b]pyridine-2-carboxamido)propanoate A mixture of methyl (R)-2-(((benzyloxy)carbonyl)amino)-3-(7-(hydroxymethyl)thieno[3,2-b]pyridine-2-carboxamido)propanoate (90 mg, 0.20 mmol) in 12 N HCl (10 mL) was stirred at 25° C. for 2 h. The mixture was concentrated in vacuo and lyophilized. The residue was then added HCl/MeOH (4M, 15 mL) and stirred at 25° C. for 2 h. The mixture was concentrated. The residue was purified by preparative-HPLC (Method M) to give compound methyl (R)-2-amino-3-(7-(hydroxymethyl)thieno[3,2-b]pyridine-2-carboxamido)propanoate (25 mg) as HCl salt.

$^1$H NMR (400 MHz, DMSO-d$_6$) δ 9.50 (br t, J=6.0 Hz, 1H), 8.79 (d, J=4.8 Hz, 1H), 8.71 (br s, 3H), 8.42 (s, 1H), 7.54 (d, J=4.8 Hz, 1H), 4.92 (s, 2H), 4.30-4.21 (m, 1H).

LCMS (MH+): m/z=310.1, $t_R$ (min, Method BB)=0.03 min.

[α]$^{20}$D=−1.8 (c=4.5 mg/mL, CH$_3$OH).

Compound 1J (R)-2-amino-3-(7-(fluoromethyl)thieno[3,2-b]pyridine-2-carboxamido)propanoic acid The overall synthesis scheme for the preparation of (R)-2-amino-3-(7-(fluoromethyl)thieno[3,2-b]pyridine-2-carboxamido)propanoic acid is shown below.

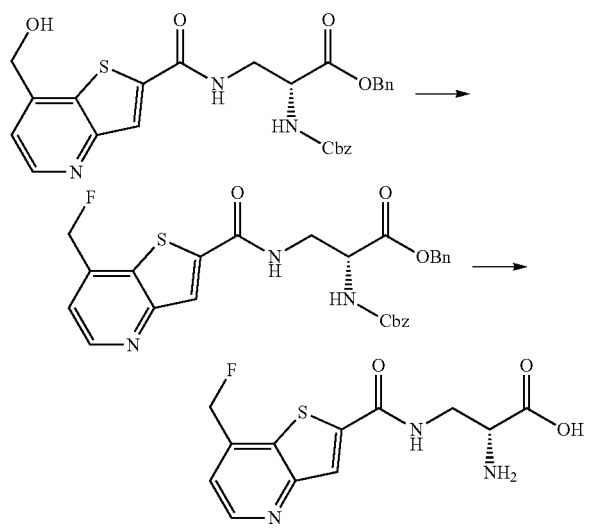

Step 1: benzyl (R)-2-(((benzyloxy)carbonyl)amino)-3-(7-(fluoromethyl)thieno[3,2-b]pyridine-2-carboxamido)propanoate

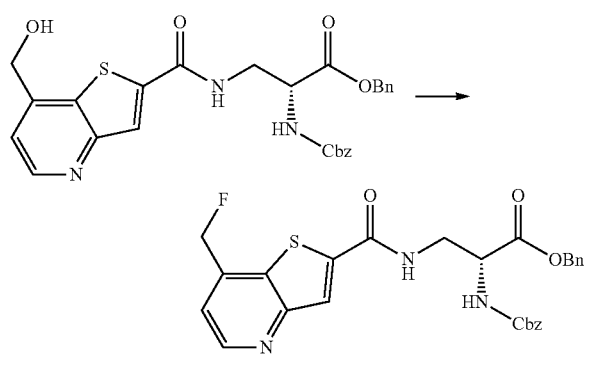

To a solution of benzyl (R)-2-(((benzyloxy)carbonyl)amino)-3-(7-(hydroxymethyl)thieno[3,2-b]pyridine-2-carboxamido)propanoate (100 mg, 0.19 mmol) in DCM (5 mL) was added DAST (62 mg, 0.38 mmol). The mixture was stirred at 20° C. for 1 hour. The reaction was quenched with water (1 mL) and concentrated. The residue was added water (10 mL), pH adjusted to 8 with 2N NaOH solution and extracted with ethyl acetate (20 mL×3). The combined organic layers were concentrated. The residue was purified by Combi Flash on silica gel (petroleum ether:ethyl acetate with ethyl acetate from 0 to 100%) to give compound benzyl (R)-2-(((benzyloxy)carbonyl)amino)-3-(7-(fluoromethyl)thieno[3,2-b]pyridine-2-carboxamido)propanoate (25 mg).

$^1$H NMR (400 MHz, CDCl$_3$) δ 8.80 (s, 1H), 8.02 (s, 1H), 7.43-7.30 (m, 12H), 6.11 (br d, J=6.4 Hz, 1H), 5.71 (d, J=46.4 Hz, 2H), 5.23 (s, 2H), 5.13 (s, 2H), 4.69-4.61 (m, 1H), 4.00-3.96 (m, 2H).

Step 2: (R)-2-amino-3-(7-(fluoromethyl)thieno[3,2-b]pyridine-2-carboxamido)propanoic acid

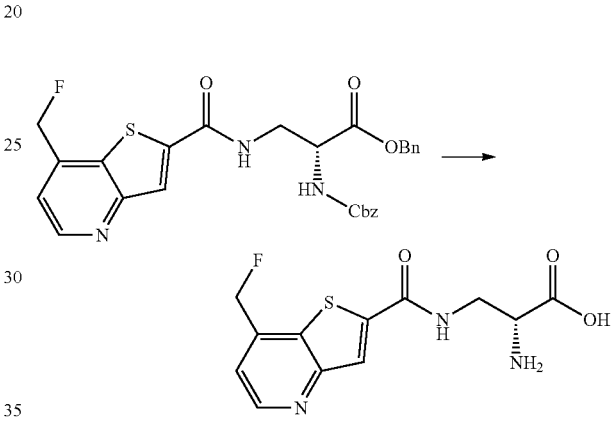

A mixture of benzyl (R)-2-(((benzyloxy)carbonyl)amino)-3-(7-(fluoromethyl)thieno[3,2-b]pyridine-2-carboxamido)propanoate (25 mg, 0.05 mmol) and 30% HBr in AcOH (3 mL) was stirred at 50° C. for 3 h. The mixture was concentrated. The residue was purified by preparative-HPLC (Method R) to give compound (R)-2-amino-3-(7-(fluoromethyl)thieno[3,2-b]pyridine-2-carboxamido)propanoic acid (9 mg) as HCl salt.

$^1$H NMR (400 MHz, DMSO-d$_6$) δ 9.44 (t, J=6.0 Hz, 1H), 8.80 (d, J=4.8 Hz, 1H), 8.54 (br d, J=3.6 Hz, 3H), 8.44 (s, 1H), 7.51 (d, J=4.4 Hz, 1H), 5.87 (d, J=46.0 Hz, 2H), 4.20-4.11 (m, 1H), 3.86-3.80 (m, 2H).

LCMS (MH+): m/z=298.1, $t_R$ (min, Method BB)=0.26.

Compound 2w

Methyl(R)-2-amino-3-(7-(fluoromethyl)thieno[3,2-b]pyridine-2-carboxamido)propanoate The overall synthesis scheme for the preparation of methyl (R)-2-amino-3-(7-(fluoromethyl)thieno[3,2-b]pyridine-2-carboxamido)propanoate is shown below.

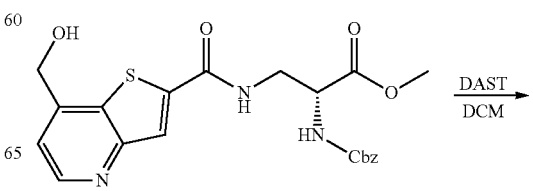

113

-continued

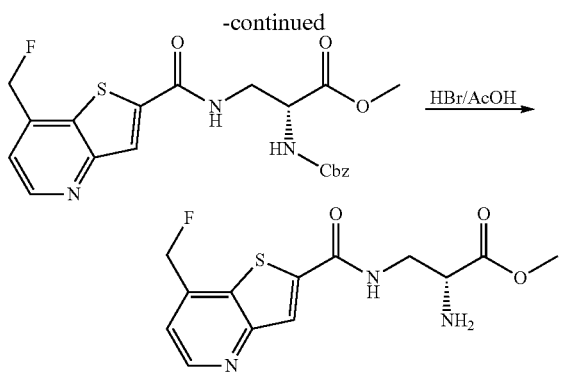

Step 1: Methyl (R)-2-(((benzyloxy)carbonyl)amino)-3-(7-(fluoromethyl)thieno[3,2-b]pyridine-2-carboxamido)propanoate

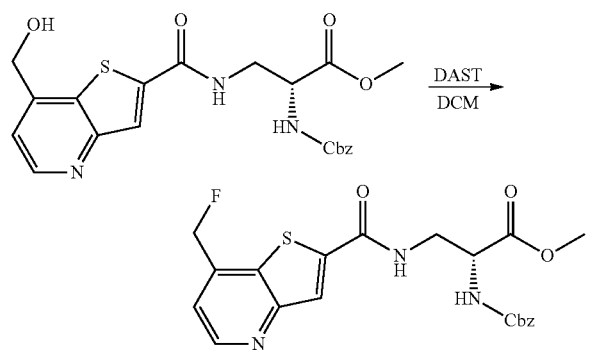

To a solution of methyl (R)-2-amino-3-(7-(hydroxymethyl)thieno[3,2-b]pyridine-2-carboxamido)propanoate (100 mg, 0.23 mmol) in DCM (8 mL) was added DAST (73 mg, 0.45 mmol). The mixture was stirred at 20° C. for 1 hour. The reaction was quenched with water (1 mL) and concentrated. The residue was added water (10 mL) and pH adjusted to 8 with 2N NaOH solution and extracted with ethyl acetate (20 mL×3). The combined organic layers were concentrated. The residue was purified by Combi Flash on silica gel (petroleum ether: ethyl acetate with ethyl acetate from 0 to 100%) to give compound methyl (R)-2-(((benzyloxy)carbonyl)amino)-3-(7-(fluoromethyl)thieno[3,2-b]pyridine-2-carboxamido)propanoate (25 mg).

$^1$H NMR (400 MHz, CDCl$_3$) δ 8.79 (d, J=4.8 Hz, 1H), 8.09 (s, 1H), 7.62 (br, 1H), 7.38 (d, J=4.8 Hz, 1H), 7.36-7.27 (m, 5H), 6.20 (br, 1H), 5.70 (d, J=46.4 Hz, 2H), 5.13 (s, 2H), 4.66-4.57 (m, 1H), 3.99-3.85 (m, 2H), 3.82 (s, 3H).

Step 2: methyl (R)-2-amino-3-(7-(fluoromethyl)thieno[3,2-b]pyridine-2-carboxamido)propanoate

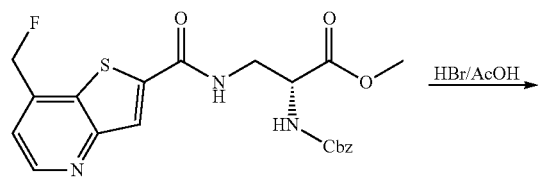

114

-continued

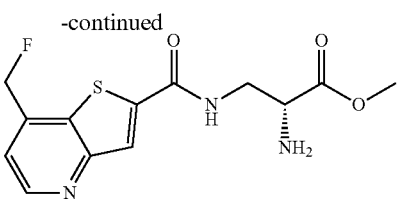

A mixture of methyl 2-(((benzyloxy)carbonyl)amino)-3-(7-(fluoromethyl)thieno[3,2-b]pyridine-2-carboxamido)propanoate (20 mg, 0.045 mmol) in 30% HBr in AcOH (3 mL) was stirred at 20° C. for 1 hour. The mixture was concentrated. The residue was purified by preparative-HPLC (Method P) to give compound methyl (R)-2-amino-3-(7-(fluoromethyl)thieno[3,2-b]pyridine-2-carboxamido)propanoate (9 mg, 52% yield) as HCl salt.

$^1$H NMR (400 MHz, DMSO-d$_6$) δ 9.41 (br, 1H), 8.80 (d, J=4.4 Hz, 1H), 8.66 (br s, 3H), 8.40 (s, 1H), 7.50 (d, J=4.8 Hz, 1H), 5.86 (d, J=46.4 Hz, 2H), 4.30-4.31 (m, 1H), 3.84-3.77 (m, 2H), 3.74 (s, 3H).

LCMS (MH+): m/z=312, $t_R$ (min, Method BB)=0.31.

[α]$^{20}$D=2.0 (c=1.0 mg/mL, CH$_3$OH).

Compound 1k (R)-2-amino-3-(6-fluoro-7-methylthieno[3,2-b]pyridine-2-carboxamido)propanoic acid The overall synthesis scheme for the preparation of (R)-2-amino-3-(6-fluoro-7-methylthieno[3,2-b]pyridine-2-carboxamido)propanoic acid is shown below.

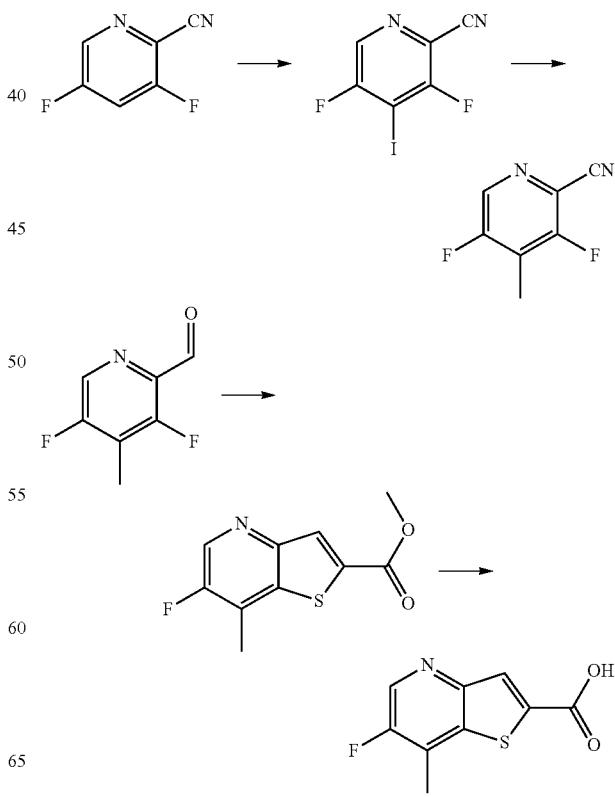

-continued

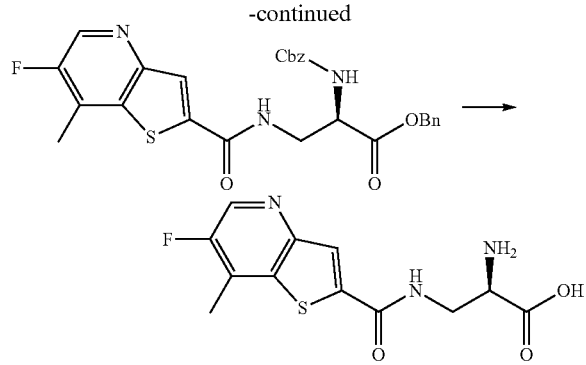

Step 1: 3,5-difluoro-4-iodopicolinonitrile

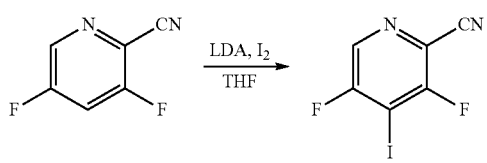 [SMILES: N#Cc1ncc(F)cc1F ; N#Cc1ncc(F)c(I)c1F ; "THF"]

To a solution of diisopropylamine (4.30 g, 42 mmol) in THF (50 mL) was added n-BuLi (17 mL, 2.5 M in hexane) at −78° C. and the reaction was stirred at −78° C. for 0.5 h. A solution of 3,5-difluoropicolinonitrile (5 g, 36 mmol) in THF (50 mL) was added at −78° C. and the reaction mixture stirred at −78° C. for 0.5 h. $I_2$ (9.51 g, 37.5 mmol) was added in portions at −78° C. and the resulting mixture was stirred at −78° C. for 1 hour. water (50 mL) was added to quench the reaction. The mixture was extracted with ethyl acetate (100 mL×3). The combined organic layers were washed with brine (50 mL×2), dried over anhydrous sodium sulfate, filtered and concentrated. The residue was purified by Combi flash (silica gel, petroleum ether/ethyl acetate with ethyl acetate from 030%) to give 3,5-difluoro-4-iodopicolinonitrile (4.5 g).
$^1$H NMR (400 MHz, $CDCl_3$) δ 8.28 (s, 1H).

Step 2: 3,5-difluoro-4-methylpicolinonitrile

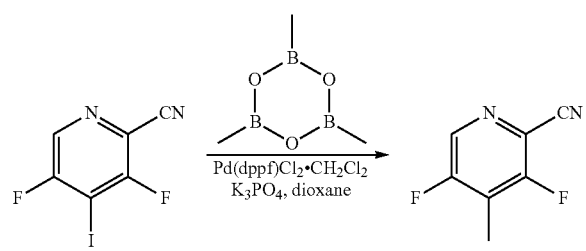

A mixture of 3,5-difluoro-4-iodopicolinonitrile (2 g, 7.52 mmol), 2,4,6-trimethyl-1,3,5,2,4,6-trioxatriborinane (5.39 g, 42.92 mmol), $Pd(dppf)Cl_2 \cdot CH_2Cl_2$ (1.84 g, 2.26 mmol) and $K_3PO_4$ (3.20 g, 15.08 mmol) in dioxane (10 mL) was degassed and purged with $N_2$ for 3 times, and then the mixture was stirred at 120° C. for 10 h under $N_2$ atmosphere. Water (10 ml) was added to the reaction and extracted with ethyl acetate (15 mL×3). The combined organic layers were washed with brine (15 mL×2), dried over anhydrous sodium sulfate, filtered and concentrated. The residue was purified by Combi flash (silica gel, petroleum ether/ethyl acetate with ethyl acetate from 020%) to give 900 mg crude product. The crude product was further purified by preparative HPLC (Method N) to give 3,5-difluoro-4-methylpicolinonitrile (270 mg).

Step 3: 3,5-difluoro-4-methylpicolinaldehyde

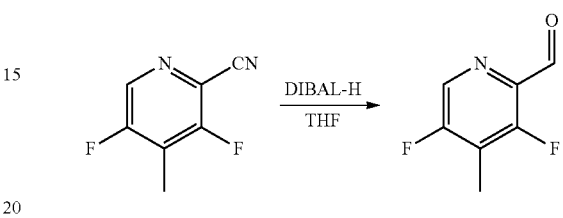

To a stirred solution of 3,5-difluoro-4-methylpicolinonitrile (270 mg, 1.75 mmol) in THF (10 mL) was added diisobutylaluminium hydride (DIBAL-H) (2.30 mL, 1M in toluene, 2.30 mmol) at −20° C. and the mixture was stirred at −20° C. for 1 hour. Water (10 mL) was added to quench the reaction and 1N HCl was added to adjust the pH to 5-6. The reaction mixture was extracted with ethyl acetate (15 mL×3). The combined organic layers were washed with brine (20 mL), dried over anhydrous sodium sulfate, filtered and concentrated to give 3,5-difluoro-4-methylpicolinaldehyde (270 mg).

Step 4: methyl 6-fluoro-7-methylthieno[3,2-b]pyridine-2-carboxylate

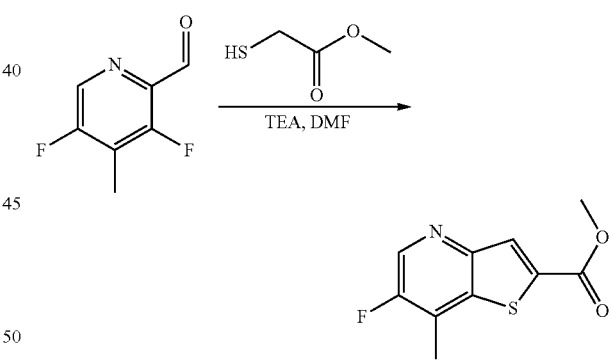

To a solution of 3,5-difluoro-4-methylpicolinaldehyde (270 mg, crude) in DMF (5 mL) was added slowly TEA (349 mg, 3.45 mmol) and methyl 2-mercaptoacetate (300 mg, 2.83 mmol) and the mixture was stirred at 100° C. for 3 h. Water (5 ml) was added and the mixture was extracted with ethyl acetate (5 mL×3). The combined organic layers were washed with brine (5 mL×2), dried over anhydrous sodium sulfate, filtered and concentrated. The residue was purified by Combi flash (silica gel, petroleum ether/ethyl acetate with ethyl acetate from 050%) to give the crude compound (200 mg). The crude compound was further purified by preparative HPLC (Method S) to give methyl 6-fluoro-7-methylthieno[3,2-b]pyridine-2-carboxylate (40 mg).
$^1$H NMR (400 MHz, $CDCl_3$) δ 8.59 (s, 1H), 8.20 (d, J=1.2 Hz, 1H), 3.99 (s, 3H), 2.55 (s, 3H).

Step 5: 6-fluoro-7-methylthieno[3,2-b]pyridine-2-carboxylic acid

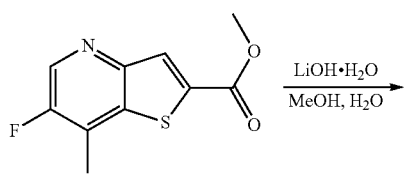

To a solution of methyl 6-fluoro-7-methylthieno[3,2-b]pyridine-2-carboxylate (40 mg, 177.59 μmol) in MeOH (4 mL) was added a solution LiOH.H₂O (22 mg, 524.26 μmol) in water (1 mL) and the resulting mixture was stirred at 30° C. for 2 h. The solvent was removed. Water (2 mL) was added, acidified with sat. KHSO₄ solution to pH 34 and extracted with ethyl acetate (10 mL×5). The combined organic layers were washed with brine (5 mL), dried over anhydrous sodium sulfate, filtered and concentrated to give 6-fluoro-7-methylthieno[3,2-b]pyridine-2-carboxylic acid (25 mg).

LC-MS: $t_R$=1.267 min, m/z=212.0[M+H]⁺.

Step 6: benzyl (R)-2-(((benzyloxy)carbonyl)amino)-3-(6-fluoro-7-methylthieno[3,2-b]pyridine-2-carboxamido)propanoate

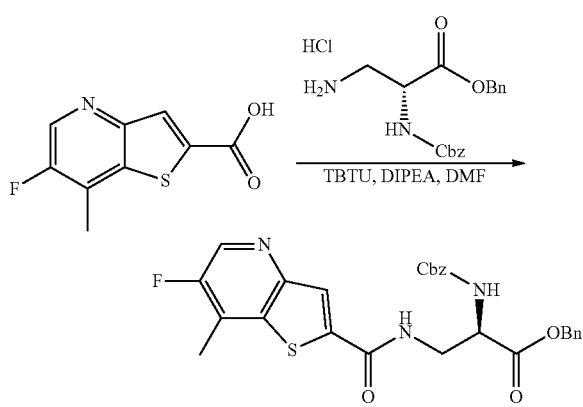

A mixture of 6-fluoro-7-methylthieno[3,2-b]pyridine-2-carboxylic acid (25 mg, 118 μmol), benzyl (R)-3-amino-2-(((benzyloxy)carbonyl)amino)propanoate (52 mg, 142 μmol, HCl salt), O-(Benzotriazol-1-yl)-N,N,N',N'-tetramethyluronium tetrafluoroborate (57 mg, 177 μmol) and N,N-diisopropylethylamine (31 mg, 241 μmol) in DMF (2 mL) was stirred at 30° C. for 4 h. Water (2 ml) was added to quench the reaction and the mixture was extracted with ethyl acetate (5 mL×3). The combined organic layers were washed with brine (5 mL×2), dried over anhydrous sodium sulfate, filtered and concentrated. The residue was purified by preparative TLC (SiO₂, Ethyl acetate:Petroleum ether=1:1) to give benzyl (R)-2-(((benzyloxy)carbonyl)amino)-3-(6-fluoro-7-methylthieno[3,2-b]pyridine-2-carboxamido)propanoate (25 mg).

¹H NMR (400 MHz, CDCl₃) δ 8.53 (s, 1H), 7.78 (s, 1H), 7.40-7.27 (m, 10H), 6.08 (br d, J=5.6 Hz, 1H), 5.30 (s, 1H), 5.21 (s, 2H), 5.11 (s, 2H), 4.69-4.55 (m, 1H), 3.92-3.85 (m, 2H), 2.52 (s, 3H).

Step 7: (R)-2-amino-3-(6-fluoro-7-methylthieno[3,2-b]pyridine-2-carboxamido)propanoic acid as HBr salt

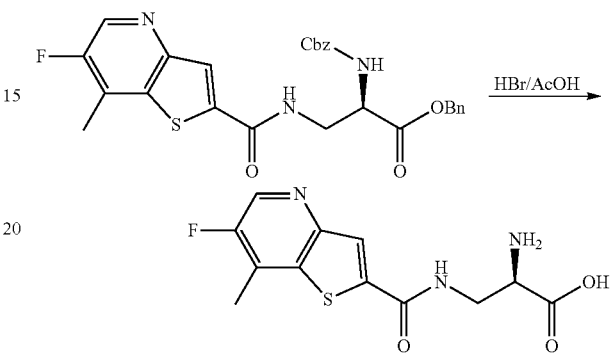

A mixture of benzyl (R)-2-(((benzyloxy)carbonyl)amino)-3-(6-fluoro-7-methylthieno[3,2-b]pyridine-2-carboxamido)propanoate (25 mg, 48 μmol) and 33% HBr in AcOH (2 mL) was stirred at 50° C. for 16 h. The solvent was removed. The residue was washed with TBME (5 mL×3), the solid was filtered and the residual solvent removed by lyophilization to give (R)-2-amino-3-(6-fluoro-7-methylthieno[3,2-b]pyridine-2-carboxamido)propanoic acid (16 mg) as HBr salt.

¹H NMR (400 MHz, DMSO-d₆) δ 9.18 (t, J=5.6 Hz, 1H), 8.71 (d, J=1.6 Hz, 1H), 8.41-8.26 (m, 3H), 8.26 (s, 1H), 4.21-4.09 (m 1H), 3.86-3.78 (m, 1H), 3.76-3.67 (m, 1H), 2.50 (s, 3H).

LCMS (MH+): m/z=298, $t_R$ (min, Method BB)=0.34.

[α]²⁰D=−16.00 (c=2 mg/mL, MeOH).

Compound 2x

Methyl (R)-2-amino-3-(6-fluoro-7-methylthieno[3,2-b]pyridine-2-carboxamido)propanoate The overall synthesis scheme for the preparation of methyl (R)-2-amino-3-(6-fluoro-7-methylthieno[3,2-b]pyridine-2-carboxamido)propanoate is shown below.

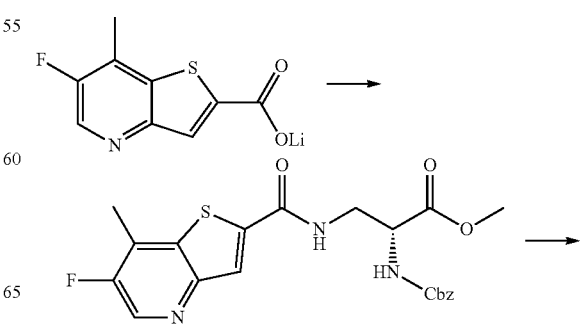

Step 1: methyl(R)-2-(((benzyloxy)carbonyl)amino)-3-(6-fluoro-7-methylthieno[3,2-b]pyridine-2-carboxamido)propanoate

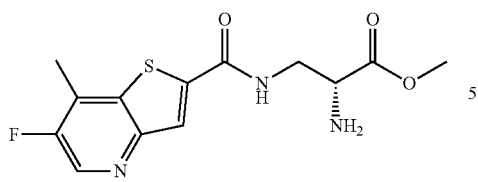

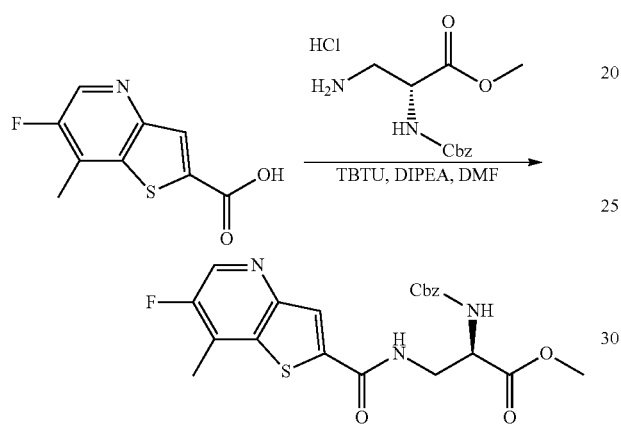

A mixture of 6-fluoro-7-methylthieno[3,2-b]pyridine-2-carboxylic acid (70 mg, 331.42 µmol), methyl (R)-3-amino-2-(((benzyloxy)carbonyl)amino)propanoate (115 mg, 0.4 mmol, HCl salt), TBTU (160 mg, 0.5 mmol) and N,N-diisopropylethylamine (89 mg, 0.69 mmol) in DMF (5 mL) was stirred at 30° C. for 16 h. Water (5 ml) was added to quench the reaction and extracted with ethyl acetate (10 mL×3). The combined organic layers were washed with brine (10 mL×2), dried over anhydrous sodium sulfate, filtered and concentrated. The residue was purified by preparative TLC (SiO2, Ethyl acetate:Petroleum ether=1:1) to give methyl (R)-2-(((benzyloxy)carbonyl)amino)-3-(6-fluoro-7-methylthieno[3,2-b]pyridine-2-carboxamido)propanoate (70 mg).

$^{1}$H NMR (400 MHz, CDCl$_3$) δ 8.46 (s, 1H), 7.80 (s, 1H), 7.41-7.19 (m, 6H), 6.01-5.85 (m, 1H), 5.05 (s, 2H), 4.59-4.41 (m, 1H), 3.95-3.76 (m, 2H), 3.73 (s, 3H), 2.45 (s, 3H).

Step 2: Methyl(R)-2-amino-3-(6-fluoro-7-methylthieno[3,2-b]pyridine-2-carboxamido)propanoate

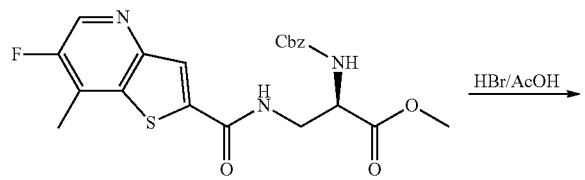

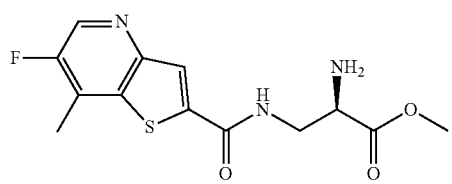

A mixture of methyl (R)-2-(((benzyloxy)carbonyl)amino)-3-(6-fluoro-7-methylthieno[3,2-b]pyridine-2-carboxamido)propanoate (70 mg, 0.16 µmol) in 33% HBr in AcOH (2 mL) was stirred at 30° C. for 1 h. The solvent was removed. The crude compound was washed with TBME (5 mL×3), filtered and the residual solvent removed by lyophilization to give methyl (R)-2-amino-3-(6-fluoro-7-methylthieno[3,2-b]pyridine-2-carboxamido)propanoate (50 mg) as HBr salt.

$^{1}$H NMR (400 MHz, DMSO-d$_6$) δ 9.21 (t, J=5.6 Hz, 1H), 8.71 (d, J=1.6 Hz, 1H), 8.63-8.37 (br s, 3H), 8.28 (s, 1H), 4.31-4.20 (m, 1H), 3.85-3.71 (m, 5H).

LCMS (MH+): m/z=312.1, t$_R$ (min, Method BB)=0.38.

[α]$^{20}$D=−2.00 (c=3 mg/mL, MeOH).

Compound 11

(R)-2-amino-3-(6,7-dimethylthieno[3,2-b]pyridine-2-carboxamido)propanoic acid The overall synthesis scheme for the preparation of (R)-2-amino-3-(6,7-dimethylthieno[3,2-b]pyridine-2-carboxamido)propanoic acid is shown below.

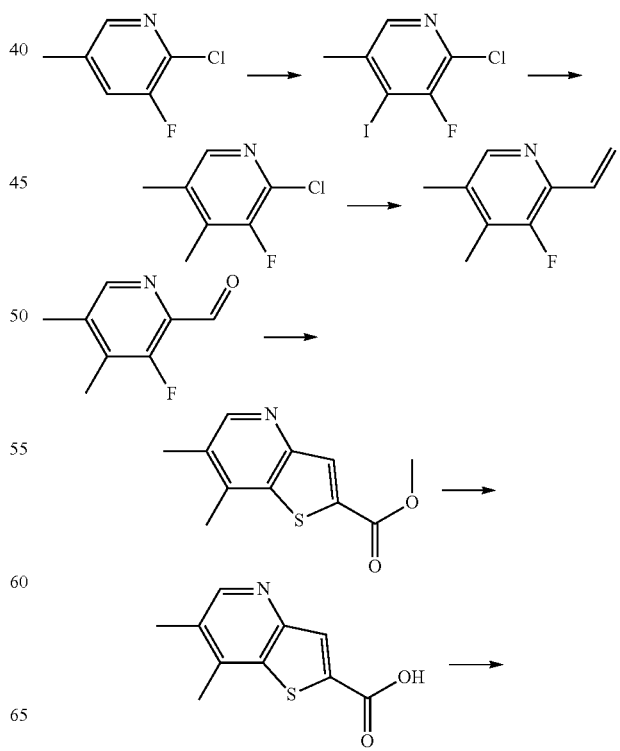

-continued

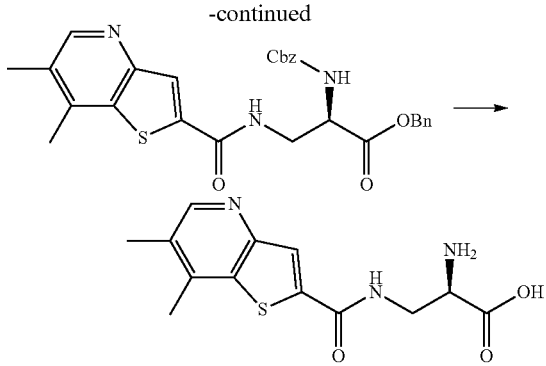

Step 1: 2-Chloro-3-fluoro-4-iodo-5-methylpyridine

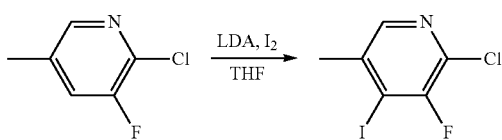

To a solution of diisopropylamine (5.8 mL, 41 mmol) in THF (50 mL) was added n-BuLi (17.5 mL, 2.5 M in hexane) at −78° C. and the reaction was stirred at −78° C. for 1 hour. A solution of 2-chloro-3-fluoro-5-methylpyridine (5.00 g, 34.4 mmol) in THF (50 mL) was added dropwise at −78° C. and the reaction mixture stirred at −78° C. for 1 hour. $I_2$ (9.50 g, 37.4 mmol) was added in portions at −78° C. and the resulting mixture was stirred at −78° C. for 1 hour. sat.$NH_4C$ (20 mL) was added to quench the reaction, followed by water (50 mL) at 0° C. and extraction with ethyl acetate (100 mL×3). The combined organic layers were washed with brine (100 mL×2), sat.$Na_2S_2O_3$ solution (100 mL), dried over anhydrous sodium sulfate, filtered and concentrated to give 2-chloro-3-fluoro-4-iodo-5-methyl-pyridine (8.2 g).

$^1$H NMR (400 MHz, CDCl$_3$) δ 7.97 (s, 1H), 2.47 (s, 3H).

Step 2: 2-Chloro-3-fluoro-4,5-dimethylpyridine

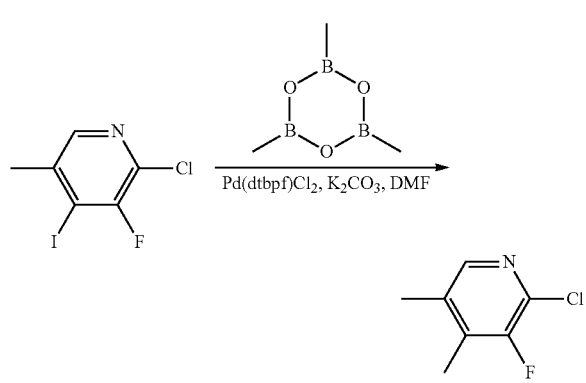

A mixture of 2-chloro-3-fluoro-4-iodo-5-methylpyridine (4.20 g, 15.5 mmol), 2,4,6-trimethyl-1,3,5,2,4,6-trioxatriborinane (4.27 g, 34.0 mmol), K$_2$CO$_3$ (4.28 g, 30.9 mmol) and pd(dtbpf)Cl$_2$ (1.01 g, 1.55 mmol) in dioxane (10 mL) was degassed by purging with N$_2$, and then the mixture was stirred at 80° C. under N$_2$ for 16 h. Then additional 2,4,6-trimethyl-1,3,5,2,4,6-trioxatriborinane (4.27 g, 34.0 mmol) was added, and the resulting mixture was stirred at 80° C. for another 16 h. Water (20 ml) was added to quench the reaction followed by extraction with ethyl acetate (20 mL×3). The combined organic layers were washed with brine (20 mL×2), dried over anhydrous sodium sulfate, filtered and concentrated. The residue was purified by Combi flash (silica gel, petroleum ether/ethyl acetate with ethyl acetate from 010%) to give 2-chloro-3-fluoro-4,5-dimethylpyridine (1.2 g).

$^1$H NMR (400 MHz, CDCl$_3$) δ 7.95 (s, 1H), 2.22-2.27 (m, 6H).

Step 3: 3-Fluoro-4,5-dimethyl-2-vinylpyridine

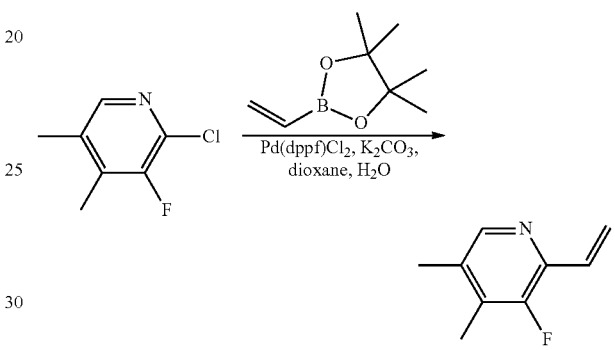

A mixture of 2-chloro-3-fluoro-4,5-dimethylpyridine (1.70 g, 10.7 mmol), 4,4,5,5-tetramethyl-2-vinyl-1,3,2-dioxaborolane (2.46 g, 15.9 mmol), Pd(dppf)Cl$_2$ (780 mg, 1.07 mmol) and K$_2$CO3 (2.94 g, 21.3 mmol) in a mixture of dioxane (80 mL) and water (8 mL) was degassed by purging with N$_2$, and then the mixture was stirred at 80° C. for 16 h under N$_2$ atmosphere. Water (50 ml) was added and the mixture was extracted with ethyl acetate (50 mL×3). The combined organic layers were washed with brine (50 mL×2), dried over Na$_2$SO$_4$, filtered and concentrated. The residue was purified by Combi flash (silica gel, petroleum ether/ethyl acetate with ethyl acetate from 0~30%) to give 3-fluoro-4,5-dimethyl-2-vinylpyridine (1.0 g).

$^1$H NMR (400 MHz, CDCl$_3$) δ 8.10 (s, 1H), 7.04-6.82 (m, 1H), 6.31 (dd, J=2.0 Hz, 17.6 Hz, 1H), 5.48 (dd, J=2.0 Hz, 11.2 Hz, 1H), 2.4 (s, 3H), 2.18 (d, J=2.0 Hz, 3H).

Step 4: 3-Fluoro-4,5-dimethylpicolinaldehyde

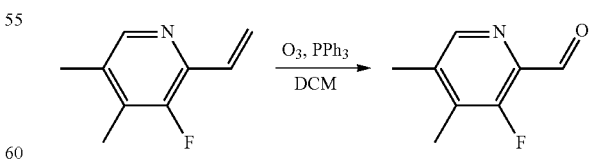

Ozone (15 psi) was bubbled through a solution of 3-fluoro-4,5-dimethyl-2-vinylpyridine (1.00 g, 6.61 mmol) in DCM (200 mL) at −70° C. for 15 min. Then PPh$_3$ (2.08 g, 7.94 mmol) was added at −70° C., the mixture was stirred at 25° C. for 2 h. The mixture was concentrated in vacuo, and the resulting residue was purified by Combi Flash on silica gel (petroleum ether:ethyl acetate with ethyl acetate from 0 to 50%) to give 3-fluoro-4,5-dimethylpicolinaldehyde (600 mg).

$^1$H NMR (400 MHz, CDCl$_3$) δ 10.16 (s, 1H), 8.37 (s, 1H), 2.39 (s, 3H), 2.30 (s, 3H).

Step 5: Methyl 6,7-dimethylthieno[3,2-b]pyridine-2-carboxylate

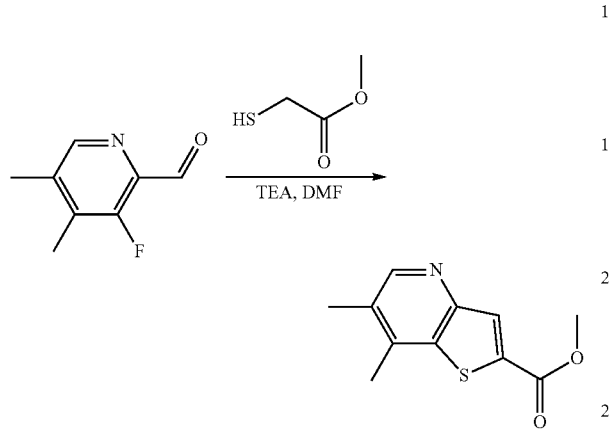

To a solution of 3-fluoro-4,5-dimethylpicolinaldehyde (550 mg, 3.59 mmol) in DMF (10 mL) was added TEA (1 mL, 7.18 mmol) and the mixture was stirred at 25° C. for 30 min, then methyl 2-sulfanylacetate (460 mg, 4.33 mmol) was added slowly. The mixture was stirred at 100° C. for 3 h. Water (10 ml) was added to quench the reaction and the mixture was extracted with ethyl acetate (10 mL×3). The combined organic layers were washed with brine (10 mL×2), dried over Na$_2$SO$_4$, filtered and concentrated to give methyl 6,7-dimethylthieno[3,2-b]pyridine-2-carboxylate (800 mg), which was used without any further purification.

$^1$H NMR (400 MHz, CDCl$_3$) δ 8.53 (s, 1H), 8.18 (s, 1H), 3.97 (s, 3H), 2.52 (s, 3H), 2.43 (s, 3H).

Step 6: 6,7-Dimethylthieno[3,2-b]pyridine-2-carboxylic acid

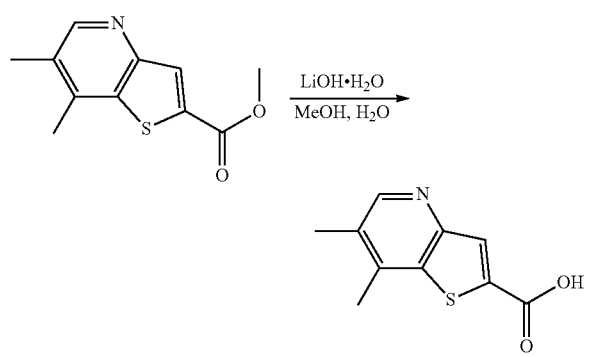

To a solution of methyl 6,7-dimethylthieno[3,2-b]pyridine-2-carboxylate (400 mg, crude) in MeOH (8 mL) was added a solution of LiOH·H$_2$O (160 mg, 3.81 mmol) in water (2 mL) and the resulting mixture was stirred at 25° C. for 1 hour. The mixture was concentrated, and water (5 mL) was added, followed by extraction with ethyl acetate (5 mL×2). The aqueous layer was acidified with sat.KHSO$_4$ solution to pH 3. The solid was filtered and dried to give 6,7-dimethylthieno[3,2-b]pyridine-2-carboxylic acid (140 mg). $^1$H NMR (400 MHz, DMSO-d$_6$) δ 13.60 (brs, 1H), 8.55 (s, 1H), 8.05 (s, 1H), 2.50 (s, 3H), 2.39 (s, 3H).

Step 7: benzyl(R)-2-(((benzyloxy)carbonyl)amino)-3-(6,7-dimethylthieno[3,2-b]pyridine-2-carboxamido)propanoate

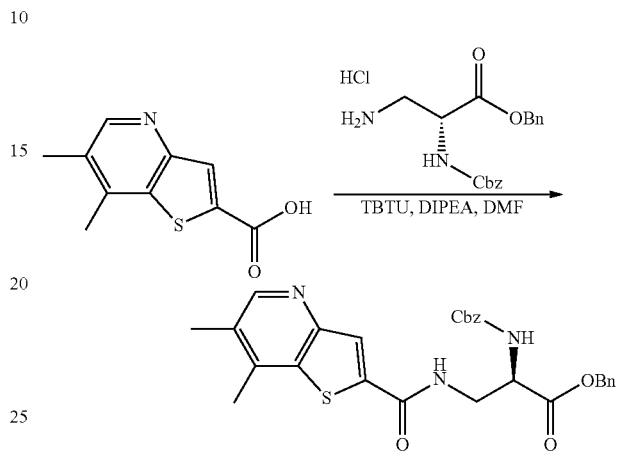

A mixture of 6,7-dimethylthieno[3,2-b]pyridine-2-carboxylic acid (70 mg, 338 μmol), benzyl (R)-3-amino-2-(((benzyloxy)carbonyl)amino)propanoate (148 mg, 406 μmol, HCl salt), O-(Benzotriazol-1-yl)-N,N,N',N'-tetramethyluronium tetrafluoroborate (163 mg, 508 μmol) and N,N-diisopropylethylamine (88.0 mg, 677 μmol) in DMF (5 mL) was stirred at 25° C. for 16 h. Water (5 mL) was added to quench the reaction and the mixture was extracted with ethyl acetate (5 mL×3). The combined organic layers were washed with brine (5 mL×2), dried over Na$_2$SO$_4$, filtered and concentrated. The residue was purified by preparative TLC (SiO$_2$, Ethyl acetate:Petroleum ether=2:1) to give benzyl (R)-2-(((benzyloxy)carbonyl)amino)-3-(6,7-dimethylthieno[3,2-b]pyridine-2-carboxamido)propanoate (100 mg).

$^1$H NMR (400 MHz, CDCl$_3$) δ 8.50 (s, 1H), 7.77 (s, 1H), 7.42-7.28 (m, 10H), 7.08 (br s, 1H), 6.01 (d, J=6.4 Hz, 1H), 5.22 (s, 2H), 5.12 (s, 2H), 4.63 (d, J=3.6 Hz, 1H), 4.00-3.81 (m, 2H), 2.51 (s, 3H), 2.42 (s, 3H).

Step 8: (R)-2-amino-3-(6,7-dimethylthieno[3,2-b]pyridine-2-carboxamido)propanoic acid

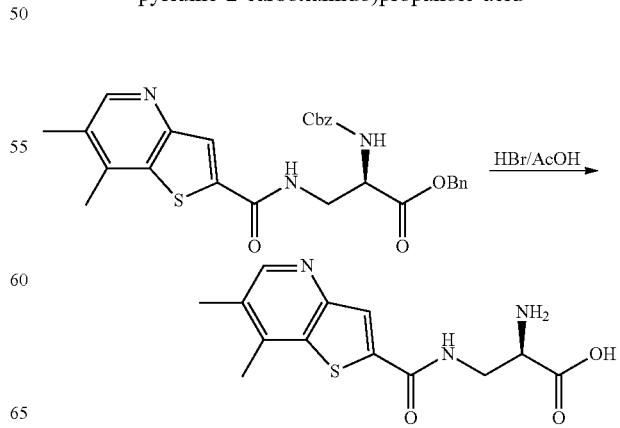

A mixture of benzyl (R)-2-(((benzyloxy)carbonyl)amino)-3-(6,7-dimethylthieno[3,2-b]pyridine-2-carboxamido)propanoate (100 mg, 193 µmol) and 33% HBr in AcOH (5 mL) was stirred at 50° C. for 16 h. The mixture was concentrated. The solid was suspended in AcOH (5 mL), filtered, and washed with additional AcOH (1 mL×2). The solvent was removed by lyophilization to give (R)-2-amino-3-(6,7-dimethylthieno[3,2-b]pyridine-2-carboxamido)propanoic acid (77 mg) as HBr salt.

$^1$H NMR (400 MHz, DMSO-$d_6$) δ 9.27 (t, J=5.2 Hz, 1H), 8.69 (s, 1H), 8.29-8.41 (m, 3H), 8.27 (s, 1H), 4.11-4.22 (m, 1H), 3.72-3.84 (m, 2H), 2.58 (s, 3H), 2.44 (s, 3H).

LCMS (MH+): m/z=294.2, $t_R$ (min, Method BB)=0.24.

$[α]^{20}$D=−3.00 (c=6 mg/mL, MeOH).

Compound 2y

Methyl(R)-2-amino-3-(6,7-dimethylthieno[3,2-b]pyridine-2-carboxamido)propanoate

The overall synthesis scheme for the preparation of methyl (R)-2-amino-3-(6,7-dimethylthieno[3,2-b]pyridine-2-carboxamido)propanoate is shown below.

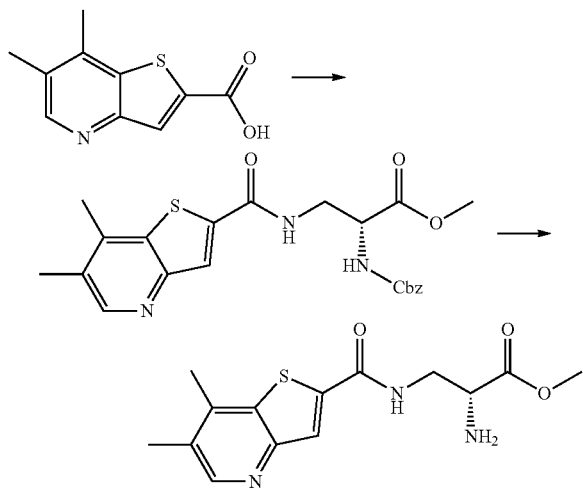

Step 1: (R)-methyl 2-(((benzyloxy)carbonyl)amino)-3-(6,7-dimethylthieno[3,2-b]pyridine-2-carboxamido)propanoate

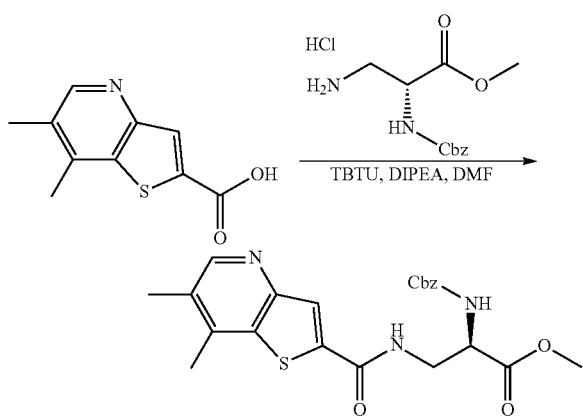

A mixture of 6,7-dimethylthieno[3,2-b]pyridine-2-carboxylic acid (70 mg, 337 µmol), (R)-methyl 3-amino-2-(((benzyloxy)carbonyl)amino)propanoate (117 mg, 0.40 mmol, HCl salt), TBTU (163 mg, 0.51 mmol) and N,N-diisopropylethylamine (88 mg, 0.68 mmol) in DMF (5 mL) was stirred at 25° C. for 16 h. Water (5 mL) was added to quench the reaction and the mixture was extracted with ethyl acetate (5 mL×3). The combined organic layers were washed with brine (5 mL×2), dried over Na$_2$SO$_4$, filtered and concentrated. The residue was purified by preparative TLC (SiO$_2$, Ethyl acetate:Petroleum ether=2:1) to give methyl (R)-2-(((benzyloxy)carbonyl)amino)-3-(6,7-dimethylthieno[3,2-b]pyridine-2-carboxamido)propanoate (100 mg).

$^1$H NMR (400 MHz, CDCl$_3$) δ 8.50 (s, 1H), 7.86 (s, 1H), 7.40-7.27 (m, 6H), 6.00 (d, J=6.4 Hz, 1H), 5.13 (s, 2H), 4.60 (m, 1H), 4.02-3.81 (m, 5H), 2.51 (s, 3H), 2.42 (s, 3H).

Step 2: methyl (R)-2-amino-3-(6,7-dimethylthieno[3,2-b]pyridine-2-carboxamido)propanoate

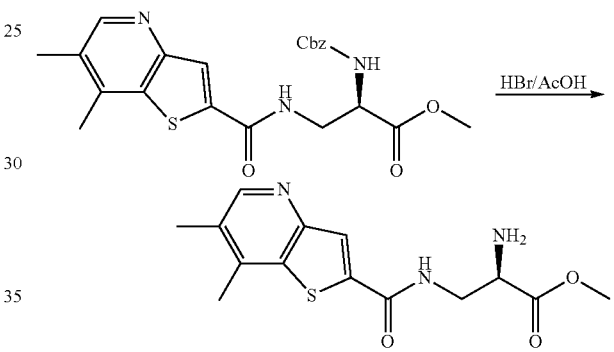

A mixture of methyl (R)-2-(((benzyloxy)carbonyl)amino)-3-(6,7-dimethylthieno[3,2-b]pyridine-2-carboxamido)propanoate (100 mg, 0.23 mmol) in 33% HBr in AcOH (5 mL) was stirred at 25° C. for 2 h. The solvent was removed. The solid was suspended in AcOH (5 mL), filtered, washed with AcOH (1 mL×2) and lyophilized to give methyl (R)-2-amino-3-(6,7-dimethylthieno[3,2-b]pyridine-2-carboxamido)propanoate (65 mg) as HBr salt.

$^1$H NMR (400 MHz, DMSO-$d_6$) δ 9.33 (t, J=5.6 Hz, 1H), 8.72 (s, 1H), 8.59-8.40 (br s, 3H), 8.29 (s, 1H), 4.42-4.17 (m, 1H), 3.80-3.73 (m, 5H), 2.60 (s, 3H), 2.45 (s, 3H).

LCMS (MH+): m/z=308.1, $t_R$ (min, Method BB)=0.30 min.

$[α]^{20}$D=−2.00 (c=5 mg/mL, MeOH).

e. In Vitro and In Vivo Characterization of Compounds of the Invention

Example 1a: Affinity Data and Permeability Data of Parent Compounds of Prodrugs of Formula I Scintillation Proximity Assay (SPA):

To determine the affinity of the compounds of the present invention a SPA is used. The assay is run in a 384-plate format (OptiPlate-384) where each well contains a mix of 5 µL of test compound, 5 µL NR1s1s2 (ligand binding domains of the NMDA receptor, MW 35.6 kDa, 0.075 ug/well final), 5 µL [3H]-MDL-105,519 (radiolabelled, high affinity N-methyl-D-aspartate (NMDA) glutamate receptor antagonist at the glycine site obtained from Sigma Aldrich, final concentration 5 nM, Kd=1.3 nM), 5 μL streptavidin coated imaging beads (Perkin Elmer cat. No.: RPNQ0273, 8 ug/well). The assay buffer contains 100 mM HEPES-NaOH, 150 mM NaCl, 1 mM EDTA, 10% glycerol at pH 7.4 in ultra-pure water. Non-specific binding is defined by inclusion of 10 μM L-689,560 (highly potent NMDA antagonist) and total binding by 1% DMSO. Following 30 minutes incubation in the dark (shaker, Multi-microplate Genie), the SPA beads are allowed to settle for 3 h after which the signal is read on a Viewlux instrument (Perkin Elmer). Normalized data are used to calculate IC50 and Ki values.

MDR1-MDCKII Permeability Assay Papp(AB)

MDR1-MDCKII cells (obtained from Piet Borst at the Netherlands Cancer Institute) were seeded onto polyethylene membranes (PET) in 96-well BD insert systems at 2.5×105 cells/mL until to 4-7 days for confluent cell monolayer formation.

Experimental Procedure:

Test compounds were diluted with the transport buffer (HBSS with 10 mM HEPES, added 1% BSA, pH 7.4) from DMSO stock solution to a concentration of 0.5 μM (DMSO: 0.4%) and applied to the apical or basolateral side of the cell monolayer. Permeation of the test compounds from A to B direction or B to A direction was determined in triplicate over a 60-minute incubation at 37° C. and 5% $CO_2$ with a relative humidity of 95%. In addition, the efflux ratio of each compound was also determined. Test and reference compounds were quantified by LC/MS/MS analysis based on the peak area ratio of analyte/IS.

Reference compounds: Fenoterol (conc: 2 μM) was used as low permeability marker and Propranolol (conc: 2 μM) was used as high permeability marker in A to B Permeability, furthermore was bi-directional permeability of a P-glycoprotein substrate (digoxin) included.

Data Analysis:

The apparent permeability coefficient Papp (cm/s) was calculated using the equation:

$$Papp = (dCr/dt) \times Vr/(A \times C0) \quad (1)$$

Where dCr/dt is the cumulative concentration of compound in the receiver chamber as a function of time (μM/s); Vr is the solution volume in the receiver chamber (0.05 mL on the apical side; 0.25 mL on the basolateral side); A is the surface area for the transport, i.e. 0.0804 $cm^2$ for the area of the monolayer; C0 is the initial concentration in the donor chamber (μM).

The efflux was calculated using the equation:

$$\text{Efflux ratio} = Papp(BA)/Papp(AB) \quad (2)$$

The mass balance (Recovery) was calculated. The mass balance is defined as: the sum of the compound recovered from the acceptor chamber and the compound remaining in the donor chamber at the end of the experiment, divided by the initial donor amount. The mass balance should be as high as possible. Criterion: Recovery <50% is insufficient.

To evaluate the integrity of the cell monolayer, Lucifer Yellow permeability was measured in one direction (A to B). The percentage of Lucifer Yellow was calculated in control wells as an estimation of the overall cell membrane integrity. The wells are considered fully acceptable if % Lucifer Yellow is less than 2%.

TABLE 3a

Permeability data and Ki data of parent compounds of the invention

| Compound | SPA Ki (nM) | Permeability Papp (AB) (values given are ×$10^{-6}$ cm/s) |
| --- | --- | --- |
| 1a | 170 | BLOQ |
| 1b | 140 | BLOQ |
| 1c | 96 | BLOQ |
| 1d | 860 | BLOQ |
| 1e | 690 | BLOQ |
| 1f | 360 | 1.03 |
| 1g | 220 | BLOQ |
| 1h | 63 | NT |
| 1i | 3900 | NT |
| 1j | 180 | NT |
| 1k | 260 | NT |
| 1l | 490 | 0.47 |

BLOQ = Below Level of Quantification
NT = Not tested

Table 3a shows that compounds of formula V have affinity to the glycine site of the NMDA receptor.

Example 1b: Permeability Data of Prodrug Compounds of the Invention

The experiments for the prodrugs were the same as for the parent compounds exemplified in Table 3a. The results are listed in table 3b. Results shows that prodrugs of the parent compounds have an improved permeability compared to the respective parent compounds.

TABLE 3b

Permeability of prodrug compounds of the invention.

| Example | Permeability Papp (AB) (values given are ×$10^{-6}$ cm/s) |
| --- | --- |
| 2a | 8.36 |
| 2b | 9.25 |
| 2c | 14.75 |
| 2d | 15.19 |
| 2e | 10.32 |
| 2f | 18.44 |
| 2g | 7.11 |
| 2h | 6.11 |
| 2i | 8.19 |
| 2j | 11.94 |
| 2k | 4.77 |
| 2l | 6.50 |
| 2m | 8.68 |
| 2n | 5.86 |
| 2o | NT |
| 2p | 0.81 |
| 2q | 1.97 |
| 2r | 5.54 |
| 2s | 12.34 |
| 2t | 4.81 |
| 2u | NT |
| 2v | 1.16 |
| 2w | 4.19 |
| 2x | 15.50 |
| 2y | 7.08 |

Example 2: In Vivo Exposure Data

In Vivo Procedure:

Brain disposition of test compound was evaluated in male Sprague Dawley rats (standard body weight range). Briefly, discrete (nominal dose: 2 mg/kg, 2 ml/kg) or cassetted (nominal dose: 1 mg/kg/compound, 2 ml/kg) test compounds were administered by intravenous bolus injection (formulated in 10% hydroxypropyl-β-cyclodextrin or 10-20% Captisol, pH=3).

Sample Collection:

Serial blood samples were collected from a lateral tail vein at designated time points (n=3 per time point) then rats were put under deep isofluorane induced anaesthesia prior to removal of brains (n=3 per time point). Blood samples were stabilized against further metabolism ex vivo by addition of an esterase inhibitor (100 µM diisopropyl fluorophosphate). Similarly, esterase inhibitor (100-125 µM) was included in the brain homogenate buffer.

Blood was collected into K3-EDTA-coated tubes and the samples are gently turned upside-down to ensure a homogenous sample. The tubes were centrifuged at 3300×g for 10 min. at max 4° C. and plasma samples were transferred to Micronic tubes. Brain samples were dissected once the animal had been sacrificed, slightly "dipped" on filter paper to remove blood overflow on the outside, and transferred into Covaris AFA tubes. Plasma and brain samples were stored at −80° C. until analysis.

Sample Preparation:

Seven calibration standards and three QC samples were prepared in plasma and brain homogenate, respectively, in the concentration range 10-10000 ng/mL. Blank samples (control matrix with internal standard) were prepared and treated in the same way as calibration standards. Prior to analysis, the brain samples were homogenized with milliQ water 1:4 (w/v) using a Covaris focused-ultrasonicator. Study samples with expected concentration above upper limit of quantification were diluted with blank matrix.

Brain homogenate and plasma from study samples, calibration standards, quality controls and blank samples were subsequently treated with the same extraction procedure, i.e. protein precipitation by adding 150 µL acetonitrile with internal standard (Tolbutamide) to 25 µL of sample. Samples were centrifuged and the supernatant from each sample was diluted 1:1 with water to lower the content of organic solvent.

LC-MS/MS:

Samples were analyzed using an AB Sciex API4000 triple quadrupole (TQ) mass spectrometer operated in positive and negative electrospray ionization and MS/MS mode (multiple reaction monitoring, MRM). The mass spectrometer was coupled to a Waters Acquity UPLC equipped with a Waters Acquity UPLC HSS C18 SB (1.7 µm, 30 mm×2.1 mm) analytical column. Chromatographic separation was achieved by a 3-minute gradient starting with 98% mobile phase A (0.1% Formic Acid in water) and 2% mobile phase B (0.1% Formic Acid in Acetonitrile) increasing to 95% mobile phase B. Flow rate was 0.6 mL/min and the column temperature was 40° C. MRM transitions (m/z) were as follows: 380→248, 350→263, Tolbutamide: 269→106 (neg) and 271→155 (pos). Quantification was performed by linear regression, 1/x2 weighting.

Concentrations of prodrug and drug in plasma and brain were quantified against matrix matched calibration standards. The blood brain deposition data is shown in the table below.

TABLE 4 in vivo exposure data of corresponding parent compound after administration a prodrug of the invention in male Sprague Dawley rats

| Compound dosed | Compound quantified | Dose mg/kg | Total Plasma concentration (ng/mL) 30 min post dose | Total Brain concentration (ng/mL) 30 min post dose |
| --- | --- | --- | --- | --- |
| 2a | 1a | 2 | 303 | 4.9 |
| 2b | 1b | 1 | 421 | 29.8 |
| 1c | 1c | 2 | 270 | 8.4 |
| 2c | 1c | 2 | 176 | 176 |
| 2d | 1c | 2 | 568 | 67 |
| 2f | 1c | 2 | 500 | BLOQ |
| 2m | 1c | 2 | 156 | 7.3 |
| 2u | 1h | 2 | 186 | BLOQ |

BLOQ = Below Level of Quantification

Example 3—Maximal Electro Shock Threshold

Naïve rats were acclimatised to the procedure room in their home cages, with food and water available ad libitum. All rats were weighed at the beginning of the study and randomly assigned to treatment groups. The individual treatment groups were dosed with either 10% hydroxypropyl-β-cyclodextrin (vehicle) or compound 2c (3, 10, or 30 mg/g), The dosing of the animals were performed by subcutaneous injection 30 min before test according to treatment groups. Rats were individually assessed for the production of a tonic hind limb extensor seizure using a Hugo Sachs Electronik stimulator, which delivered an adjustable constant current (1-300 mA) of 0.3 seconds duration via corneal electrodes. The stimulus intensity was varied, from a typical baseline of 25 mA, by an 'up and down' method of shock titration. Thus, the first rat within a treatment group was given a shock at the expected or estimated seizure threshold ($CC_{50}$) current, that is, the current producing tonic hind limb extensor seizure in 50% of animals. For subsequent animals, the stimulus intensity was lowered or raised in log $0.06:10^{\wedge}(1+x*0.06)$ mA intervals if the preceding rat did or did not show tonic hind limb extension, respectively. This procedure continued for all rats within a treatment group. Data generated from treatment groups of n=12-16 were used to calculate the $CC_{50}$ values according to the method of Kimball et al. (Kimball A, Burnett W, Doherty D. Chemical protection against ionizing radiation. I. Sampling methods for screening compounds in radiation protection studies with mice. Radiat Res. 1957; 7(1):1-12). Significant differences between drug-treated animals and vehicle were assessed according to Litchfield and Wilcoxon (Litchfield J, Wilcoxon F. A simplified method for evaluating dose-effect experiments. J Pharmacol Exp Ther. 1949; 96(1): 99-113).

Figure 1:
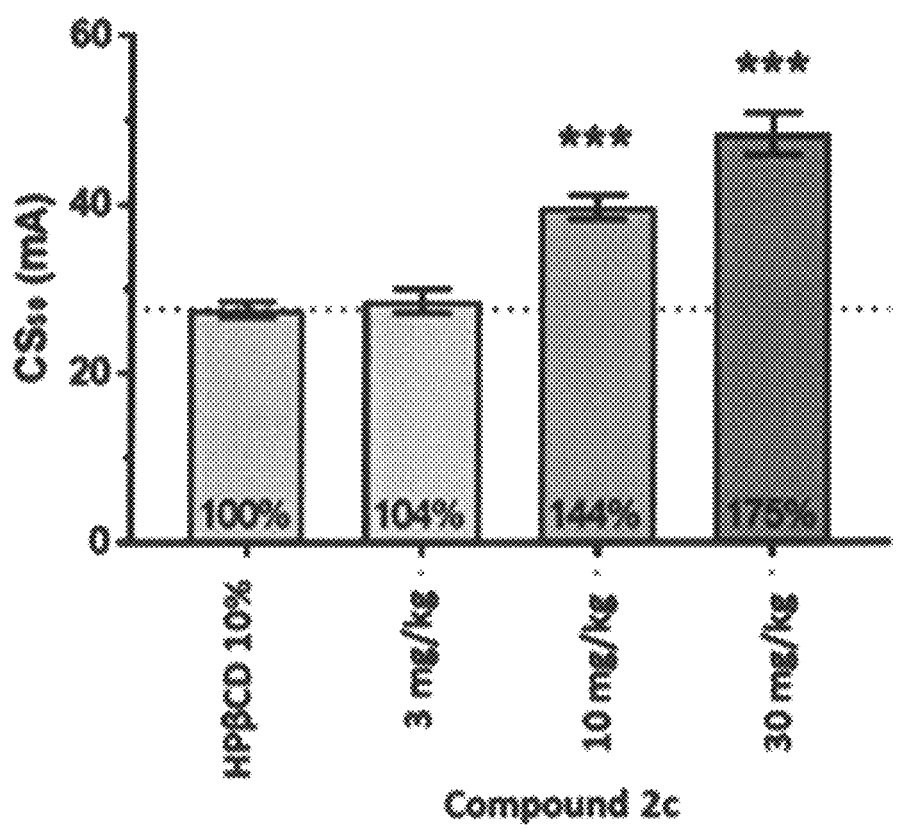
FIG. 1: Effects of compound 2c in the MEST model.
Y-axis: Estimated seizure threshold ($CC_{50}$) current (mA); X-axis: bar furthest to the left: vehicle 10% HPβCD; bar second to the left: 3 mg/kg of compound 2c; bar third to the left: 10 mg/kg of compound 2c; bar furthest to the right: 30 mg/kg of compound 2c.

As shown in FIG. 1, administration of compound 2c dosed at 3, 10 and 30 mg/kg subcutaneously showed dose dependent effects on the maximal electro shock threshold.

Example 4—Forced Swim Test

Adult male Wistar Kyoto rats from Envigo (former Harlan; Blackthorn, UK). Animals are maintained under controlled conditions (21±1° C., 37±1%, 12/12 h light/dark cycles, lights on at 8 a.m.) with food and water available ad libitum. In all studies WKY rats were randomly allocated to a maximum of 5 treatment groups (n=20 per group). WKY rats received either a single administration of either saline (vehicle), ketamine (5 mg/kg) or compound 2c (3, 10, or 30 mg/kg) according to treatment group. The dosing of the animals were performed by subcutaneous injection 24 h before test g. The WKY rats were individually placed into a glass cylinder (50 cm height, 20 cm diameter) containing 30 cm of water at 25±1° C. for a 5 min test phase. The test session recorded (using a video camera placed above the cylinder for subsequent behavioural analysis) the time of immobility (s). One-way analysis of variance (ANOVA) was used to detect statistical significance in the FST data. The Fisher least significant difference (LSD) test was used for post hoc analyses. Probability values of P<0.05 were considered as statistically significant. Statistical analyses were performed using SPSS.

As shown in FIG. 2, administration of compound 2c dosed at 3, 10 and 30 mg/kg subcutaneously showed significant effects in time of immobility at the 30 mg/kg dose.

Example 5—Resting State Electroencephalography (rsEEG) in Rats

Surgical Procedure

On the day of surgery, rats (270-300 g) were anesthetized with a 0.25 ml/100 g subcutaneous (SC) injection of 1:1 hypnorm/Dormicum and mounted in a stereotaxic frame (David Kopf Instruments, Tujunga, Calif., USA) with blunt ear bars. Marcain (0.2 ml SC) was injected under the scalp, and gel (Neutral Opthta Eye Gel) put on the eyes to prevent the mucous membrane drying out. Holes were burred in the skull to allow for placement of two depth electrodes (E363-series; PlasticsOne, Roanoke, Va., USA) in left and right pre/infralimbic PFC (AP: 3.0 mm from the bregma suture, Medial-Lateral (ML): +/−0.7 mm from the sagittal suture and DV: 3.0 mm from the dura) and thalamus (AP: −2.8 mm from the bregma suture, ML: +0.7 mm from the sagittal suture and DV: 4.4 mm from the dura) and three screw electrodes at vertex (AP: −2 mm from the bregma suture, ML: +2.0 mm from the sagittal suture), a reference electrode (AP: +8.0 mm and ML: −2.0 mm), and a ground electrode (AP: −5 mm, ML: +5 mm). During surgeries, nails were cut to prevent rats from scratching wounds following surgery. After completion of surgeries, rats were placed under warming lamps until recovery of consciousness (maximum 4 hrs). Water soaked food pellets were placed in the home cage, so the rat easily and quickly could start feeding. Extra muesli was supplied to aid the recovery. Rats were treated with Norodyl and Noromox for 5 days in total and closely observed during a 10-14-day post-surgery recovery period. Animal bodyweights were recorded daily. No rats lost more than 10% of their pre-surgery bodyweight. Sutures were removed after 7-10 days. At the end of experiments electrical lesions were performed in all recording electrodes and brains were cut for visual microscopy inspection of electrode placement. The differences between depth- and screw-electrode impedances were handled by investigating relative power changes and common-mode noise sources were reduced from recording in shielded boxes and excluding power estimates around 50, 100, and 150 Hz from analyses.

Electrophysiological Recordings

Rats were handled daily and habituated to recording box the week before recording sessions. Recordings were performed during the dark phase of the light/dark cycle. At 8 AM, rats (400-500 g) were individually transferred to an acrylic chamber (30 cm wide 45 cm deep 55 cm high) placed within an electrically shielded sound-proof box (90 cm wide 55 cm deep 65 cm high) and were tethered to a six-pin wire suspended from a rotating swivel, allowing free movement within the recording box. Rats were habituated for 2-h followed by 45 minutes of baseline recording, where after rats were injected subcutaneously with 10% hydroxypropyl-β-cyclodextrin (vehicle), 10 mg/kg ketamine in saline, or 20 mg/kg compound 2c in 10% HPCD and left in the box for two more h. Rats only went through recording sessions once a week with at least six days between recordings to allow for wash-out of compounds. The analog LFP/ECoG signals were amplified and band-pass filtered at 0.01-300 Hz (Precision Model 440; Brownlee, Palo Alto, Calif., USA) and converted to a digital signal at a sampling rate of 1 kHz (CED Power 1401, Power 1 (625 kHz, 16 bit) and CED Expansion ADC16; CED, Cambridge, England). An analog 50 Hz notch filter (Precision Model 440, Brownlee) was applied to the LFP/ECoG signals of the first dataset but was not applied in the following pharmaco-EEG experiments. Video recordings were processed in EthoVision producing the mobility signal, which was subsequently collected in Spike2 along with the LFP/ECoG signals with a delay used subsequently to synchronize the signals.

Data Analysis

The development of the locomotive state-detection algorithm and the state-specific pharmaco-EEG analyses were carried out in MATLAB R2017a (The MathWorks, Inc., Natick, Mass., USA) using functions from the sigTOOL toolbox. Significant differences between drug-treated animals and vehicle were assessed according to Turkey's honest significant difference. As shown in FIGS. 3A-3D administration of compound 2c dosed at 20 mg/kg subcutaneously showed significant effects in high frequency oscillation in resting state Electroencephalography and showing similarities to that observed with ketamine.

Example 6—Microdialysis Studies in Rats

Male Sprague-Dawley rats, initially weighing 275-300 g, were used. The animals were housed under a 12-hr light/dark cycle under controlled conditions for regular in-door temperature (21±2° C.) and humidity (55±5%) with food and tap water available ad libitum. Rats were anaesthetised with hypnorm/dormicum (2 ml/kg) and intracerebral guide cannulas (CMA/12) were stereotaxically implanted into the brain, aiming to position the dialysis probe tip in the ventral hippocampus (co-ordinates: 5.6 mm posterior to bregma, lateral −4.8 mm, 7.0 mm ventral to dura. Anchor screws and acrylic cement were used for fixation of the guide cannulas. The body temperature of the animals was monitored by rectal probe and maintained at 37° C. The rats were allowed to recover from surgery for 2 days, housed singly in cages.

On the day of the experiment a microdialysis probe (CMA/12, 0.5 mm diameter, 3 mm length) was inserted through the guide cannula. The probe was connected via a dual channel swivel to a microinjection pump. Perfusion of the microdialysis probe with filtered Ringer solution (145 mm NaCl, 3 mM KCl, 1 mM MgCl2, 1.2 mM CaCl2)) was begun shortly before insertion of the probe into the brain and continued for the duration of the experiment at a constant flow rate of 1 μl/min. After 180 min of stabilisation, the experiments were initiated. Dialysates were collected every 20 min into polystyrene microvials containing trifluoroacetic acid (final concentration 0.25%) at 4° C. After the experiments the animals were sacrificed and the brains removed and the probe placement was verified.

In vitro recovery of the probes was determined by using stock solutions of compound 2c and compound 1c at 1000 ng/ml. The experiments were performed at room temperature. For each compound three microdialysis probes (CMA/3) were inserted into tubes containing stock solutions. Perfusion of the microdialysis probe with filtered Ringer solution was begun shortly before insertion of the probe into the stock solutions and continued for the duration of the experiment at a constant flow rate of 1 µl/min. After 60 min of stabilisation 3 consecutive 20-min samples were sampled by each probe.

As shown in FIG. 4, considerable extracellular levels of compound 1c in the rat ventral hippocampus after systemic administration of compound 2c dosed at 30 mg/kg subcutaneously were observed.

The invention claimed is:

1. A compound of Formula I, or a pharmaceutically acceptable salt thereof, wherein:

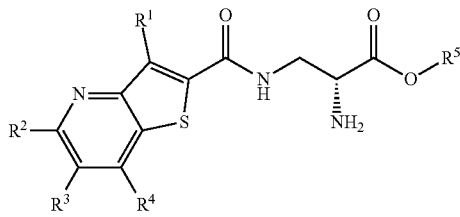

I $R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $NR^aR^b$, $OR^6$, L-($OR^6$), and $R^7$;

$R^a$ and $R^b$ are independently selected from the group consisting of hydrogen, and $C_{1-4}$ alkyl;

$R^6$ is selected from the group consisting of hydrogen, halogen, $C_{1-4}$ alkyl, $C_{1-4}$ haloalkyl, $C_{1-4}$ hydroxyalkyl, and $C_{1-4}$ hydroxyhaloalkyl;

L represents $C_{1-3}$ alkylene;

$R^7$ is selected from the group consisting of $C_{3-6}$ cycloalkyl, phenyl, a 4, 5, or 6 membered heterocycle, and a 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F;

$R^5$ is selected from the group consisting of $C_{1-5}$ alkyl, $C_{1-4}$ haloalkyl, hydroxyalkyl, $C_{1-4}$ hydroxyhaloalkyl, $R^8$, $WR^8$, and W($OR^9$);

W is selected from the group consisting of $C_{1-3}$ alkylene and —$CH_2C(O)$—;

$R^8$ is selected from the group consisting of $C_{3-6}$ cycloalkyl, phenyl, a 4, 5, or 6 membered heterocycle, and a 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F; and $R^9$ is $C_{1-3}$ alkyl unsubstituted or substituted with 1, 2 or 3 F.

2. The compound according to claim 1, or a pharmaceutically acceptable salt thereof, wherein:

$R^1$ is selected from the group consisting of a hydrogen, halogen, and $C_{1-4}$ alkyl;

$R^2$ is selected from the group consisting of hydrogen, halogen, and $C_{1-4}$ alkyl;

$R^3$ is selected from the group consisting of hydrogen, halogen, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $OR^6$, and $R^7$;

$R^6$ is selected from the group consisting of hydrogen, $C_{1-4}$ alkyl, and $C_{1-4}$ haloalkyl;

$R^7$ is selected from the group consisting of a $C_{3-6}$ cycloalkyl and phenyl, wherein said cycloalkyl and phenyl are independently unsubstituted or substituted with 1, 2 or 3 substituents independently selected from halogen, $C_{1-3}$ alkyl, and $C_{1-3}$ alkoxy, wherein said $C_{1-3}$ alkyl and $C_{1-3}$ alkoxy are independently unsubstituted or substituted with 1, 2 or 3 F;

$R^5$ is selected from the group consisting of $C_{1-4}$ alkyl, $R^8$, $WR^8$, W($OR^9$);

W is $C_{1-3}$ alkylene;

$R^8$ is selected from the group consisting of $C_{3-6}$ cycloalkyl and phenyl, wherein said cycloalkyl and phenyl is independently unsubstituted or substituted with 1, 2 or 3 substituents independently selected from halogen, $C_{1-3}$ alkyl, and $C_{1-3}$ alkoxy, wherein said $C_{1-3}$ alkyl and $C_{1-3}$ alkoxy are independently unsubstituted or substituted with 1, 2 or 3 F; and $R^9$ is $C_{1-3}$ alkyl unsubstituted or substituted with 1, 2 or 3 F.

3. The compound according to claim 1, or a pharmaceutically acceptable salt thereof, wherein $R^1$ is hydrogen.

4. The compound according to claim 1, or a pharmaceutically acceptable salt thereof, wherein $R^2$ is hydrogen.

5. The compound according to claim 1, or a pharmaceutically acceptable salt thereof, wherein $R^3$ is selected from the group consisting of hydrogen, $C_{1-4}$ alkyl, and halogen.

6. The compound according to claim 5, or a pharmaceutically acceptable salt thereof, wherein $R^3$ is selected from the group consisting of hydrogen, fluorine, and methyl.

7. The compound according to claim 6, or a pharmaceutically acceptable salt thereof, wherein $R^3$ is hydrogen.

8. The compound according to claim 1, or a pharmaceutically acceptable salt thereof, wherein $R^1$, $R^2$, and $R^3$ are hydrogen.

9. The compound according to claim 1, or a pharmaceutically acceptable salt thereof, wherein $R^4$ is $C_{1-4}$ alkyl.

10. The compound according to claim 1, or a pharmaceutically acceptable salt thereof, wherein $R^4$ is methyl.

11. The compound according to claim 1, or a pharmaceutically acceptable salt thereof, wherein $R^4$ is $C_{1-4}$ fluoroalkyl.

12. The compound according to claim 1, or a pharmaceutically acceptable salt thereof, wherein $R^4$ is halogen.

13. The compound according to claim 1, or a pharmaceutically acceptable salt thereof, wherein $R^4$ is phenyl unsubstituted or substituted with $C_{1-3}$ alkyl.

14. The compound according to claim 1, or a pharmaceutically acceptable salt thereof, wherein $R^4$ is $C_{1-4}$ alkoxy.

15. The compound according to claim 1, or a pharmaceutically acceptable salt thereof, wherein $R^4$ is selected from the group consisting of $C_{1-4}$ alkyl, $C_{1-4}$ fluoroalkyl, $NR^aR^b$, $C_{1-4}$ hydroxyalkyl, $C_{1-4}$ alkoxy, halogen, and phenyl unsubstituted or substituted with ethyl.

16. The compound according to claim 1, or a pharmaceutically acceptable salt thereof, wherein $R^4$ is selected from the group consisting of methyl, ethyl, isopropyl, cyclopropyl, fluoromethyl, difluoromethyl, trifluoromethyl, hydroxymethyl, isopropoxy, ethoxy, methoxy, bromo, fluoro, dimethylamino, and ethylphenyl.

17. The compound, or a pharmaceutically acceptable salt thereof, according to claim 1 having the formula Ia, or a pharmaceutically acceptable salt thereof, wherein:

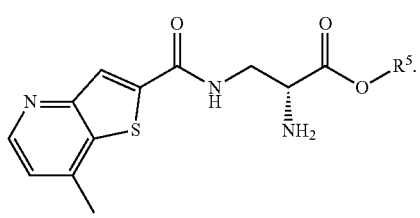

Ia

18. The compound according to claim 1, or a pharmaceutically acceptable salt thereof, wherein $R^5$ is selected from the group consisting of methyl, ethyl, propyl, isopropyl, cyclopropyl, butyl, isobutyl, —$CH_2$-cyclopropyl, 2-methoxyethyl, isopentyl, benzyl, cyclohexyl, 2-oxo-2-(pyrrolidin-1-yl)ethyl, and phenyl.

19. The compound according to claim 1, or a pharmaceutically acceptable salt thereof, wherein $R^5$ is $C_{1-5}$ alkyl.

20. The compound according to claim 1, or a pharmaceutically acceptable salt thereof, wherein $R^5$ is selected from the group consisting of methyl, ethyl, propyl, butyl, and isopropyl.

21. The compound according to claim 1, or a pharmaceutically acceptable salt thereof, wherein $R^5$ is selected from the group consisting of methyl, ethyl, propyl, and butyl.

22. The compound according to claim 1, or a pharmaceutically acceptable salt thereof, wherein $R^5$ is selected from the group consisting of methyl and ethyl.

23. The compound according to claim 1, or a pharmaceutically acceptable salt thereof, wherein $R^5$ is methyl.

24. The compound according to claim 1, or a pharmaceutically acceptable salt thereof, wherein $R^5$ is ethyl.

25. The compound, or a pharmaceutically acceptable salt thereof, according to claim 1 selected from the group consisting of:
methyl (R)-2-amino-3-(7-(difluoromethyl)thieno[3,2-b]pyridine-2-carboxamido)propanoate;
methyl (R)-2-amino-3-(7-cyclopropylthieno[3,2-b]pyridine-2-carboxamido) propanoate;
methyl (R)-2-amino-3-(7-methylthieno[3,2-b]pyridine-2-carboxamido)propanoate;
ethyl (R)-2-amino-3-(7-methylthieno[3,2-b]pyridine-2-carboxamido)propanoate;
propyl (R)-2-amino-3-(7-methylthieno[3,2-b]pyridine-2-carboxamido)propanoate;
isopropyl (R)-2-amino-3-(7-methylthieno[3,2-b]pyridine-2-carboxamido)propanoate;
cyclopropyl (R)-2-amino-3-(7-methylthieno[3,2-b]pyridine-2-carboxamido)propanoate;
butyl (R)-2-amino-3-(7-methylthieno[3,2-b]pyridine-2-carboxamido)propanoate;
isobutyl (R)-2-amino-3-(7-methylthieno[3,2-b]pyridine-2-carboxamido)propanoate;
cyclopropylmethyl (R)-2-amino-3-(7-methylthieno[3,2-b]pyridine-2-carboxamido)propanoate;
2-methoxyethyl (R)-2-amino-3-(7-methylthieno[3,2-b]pyridine-2-carboxamido)propanoate;
isopentyl (R)-2-amino-3-(7-methylthieno[3,2-b]pyridine-2-carboxamido)propanoate;
benzyl (R)-2-amino-3-(7-methylthieno[3,2-b]pyridine-2-carboxamido)propanoate;
cyclohexyl (R)-2-amino-3-(7-methylthieno[3,2-b]pyridine-2-carboxamido)propanoate;
phenyl (R)-2-amino-3-(7-methylthieno[3,2-b]pyridine-2-carboxamido)propanoate;
(2-oxo-2-pyrrolidin-1-yl-ethyl) (R)-2-amino-3-(7-methylthieno[3,2-b]pyridine-2-carboxamido)propanoate;
methyl (R)-2-amino-3-(7-(2-ethylphenyl)thieno[3,2-b]pyridine-2-carboxamido)propanoate;
methyl (R)-2-amino-3-(7-methoxythieno[3,2-b]pyridine-2-carboxamido)propanoate;
methyl (R)-2-amino-3-(7-(trifluoromethyl)thieno[3,2-b]pyridine-2-carboxamido)propanoate;
methyl (R)-2-amino-3-(7-isopropoxythieno[3,2-b]pyridine-2-carboxamido)propanoate;
methyl (R)-2-amino-3-(7-bromothieno[3,2-b]pyridine-2-carboxamido)propanoate;
methyl (R)-2-amino-3-(7-(hydroxymethyl)thieno[3,2-b]pyridine-2-carboxamido)propanoate;
methyl (R)-2-amino-3-(7-(fluoromethyl)thieno[3,2-b]pyridine-2-carboxamido)propanoate;
methyl (R)-2-amino-3-(6-fluoro-7-methyl-thieno[3,2-b]pyridine-2-carboxamido)propanoate; and
methyl (R)-2-amino-3-(6,7-dimethylthieno[3,2-b]pyridine-2-carboxamido)propanoate; and pharmaceutically acceptable salts thereof.

26. The compound, or a pharmaceutically acceptable salt thereof, according to claim 1 selected from the group consisting of:
methyl (R)-2-amino-3-(7-methylthieno[3,2-b]pyridine-2-carboxamido)propanoate;
ethyl (R)-2-amino-3-(7-methylthieno[3,2-b]pyridine-2-carboxamido)propanoate;
propyl (R)-2-amino-3-(7-methylthieno[3,2-b]pyridine-2-carboxamido)propanoate;
isopropyl (R)-2-amino-3-(7-methylthieno[3,2-b]pyridine-2-carboxamido)propanoate;
cyclopropyl (R)-2-amino-3-(7-methylthieno[3,2-b]pyridine-2-carboxamido)propanoate;
butyl (R)-2-amino-3-(7-methylthieno[3,2-b]pyridine-2-carboxamido)propanoate;
isobutyl (R)-2-amino-3-(7-methylthieno[3,2-b]pyridine-2-carboxamido)propanoate;
cyclopropylmethyl (R)-2-amino-3-(7-methylthieno[3,2-b]pyridine-2-carboxamido)propanoate;
2-methoxyethyl (R)-2-amino-3-(7-methylthieno[3,2-b]pyridine-2-carboxamido)propanoate;
isopentyl (R)-2-amino-3-(7-methylthieno[3,2-b]pyridine-2-carboxamido)propanoate;
benzyl (R)-2-amino-3-(7-methylthieno[3,2-b]pyridine-2-carboxamido)propanoate;
cyclohexyl (R)-2-amino-3-(7-methylthieno[3,2-b]pyridine-2-carboxamido)propanoate; and
phenyl (R)-2-amino-3-(7-methylthieno[3,2-b]pyridine-2-carboxamido)propanoate; and pharmaceutically acceptable salts thereof.

27. The compound, or a pharmaceutically acceptable salt thereof, according to claim 1 selected from the group consisting of:
methyl (R)-2-amino-3-(7-methylthieno[3,2-b]pyridine-2-carboxamido)propanoate;
ethyl (R)-2-amino-3-(7-methylthieno[3,2-b]pyridine-2-carboxamido)propanoate;
propyl (R)-2-amino-3-(7-methylthieno[3,2-b]pyridine-2-carboxamido)propanoate; and
isobutyl (R)-2-amino-3-(7-methylthieno[3,2-b]pyridine-2-carboxamido)propanoate; and pharmaceutically acceptable salts thereof.

28. A pharmaceutical composition comprising a compound, or a pharmaceutically acceptable salt thereof, according to claim 1, and one or more pharmaceutically acceptable carriers or diluents.

29. The compound, or a pharmaceutically acceptable salt thereof, according to claim 1 wherein said compound is methyl (R)-2-amino-3-(7-methylthieno[3,2-b]pyridine-2-carboxamido)propanoate.

30. The compound, or a pharmaceutically acceptable salt thereof, according to claim 1 wherein said compound is ethyl (R)-2-amino-3-(7-methylthieno[3,2-b]pyridine-2-carboxamido)propanoate.

31. The compound, or a pharmaceutically acceptable salt thereof, according to claim 1 wherein said compound is propyl (R)-2-amino-3-(7-methylthieno[3,2-b]pyridine-2-carboxamido)propanoate.

32. The pharmaceutical composition according to claim 28, comprising methyl (R)-2-amino-3-(7-methylthieno[3,2-b]pyridine-2-carboxamido)propanoate or a pharmaceutically acceptable salt thereof.

33. The pharmaceutical composition according to claim 28, comprising ethyl (R)-2-amino-3-(7-methylthieno[3,2-b]pyridine-2-carboxamido)propanoate or a pharmaceutically acceptable salt thereof.

34. The pharmaceutical composition according to claim 28, comprising propyl (R)-2-amino-3-(7-methylthieno[3,2-b]pyridine-2-carboxamido)propanoate or a pharmaceutically acceptable salt thereof.

35. A method for the treatment of depression comprising the administration of a therapeutically effective amount of the compound or pharmaceutically acceptable salt thereof according to claim 1 to a patient in need thereof.

36. The method for the treatment of depression according to claim 35, wherein the depression is selected from the group consisting of major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

* * * * *